(12) United States Patent
Hoyt et al.

(10) Patent No.: US 9,382,226 B2
(45) Date of Patent: Jul. 5, 2016

(54) ALDOSTERONE SYNTHASE INHIBITORS

(75) Inventors: Scott B. Hoyt, Hoboken, NJ (US); Min K. Park, Whippany, NJ (US); Clare London, Chatham, NJ (US); Yusheng Xiong, Plainsboro, NJ (US); D. Jonathan Bennett, Aberdour (GB); Jiaqiang Cai, Glasgow (GB); Paul Ratcliffe, Strathaven (GB); Andrew Cooke, East Kilbride (GB); Emma Carswell, Eaglesham (GB); John MacLean, Kilmarnock (GB); Rohit Saxena, Uttar Pradesh (IN); Bheemashankar A. Kulkarni, Karnataka State (IN); Archana Gupta, Uttar Pradesh (IN)

(73) Assignee: Merck Sharp & Dohme Corp., Rahway, NJ (US)

( * ) Notice: Subject to any disclaimer, the term of this patent is extended or adjusted under 35 U.S.C. 154(b) by 86 days.

(21) Appl. No.: 13/811,059

(22) PCT Filed: Jul. 20, 2011

(86) PCT No.: PCT/US2011/044598
§ 371 (c)(1),
(2), (4) Date: Jul. 15, 2013

(87) PCT Pub. No.: WO2012/012478
PCT Pub. Date: Jan. 26, 2012

(65) Prior Publication Data
US 2013/0317057 A1  Nov. 28, 2013

Related U.S. Application Data

(60) Provisional application No. 61/366,243, filed on Jul. 21, 2010, provisional application No. 61/473,471, filed on Apr. 8, 2011.

(51) Int. Cl.
| | |
|---|---|
| *C07D 401/04* | (2006.01) |
| *C07D 413/14* | (2006.01) |
| *C07D 471/04* | (2006.01) |
| *A61K 31/4375* | (2006.01) |
| *A61K 31/4439* | (2006.01) |
| *A61K 31/4184* | (2006.01) |
| *A61K 31/4709* | (2006.01) |

(52) U.S. Cl.
CPC .......... *C07D 401/04* (2013.01); *A61K 31/4184* (2013.01); *A61K 31/4375* (2013.01); *A61K 31/4439* (2013.01); *A61K 31/4709* (2013.01); *C07D 413/14* (2013.01); *C07D 471/04* (2013.01)

(58) Field of Classification Search
CPC ........... A61K 31/4184; A61K 31/4375; A61K 31/4439; A61K 31/4709; C07D 401/04; C07D 413/14; C07D 471/00

USPC ........ 514/300, 314, 338; 546/122, 144, 272.1
See application file for complete search history.

(56) References Cited

U.S. PATENT DOCUMENTS

| 5,387,592 A | 2/1995 | Bradbury et al. |
|---|---|---|
| 2006/0014756 A1 | 1/2006 | Edwards et al. |

FOREIGN PATENT DOCUMENTS

| EP | 1162196 A1 | 12/2001 |
|---|---|---|
| WO | WO0151473 A1 | 7/2001 |
| WO | WO2004041209 | * 5/2004 |
| WO | WO2005118555 A1 | 12/2005 |
| WO | WO2007103755 A2 | 9/2007 |
| WO | WO2010130796 A1 | 11/2010 |

OTHER PUBLICATIONS

Wilfred et al. (Synlett, 2004, No. 9, pp. 1628-1630).*
Dhanak et al.2007, Abstract, WO 2007103755.*
Cao et al. (Current medicinal chemistry, 2008, vol. 15, abstract).*
Matsushita H. et al., "Smart cleavage reactions: the synthesis of benzimidazoles and benzothiazoles from polymer-bound esters", Tetrahedron Letters, vol. 45, No. 2, Jan. 5, 2004, pp. 313-316.
Ulrike E Hille et al., "First selective CYP11B1 Inhibitors for the Treatment of Cortisol-Dependent Diseases", ACS Medicinal Chemistry Letters, American Chemical Society, US, vol. 2, No. 1, Oct. 22, 2010, pp. 2-6.
Zimmer, C., et al. "N-(Pyridin-3-yl)benzamides as selective inhibitors of human aldosterone synthase (CYP11B2)", Bioorganic & Medicinal Chemistry Letters, vol. 21, No. 1, Nov. 12, 2010, pp. 186-190.

(Continued)

*Primary Examiner* — Savitha Rao
(74) *Attorney, Agent, or Firm* — Janet E. Fair; Anna L. Cocuzzo

(57) ABSTRACT

The invention involves compounds of structural Formula (I) and the pharmaceutically acceptable salts thereof. The compounds of the invention are effective at selectively inhibiting CYP11B2, and are therefore useful for the treatment or prophylaxis of disorders that are associated with elevated aldosterone levels, including, but not limited to, hypertension and heart failure.

(I)

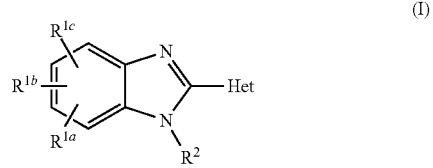

16 Claims, No Drawings

(56) References Cited

OTHER PUBLICATIONS

Gilbert, K.C., et al., "Aldosterone and Inflammation", Curr. Opin. Endocrinol. Diabetes Obes., vol. 17, 2010, pp. 199-204.
Pitt, B., et al., "The Effect of Spironolactone on morbitiy and mortality in patients with severe heart failure", New Engl. J. Med., vol. 341, 1999, pp. 709-717.
Pitt, B., et al., "Eplerenone, a Selective Aldosterone Blocker, in Patients with Left Ventricular Dysfunction after Myocardial Infarction", New Engl. J. Med., vol. 348, 2003, pp. 1309-1321.
MacFadyen, R. J., et al., "Aldosterone blockade reduces vascular collagen turnover, improves heart rate variability and reduces early morning rise in heart rate in heart failure patients", Cardiovasc Res., vol. 35, 1997, pp. 30-34.
Soberman, J. E., et al., "Spironolactone in Congestive Heart Failure", Curr. Hypertens. Rep., vol. 2, 2000, pp. 451-456.
Kawamoto, T., et. al, "Role of steroid 11 B-hydroxylase and steroid 18-hydroxylase in the biosynthesis of glucocorticoids and mineralocorticolds in humans", Proc. Natl. Acad. Sci, vol. 89, 1992, pp. 1458-1462.
Taymans, S. E., et al., "Human CYP11B2 (Aldosterone Synthase) maps to Chromosome 8q24.3", J. Clin. Endocrinol. Metab., vol. 83, 1998, pp. 1033-1036.
Supplementary EP Search Report for Application No. EP 11 81 0313 dated Nov. 13, 2013, 4 pages.
EP Search Report (Form PCT/ISA/210), mailing date: Dec. 12, 2011.
Database Caplus, Chemical Abstracts Service: RN 1308670-03-2, Jun. 10, 2011; RN 1308660-48-8, Jun. 10, 2011; RN 1255871-21-6, Dec. 8, 2010; RN 1246929-32-7, Nov. 25, 2010; RN 1196131-46-0, Dec. 7, 2009; RN 1038408-43-3, Aug. 4, 2008; RN 864274-88-4, Sep. 30, 2005; RN 548739-20-4, Jul. 16, 2003; RN 548739-19-1, Jul. 16, 2003; RN 548739-18-0, Jul. 16, 2003; RN 548739-17-9, Jul. 16, 2003; RN 297149-01-0, Oct. 19, 2000.
Jung, M. H. et al., Synthesis of 2-(1-Methyl-1,2,5,6-tetrahydropyridin-3-yl)benzimidazoles, J. Heterocyclic Chem, 2003, p. 37-40, vol. 40.

* cited by examiner

ALDOSTERONE SYNTHASE INHIBITORS

CROSS REFERENCE TO RELATED APPLICATIONS

This application is the National Stage of International Application No. PCT/US2011/044598 filed on Jul. 20, 2011, which claims the benefit under 35 U.S.C. 119(e) of U.S. Provisional Application Nos. 61/366,243, filed Jul. 21, 2010, and 61/473,471, filed Apr. 8, 2011.

RELATED APPLICATIONS

This application claims benefit of provisional application U.S. Ser. No. 61/366,231, filed Jul. 21, 2010, and provisional application U.S. Ser. No. 61/473,417, filed Apr. 8, 2010, both herein incorporated by reference.

BACKGROUND OF THE INVENTION

Aldosterone is a steroid hormone secreted in the adrenal cortex. In primary cells of the distal tubules and collecting ducts of the kidney, aldosterone binding to the mineralocorticoid receptor (MR) results in the retention of sodium and water and excretion of potassium, which in turn leads to increased blood pressure. Aldosterone also causes inflammation that leads to fibrosis and remodeling in the heart, vasculature and kidney. This inflammation may proceed by MR-dependent as well as MR-independent mechanisms (Gilbert, K. C. et al., Curr. Opin. Endocrinol. Diabetes Obes., vol. 17, 2010, pp. 199-204).

Mineralocorticoid receptor antagonists (MRAs) such as spironolactone and eplerenone have been used previously to block the effects of aldosterone binding to MR. When given in addition to standard therapies such as angiotensin-converting enzyme (ACE) inhibitors and loop diuretics, the nonselective MRA spironolactone and the selective MRA eplerenone significantly reduced morbidity and mortality in patients with heart failure or myocardial infarction (Pitt, B. et al., New Engl. J. Med., vol. 341, 1999, pp. 709-717; Pitt, B. et al., New Engl. J. Med., vol. 348, 2003, pp. 1382-1390). However, the nonselective MRA spironolactone can also bind to and act at other steroid receptors, and as a consequence its use is associated with sexual side effects such as gynecomastia, dysmenorrhoea and impotence (Pitt, B. et al., New Engl. J. Med., vol. 341, 1999, pp. 709-717; MacFadyen, R. J. et al., Cardiovasc. Res., vol. 35, 1997, pp 30-34; Soberman, J. E. et al., Curr. Hypertens. Rep., vol. 2, 2000, pp 451-456). Additionally, both spironolactone and eplerenone are known to cause elevated plasma potassium levels (hyperkalemia) and elevated aldosterone levels.

An alternative method of blocking the effects of aldosterone is to inhibit its biosynthesis. CYP11B2 (aldosterone synthase) is a mitochondrial cytochrome P450 enzyme that catalyzes the final oxidative steps in the conversion of 11-deoxycorticosterone, a steroidal precursor, to aldosterone (Kawamoto, T. et al., Proc. Natl. Acad. Sci. USA, vol. 89, 1992, pp. 1458-1462). Compounds that inhibit CYP11B2 should thus inhibit the formation of aldosterone. Such compounds, particularly those of nonsteroidal structure, should provide the beneficial effects of MRAs, without the adverse effects derived from steroid receptor binding or MR-independent inflammatory pathways.

CYP11B1 (steroid-11β-hydroxylase) is a related enzyme that catalyzes the formation of glucocorticoids such as cortisol, an important regulator of glucose metabolism. Because human CYP11B2 and CYP11B1 are greater than 93% homologous, it is possible for nonselective compounds to inhibit both enzymes (Kawamoto, T. et al., Proc. Natl. Acad. Sci. USA, vol. 89, 1992, pp 1458-1462; Taymans, S. E. et al., J. Clin. Endocrinol. Metab., vol. 83, 1998, pp 1033-1036). It would be preferable, however, for therapeutic agents to selectively inhibit CYP11B2 and the formation of aldosterone with diminished inhibition of, or affect on, CYP11B1 and the production of cortisol. The compounds of the invention provide an alternative to previous treatments for elevated aldosterone levels and selectively inhibit CYP11B2 as compared to CYP11B1.

SUMMARY OF THE INVENTION

In it many embodiments, the present invention provides for a novel class of benzimidazole analogues, which are inhibitors of CYP11B2, or metabolites, stereoisomers, solvates or polymorphs thereof, processes of preparing such compounds, pharmaceutical compositions comprising one or more such compounds, processes of preparing pharmaceutical compositions comprising one or more such compounds and methods of treatment, prevention, inhibition or amelioration of one or more disease states associated with inhibiting CYP11B2 by administering an effective amount at least one of the inventive benzimidazole analogues to a patient in need thereof.

In one aspect, the present application discloses a compound or a pharmaceutically acceptable salt, metabolite, solvate, prodrug or polymorph of said compound, said compound having the general structure shown in Formula I

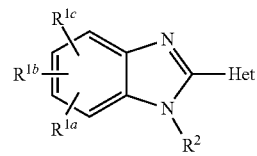

I or a pharmaceutically acceptable salt thereof
wherein:
Het is a heteroaromatic ring of the formula:

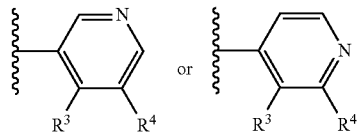

$R^{1a}$, $R^{1b}$ and $R^{1c}$ are independently:
  H; halogen; —CN; —NO$_2$; —OR$^5$; —NR$^8$R$^9$; —N(R$^{13}$)C(O)R$^{10}$; —N(R$^{13}$)SO$_2$—R$^{10}$; —C(O)R$^{10}$; —C(O)N(R$^6$)(R$^7$), —C(O)OR$^{10}$; —SO$_2$N(R$^6$)(R$^7$) or —S(O)$_m$—R$^{10}$; alkyl optionally substituted one or more times by halogen, —CN, —OR$^5$, —N(R$^{13}$)C(O)R$^{10}$ or —C(O)N(R$^6$)(R$^7$); cycloalkyl optionally substituted one or more times by halogen, alkyl, or haloalkyl; aryl optionally substituted one or more times by halogen, —OR$^5$, alkyl, or haloalkyl or heteroaryl optionally substituted one or more times by halogen, —OR$^5$, alkyl or haloalkyl;

$R^2$ is:
  —OR$^5$, alkyl; alkyl-R$^{11}$; cycloalkyl optionally substituted one or more times by alkyl and halogen; and —C$_1$-C$_2$ alkyl-cycloalkyl wherein the cycloalkyl group is optionally substituted one or more times by alkyl and halogen;

$R^3$ is:
  H; halogen; —CN; —NO$_2$; —OR$^{5a}$; —NR$^8$R$^9$; —N(R$^{13}$)C(O)R$^{10}$; —C(O)R$^{10}$—C(O)N(R$^6$)(R$^7$), —C(O)OR$^{10}$ or —S(O)$_m$—R$^{10}$; alkyl optionally substituted one or more times by halogen or OR$^{5a}$; cycloalkyl optionally substituted one or more times by halogen, —OR$^{5a}$, alkyl, or haloalkyl; aryl optionally substituted one or more times by halogen, —OR$^{5a}$, alkyl, or haloalkyl or heteroaryl optionally substituted one or more times by halogen, —OR$^{5a}$, alkyl or haloalkyl;

$R^4$ is:
  H; halogen; —CN; —NO$_2$; —OR$^{5b}$; —NR$^8$R$^9$; —N(R$^{13}$)C(O)R$^{10}$; —C(O)R$^{10}$—C(O)N(R$^6$)(R$^7$), —C(O)OR$^{10}$ or —S(O)$_m$—R$^{10}$; alkyl optionally substituted one or more times by halogen or —OR$^{5b}$; cycloalkyl optionally substituted one or more times by halogen, —OR$^{5b}$, alkyl, or haloalkyl; aryl optionally substituted one or more times by halogen, —OR$^{5b}$, alkyl, or haloalkyl or heteroaryl optionally substituted one or more times by halogen, —OR$^{5b}$, alkyl or haloalkyl;

or $R^3$ and $R^4$ are joined together to form a 5-7 membered carbocyclic or heterocyclic ring that is fused to the pyridyl ring to which $R^3$ and $R^4$ are attached, wherein the ring formed by $R^3$ and $R^4$ is optionally substituted with 1 to 3 of $R^{12}$;

$R^5$, $R^{5a}$ and $R^{5b}$ are each independently H; alkyl optionally substituted with halogen; or aralkyl wherein the aryl ring is optionally substituted one or more times by halogen, —OR$^{5c}$, alkyl or haloalkyl;

$R^{5c}$ is H or alkyl optionally substituted with halogen;

$R^6$ and $R^7$ are each independently:
  H, alkyl optionally substituted with halogen; cycloalkyl optionally substituted with alkyl or halogen; aryl optionally substituted one or more times by halogen, —OR$^5$, alkyl, or haloalkyl or heteroaryl optionally substituted one or more times by halogen, —OR$^5$, alkyl or haloalkyl;

or $R^6$ and $R^7$ join together with the nitrogen to which they are attached to form a 3-7 membered saturated heterocyclic ring;

$R^8$ and $R^9$ are each independently:
  H; alkyl; or aralkyl wherein the aryl ring is optionally substituted one or more times by halogen, —OR$^5$, alkyl or haloalkyl;

$R^{10}$ is independently H; alkyl optionally substituted one or more times with halogen; cycloalkyl optionally substituted one or more times by halogen, alkyl or haloalkyl; or aryl wherein the aryl ring is optionally substituted one or more times by halogen, —OR$^5$, alkyl or haloalkyl $R^{11}$ is haloalkyl or —OR$^5$;

$R^{12}$ is independently halogen or alkyl optionally substituted one or more time by halogen;

$R^{13}$ is H or alkyl; and m is 0, 1 or 2.

The compounds of the invention are effective at selectively inhibiting CYP11B2, and are therefore useful for the treatment or prophylaxis of disorders that are associated with elevated aldosterone levels, including, but not limited to, hypertension and heart failure. Therefore, an object of the invention is to provide methods of treatment comprising administering a therapeutically or prophylactically effective amount of a compound of Formula I to a patient in need of treatment for elevated aldosterone levels. A further object is to provide the use of compounds of Formula I in combination with other therapeutically effective agents, including one or more additional drugs useful for the treatment of hypertension, heart failure or other medical conditions found in such patients. The invention furthermore relates to processes for preparing compounds of Formula I, and pharmaceutical compositions which comprise compounds of Formula I. Moreover, the compounds of this invention may be used to validate in vitro assays, such as, for example the V79 Human CYP11B2 and V79 Human CYP11B1 assays discussed later in the application. These and other objects will be evident from the description contained herein.

DETAILED DESCRIPTION OF THE INVENTION

In an embodiment, the present invention provides compounds represented by structural Formula I or pharmaceutically acceptable salt thereof, wherein the various moieties are as described as above.

Another embodiment of the present invention is compounds or their pharmaceutically acceptable salts of Formula I represented by structural Formula Ia

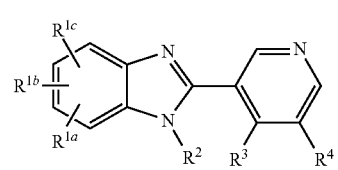

Ia or a pharmaceutically acceptable salt thereof wherein:

$R^{1a}$, $R^{1b}$ and $R^{1c}$ are independently selected from the group consisting of:
  —H, —F, —Br, —CN, —OR$^5$, —SO$_2$NR$^6$R$^7$,
  —C$_1$-C$_6$ alkyl optionally substituted with 1 to 3 of —F,
  —C$_3$-C$_7$ cycloalkyl optionally substituted with 1 to 3 substituents independently selected from the group consisting of —CH$_3$ or —F;

$R^2$ is selected from the group consisting of:
  (a) —C$_1$-C$_5$ alkyl-R$^{11}$, (b) —C$_1$-C$_4$ alkyl; (c) cyclopropyl optionally substituted with 1 or 2 substituents independently selected from the group consisting of —CH$_3$ or —F or (d) —C$_1$-C$_2$ alkyl-cyclopropyl wherein cyclopropyl is optionally substituted with 1 or 2 substituents independently selected from the group consisting of —CH$_3$ or —F;

$R^3$ is selected from the group consisting of:
  —H, —F, —Cl, —Br, —CN, —OR$^{5a}$, —C$_1$-C$_6$ perfluoroalkyl,
  —C$_1$-C$_6$ alkyl optionally substituted with 1 to 3 of —F and optionally substituted with OH, or
  —C$_3$-C$_7$ cycloalkyl optionally substituted with 1 to 3 substituents independently selected from the group consisting of —CH$_3$ or —F;

$R^4$ is selected from the group consisting of:
  (a) —H, —F, —Cl, —Br, —CN, —OR$^{5b}$, —NR$^8$R$^9$, —CO$_2$R$^{10}$ or —COR$^{10}$,
  (b) —C$_1$-C$_6$ perfluoroalkyl,
  (c) —C$_1$-C$_7$ alkyl optionally substituted with 1 to 6 of —F and optionally substituted with 1 or 2 substituents independently selected from the group consisting of (i) —OR$^{5b}$ or (ii) aryl optionally substituted with 1 to 3 substituents independently selected from the group consisting of —F, —Cl and —C$_1$-C$_3$ alkyl optionally substituted with 1 to 3 of —F,
  (d) —C$_3$-C$_7$ cycloalkyl optionally substituted with 1 or 2 substituents independently selected from the group consisting of —C$_1$-C$_6$ alkyl, —CF$_3$ or —F, (e) aryl optionally substituted with 1 to 3 substituents independently selected from the group consisting of —F, —Cl and —$C_1$-$C_3$ alkyl optionally substituted with 1 to 3 of —F or (f) heteroaryl optionally substituted with 1 to 3 substituents independently selected from the group consisting of —F, —Cl and —$C_1$-$C_3$alkyl optionally substituted with 1 to 3 of —F;

or $R^3$ and $R^4$ are joined together to form a 5-7 membered carbocyclic or heterocyclic ring that is fused to the pyridyl ring to which $R^3$ and $R^4$ are attached, wherein the ring formed by $R^3$ and $R^4$ is optionally substituted with 1 to 3 of $R^{12}$;

$R^5$, $R^{5a}$ and $R^{5b}$ are each independently selected from the group consisting of —H or —$C_1$-$C_6$ alkyl optionally substituted with 1 to 3 of —F;

$R^6$ and $R^7$ are each independently selected from the group consisting of
(a) —$C_1$-$C_6$ alkyl optionally substituted with 1 to 3 of —F,
(b) —$C_3$-$C_7$ cycloalkyl optionally substituted with 1 or 2 substituents independently selected from the group consisting of —$CH_3$ and —F, (c) aryl or (d) heteroaryl, or $R^6$ and $R^7$ join together with the nitrogen to which they are attached to form a 3-7 membered saturated heterocyclic ring;

$R^8$ and $R^9$ are each independently selected from the group consisting of
—H, or —$C_1$-$C_6$ alkyl, or —$CH_2$-phenyl wherein phenyl is optionally substituted with 1 to 3 substituents independently selected from the group consisting of —F, —Cl or —$CF_3$;

$R^{10}$ is selected from the group consisting of
—$C_1$-$C_6$ alkyl optionally substituted with 1 to 3 of —F,
—$C_3$-$C_7$ cycloalkyl optionally substituted with 1 or 2 substituents independently selected from the group consisting of —$CH_3$ and —F; or
-phenyl which is optionally substituted with 1 to 3 substituents independently selected from the group consisting of —F, —Cl or —$CF_3$ $R^{11}$ is selected from the group consisting of —$CH_2F$, —$CHF_2$ or —$CF_3$;

$R^{12}$ is independently selected at each occurrence from the group consisting of —F, —Cl or
—$C_1$-$C_3$alkyl optionally substituted with 1 to 3 of —F.

Another embodiment of the present invention is compounds or their pharmaceutically acceptable salts of Formula I represented by structural Formula Ib

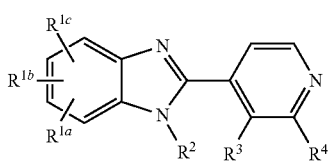

Ib or a pharmaceutically acceptable salt thereof wherein
$R^{1a}$, $R^{1b}$ and $R^{1c}$ are independently selected from the group consisting of:
—H, —F, —Cl, —Br, —CN, —ORS, —$SO_2NR^6R^7$, —C(O)$OR^{10}$
—$C_1$-$C_6$ alkyl optionally substituted with 1 to 3 of —F, or
—$C_3$-$C_7$ cycloalkyl optionally substituted with 1 to 3 substituents independently selected from the group consisting of —$CH_3$ and —F;

$R^2$ is selected from the group consisting of:
(a) —$C_1$-$C_5$ alkyl-$R^{11}$, (b) —$C_1$-$C_4$ alkyl; (c) cyclopropyl optionally substituted with 1 or 2 substituents independently selected from the group consisting of —$CH_3$ or —F or (d) —$C_1$-$C_2$ alkyl-cyclopropyl wherein cyclopropyl is optionally substituted with 1 or 2 substituents independently selected from the group consisting of —$CH_3$ or —F;

$R^3$ is selected from the group consisting of:
—H, —F, —Cl, —Br, —CN, —$OR^{5a}$, —$C_1$-$C_6$ perfluoroalkyl,
—$C_1$-$C_6$ alkyl optionally substituted with 1 to 3 of —F and optionally substituted with OH, or
—$C_3$-$C_7$ cycloalkyl optionally substituted with 1 to 3 substituents independently selected from the group consisting of —$CH_3$ or —F;

$R^4$ is selected from the group consisting of:
(a) —H, —F, —Cl, —Br, —CN, —$OR^{5b}$, —$NR^8R^9$, —$CO_2R^{10}$ or —$COR^{10}$,
(b) —$C_1$-$C_6$ perfluoroalkyl,
(c) —$C_1$-$C_7$ alkyl optionally substituted with 1 to 6 of —F and optionally substituted with 1 or 2 substituents independently selected from the group consisting of (i) —$OR^{5b}$ or (ii) aryl optionally substituted with 1 to 3 substituents independently selected from the group consisting of —F, —Cl or —$C_1$-$C_3$alkyl optionally substituted with 1 to 3 of —F,
(d) —$C_3$-$C_7$ cycloalkyl optionally substituted with 1 or 2 substituents independently selected from the group consisting of —$C_1$-$C_6$ alkyl, —$CF_3$ or —F,
(e) aryl optionally substituted with 1 to 3 substituents independently selected from the group consisting of —F, —Cl or —$C_1$-$C_3$alkyl optionally substituted with 1 to 3 of —F and
(f) heteroaryl optionally substituted with 1 to 3 substituents independently selected from the group consisting of —F, —Cl or —$C_1$-$C_3$alkyl optionally substituted with 1 to 3 of —F;

or $R^3$ and $R^4$ are joined together to form a 5-7 membered carbocyclic or heterocyclic ring that is fused to the pyridyl ring to which $R^3$ and $R^4$ are attached, wherein the ring formed by $R^3$ and $R^4$ is optionally substituted with 1 to 3 of $R^{12}$;

$R^5$, $R^{5a}$ and $R^{5b}$ are each independently selected from the group consisting of —H or —$C_1$-$C_6$ alkyl optionally substituted with 1 to 3 of —F;

$R^6$ and $R^7$ are each independently selected from the group consisting of
(a) —$C_1$-$C_6$ alkyl optionally substituted with 1 to 3 of —F,
(b) —$C_3$-$C_7$ cycloalkyl optionally substituted with 1 or 2 substituents independently selected from the group consisting of —$CF_3$ or —F, (c) aryl or (d) heteroaryl, or $R^6$ and $R^7$ join together with the nitrogen to which they are attached to form a 3-7 membered saturated heterocyclic ring;

$R^8$ and $R^9$ are each independently selected from the group consisting of
—H, —$C_1$-$C_6$ alkyl or —$CH_2$-phenyl wherein phenyl is optionally substituted with 1 to 3 substituents independently selected from the group consisting of —F, —Cl or —$CF_3$;

$R^{10}$ is selected from the group consisting of
—$C_1$-$C_6$ alkyl optionally substituted with 1 to 3 of —F,
—$C_3$-$C_7$ cycloalkyl optionally substituted with 1 or 2 substituents independently selected from the group consisting of —$CH_3$ or —F; or -phenyl which is optionally substituted with 1 to 3 substituents independently selected from the group consisting of —F, —Cl or —CF$_3$;

R$^{11}$ is selected from the group consisting of —CH$_2$F, —CHF$_2$ or —CF$_3$;

R$^{12}$ is independently selected at each occurrence from the group consisting of —F, —Cl or
—C$_1$-C$_3$alkyl optionally substituted with 1 to 3 of —F.

Another embodiment of this invention is compounds of Formula I, Ia or Ib wherein R$^3$ is selected from the group consisting of:
—H, —F, —Cl, —Br, —CN, —OR$^{5a}$, —C$_1$-C$_6$ perfluoroalkyl, —C$_1$-C$_6$ alkyl optionally substituted with 1 to 3 of —F, or
—C$_3$-C$_7$ cycloalkyl optionally substituted with 1 to 3 substituents independently selected from the group consisting of —CH$_3$ or —F.

Another embodiment of this invention is compound of any of the embodiments above wherein at least one R$^{1a}$, R$^{1b}$ or R$^{1c}$ is selected from the group consisting of —H, —F, —Br, —NO$_2$, —CN, C$_1$-C$_6$ alkyl (e.g., methyl, ethyl, isopropyl), C$_1$-C$_6$ alkyl substituted with —OH, halogen, or N(R$^{13}$)C(O)—C$_1$-C$_6$ alkyl, —OC$_1$-C$_6$ alkyl (e.g., methoxy, ethoxy, isopropyloxy), —N(R$^{13}$)C(O)—C$_1$-C$_6$ alkyl, —C(O)N(H)C$_1$-C$_6$ alkyl, —NH$_2$, —NH(C$_1$-C$_6$ alkyl), —N(C$_1$-C$_6$ alkyl)(C$_1$-C$_6$ alkyl), —C(O)OH, —C(O)O—C$_1$-C$_6$alkyl, —S—C$_1$-C$_6$ alkyl, —S(O)—C$_1$-C$_6$ alkyl, —S(O)$_2$—C$_1$-C$_6$ alkyl, —N(R$^{13}$)S(O)$_2$—C$_1$-C$_6$ alkyl, or optionally C$_1$-C$_6$ alkyl substituted heteroaryl, wherein the heteroaryl is an isooxazolyl, pyrazolyl, oxazolyl, imidazolyl or pyridyl ring.

Another embodiment of this invention are compounds of any of the embodiments above wherein R$^2$ is —OH, C$_1$-C$_6$ alkyl (e.g., methyl, ethyl, isopropyl), C$_1$-C$_6$ alkyl substituted with —OH or halogen, —O—C$_1$-C$_6$ alkyl (e.g., methoxy, ethoxy, isopropyloxy), cyclopropyl optionally substituted by halogen, —OH or —O—C$_1$-C$_6$ alkyl or —OCH$_2$-phenyl, wherein the phenyl ring is optionally substituted by halogen, —OH or —O—C$_1$-C$_6$ alkyl.

Another embodiment of this invention are compounds of any of the embodiments above where R$^3$ and R$^4$ are independently H, halogen —CN, —C$_1$-C$_6$ alkyl substituted optionally substituted with —OH, —O—C$_1$-C$_6$ alkyl, or halogen, —O—C$_1$-C$_6$ alkyl (e.g., methoxy, ethoxy, isopropyloxy), —C(O)C$_1$-C$_6$alkyl, —C(O)OH, —C(O)O—C$_1$-C$_6$ alkyl, —S—C$_1$-C$_6$ alkyl, —S(O)—C$_1$-C$_6$ alkyl, —S(O)$_2$—C$_1$-C$_6$ alkyl, —NH$_2$, —NH(C$_1$-C$_6$ alkyl), —N(C$_1$-C$_6$ alkyl)(C$_1$-C$_6$ alkyl), optionally halo substituted phenyl, or optionally C$_1$-C$_6$ alkyl substituted heteroaryl, wherein the heteroaryl is an isooxazolyl, pyrazolyl, oxazolyl, imidazolyl or pyridyl ring or R$^3$ and R$^4$ together with the pyridyl ring form:

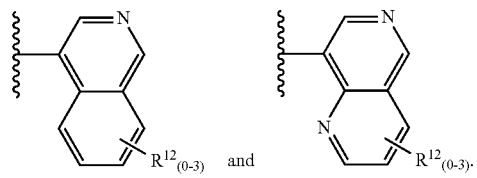

Another embodiment of this invention is compounds of Formula Ia or Ib having structural Formula II or the pharmaceutically acceptable salts thereof wherein R$^{1c}$ is —H, R$^2$ is cyclopropyl optionally substituted with 1 or 2 substituents independently selected from the group consisting of —CH$_3$ or —F, and the variables R$^{1a}$, R$^{1b}$, R$^3$ and R$^4$ are as defined in Formula Ia or Ib:

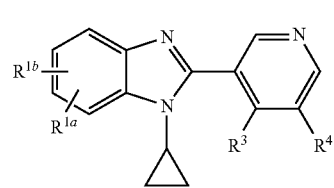

II wherein cyclopropyl is optionally substituted as described above in Formula Ia or Ib.

Another embodiment of this invention is compounds or pharmaceutically acceptable salts thereof of any of the embodiments identified above wherein (a) R$^3$ is —H and R$^4$ is selected from the group consisting of —H, —F, —Cl, —Br, —CN or —C$_1$-C$_7$ alkyl optionally substituted with 1 to 6 of —F, particularly wherein one or two terminal carbons is —CF$_3$, and optionally substituted with 1 or 2 of —OR$^{5b}$; or (b) R$^3$ and R$^4$ are joined together to form a 5-7 member carbocyclic or heterocyclic ring that is fused to the pyridyl ring to which R$^3$ and R$^4$ are attached wherein the ring formed by R$^3$ and R$^4$ is optionally substituted with 1 to 3 of R$^{12}$. Another aspect of this embodiment is compounds where R$^{12}$ is alkyl or halogen. Alternatively, another embodiment of this invention is compounds of pharmaceutically acceptable salts thereof of any of the embodiments identified wherein R$^4$ is

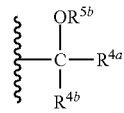

wherein R$^{5b}$ is —H or —C$_1$-C$_3$ alkyl optionally substituted with 1 to 3 of —F, and R$^{4a}$ and R$^{4b}$ are each independently selected from the group consisting of (a) —C$_1$-C$_3$ alkyl or (b) —C$_1$-C$_3$ alkyl substituted with 1 to 3 of —F, preferably wherein the terminal carbon is —CF$_3$.

A further embodiment of this invention is compounds of Formula Ia or Ib or the pharmaceutically acceptable salts thereof wherein:

R$^{1a}$, R$^{1b}$ and R$^{1c}$ are each independently selected from —H, —F, —CF$_3$ or —OCH$_3$; and/or R$^2$ is selected from (a) —C$_1$-C$_3$alkyl, (b) —C$_1$-C$_2$alkyl-R$^{11}$, (c) —(CH$_2$)$_{(1-2)}$-cyclopropyl wherein cyclopropyl is optionally substituted with —CH$_3$ or —F, or (d) cyclopropyl optionally substituted with —CH$_3$ or —F; and/or R$^3$ is —H or is joined together with R$^4$ to form a 5-7 membered carbocyclic or heterocyclic ring that is fused to the pyridyl ring to which R$^3$ and R$^4$ are attached selected from the group consisting of

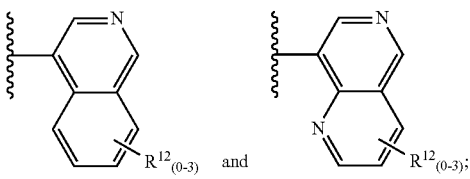

and/or

R⁴, when not joined with R³, is selected from —H, —F, —CN, —OCH₃, —COCH₃, —COOCH₃, —CF₃, or

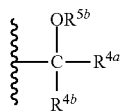

wherein $R^{5b}$ is —H or —CH₃, and $R^{4a}$ and $R^{4b}$ are each independently selected from the group consisting of —CH₃ and —CF₃; and/or $R^5$ and $R^{5a}$ are each independently selected from the group consisting of —H, —CH₃ and —CF₃.

A further embodiment of this invention is compounds of Formula Ia or Ib described above or their pharmaceutically acceptable salts wherein $R^6$ and $R^7$ are each —$C_1$-$C_3$ alkyl optionally substituted with 1 to 3 of —F. A further embodiment of this embodiment of the inventions are compounds or their pharmaceutically acceptable salts wherein $R^6$ and $R^7$ are each —$C_1$-$C_3$alkyl optionally substituted with 1 to 3 of —F; and/or $R^8$ and $R^9$ are each independently selected from the group consisting of —H, or —$C_1$-$C_3$ alkyl.

In another embodiment are compounds of Formula Ia or Ib or the pharmaceutically acceptable salts thereof wherein $R^3$ is —H and $R^4$ is selected from —H, —C(OH)(CH₃)₂ or —C(OCH₃)(CH₃)₂.

As used herein except if noted otherwise, "alkyl" is intended to include both branched- and straight-chain saturated aliphatic hydrocarbon groups having the specified number of carbon atoms. Commonly used abbreviations for alkyl groups are used throughout the specification. For example the term "$C_{1-6}$ alkyl" (or "$C_1$-$C_6$ alkyl"), means linear or branched chain alkyl groups, including all isomers, having the specified number of carbon atoms and includes all of the hexyl and pentyl isomers as well as n-, iso-, sec- and tert-butyl (butyl, s-butyl, i-butyl, t-butyl; Bu=butyl), n- and i-propyl (Pr=propyl), ethyl (Et) and methyl (Me).

"Halo" refers to fluorine, chlorine, bromine or iodine radicals. Preferred are fluoro, chloro or bromo, and more preferred are fluoro and chloro.

"Halogen" means fluorine, chlorine, bromine, or iodine.

"Haloalkyl" means a halo-alkyl-group in which the alkyl group is as previously described. The bond to the parent moiety is through the alkyl. Non-limiting examples of suitable haloalkyl groups include fluoromethyl, difluoromethyl, —CH₂CF₃, —CH₂CHF₂—CH₂CH₂F, or an alkyl group with one or more terminal carbons tri-substituted with a halogen (e.g., —F) such as, for example —$C_1$-$C_3$alkyl-CF₃, —CH(CH₃)(CF₃), —CH(CF₃)₂ and the like.

"Cycloalkyl" is a cyclized alkyl ring having the indicated number of carbon atoms. Examples of cycloalkyl include cyclopropyl, cyclobutyl, cyclopentyl, cyclohexyl and cycloheptyl. The cycloalkyl ring may be substituted on any available carbon which results in the creation of a stable structure, including the ring carbon which serves as the point of attachment to the rest of the molecule.

"Aryl" unless otherwise indicated, means mono- and bicyclic aromatic rings containing 6-12 carbon atoms. Examples of aryl include phenyl, naphthyl, indenyl and the like. "Aryl" also includes monocyclic rings fused to an aryl group. Examples include tetrahydronaphthyl, indanyl and the like. Phenyl is preferred in all embodiments of this invention.

"Heteroaryl" unless otherwise indicated, means a mono- or bicyclic aromatic ring or ring system containing at least one heteroatom selected from O, S and N, with each heteroaryl containing 5 to 10 atoms. Examples include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, and the like. Heteroaryl also includes a 5-6 membered heteroaryl ring fused to a non-aromatic or partially or fully aromatic ring which optionally contains one or more heteroatoms. Heteroaryl also includes such groups in charged form, e.g., pyridinium, and heteroaryls substituted with oxo (=O).

"Aralkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

$R^6$ and $R^7$ can be joined together with the nitrogen to which they are attached to form a 3-7 membered saturated heterocyclic ring, wherein the ring is composed of carbon atoms and at least one N atom and optionally one or two additional heteroatoms selected from N, S and O. Examples include but are not limited to aziridinyl, azetidinyl, pyrrolidinyl, imidazolidinyl, piperidinyl, piperazinyl, morpholinyl, thiomorpholinyl, azepanyl, 1,4-diazepanyl, 1,4-oxazepanyl, 1.5 and 1,4-thiazepanyl.

When $R^3$ and $R^4$ are joined together to form a 5-7 membered carbocyclic ring that is fused to the pyridyl ring to which $R^3$ and $R^4$ are attached, "carbocyclic" means a cycloalkyl, aryl or partially unsaturated ring composed of 5-7 carbon atoms wherein two of the carbons are shared between the fused rings. When $R^3$ and $R^4$ are joined together to form a 5-7 membered heterocyclic ring fused to the pyridyl ring to which $R^3$ and $R^4$ are attached, "heterocyclic" means fully saturated, partially unsaturated or aryl ring composed of carbon atoms and one, two or three heteroatoms selected from N, S and O, wherein two carbons are shared between the fused rings. Examples of such fused ring systems wherein $R^3$ and $R^4$ together represent a 6-membered carbocyclic ring and a 6 membered heterocyclic ring, respectively, include but are not limited to:

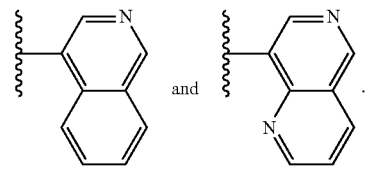 [SMILES: *c1cncc2ccccc12 ; "and" ; *c1cncc2cccnc12]

When a moiety can be optionally substituted, it means that each carbon and heteroatom (when present) available for substitution in the given moiety may be independently unsubstituted or substituted with the specified number of substituents that are the same or different at each occurrence and which result in the creation of a stable structure as is understood to be reasonable by one skilled in the art, unless specified otherwise.

In some instances the number of substituents which may be optionally present on a moiety is specified, for example but not limited to, 1 to 3 of —F (fluoro). For example, an alkyl group that can be optionally substituted with 1 to 3 of —F includes, but is not limited to, —CH₃, —CH₂F, —CHF₂, —CF₃, —CH₂CH₃, —CH₂—CH₂F, —CH₂—CHF₂, —CHF—CH₂F, —CH₂CF₃, —CHF—CHF₂, —(CH₂)₂CH₃, —CH(CF₃)—CH₃, —(CH₂)₃—CF₃, —(CH₂)₂CH(CF₃) CH₃, and —(CH₂)₅—CF₃, as appropriate for the defined number of carbon atoms for the given alkyl group. An alkyl group with one or more terminal carbons tri-substituted with —F is preferred, e.g., —$C_1$-$C_3$alkyl-$CF_3$, —$CH(CH_3)(CF_3)$, $CH(CF_3)_2$ and the like; —$CF_3$ is most preferred. "Perfluoroalkyl" means an alkyl group wherein all hydrogens are replaced with fluoro.

Halo, halide or halogen refers to —F (fluoro), —Cl (chloro), —Br (bromo) and —I (iodo). Unless expressly depicted or described otherwise, variables depicted in a structural formula with a "floating" bond, such as each of substituents $R^{1a}$, $R^{1b}$, and $R^{1c}$ in structural Formula I, are permitted on any available carbon atom in the ring to which each is attached.

The present invention encompasses all stereoisomeric forms of the compounds of Formula Ia. Centers of asymmetry that are present in the compounds of Formula I can all independently of one another have (R) configuration or (S) configuration. When bonds to the chiral carbon are depicted as straight lines in the structural Formulas of the invention, it is understood that both the (R) and (S) configurations of the chiral carbon, and hence both enantiomers and mixtures thereof, are embraced within the Formula. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I or it can be done on a final racemic product. Absolute stereochemistry may be determined by X-ray crystallography of crystalline products or crystalline intermediates which are derivatized, if necessary, with a reagent containing a stereogenic center of known configuration. Where compounds of this invention are capable of tautomerization, all individual tautomers as well as mixtures thereof are included in the scope of this invention. The present invention includes all such isomers, as well as salts, solvates (including hydrates) and solvated salts of such isomers including racemates, enantiomers, diastereomers and tautomers and mixtures thereof.

Reference to the compounds of this invention as those of a specific formula or embodiment, e.g., Formula I, or any other generic structural formula, embodiment or specific compound described or claimed herein, is intended to encompass the specific compound or compounds falling within the scope of the formula or embodiment, including salts thereof, particularly pharmaceutically acceptable salts, solvates of such compounds and solvated salt forms thereof, where such forms are possible unless specified otherwise.

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of Formula I. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within Formula I can be prepared without undue experimentation by conventional techniques well known to those skilled in the art or by processes analogous to those described in the Schemes and Examples herein using appropriate isotopically-enriched reagents and/or intermediates.

When the compounds of Formula I contain one or more acidic or basic groups the invention also includes the corresponding physiologically or toxicologically acceptable salts, in particular the pharmaceutically utilizable salts. Thus, the compounds of Formula I which contain acidic groups can be used according to the invention, for example, as alkali metal salts, alkaline earth metal salts or as ammonium salts. Examples of such salts include but are not limited to sodium salts, potassium salts, calcium salts, magnesium salts or salts with ammonia or organic amines such as, for example, ethylamine, ethanolamine, triethanolamine or amino acids. Compounds of Formula I which contain one or more basic groups, i.e. groups which can be protonated, can be used according to the invention in the form of their acid addition salts with inorganic or organic acids as, for example but not limited to, salts with hydrogen chloride, hydrogen bromide, phosphoric acid, sulfuric acid, nitric acid, benzenesulfonic acid, methanesulfonic acid, p-toluenesulfonic acid, naphthalenedisulfonic acids, oxalic acid, acetic acid, trifluoroacetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, mile acid, sulfaminic acid, phenylpropionic acid, gluconic acid, ascorbic acid, isonicotinic acid, citric acid, adipic acid, etc. If the compounds of Formula Ia simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of physiologically (i.e., pharmaceutically) acceptable salts.

Furthermore, compounds of the present invention may exist in amorphous form and/or one or more crystalline forms, and as such all amorphous and crystalline forms and mixtures thereof of the compounds of Formula I are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with un-solvated and anhydrous forms.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO⁻ depending on the pH of the fluid or tissue where conversion takes place) or hydroxy form particularly in vivo and as such are encompassed within the scope of this invention. Examples of pharmaceutically acceptable pro-drug modifications include, but are not limited to, —$C_{1-6}$alkyl esters and —$C_{1-6}$alkyl substituted with phenyl esters.

Accordingly, the compounds within the generic structural formulas, embodiments and specific compounds described and claimed herein encompass salts, isomers, tautomers, physical forms (e.g., amorphous and crystalline forms) and solvated forms thereof and any combination of these forms, as well as pro-drug forms thereof, unless specified otherwise.

Compounds of the present invention are effective at inhibiting the synthesis of aldosterone by inhibiting CYP11B2 (aldosterone synthase), and they are therefore useful agents for the therapy and prophylaxis of disorders that are associated with elevated aldosterone levels. Accordingly, an object of the instant invention is to provide a method for inhibiting aldosterone synthase, and more particularly selectively inhibiting CYP11B2, in a patient in need thereof, comprising administering a compound of Formula I to the patient in an amount effective to inhibit aldosterone synthesis, or more particularly to selectively inhibit CYP11B2, in the patient. A selective inhibitor of CYP11B2 is intended to mean a compound that preferentially inhibits CYP11B2 as compared to CYP11B1. The inhibition of CYP11B2, as well inhibition of CYP11B1, by the compounds of Formula I can be examined, for example, in the inhibition assays described below.

In general, compounds that have activity as aldosterone synthase inhibitors can be identified as those compounds which have an $IC_{50}$ of less than or equal to about 10 μM; preferably less than or equal to about 250 nM; and most preferably less than or equal to about 100 nM, in the V79-Human-CYP11B2 Assay described below. In general, aldosterone synthase inhibitors that are selective for inhibition of CYP11B2 as compared to CYP11B1 are those that show at least 3-fold greater inhibition for CYP11B2 compared to CYP11B1; preferably at least 20-fold inhibition for CYP11B2 compared to CYP11B1; and more preferably at least 100-fold greater inhibition for CYP11B2 compared to CYP11B1, in the V79-Human-CYP11B2 Assay as compared to the V79-Human-CYP11B1 Assay.

Due to their ability to inhibit aldosterone synthase, the compounds of the present invention are useful to treat and/or reduce the risk for hypertension, heart failure such as congestive heart failure, diastolic dysfunction, left ventricular diastolic dysfunction, diastolic heart failure, systolic dysfunction, hypokalemia, renal failure, in particular chronic renal failure, restenosis, metabolic syndrome, nephropathy, post-myocardial infarction, coronary heart diseases, increased formation of collagen, fibrosis and remodeling following hypertension and endothelial dysfunction, cardiovascular diseases such as atherosclerosis, renal dysfunction, liver diseases, vascular diseases, cerebrovascular diseases, retinopathy, neuropathy, insulinopathy, endothelial dysfunction, ischemia, myocardial and vascular fibrosis, myocardial necrotic lesions, vascular damage, myocardial infarction, left ventricular hypertrophy, cardiac lesions, vascular wall hypertrophy, endothelial thickening, and fibrinoid necrosis of coronary arteries.

The dosage amount of the compound to be administered depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to compounds of Formula Ia. A consideration of these factors is well within the purview of the ordinarily skilled clinician for the purpose of determining the therapeutically effective or prophylactically effective dosage amount needed to prevent, counter, or arrest the progress of the condition. It is expected that the compound will be administered chronically on a daily basis for a length of time appropriate to treat or prevent the medical condition relevant to the patient, including a course of therapy lasting days, months, years or the life of the patient.

In general, a daily dose of approximately 0.001 to 30 mg/kg, preferably 0.001 to 20 mg/kg, in particular 0.01 to 10 mg/kg (in each case mg per kg of bodyweight) is appropriate for administration to an adult weighing approximately 75 kg in order to obtain the desired results. The daily dose is preferably administered in a single dose or, in particular when larger amounts are administered, can be divided into several, for example two, three or four individual doses, and may be, for example but not limited to, 0.1 mg, 0.25 mg, 0.5 mg, 0.75 mg, 1 mg, 1.25 mg, 2.5 mg, 5 mg, 10 mg, 20 mg, 40 mg, 50 mg, 75 mg, 100 mg, etc., on a daily basis. In some cases, depending on the individual response, it may be necessary to deviate upwards or downwards from the given daily dose.

The term "patient" includes animals, preferably mammals and especially humans, who use the instant active agents for the prevention or treatment of a medical condition. Administering of the drug to the patient includes both self-administration and administration to the patient by another person. The patient may be in need of treatment for an existing disease or medical condition, or may desire prophylactic treatment to prevent or reduce the risk of said disease or medical condition.

The term therapeutically effective amount is intended to mean that amount of a drug or pharmaceutical agent that will elicit the biological or medical response of a tissue, a system, animal or human that is being sought by a researcher, veterinarian, medical doctor or other clinician. A prophylactically effective amount is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. It is understood that a specific daily dosage amount can simultaneously be both a therapeutically effective amount, e.g., for treatment of hypertension, and a prophylactically effective amount, e.g., for prevention of myocardial infarction.

In the methods of treatment of this invention, the compound may be administered via any suitable route of administration such as, for example, orally, parenterally, or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. Oral formulations are preferred, particularly solid oral dosage units such as pills, tablets or capsules.

Accordingly, this invention also provides pharmaceutical compositions comprised of a compound of Formula I and a pharmaceutically acceptable carrier. For oral use, the pharmaceutical compositions of this invention containing the active ingredient may be in forms such as pills, tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients, which are suitable for the manufacture of tablets. These excipients may be for example, inert diluents, such as calcium carbonate, sodium carbonate, lactose, mannitol, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. Pharmaceutical compositions may also contain other customary additives, for example, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

Oral immediate-release and time-controlled release dosage forms may be employed, as well as enterically coated oral dosage forms. Tablets may be uncoated or they may be coated by known techniques for aesthetic purposes, to mask taste or for other reasons. Coatings can also be used to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an anti-oxidant such as ascorbic acid. Syrups and elixirs may be formulated with sweetening agents, for example glycerol, propylene glycol, sorbitol or sucrose.

The instant invention also encompasses a process for preparing a pharmaceutical composition comprising combining a compound of Formula I with a pharmaceutically acceptable carrier. Also encompassed is the pharmaceutical composition which is made by combining a compound of Formula I with a pharmaceutically acceptable carrier. The carrier is comprised of one or more pharmaceutically acceptable excipients. Furthermore, a therapeutically effective amount of a compound of this invention can be used for the preparation of a medicament useful for inhibiting aldosterone synthase, inhibiting CYP11B2, for normalizing a disturbed aldosterone balance, or for treating or preventing any of the medical conditions described herein, in dosage amounts described herein.

The amount of active compound of Formula I and its pharmaceutically acceptable salts in the pharmaceutical composition may be, for example but not limited to, from 0.1 to 200 mg, preferably from 0.1 to 50 mg, per dose on a free acid/free base weight basis, but depending on the type of the pharmaceutical composition and potency of the active ingredient it could also be lower or higher. Pharmaceutical compositions usually comprise 0.5 to 90 percent by weight of the active compound on a free acid/free base weight basis.

Since the compounds of Formula I inhibit aldosterone synthase, apart from use as pharmaceutically active compounds in human medicine and veterinary medicine, they can also be employed as a scientific tool or as aid for biochemical investigations in which such an effect on aldosterone synthase and aldosterone levels is intended, and also for diagnostic purposes, for example in the in vitro diagnosis of cell samples or tissue samples. The compounds of Formula Ia can also be employed as intermediates for the preparation of other pharmaceutically active compounds.

One or more additional pharmacologically active agents may be administered in combination with a compound of Formula I. An additional active agent (or agents) is intended to mean a pharmaceutically active agent (or agents) different from the compound of Formula Ia. Generally, any suitable additional active agent or agents, including but not limited to anti-hypertensive agents, anti-atherosclerotic agents such as a lipid modifying compound, anti-diabetic agents and/or anti-obesity agents may be used in any combination with the compound of Formula I in a single dosage formulation (a fixed dose drug combination), or may be administered to the patient in one or more separate dosage formulations which allows for concurrent or sequential administration of the active agents (co-administration of the separate active agents). Examples of additional active agents which may be employed include but are not limited to angiotensin converting enzyme (ACE) inhibitors (e.g, alacepril, benazepril, captopril, ceronapril, cilazapril, delapril, enalapril, enalaprilat, fosinopril, imidapril, lisinopril, moexepril, moveltipril, perindopril, quinapril, ramipril, spirapril, temocapril, or trandolapril); dual inhibitors of angiotensin converting enzyme (ACE) and neutral endopeptidase (NEP) such as omapatrilat, sampatrilat and fasidotril; angiotensin II receptor antagonists (e.g., candesartan, eprosartan, irbesartan, losartan, olmesartan, telmisartan, valsartan) neutral endopeptidase inhibitors (e.g., thiorphan and phosphoramidon), aldosterone antagonists, renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including dial sulfonamides and sulfinyls (U.S. Pat. No. 5,098,924), N-morpholino derivatives (U.S. Pat. No. 5,055, 466), N-heterocyclic alcohols (U.S. Pat. No. 4,885,292) and pyrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643), enalkrein, RO 42-5892, A 65317, CP 80794, ES 1005, ES 8891, SQ 34017, aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635), endothelin receptor antagonists, vasodilators, calcium channel blockers (e.g., amlodipine, bepridil, diltiazem, felodipine, gallopamil, nicardipine, nifedipine, niludipine, nimodipine, nisoldipine veraparmil), potassium channel activators (e.g., nicorandil, pinacidil, cromakalim, minoxidil, aprilkalim, loprazolam), diuretics (e.g., hydrochlorothiazide) including loop diuretics such as ethacrynic acid, furosemide, bumetanide and torsemide, sympatholitics, beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazocin, prazocin or alpha methyldopa) central alpha adrenergic agonists, peripheral vasodilators (e.g. hydralazine), lipid lowering agents (e.g., simvastatin, lovastatin, pravastatin, fluvastatin, atorvastatin, rosuvastatin, ezetimibe); niacin in immediate-release or controlled release forms, and particularly in niacin in combination with a DP antagonist such as laropiprant (TREDAPTIYE®) and/or with an HMG-CoA reductase inhibitor; niacin receptor agonists such as acipimox and acifran, as well as niacin receptor partial agonists; or with other drugs beneficial for the prevention or the treatment of the above-mentioned diseases including nitroprusside and diazoxide.

Additional active agents may be administered in combination with a compound of this invention include metabolic altering agents such as (1) insulin sensitizing agents, for example (i) PPARγ agonists, such as the glitazones (e.g. pioglitazone, rosiglitazone, netoglitazone, rivoglitazone, and balaglitazone) and other PPAR ligands, including (a) PPARα/γ dual agonists, such as muraglitazar, aleglitazar, sodelglitazar, and naveglitazar, (b) PPARα agonists, such as fenofibric acid derivatives (gemfibrozil, clofibrate, ciprofibrate, fenofibrate and bezafibrate), (ii) biguanides, such as metformin and its pharmaceutically acceptable salts, in particular, metformin hydrochloride; (2) insulin or insulin analogs, such as insulin lispro, insulin detemir, insulin glargine, insulin glulisine, and inhalable formulations of each thereof; (3) sulfonylurea and non-sulfonylurea insulin secretagogues, such as tolbutamide, glyburide, glipizide, glimepiride, mitiglinide, and meglitinides, such as nateglinide and repaglinide; and (4) incretin mimetics, such as GLP-1, GLP-1 analogs, derivatives, and mimetics, and GLP-1 receptor agonists such as exenatide, liraglutide and taspoglutide.

Dipeptidyl peptidase-IV (DPP-4) inhibitors can be used in combination with compounds of this invention including, but not limited to, sitagliptin (disclosed in U.S. Pat. No. 6,699,871), vildagliptin, saxagliptin, alogliptin, denagliptin, carmegliptin, dutogliptin, melogliptin, and linagliptin. Antiobesity compounds can be combined with compounds of this invention, for example, topiramate, zonisamide, naltrexone, phentermine, bupropion, fenfluramine, dexfenfluramine, sibutramine; lipase inhibitors, such as orlistat and cetilistat; neuropeptide $Y_1$ or $Y_5$ antagonists such as MK-0557; and CB1 receptor inverse agonists and antagonists such as rimonabant and taranabant. Any active agent used in combination with a compound of this invention may be in a pharmaceutically acceptable salt form thereof.

The compounds of the present invention can be prepared according to the procedures of the following Schemes using appropriate materials and are further exemplified by the specific Examples which follow. Moreover, by utilizing the procedures described herein, one of ordinary skill in the art can readily prepare additional compounds of the present invention claimed herein.

Throughout the synthetic schemes, abbreviations are used with the following meanings unless otherwise indicated: Ac acetate; aq, aq.=aqueous; Ar=aryl; BOC, Boc=t-butyloxycarbonyl; Bn=benzyl; BSA=bovine serum albumin; Bu=butyl, t-Bu=tert-butyl; BuLi, n-BuLi=n-butyllithium; CBZ, Cbz=Benzyloxycarbonyl; conc, conc.=concentrated; cPr=cyclopropyl; DAST=(diethylamino)sulfur trifluoride; dba=dibenzylideneacetone; DCM=dichloromethane; DIAD=diisopropylazodicarboxylate; DIBAL, DIBAL-H=diisobutylaluminum hydride; DIEA=diisopropylethylamine; DMAC, DMA=dimethylacetamide; DME=1,2-dimethoxyethane; DMEM=Dulbecco's modified eagle medium; DMAP=4-dimethylaminopyridine; DMF=N,N-dimethylformamide; DMSO=dimethylsulfoxide; eq.=equivalent(s); EDC=N-[3-(dimethylamino)propyl]-N-ethylcarbodiimide; EDTA=ethylenediaminetetraacetic acid; ESI=electrospray ionization; Et=ethyl; EtOAc=ethyl acetate; EtOH=ethanol; FBS=Fetal Bovine Serum; h, hr=hour; HATU=N-[(dimethylamino)-1H-1,2,3-triazolo[4,5-b]pyridin-1-ylmethylene]-N-methylmethanaminium hexafluorophosphate N-oxide; HOAc=acetic acid; HOAt=3H-[1,2,3]-triazolo[4,5-b]pyridin-3-ol; HOBt=1H-benzotriazol-1-ol; HPLC=High pressure liquid chromatography; HTRF=homogenous time resolved fluorescence; IPA, i-PrOH=isopropanol; iPr=isopropyl; LAH=Lithium aluminum hydride; LCMS=liquid chromatography-mass spectroscopy; LHMDS=lithium bis(trimethylsilyl)amide; Me=methyl; MeOH=methanol; min, min.=minute; μW=microwave; NMP=N-methylpyrrolidinone; NMR=nuclear magnetic resonance; OMs, mesyl=methanesulfonyl; Oxone, OXONE=potassium peroxymonosulfate; PBS=phosphate buffered saline; $Pd_2dba_3$=tris(dibenzylidineacetone)dipalladium; Pd/C=palladium on activated carbon; Ph=phenyl; Pr=propyl; Py=pyridyl; RT, rt=room temperature; sat.=saturated; TBAF=tetrabutylammonium fluoride; TBAI=tetrabutylammonium iodide; TFA=trifluoroacetic acid; THF=tetrahydrofuran; TLC=thin layer chromatography; prep TLC=preparative thin layer chromatography; Tosyl=toluenesulfonyl; triflate, OTf=trifluoromethanesulfonate; triflic=trifluoromethanesulfonic; Xantphos=4,5-bis(diphenylphosphino)-9,9-dimethylxanthene.

Pyridine aldehydes may be obtained commercially, are known in the literature, and may be prepared by a variety of methods by those skilled in the art. One such method, shown in Scheme 1, involves reaction of ketone 1 with a Grignard reagent in a solvent such as tetrahydrofuran at low temperature to give alcohol 2. Heating of 2 in the presence of a catalyst such as $Pd(OAc)_2$, a ligand such as Xantphos, carbon monoxide, and a base such as triethylamine in a solvent such as methanol may then provide pyridine ester 3. Exposure of ester 3 to a reducing agent such as diisobutylaluminum hydride in a mixed solvent system such as toluene and dichloromethane at low temperature affords pyridine aldehyde 4.

Scheme 1

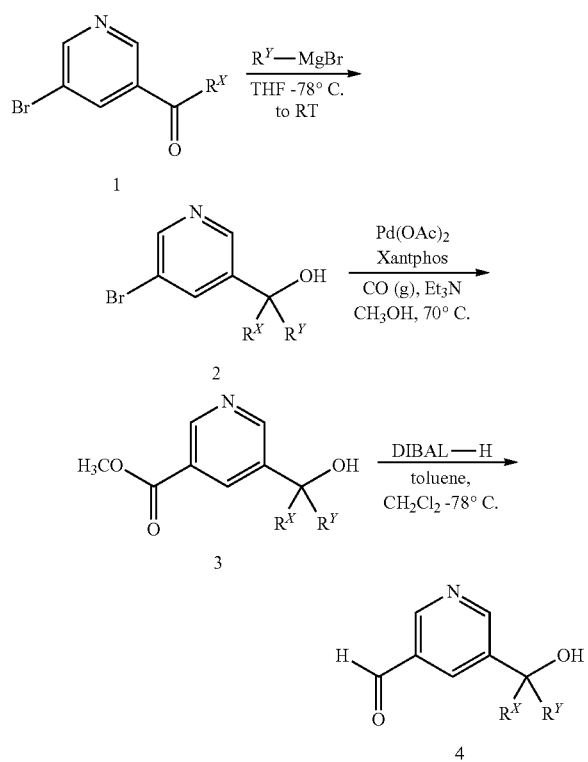

Where $R^Y=CF_3$, such pyridine aldehydes may be prepared by a variety of methods by those skilled in the art. One such method, outlined in Scheme 2, involves treatment of ketone 5 with (trifluoromethyl)trimethylsilane and tetrabutylammonium fluoride in a solvent such as tetrahydrofuran at room temperature to provide alcohol 6. Alcohol 6 may then be converted to aldehyde 8 by the same method described in Scheme 1 for the conversion of alcohol 2 to aldehyde 4.

Scheme 2

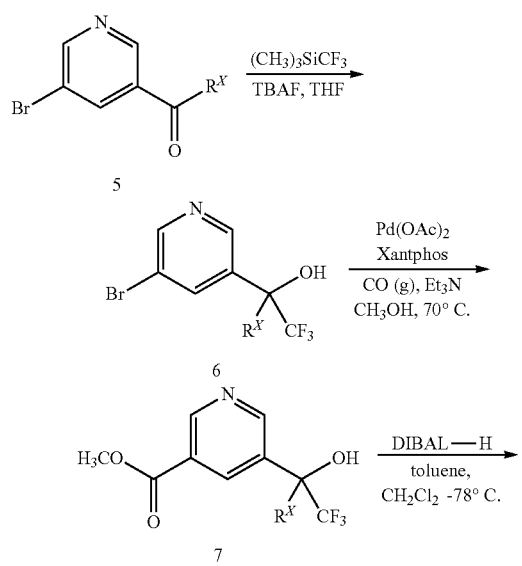

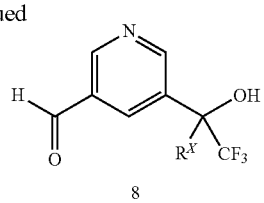

Heteroaryl aldehydes such as napthyridine aldehydes may be prepared by a variety of methods by those skilled in the art. One method for napthyridine synthesis is shown in Scheme 3, and involves ozonolysis of known napthyridine 9 (*Chem. Pharm. Bull.* 1986, 34, 2018-2023) in a mixed solvent system such as dichloromethane and methanol to provide napthyridine aldehyde 10.

Scheme 3

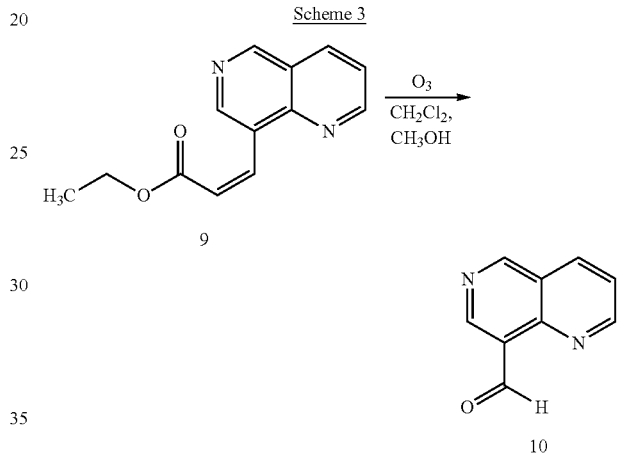

Pyridine carboxylic acids may be obtained commercially, are known in the literature, and may be prepared by a variety of methods by those skilled in the art. One such method, outlined in Scheme 4, involves treatment of known ester 11 (*Montash. Chem.* 1995, 126, 805-809) with a base such as aqueous sodium hydroxide in a solvent such as methanol at room temperature to provide carboxylic acid 12.

Scheme 4

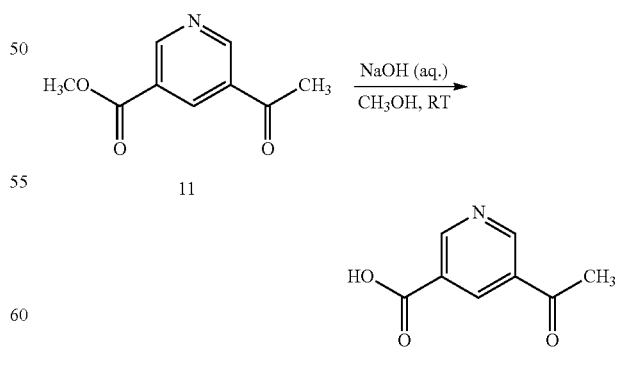

2-Heteroaryl benzimidazoles may be prepared by a variety of methods by those skilled in the art. One such method, shown in Scheme 5, involves heating of fluoronitrobenzene 13 in the presence of an amine, a base such as K₂CO₃, and an additive such as KF to afford nitroaniline 14. Exposure of 14 to a catalyst such as Pd/C under an atmosphere of hydrogen in a solvent such as methanol effects reduction to give diamine 15. Diamine 15 may then be condensed with a heteroaryl aldehyde 16 in the presence of OXONE® in a mixed solvent system such as DMF and H₂O at room temperature to yield 2-heteroaryl benzimidazole 17. Alternatively, diamine 15 may be condensed with 16 in the presence of Na₂S₂O₅ in a solvent such as DMF at elevated temperature to provide 17. The heteroaryl aldehydes 16 employed in these reactions may be obtained commercially, or may synthesized according to procedures outlined in Schemes 1-3

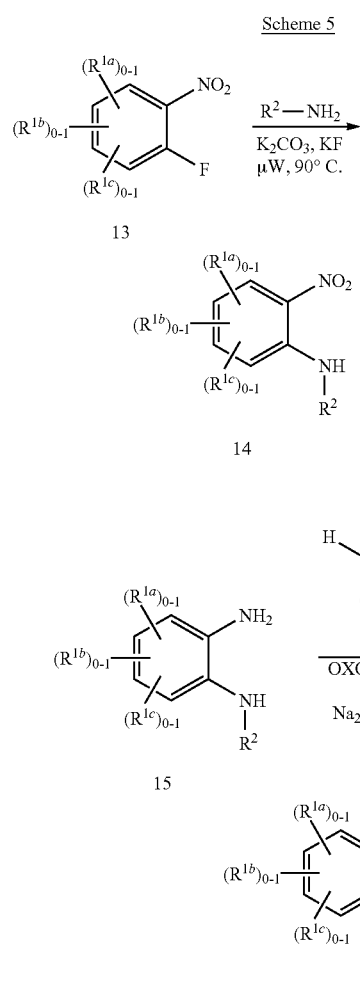

An alternative method for the synthesis of 2-heteroaryl benzimidazoles is outlined in Scheme 6. In this approach, diamine 15 may be coupled to a heteroaryl carboxylic acid 18 using standard methods for amide bond formation. For example, 15 and 18 may be coupled in the presence of N-[3-(dimethylamino)propyl]-N-ethylcarbodiimide (EDC), 1H-benzotriazol-1-ol (HOBt), and a base such as diisopropylethylamine in a solvent such as dichloromethane at room temperature to afford amide 19. Alternatively, 15 and 18 may be coupled in the presence of N-[(dimethylamino)-1H-1,2,3-triazolo[4,5-b]pyridin-1-ylmethylene]-N-methylmethanaminium hexafluorophosphate N-oxide (HATU), 3H[1,2,3]-triazolo[4,5-b]pyridin-3-ol (HOAt), and a base such as diisopropylethylamine in a solvent such as dichloromethane to provide amide 19. Amide 19 may then be cyclized to benzimidazole 17 by heating in the presence of an acid such as acetic acid.

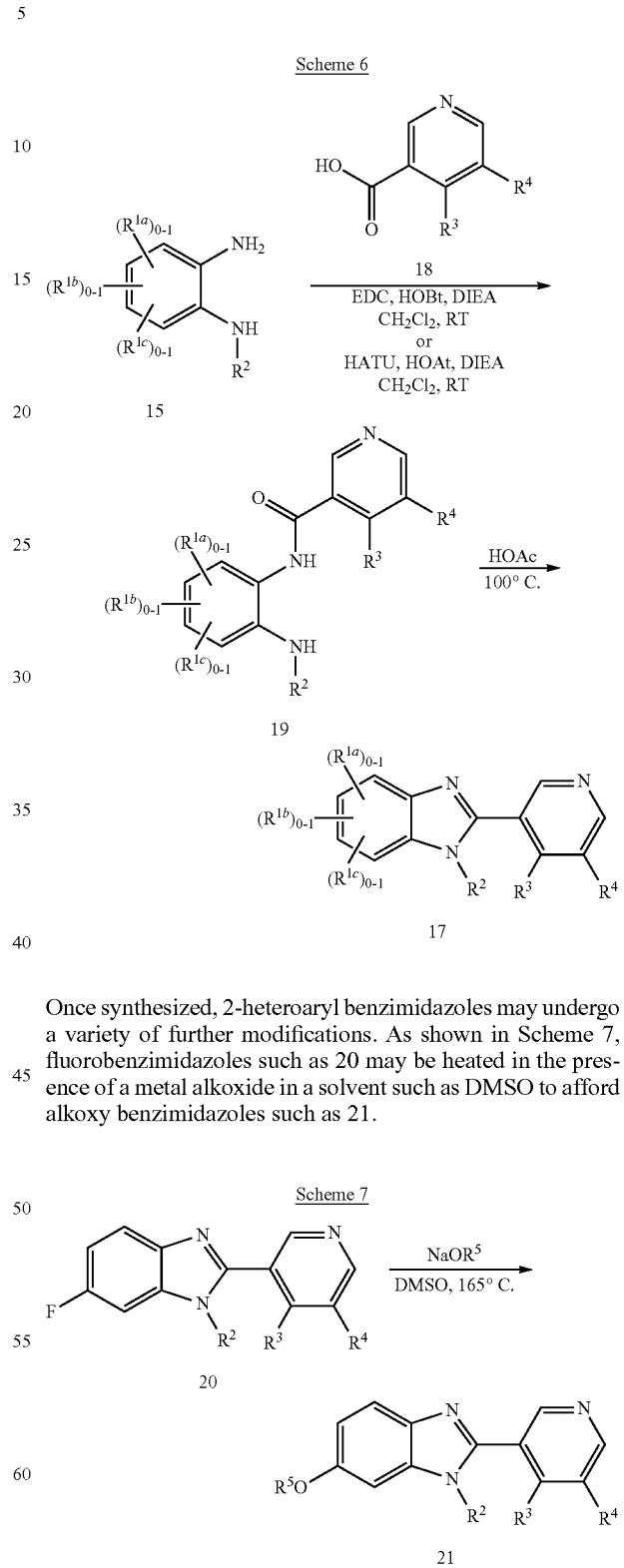

Once synthesized, 2-heteroaryl benzimidazoles may undergo a variety of further modifications. As shown in Scheme 7, fluorobenzimidazoles such as 20 may be heated in the presence of a metal alkoxide in a solvent such as DMSO to afford alkoxy benzimidazoles such as 21.

2-Heteroaryl benzimidazoles such as 22 may also undergo modifications such as those outlined in Scheme 8. Treatment of 22 with a base such as sodium hydride and an alkyl iodide $R^5$—I in a solvent such as tetrahydrofuran may provide alkylated product 23.

Scheme 8

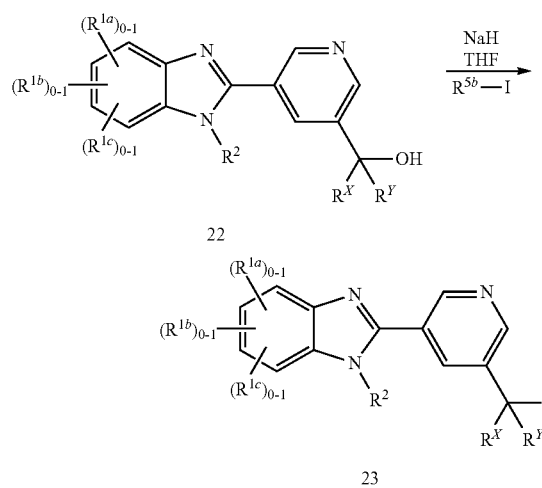

In yet another route, compounds of general Formula Ia can be synthesized according to Scheme 9. Bisaniline 15 was treated with carbonyldiimidazole to give benzimidazolone 24 which was then converted to 2-bromobenzimidazole 25 by heating with oxyphosphorus bromide. A Suzuki coupling between 25 and boronic ester 26 gives desired compound 17.

Scheme 9

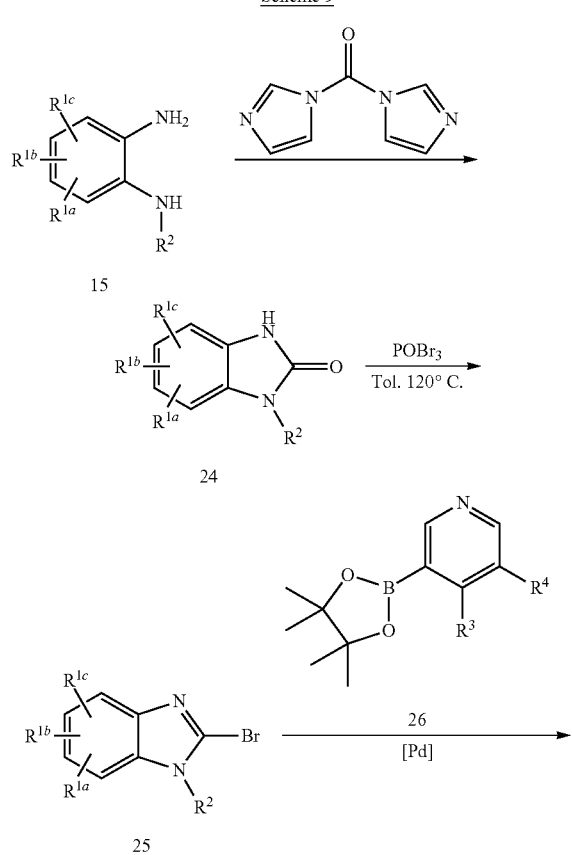

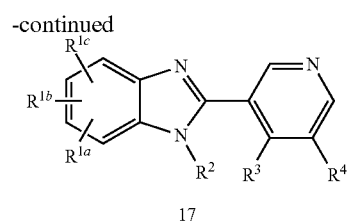

The desired boronic ester 26 can be synthesized according to Scheme 10. Lithiation of 3-bromo-5-fluoropyridine with LDA followed by methylation gives intermediate 28 which was then converted to corresponding boronic ester 26 by a standard palladium chemistry.

Scheme 10

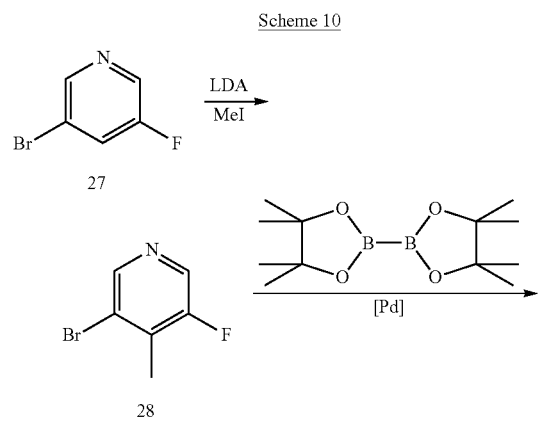

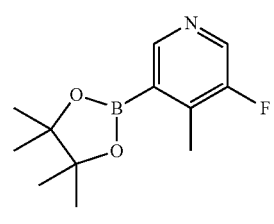

As will be known to those skilled in the art, in all schemes, the products of Formula Ia and all synthetic intermediates may be purified from unwanted side products, reagents and solvents by recrystallization, trituration, preparative thin layer chromatography, flash chromatography on silica gel as described by W. C. Still et al, 3. Org. Chem. 1978, 43, 2923, or reverse-phase HPLC. Compounds purified by HPLC may be isolated as the corresponding salt.

Additionally, in some instances the final compounds of Formula Ia and synthetic intermediates may be comprised of a mixture of cis and trans isomers, enantiomers or diastereomers. As will be known to those skilled in the art, such cis and trans isomers, enantiomers and diastereomers may be separated by various methods including crystallization, chromatography using a homochiral stationary phase and, in the case of cis/trans isomers and diastereomers, normal-phase and reverse-phase chromatography.

Chemical reactions were monitored by LCMS, and the purity and identity of the reaction products were assayed by LCMS (electrospray ionization) and NMR. LCMS spectra were recorded on an Agilent 1100 series instrument equipped with an Xterra MS C18 column (3.5 µM, 3.0×50 mm i.d.) and UV detector. $^1$H NMR spectra were recorded on a Varian 500

MHz spectrometer, and are internally referenced to residual protio solvent signals. Data for $^1$H NMR are reported with chemical shift (δ ppm), multiplicity (s=singlet, d=doublet, t triplet, q=quartet, m=multiplet, br s broad singlet, br m=broad multiplet), coupling constant (Hz), and integration. Unless otherwise noted, all LCMS ions listed are [M+H]. All temperatures are degrees Celsius unless otherwise noted.

Intermediates and final compounds having a chiral carbon can be prepared as racemates, or chiral intermediates can be resolved and the enantiomers used separately to synthesize enantiomeric downstream intermediates and final products. In the instances where chiral compounds were separated by chiral HPLC purification, the term "enantiomer A" refers to the first eluting enantiomer and the term "enantiomer B" refers to the second eluting enantiomer under the specified conditions. As a result, the chemical nomenclature may indicate that an S and/or an R enantiomer was obtained, but the absolute stereochemistry of the separate enantiomers A and/or B was not determined.

Preparative HPLC was performed using a SunFire Prep C18 OBD column (5 μM, 19×100 mm i.d.) on Gilson instruments equipped with UV detectors. Flash chromatography on silica gel was performed using pre-packed silica gel columns on Biotage Horizon or Biotage SP-1 instruments equipped with UV detectors.

The following examples are provided so that the invention might be more fully understood. They should not be construed as forming the only genus that is considered as the invention nor limiting the invention in any way.

EXAMPLE 1

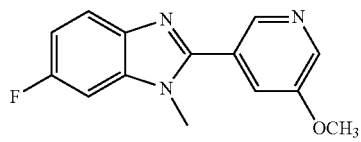 [SMILES: COc1cncc(-c2nc3ccc(F)cc3n2C)c1]

Step A. 5-Fluoro-N-methyl-2-nitroaniline

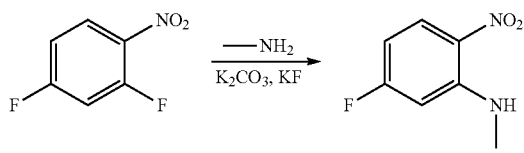

2,4-Difluoronitrobenzene (1.00 g, 6.29 mmol), potassium fluoride (0.365 g, 6.29 mmol), potassium carbonate (0.869 g, 6.29 mmol), and 40% methylamine in water (0.58 mL, 7.5 mmol) were added to a vial and heated in a microwave at 90° C. for 10 min. The reaction was then diluted with dichloromethane, washed with water and brine, dried over magnesium sulfate, and concentrated to provide the title compound:

$^1$H NMR (500 MHz, CDCl$_3$) δ 8.22 (dd, J=9.4, 6.1 Hz, 1 H), 8.16 (br s, 1 H), 6.48 (dd, J=11.5, 2.6 Hz, 1 H), 6.40-6.36 (m, 1 H), 3.01 (d, J=5.0 Hz, 3 H).

Step B. 4-Fluoro-N$^2$-methylbenzene-1,2-diamine

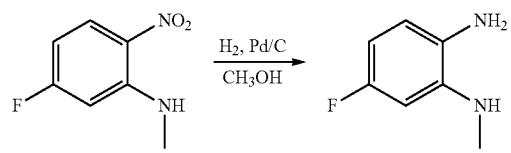

To the title compound from Example 1 Step A (0.267 g, 1.57 mmol) were added palladium on carbon (0.027 g) and methanol (7.85 mL). The resulting mixture was stirred under an atmosphere of hydrogen at room temperature overnight. The mixture was then filtered through CELITE® using dichloromethane, and the filtrate was concentrated. Purification by flash chromatography (50% ethyl acetate in hexanes, then 100% ethyl acetate) provided the title compound: $^1$H NMR (500 MHz, CDCl$_3$) δ 6.61 (dd, J=8.2, 5.6 Hz, 1 H), 6.36-6.30 (m, 2 H), 3.22 (br s, 3 H), 2.84 (s, 3 H).

Step C. 6-Fluoro-2-(5-methoxypyridin-3-yl)-1-methyl-1 H-benzimidazole

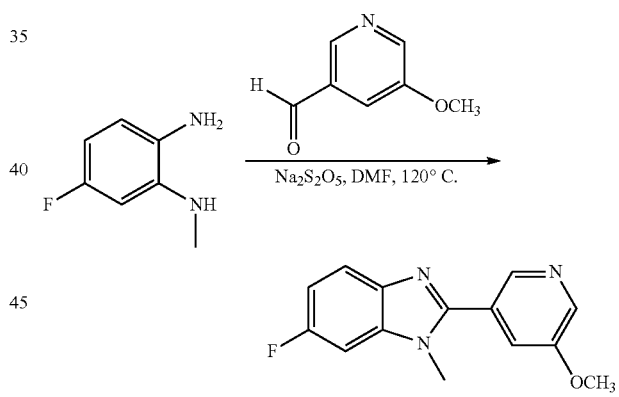

To a solution of 5-methoxypyridine-3-carbaldehyde (0.052 g, 0.378 mmol) in DMF (1.89 mL) were added the title compound from Example 1 Step B (0.053 g, 0.38 mmol) and Na$_2$S$_2$O$_5$ (0.288 g, 1.51 mmol). The resulting mixture was stirred at 120° C. overnight, then cooled to room temperature and diluted with water and ethyl acetate. The organic layer was separated, washed with water and brine, dried over magnesium sulfate, filtered, and concentrated. Purification by flash chromatography on silica gel (50% ethyl acetate in hexanes, then 100% ethyl acetate) provided the title compound: LCMS m/z 258.17 [M+H]$^+$; $^1$H NMR (500 MHz, CDCl$_3$) δ 8.56 (d, J=1.6 Hz, 1 H), 8.46 (d, J=2.9 Hz, 1 H), 7.66 (dd, J=8.6, 4.8 Hz, 1 H), 7.65 (t, J=2.1, 2.1 Hz, 1 H), 7.12-7.06 (m, 2 H), 3.95 (s, 3 H), 3.88 (s, 3 H).

The compounds in Table 1 were all prepared using chemistry described in Example 1.

TABLE 1

| Example | Structure | IUPAC Name | LCMS |
|---|---|---|---|
| 2 | 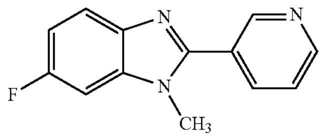 [SMILES: Cn1c(-c2cccnc2)nc2ccc(F)cc21] | 6-fluoro-1-methyl-2-(pyridin-3-yl)-1H-benzimidazole | 228.22 |
| 3 | 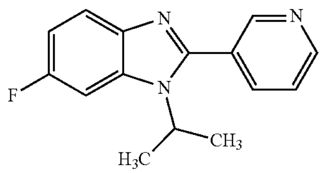 [SMILES: CC(C)n1c(-c2cccnc2)nc2ccc(F)cc21] | 6-fluoro-1-(propan-2-yl)-2-(pyridin-3-yl)-1H-benzimidazole | 256.12 |
| 4 | 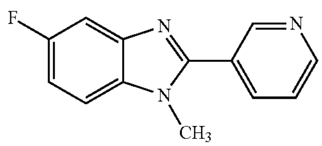 | 5-fluoro-1-methyl-2-(pyridin-3-yl)-1H-benzimidazole | 228.22 |

EXAMPLE 5

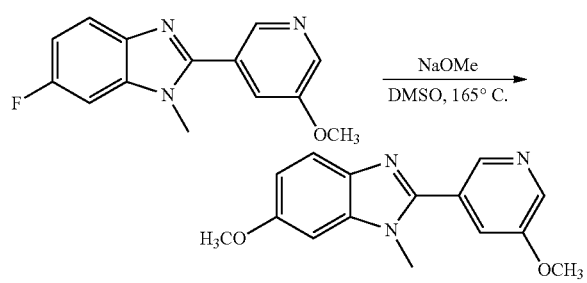

6-Methoxy-2-(5-methoxypyridin-3-yl)-1-methyl-1H-benzimidazole

To a solution of the title compound from Example 1 Step C (0.010 g, 0.038 mmol) in dimethylsulfoxide (0.2 mL) was added a solution of sodium methoxide in methanol (25 wt %, 0.018 mL, 0.078 mmol). The reaction was heated at 165° C. for 1 hour, then cooled to room temperature and purified by flash chromatography (50% ethyl acetate in hexanes, then 100% ethyl acetate) to provide the title compound: LCMS m/z 270.25 [M+H]$^+$; $^1$H NMR (500 MHz, CDCl$_3$) δ 8.55 (d, 1.5 Hz, 1 H), 8.43 J=2.7 Hz, 1H), 7.72 (d, J=8.8 Hz, 1 H), 7.66 (dd, J=2.5, 1.8 Hz, 1 H), 6.98 (dd, J=8.8, 2.3 Hz, 1 H), 6.86 (d, J=2.3 Hz, 1 H), 3.95 (s, 3 H), 3.92 (s, 3 H), 3.88 (s, 3 H).

EXAMPLES 6 AND 7

Racemate and Enantiomers

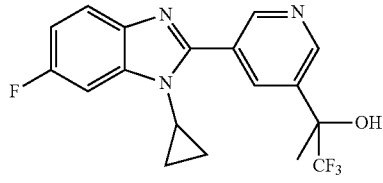

Step A.
2-(5-Bromopyridin-3-yl)-1,1,1-trifluoropropan-2-ol

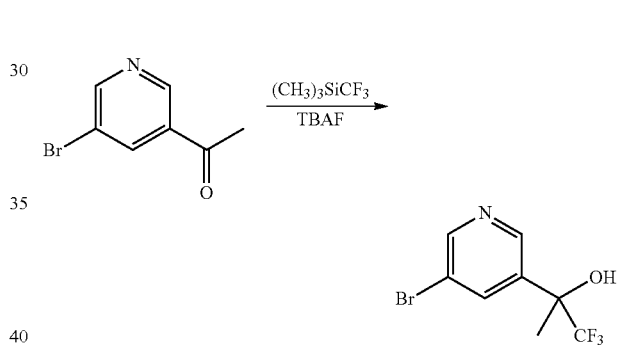

To a solution of 3-acetyl-5-bromopyridine (0.20 g, 1.0 mmol) in tetrahydrofuran (3.3 mL) were added a solution of trimethyl(trifluoromethyl)silane in tetrahydrofuran (0.5 M, 4.0 mL, 2.0 mmol) and a solution of tetrabutylammonium fluoride in tetrahydrofuran (1.0 M, 0.1 mL, 0.1 mmol). The resulting reaction mixture was stirred at room temperature for 1 h, then diluted with water and dichloromethane. The organic layer was separated, dried over magnesium sulfate, filtered and concentrated. Purification by flash chromatography on silica gel (0 to 6% dichloromethane in acetone) provided the title compound: LCMS m/z 271.75 [M+H]$^+$; $^1$H NMR (500 MHz, CDCl$_3$) δ 8.71 (s, 1 H), 8.68 (s, 1 H), 8.11 (s, 1 H), 3.12 (br s, 1 H), 1.82 (s, 3H).

Step B. Methyl 5-(1,1,1-trifluoro-2-hydroxypropan-2-yl)pyridine-3-carboxylate

-continued

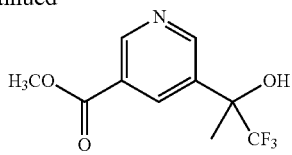

A mixture of the title compound from Step A (0.170 g, 0.628 mmol), Pd(OAc)$_2$ (2.8 mg, 0.013 mmol), Xantphos (0.015 g, 0.025 mmol), methanol (0.254 mL, 6.28 mmol), and triethylamine (8.96 mL, 1.25 mmol) was stirred under an atmosphere of carbon monoxide at 70° C. overnight. The reaction mixture was cooled to room temperature, diluted with ethyl acetate, filtered through Celite using ethyl acetate and concentrated under reduced pressure. Purification by column chromatography on silica gel (30% ethyl acetate in hexanes) provided the title compound: LCMS m/z 250.02 [M+H]$^+$; $^1$H NMR (500 MHz, CDCl$_3$) δ 9.22 (s, 1 H), 9.00 (s, 1 H), 8.52 (s, 1 H), 3.98 (s, 3 H), 2.94 (br s, 1 H), 1.86 (s, 3 H).

Step C. 5-(1,1,1-Trifluoro-2-hydroxypropan-2-yl)pyridine-3-carbaldehyde

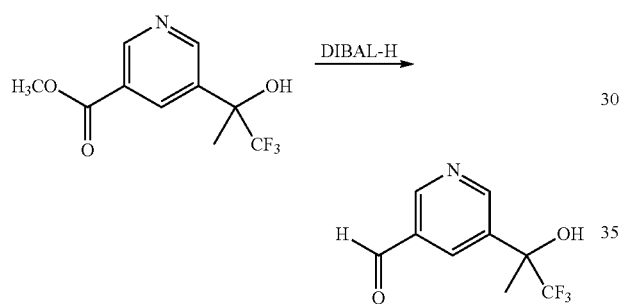

To a cooled (−78° C.) solution of the title compound from Step B (0.14 g, 0.56 mmol) in toluene (3.23 mL) and dichloromethane (3.23 mL) was added a solution of di-isobutyl aluminum hydride in toluene (1.0 M, 1.29 mL, 1.29 mmol). After 10 min, the reaction was quenched with water (1 mL), allowed to warm to room temperature, and dried over magnesium sulfate. Concentration of the filtrate under reduced pressure provided the title compound: $^1$H NMR (500 MHz, CDCl$_3$) δ 10.16 (s, 1 H), 9.08 (s, 1 H), 9.07 (s, 1 H), 8.41 (s, 1 H), 3.30 (br s, 1 H), 1.88 (s, 3 H).

Step D. N-cyclopropyl-5-fluoro-2-nitroaniline

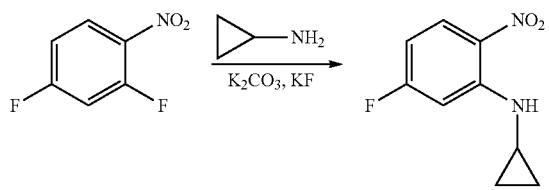

2,4-Difluoronitrobenzene (1.00 g, 6.29 mmol), potassium fluoride (0.365 g, 6.29 mmol), potassium carbonate (0.869 g, 6.29 mmol), and cyclopropylamine (0.52 mL, 7.54 mmol) were added to a vial and heated in a microwave at 90° C. for 10 min. The reaction was then diluted with dichloromethane, washed with water and brine, dried over magnesium sulfate, and concentrated to provide the title compound: LCMS m/z 196.95 [M+H]$^+$; $^1$H NMR (500 MHz, CDCl$_3$) δ 8.20 (dd, J=9.5, 6.0 Hz, 2 H), 6.95 (dd, J=11.4, 2.6 Hz, 1 H), 6.43-6.39 (m, 1 H), 2.58-2.53 (m, 1 H), 0.96-0.92 (m, 2 H), 0.69-0.66 (m, 2 H).

Step E. N$^2$-cyclopropyl-4-fluorobenzene-1,2-diamine

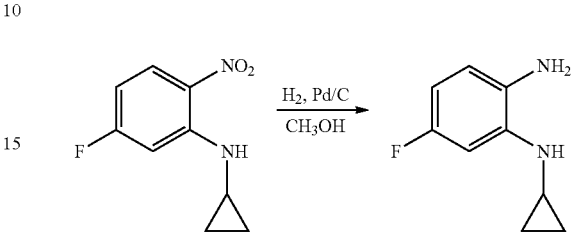

To the title compound from Step D (1.23 g, 6.27 mmol) were added 10% palladium on carbon (0.123 g, 1.16 mmol) and methanol (31.3 mL). The resulting mixture was stirred under an atmosphere of hydrogen at room temperature overnight. The reaction mixture was then filtered through CELITE° using dichloromethane and concentrated under reduced pressure. Purification by flash chromatography on silica gel (0 to 30% ethyl acetate in hexanes) provided the title compound: $^1$H NMR (500 MHz, CDCl$_3$) δ 6.76 (dd, J=10.9, 2.8 Hz, 1 H), 6.60 (dd, J=8.4, 5.6 Hz, 1 H), 6.34 (ddd, J=11.2, 8.4, 2.8 Hz, 1 H), 4.17 (br s, 1 H), 3.01 (br s, 2 H), 2.42-2.38 (m, 1 H), 0.77-0.72 (m, 2 H), 0.54-0.51 (m, 2 H).

Step F. 2-[5-(1-cyclopropyl-6-fluoro-1H-benzimidazol-2-yl)pyridin-3-yl]-1,1,1-trifluoropropan-2-ol

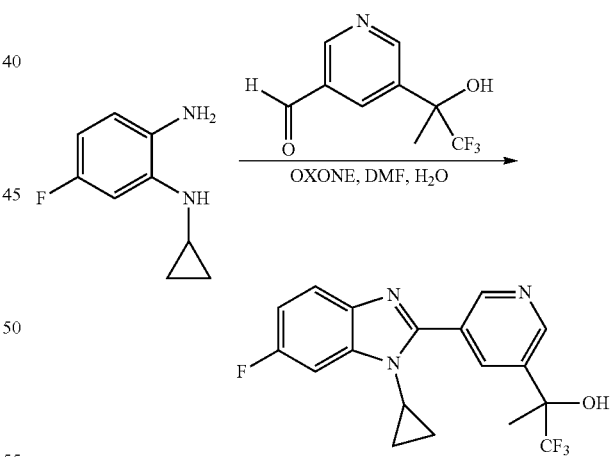

To a solution of the title compound from Step E (0.058 g, 0.35 mmol) in DMF (1.68 mL) and water (0.06 mL) were added the title compound from Step C (0.076 g, 0.35 mmol) and OXONE® (0.139 g, 0.226 mmol). The resulting mixture was stirred at room temperature for 1 hour, then diluted with ethyl acetate and water. Solid potassium carbonate was added until the aqueous layer was basic (pH ~9). Ethyl acetate was then added, and the organic layer was separated, washed with water and brine, dried over magnesium sulfate, filtered, and concentrated. Purification by flash column chromatography on silica gel (10% acetone in dichloromethane, then 30% acetone in dichloromethane) provided the title compound as a racemic mixture. That racemic mixture was then separated into two enantiomers by HPLC (ChiralCel AS column, 25% MeOH (0.2% DEA)/CO$_2$, 70 mL/min, 100 bar, 35° C.). Data for EXAMPLE 6 (Enantiomer A): LCMS m/z 365.99 [M+H]$^+$; $^1$H NMR (500 MHz, CDCl$_3$) δ 9.14 (s, 1 H), 8.85 (s, 1 H), 8.59 (s, 1 H), 7.76 (dd, J=8.8, 4.8 Hz, 1 H), 7.30 (dd, J=8.5, 2.1 Hz, 1 H), 7.11-7.07 (m, 1 H), 4.85 (br s, 1 H), 3.55-3.53 (m, 1 H), 1.79 (s, 3 H), 1.22-1.12 (m, 2 H), 0.80-0.72 (m, 2 H). Data for Example 7 (Enantiomer B): LCMS m/z 365.97 [M+H]$^+$; $^1$H NMR (500 MHz, CDCl$_3$) δ 9.16 (s, 1 H), 8.88 (s, 1 H), 8.57 (s, 1 H), 7.76 (dd, J=8.8, 4.8 Hz, 1 H), 7.30 (dd, J=8.5, 2.0 Hz, 1 H), 7.10-7.05 (m, 1 H), 3.91 (br s, 1 H), 3.56-3.55 (m, 1 H), 1.84 (s, 3 H), 1.18-1.15 (m, 2 H), 0.80-0.71 (m, 2 H).

EXAMPLE 8

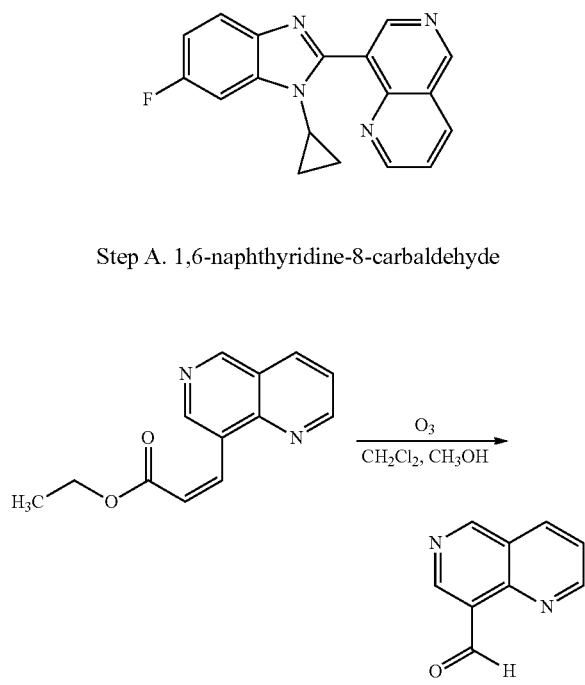

Step A. 1,6-naphthyridine-8-carbaldehyde

A solution of ethyl (2Z)-3-(1,6-naphthyridin-8-yl)prop-2-enoate (30 g) in dichloromethane (500 mL) and methanol (125 mL) was cooled to −78° C. and reacted with ozone until the color of the reaction mixture became light blue (~3 h). The reaction was purged with nitrogen to remove the residual ozone. Methyl sulfide (60 mL) was then added, and the reaction was allowed to warm to room temperature and then concentrated. The resulting residue was dissolved in dichloromethane (300 mL), washed with water (100 mL) and saturated aqueous sodium bicarbonate (100 mL) and dried over sodium sulfate. The solvent was removed and product was slurried in heptane/ethyl acetate mixture (5:1). The solid was then filtered and dried under reduced pressure to provide the title compound: LCMS m/z 158.97 [M+H]$^+$; $^1$H NMR (500 MHz, CDCl$_3$) δ 11.39 (s, 1 H), 9.09 (s, 1 H), 9.13 (m, 1 H), 9.07 (s, 1 H), 8.43 (d, J=8.3 Hz, 1 H), 7.78 (dd, J=8.7, 4.8 Hz, 1 H), 7.63 (dd, J=8.2, 4.2 Hz, 1 H), 7.34 (dd, J=8.7, 2.2 Hz, 1 H), 7.07 (m, 1 H), 3.55-3.53 (m, 1 H), 0.62-0.61 (m, 4 H).

Step B. 8-(1-cyclopropyl-6-fluoro-1H-benzimidazol-2-yl)-1,6-naphthyridine

To a solution of N$^2$-cyclopropyl-4-fluorobenzene-1,2-diamine (0.080 g, 0.48 mmol) in DMF (1.17 mL) and water (0.04 mL) were added the title compound from Example 8 Step A (0.084 g, 0.53 mmol) and OXONE® (0.192 g, 0.313 mmol). The resulting mixture was stirred at room temperature for 1 hour, then diluted with ethyl acetate and water. Solid potassium carbonate was added until the aqueous layer was basic (pH ~9). Ethyl acetate was added, and the organic layer was separated, washed with water and brine, dried over magnesium sulfate, filtered and concentrated. Purification by flash chromatography on silica gel (50% ethyl acetate in hexanes, then 100% ethyl acetate) provided the title compound: LCMS m/z 304.99 [M+H]$^+$; $^1$H NMR (500 MHz, CDCl$_3$) δ 9.09 (s, 1 H), 9.13 (m, 1 H), 9.07 (s, 1 H), 8.43 (d, J=8.3 Hz, 1 H), 7.78 (dd, J=8.7, 4.8 Hz, 1 H), 7.63 (dd, J=8.2, 4.2 Hz, 1 H), 7.34 (dd, J=8.7, 2.2 Hz, 1 H), 7.07 (m, 1 H), 3.55-3.53 (m, 1 H), 0.62-0.61 (m, 4 H).

The compounds in Table 2 were all prepared using the synthetic procedures described in Examples 6-8.

TABLE 2

| Example | Structure | IUPAC Name | LCMS |
|---|---|---|---|
| 9 | 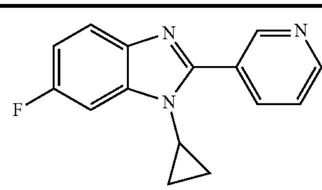 | 1-cyclopropyl-6-fluoro-2-(pyridin-3-yl)-1H-benzimidazole | 254.26 |

TABLE 2-continued

| Example | Structure | IUPAC Name | LCMS |
|---|---|---|---|
| 10 | 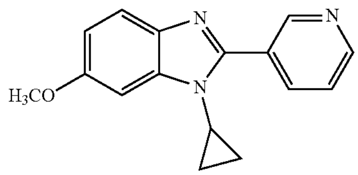 [SMILES: COc1ccc2nc(-c3cccnc3)n(C3CC3)c2c1] | 1-cyclopropyl-6-methoxy-2-(pyridin-3-yl)-1H-benzimidazole | 266.28 |
| 11 | 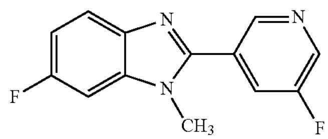 [SMILES: Cn1c(-c2cncc(F)c2)nc2ccc(F)cc21] | 6-fluoro-2-(5-fluoropyridin-3-yl)-1-methyl-1H-benzimidazole | 246.23 |
| 12 | 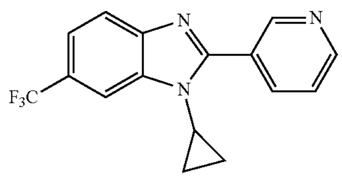 [SMILES: FC(F)(F)c1ccc2nc(-c3cccnc3)n(C3CC3)c2c1] | 1-cyclopropyl-2-(pyridin-3-yl)-6-(trifluoromethyl)-1H-benzimidazole | 304.2 |
| 13 | 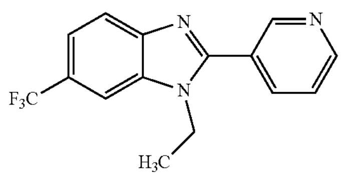 [SMILES: CCn1c(-c2cccnc2)nc2ccc(C(F)(F)F)cc21] | 1-ethyl-6-fluoro-2-(pyridin-3-yl)-1H-benzimidazole | 242.22 |
| 14 | 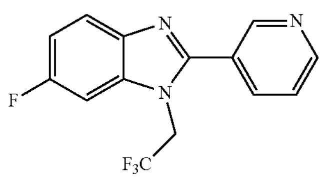 [SMILES: Fc1ccc2nc(-c3cccnc3)n(CC(F)(F)F)c2c1] | 6-fluoro-2-(pyridin-3-yl)-1-(2,2,2-trifluoroethyl)-1H-benzimidazole | 296.18 |
| 15 | 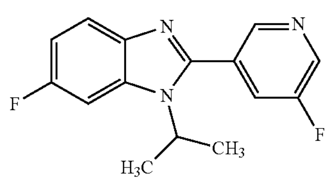 [SMILES: CC(C)n1c(-c2cncc(F)c2)nc2ccc(F)cc21] | 6-fluoro-2-(5-fluoropyridin-3-yl)-1-(propan-2-yl)-1H-benzimidazole | 274.22 |
| 16 | 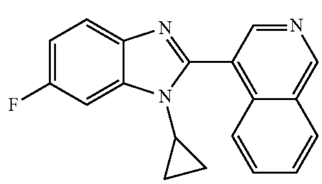 [SMILES: Fc1ccc2nc(-c3cncc4ccccc34)n(C3CC3)c2c1] | 4-(1-cyclopropyl-6-fluoro-1H-benzimidazol-2-yl)isoquinoline | 304.21 |
| 17 | 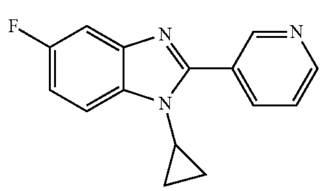 [SMILES: Fc1ccc2c(c1)nc(-c1cccnc1)n2C1CC1] | 1-cyclopropyl-5-fluoro-2-(pyridin-3-yl)-1H-benzimidazole | 254.26 |

TABLE 2-continued

| Example | Structure | IUPAC Name | LCMS |
|---|---|---|---|
| 18 | 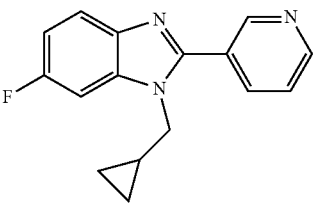 [SMILES: Fc1ccc2nc(-c3cccnc3)n(CC3CC3)c2c1] | 1-(cyclopropylmethyl)-6-fluoro-2-(pyridin-3-yl)-1H-benzimidazole | 268.02 |
| 19 | 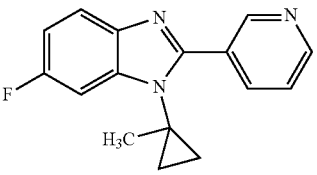 [SMILES: CC1(n2c(-c3cccnc3)nc3ccc(F)cc32)CC1] | 6-fluoro-1-(1-methylcyclopropyl)-2-(pyridin-3-yl)-1H-benzimidazole | 268.23 |
| 20 | 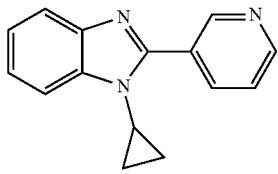 [SMILES: c1cncc(-c2nc3ccccc3n2C2CC2)c1] | 1-cyclopropyl-2-(pyridin-3-yl)-1H-benzimidazole | 236.3 |
| 21 | 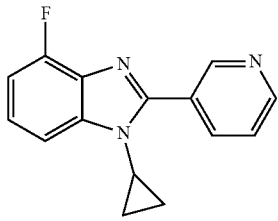 [SMILES: Fc1cccc2c1nc(-c1cccnc1)n2C1CC1] | 1-cyclopropyl-4-fluoro-2-(pyridin-3-yl)-1H-benzimidazole | 254.16 |
| 22 | 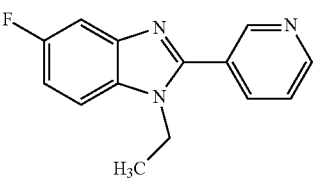 [SMILES: CCn1c(-c2cccnc2)nc2cc(F)ccc21] | 1-ethyl-5-fluoro-2-(pyridin-3-yl)-1H-benzimidazole | 242.11 |
| 23 | 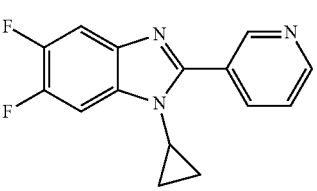 [SMILES: Fc1cc2nc(-c3cccnc3)n(C3CC3)c2cc1F] | 1-cyclopropyl-5,6-difluoro-2-(pyridin-3-yl)-1H-benzimidazole | 272.04 |
| 24 | 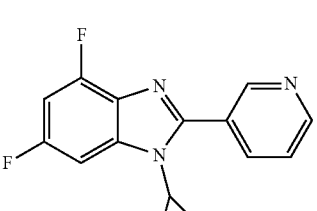 | 1-cyclopropyl-4,6-difluoro-2-(pyridin-3-yl)-1H-benzimidazole | 272.07 |
| 25 | 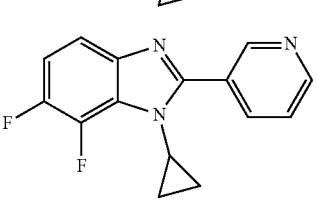 | 1-cyclopropyl-6,7-difluoro-2-(pyridin-3-yl)-1H-benzimidazole | 272.03 |

TABLE 2-continued

| Example | Structure | IUPAC Name | LCMS |
|---|---|---|---|
| 26 | 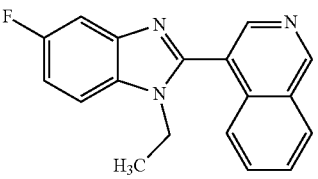 [SMILES: CCn1c(-c2cncc3ccccc23)nc2cc(F)ccc21] | 4-(1-ethyl-5-fluoro-1H-benzimidazol-2-yl)isoquinoline | 292.11 |
| 27 | 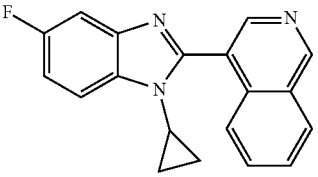 [SMILES: Fc1ccc2c(c1)nc(-c1cncc3ccccc13)n2C1CC1] | 4-(1-cyclopropyl-5-fluoro-1H-benzimidazol-2-yl)isoquinoline | 304.13 |
| 28 | 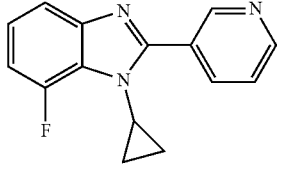 [SMILES: Fc1cccc2nc(-c3cccnc3)n(C3CC3)c12] | 1-cyclopropyl-7-fluoro-2-(pyridin-3-yl)-1H-benzimidazole | 254.19 |
| 29 | 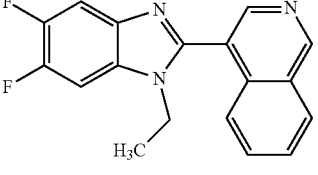 | 4-(1-ethyl-5,6-difluoro-1H-benzimidazol-2-yl)isoquinoline | 310.03 |
| 30 | 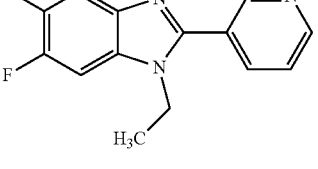 | 1-ethyl-5,6-difluoro-2-(pyridin-3-yl)-1H-benzimidazole | 260.2 |
| 31 | 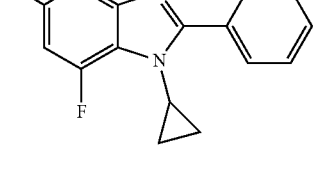 | 1-cyclopropyl-5,7-difluoro-2-(pyridin-3-yl)-1H-benzimidazole | 272.05 |
| 32 | 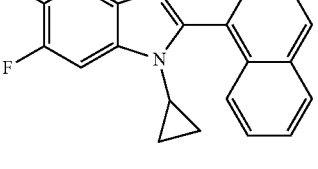 | 4-(1-cyclopropyl-5,6-difluoro-1H-benzimidazol-2-yl)isoquinoline | 322.05 |
| 33 | 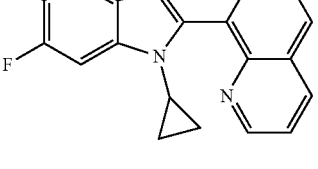 | 8-(1-cyclopropyl-5,6-difluoro-1H-benzimidazol-2-yl)-1,6-naphthyridine | 323.01 |

TABLE 2-continued

| Example | Structure | IUPAC Name | LCMS |
|---|---|---|---|
| 34 | 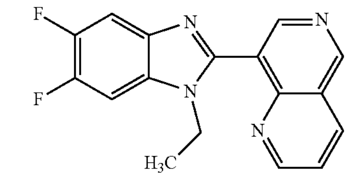 [SMILES: CCn1c(-c2cncc3ccccc23)nc2cc(F)c(F)cc21] | 8-(1-ethyl-5,6-difluoro-1H-benzimidazol-2-yl)-1,6-naphthyridine | 311.17 |
| 35 | 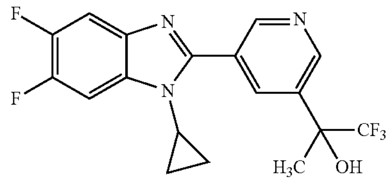 [SMILES: CC(O)(c1cncc(-c2nc3cc(F)c(F)cc3n2C2CC2)c1)C(F)(F)F] | 2-[5-(1-cyclopropyl-5,6-difluoro-1H-benzimidazol-2-yl)pyridin-3-yl]-1,1,1-trifluoropropan-2-ol | 384.37 |
| 36 | 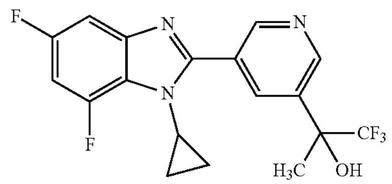 [SMILES: CC(O)(c1cncc(-c2nc3cc(F)cc(F)c3n2C2CC2)c1)C(F)(F)F] | 1-cyclopropyl-5,7-difluoro-2-[5-(1,1,1-trifluoro-2-methoxypropan-2-yl)pyridin-3-yl]-1H-benzimidazole | 383.94 |

EXAMPLE 37

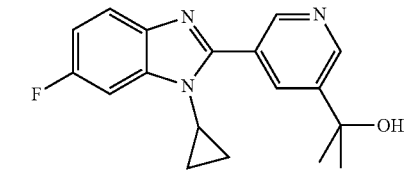

Step A. 2-(5-Bromopyridin-3-yl)propan-2-ol

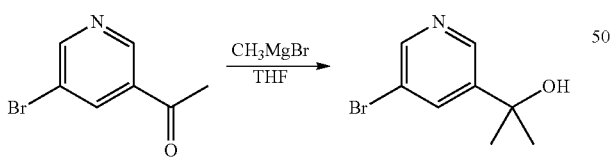

To a cooled (−78° C.) solution of 3-acetyl-5-bromo pyridine (1.98 g, 9.90 mmol) in tetrahydrofuran (33 mL) was added dropwise a solution of methyl magnesium bromide in diethyl ether (3.0 M, 6.60 mL, 19.8 mmol). The reaction was warmed to room temperature, and the resulting mixture was stirred at room temperature overnight. The reaction was then quenched with saturated aqueous ammonium chloride solution and extracted with diethyl ether. The organic extracts were combined, washed with brine, dried over magnesium sulfate, filtered and concentrated. Purification by flash chromatography on silica gel (0-60% ethyl acetate in hexanes) provided the title compound: LCMS m/z 217.83 [M+H]$^+$; $^1$H NMR (500 MHz, CDCl$_3$) δ 8.61 (s, 1 H), 8.53 (s, 1 H), 8.01 (d, J=1.9 Hz, 1 H), 2.38 (br s, 1 H), 1.61 (6 H).

Step B. Methyl 5-(2-hydroxypropan-2-yl)pyridine-3-carboxylate

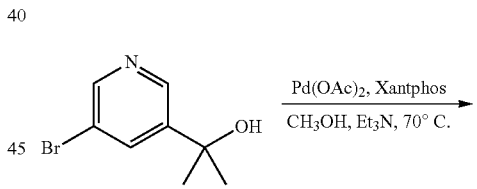

A mixture of the title compound from Step A (1.99 g, 9.21 mmol), palladium acetate (0.041 g, 0.041 Xantphos (0.213 g, 0.368 mmol), methanol (3.73 mL, 92.1 mmol), and triethylamine (18.33 mL, 132.0 mmol) was stirred under an atmosphere of carbon monoxide at 70° C. overnight. The reaction was then cooled to room temperature, diluted with ethyl acetate, filtered through CELITE© and concentrated under reduced pressure. Purification by flash chromatography on silica gel (30% ethyl acetate in hexanes) provided the title compound: LCMS m/z 195.99 [M+H]$^+$; $^1$H NMR (500 MHz, CDCl$_3$) δ 9.09 (d, J=1.8 Hz, 1 H), 8.92 (d, J=2.2 Hz, 1 H), 8.41 (t, J=2.0 Hz, 1 H), 3.96 (s, 3 H), 2.27 (br s, 1 H), 1.64 (s, 6 H).

Step C.
5-(2-Hydroxypropan-2-yl)pyridine-3-carbaldehyde

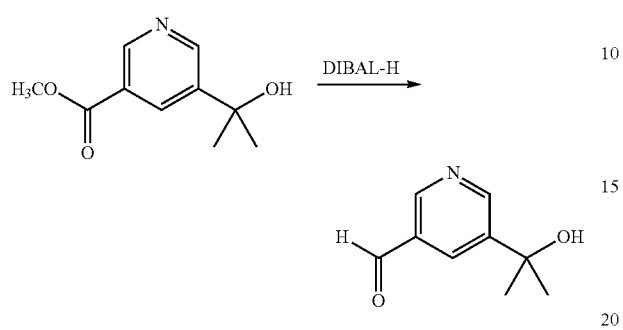

To a cooled (−78° C.) solution of the title compound from Step B (0.50 g, 2.6 mmol) in toluene (15 mL) and dichloromethane (15 mL) was added a solution of diisobutyl aluminum hydride in toluene (1.0 M, 6.0 mL, 6.0 mmol). After 10 min, the reaction was quenched with water (5 mL), allowed to warm to room temperature and dried with magnesium sulfate. Concentration of the filtrate under reduced pressure provided the title compound: $^1$H NMR (500 MHz, CDCl$_3$) δ 10.10 (s, 1 H), 8.99 (d, J=2.3 Hz, 1 H), 8.93 (s, 1 H), 8.30 (s, 1 H), 2.22 (br s, 1 H), 1.67 (s, 6 H).

Step D. 2-[5-(1-cyclopropyl-6-fluoro-1H-benzimidazol-2-yl)pyridin-3-yl]propan-2-ol

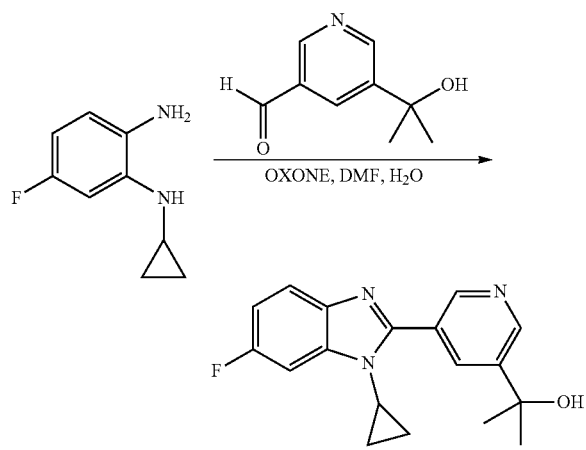

To a solution of N$^2$-cyclopropyl-4-fluorobenzene-1,2-diamine (0.479 g, 2.88 mmol) in DMF (6.97 mL) and water (0.23 mL) were added the title compound from Step C (0.302 g, 1.83 mmol) and OXONE® (0.729 g, 1.19 mmol). The resulting mixture was stirred at room temperature for 1 hour, then diluted with ethyl acetate and water. Solid potassium carbonate was added until the aqueous layer was basic (pH ~9). Ethyl acetate was added, and the organic layer was separated, washed with water and brine, dried over magnesium sulfate, filtered and concentrated. Purification by flash chromatography on silica gel (100% ethyl acetate) provided a product that was further purified by reverse phase HPLC(C18 OBD column, 20 to 90% acetonitrile/water, both 0.1% v/v trifluoroacetitic acid). Fractions containing the desired product were combined, washed sequentially with aqueous 1 N sodium hydroxide solution and brine, dried over magnesium sulfate, filtered and concentrated to provide the title compound: LCMS m/z 312.01 [M+H]$^+$; $^1$H NMR (500 MHz, CDCl$_3$) δ 9.09 (d, J=1.7 Hz, 1 H), 9.85 (d, J=1.9 Hz, 1 H), 8.40 (s, 1 H), 7.73 (dd, J=8.8, 4.8 Hz, 1 H), 7.29 (dd, J=8.7, 2.2 Hz, 1 H), 7.08-7.04 (m, 1 H), 3.57-3.55 (m, 1 H), 2.21 (br s, 1 H), 1.69 (s, 6 H), 1.20-1.16 (m, 2 H), 0.79-0.75 (m, 2 H).

EXAMPLE 38

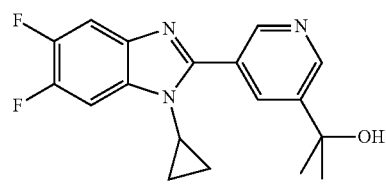 [SMILES: CC(C)(O)c1cncc(-c2nc3cc(F)c(F)cc3n2C2CC2)c1]

Step A. N-cyclopropyl-4,5-difluoro-2-nitroaniline

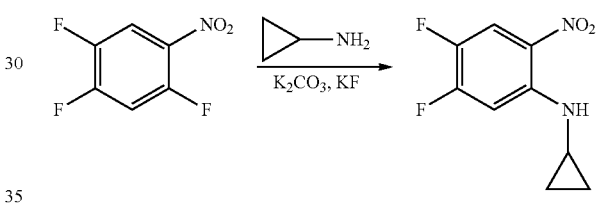

2,4,5-Trifluoronitrobenzene (2.00 g, 11.3 mmol), potassium fluoride (0.656 g, 11.3 mmol), potassium carbonate (1.561 g, 11.29 mmol), and cyclopropylamine (0.93 ml, 13.55 mmol) were added to a vial and heated in a microwave at 90° C. for 10 min. The reaction was then diluted with dichloromethane, washed with water and brine, dried over magnesium sulfate, and concentrated under reduced pressure. Purification by flash chromatography on silica gel (0-15% ethyl acetate in hexanes) provided the title compound: $^1$H NMR (500 MHz, CDCl$_3$) δ 8.04 (dd, J=10.4, 8.5 Hz, 1 H), 7.09 (dd, J=12.6, 7.0 Hz, 1 H), 2.55-2.54 (m, 1 H), 0.97-0.93 (m, 2 H), 0.69-0.66 (m, 2 H).

Step B.
N-cyclopropyl-4,5-difluorobenzene-1,2-diamine

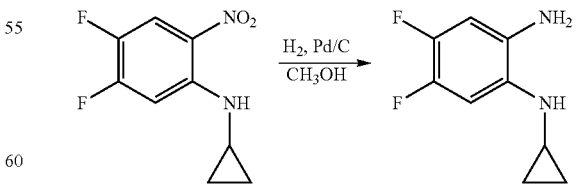

To the title compound from Step A (1.22 g, 5.69 mmol) were added 10% palladium on carbon (0.122 g, 1.15 mmol) and methanol (28.5 mL). The resulting mixture was stirred under an atmosphere of hydrogen at room temperature overnight. The mixture was then filtered through CELITE® using dichloromethane, and the filtrate was concentrated. Purification by flash chromatography on silica gel (0-30% ethyl acetate in hexanes) provided the title compound: $^1$H NMR (500 MHz, CDCl$_3$) δ 6.83 (dd, J=12.4, 7.9 Hz, 1 H), 6.51 (dd, J=11.3, 7.8 Hz, 1 H), 3.82 (br s, 1 H), 3.15 (br s, 2 H), 2.40-2.37 (m, 1 H), 0.77-0.73 (m, 2 H), 0.52-0.50 (m, 2 H).

Step C.
5-(2-Hydroxypropan-2-yl)pyridine-3-carboxylic acid

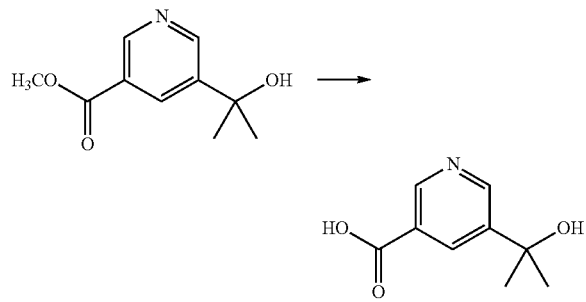

To a solution of methyl 5-(2-hydroxypropan-2-yl)pyridine-3-carboxylate (0.179 g, 0.915 mmol) in methanol (4.57 mL) was added 1 N aqueous sodium hydroxide solution (2.74 mL, 2.74 mmol). The reaction was stirred at room temperature for 30 min and then concentrated under reduced pressure. The resulting residue was acidified via the addition of 1 N aqueous hydrogen chloride solution until the pH was 2. Ethyl acetate was then added, and the extracted organics were dried over magnesium sulfate, filtered and concentrated to provide the title compound: LCMS m/z 182.01 [M+H]$^+$; $^1$H NMR (500 MHz, CD$_3$OD) δ 8.91 (s, 1 H), 8.79 (d, J=1.8 Hz, 1 H), 8.43 (d, J=1.9 Hz, 1 H), 1.51 (s, 6 H).

Step D. N-[2-(cyclopropylamino)-4,5-difluorophenyl]-5-(2-hydroxypropan-2-yl)pyridine-3-carboxamide

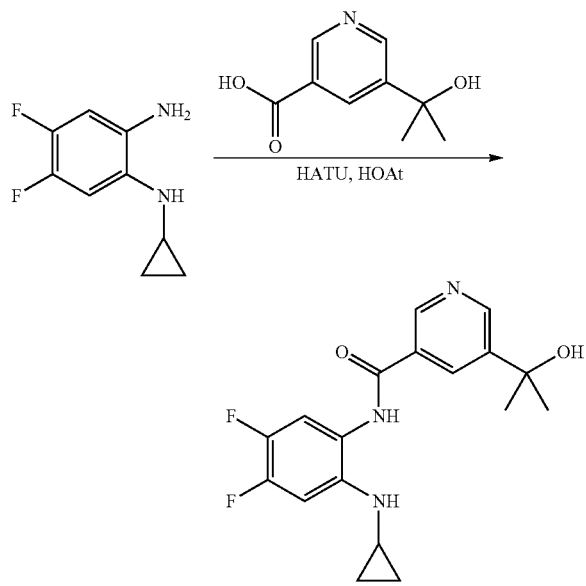

To a solution of the title compound from Step B (0.074 g, 0.40 mmol) in dichloromethane (2.1 mL) were added the title compound from Step C (0.080 g, 0.44 mmol), HATU (0.168 g, 0.442 mmol), HOAt (0.060 g, 0.44 mmol) and diisopropylethylamine (0.285 mL, 1.61 mmol). The reaction was stirred at room temperature for 1 hour, then diluted with dichloromethane, washed sequentially with water and brine, dried over magnesium sulfate, filtered and concentrated under reduced pressure. Purification by flash chromatography on silica gel (50-100% ethyl acetate in hexanes) provided the title compound: LCMS m/z 330.04 [M+H]$^+$; $^1$H NMR (500 MHz, CDCl$_3$) δ 8.96 (s, 1 H), 8.90 (d, J=7.2 Hz, 1 H), 8.35 (s, 1 H), 7.66 (br s, 1 H), 7.31 (d, J=10.7 Hz, 1 H), 7.04-7.00 (m, 1 H), 4.31 (br s, 1 H), 2.80 (br s, 1 H), 2.44 (t, J=6.1, 3.1 Hz, 1 H), 1.66 (s, 6 H), 0.78-0.77 (m, 2 H), 0.53-0.51 (m, 2 H).

Step E. 2-[5-(1-Cyclopropyl-5,6-difluoro-1H-benzimidazol-2-yl)pyridin-3-yl]propan-2-ol

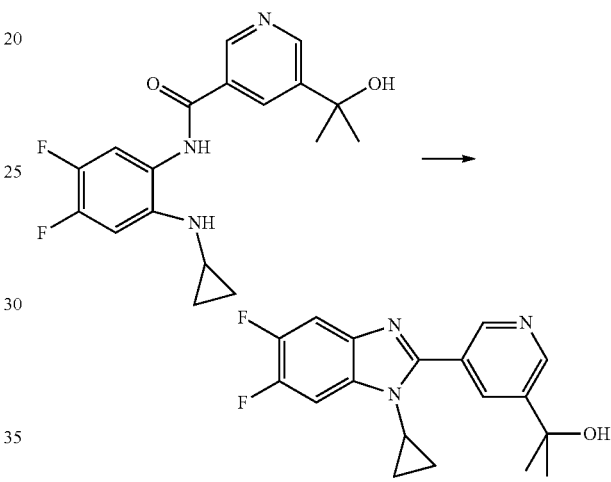

A solution of the title compound from Step D (0.070 g, 0.20 mmol) in acetic acid (1.0 mL) was heated at 100° C. for 1 hour, and then cooled to room temperature. The resulting mixture was concentrated under reduced pressure, diluted with ethyl acetate, washed sequentially with aqueous 1 N sodium hydroxide solution and brine, dried over magnesium sulfate, filtered and concentrated. Purification by flash chromatography on silica gel (50-80% ethyl acetated in hexanes) provided the title compound: LCMS m/z 330.04 [M+H]$^+$; $^1$H NMR (500 MHz, CDCl$_3$) δ 9.09 (s, 1 H), 8.87 (s, 1 H), 8.44 (d, J=1.8 Hz, 1 H), 7.58 (dd, J=10.3, 7.3 Hz, 1 H), 7.40 (dd, J=9.7, 7.0 Hz, 1 H), 3.59-3.58 (m, 1 H), 2.89 (br s, 1 H), 1.69 (s, 6 H), 1.22-1.19 (m, 2 H), 0.79-0.78 (m, 2 H).

EXAMPLE 39

1-cyclopropyl-5,6-difluoro-2-[5-(2-methoxypropan-2-yl)pyridin-3-yl]-1H-benzimidazole

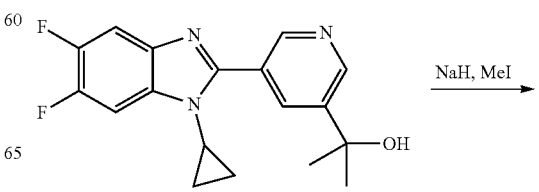

-continued

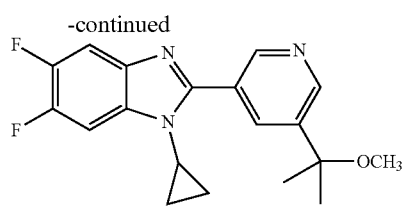

To a cooled (0° C.) solution of 2-[5-(1-Cyclopropyl-5,6-difluoro-1H-benzimidazol-2-yl)pyridin-3-yl]propan-2-ol (from Example 38 Step E) (0.086 g, 0.26 mmol) in tetrahydrofuran (1.3 mL) was added sodium hydride (60% dispersion in mineral oil, 0.026 g, 0.65 mmol). After 1 hour, iodomethane (0.024 mL, 0.389 mmol) was added. The reaction was then warmed to room temperature and stirred overnight. The reaction mixture was diluted with ethyl acetate, washed with water and brine, dried over magnesium sulfate, filtered and concentrated. Purification by flash chromatography on silica gel (30-60% ethyl acetate in hexanes) provided the title compound: LCMS m/z 344.03 [M+H]+; $^1$H NMR (500 MHz, CDCl$_3$) δ 9.09 (d, J=1.9 H, 1 H), 8.79 (d, J=2.0 Hz, 1 H), 8.29 (t, J=2.0, 2.0 Hz, 1 H), 7.58 (dd, J=10.3, 7.3 Hz, 1 H), 7.40 (dd, J=9.7, 7.1 Hz, 1 H), 3.59-3.57 (m, 1 H), 3.16 (s, 3 H), 1.63 (s, 3 H), 1.60 (s, 3 H), 1.20-1.17 (m, 2 H), 0.79-0.76 (m, 2 H).

EXAMPLE 40

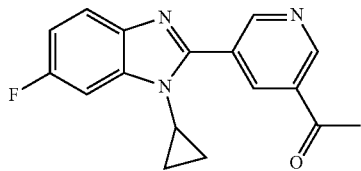 [SMILES: CC(=O)c1cncc(-c2nc3ccc(F)cc3n2C2CC2)c1]

Step A. 5-acetylpyridine-3-carboxylic acid

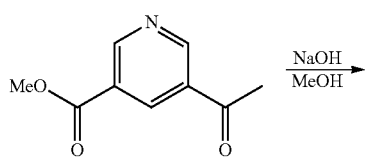

To a solution of methyl 5-acetylpyridine-3-carboxylate (0.15 g, 0.84 mmol) in methanol (2.10 mL) was added aqueous 1N sodium hydroxide solution (2.51 mL, 2.51 mmol). The resulting mixture was stirred at room temperature for 1 hour, then concentrated under reduced pressure to give a residue that was acidified with aqueous 1 N hydrogen chloride solution and extracted with ethyl acetate. The organic extracts were combined, dried over magnesium sulfate, filtered and concentrated to provide the title compound: $^1$H NMR (500 MHz, CDCl$_3$) δ 9.43 (d, J=1.4 Hz, 1 H), 9.36 (s, 1 H), 8.84 (s, 1 H), 2.70 (s, 3 H).

Step B. 5-acetyl-N-[2-(cyclopropylamino)-4-fluorophenyl]pyridine-3-carboxamide

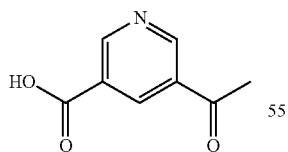

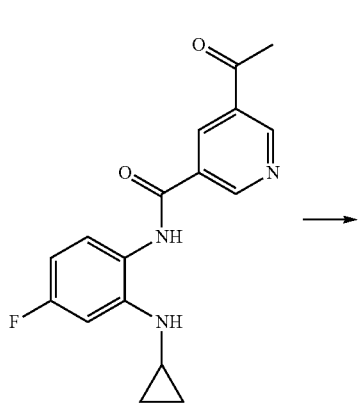

To a solution of N$^2$-cyclopropyl-4-fluorobenzene-1,2-diamine (0.082 g, 0.495 mmol) in dichloromethane were added the title compound from Step A (0.090 g, 0.545 mmol), HATU (0.207 g, 0.545 mmol), HOAt (0.074 g, 0.545 mmol), and diisopropylethylamine (0.35 mL, 1.98 mmol). The reaction was stirred at room temperature for 1 hour, then diluted with dichloromethane, washed with water and brine, dried over magnesium sulfate, filtered and concentrated. Purification by flash chromatography on silica gel (30-60% ethyl acetate in hexanes) provided the title compound: LCMS m/z 314.14 [M+H]+; $^1$H NMR (500 MHz, CDCl$_3$) δ 9.33 (s, 1 H), 9.29 (s, 1 H), 8.72 (s, 1 H), 8.02 (br s, 1 H), 7.19-7.16 (m, 1 H), 6.91 (d, J=10.5 Hz, 1 H), 6.50-6.47 (m, 1 H), 4.64 (br s, 1 H), 2.69 (s, 3 H), 2.45-2.44 (m, 1 H), 0.78-0.77 (m, 2 H), 0.52-0.51 (m, 2 H).

Step C. 1-[5-(1-cyclopropyl-6-fluoro-1H-benzimidazol-2-yl)pyridin-3-yl]ethanone

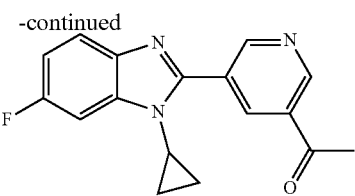

A solution of the title compound from Step B (0.10 g, 0.32 mmol) in acetic acid (1.60 mL) was heated at 100° C. for 1 hour, then cooled to room temperature and concentrated under reduced pressure. The resulting residue was diluted with ethyl acetate, washed sequentially with aqueous 1 N sodium hydroxide solution and brine, dried over magnesium sulfate, filtered and concentrated. Purification by flash chromatography on silica gel (50-80% ethyl acetate in hexanes) provided the title compound: LCMS m/z 296.07 [M+H]+; 1H NMR (500 MHz, CDCl3) δ 9.41 (d, J=1.9 Hz, 1 H), 9.26 (d, J=1.9 Hz, 1 H), 8.22 (m, 1 H), 7.75 (dd, J=8.8, 4.8 Hz, 1 H), 7.32 (dd, J=8.6, 2.3 Hz, 1 H), 7.10-7.06 (m, 1 H), 3.65-3.61 (m, 1 H), 2.73 (s, 3H), 1.26-1.20 (m, 2 H), 0.81-0.77 (m, 2 H).

EXAMPLE 41

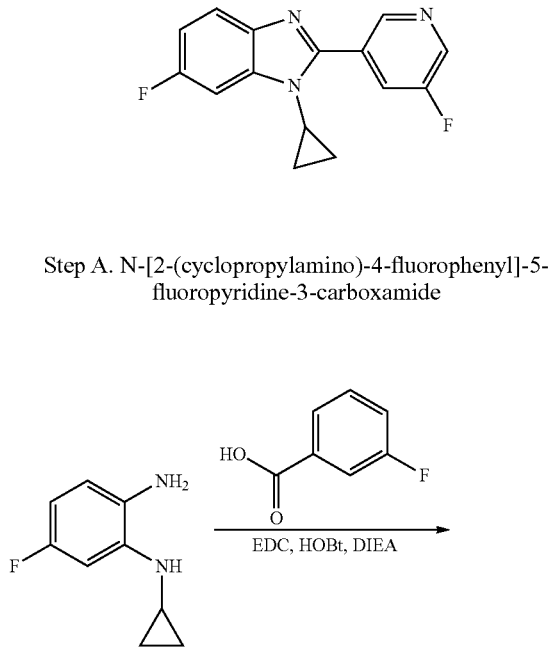

Step A. N-[2-(cyclopropylamino)-4-fluorophenyl]-5-fluoropyridine-3-carboxamide

To a solution of the title compound from N2-cyclopropyl-4-fluorobenzene-1,2-diamine (0.065 g, 0.39 mmol) in dichloromethane (1.96 mL) were added 5-fluoropyridine-3-carboxylic acid (0.061 g, 0.43 mmol), EDC (0.082 g, 0.43 mmol), HOBt (0.066 g, 0.43 mmol), and diisopropylethylamine (0.280 mL, 1.56 mmol). The reaction was stirred at room temperature overnight, then diluted with dichloromethane, washed sequentially with water and brine, dried over magnesium sulfate, filtered and concentrated. Purification by flash chromatography on silica gel (30-50% ethyl acetate in hexanes) provided the title compound: LCMS m/z 290.14 [M+H]+; 1H NMR (500 MHz, CDCl3) δ 8.90 (s, 1 H), 8.66 (d, J=2.0 Hz, 1 H), 7.97 (d, J=8.3 Hz, 1 H), 7.48 (br s, 1 H), 7.19 (m, 1 H), 6.92 (d, J=10.9 Hz, 1 H), 6.52-6.49 (m, 1 H), 4.50 (br s, 1 H), 2.47-2.44 (m, 1 H), 0.81-0.77 (m, 2 H), 0.54-0.51 (m, 2 H).

Step B. 1-cyclopropyl-6-fluoro-2-(5-fluoropyridin-3-yl)-1H-benzimidazole

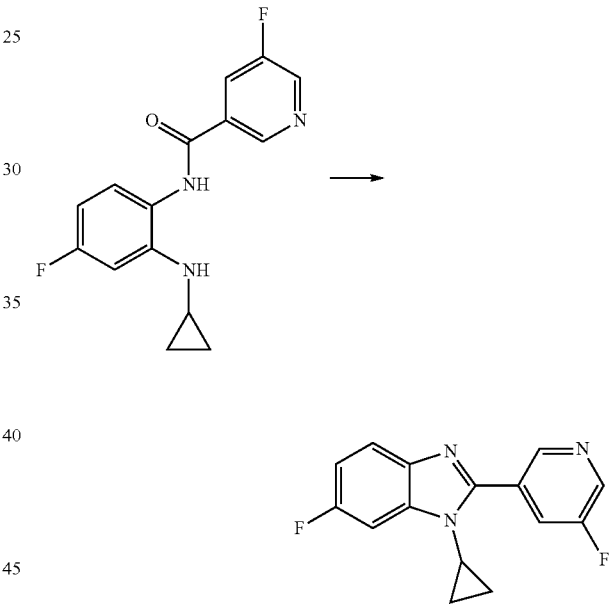

A solution of the title compound from Step A (0.038 g, 0.131 mmol) in acetic acid (0.66 mL) was heated at 100° C. for 1 hour, then cooled to room temperature and concentrated under reduced pressure. The resulting residue was diluted with ethyl acetate, washed sequentially with aqueous 1 N sodium hydroxide solution and brine, dried over magnesium sulfate, filtered and concentrated. Purification by flash chromatography (30-50% ethyl acetate in hexanes) provided the title compound: LCMS m/z 272.16 [M+H]+; 1H NMR (500 MHz, CDCl3) δ 9.06 (s, 1 H), 8.60 (d, J=2.7 Hz, 1 H), 8.03 (m, 1 H), 7.73 (dd, J=8.8, 4.8 Hz, 1 H), 7.30 (dd, J=8.6, 2.4 Hz, 1 H), 7.10-7.06 (m, 1 H), 3.59-3.55 (m, 1 H), 1.25-1.22 (m, 2 H), 0.83-0.80 (m, 2 H).

The compounds in Table 3 were prepared using the synthetic procedures described in Examples 37-41.

TABLE 3

| Example | Structure | IUPAC Name | LCMS |
|---|---|---|---|
| 42 | 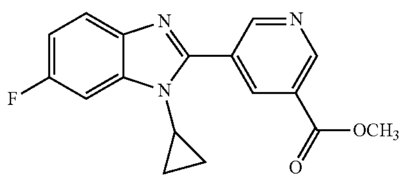 [SMILES: COC(=O)c1cncc(-c2nc3ccc(F)cc3n2C2CC2)c1] | methyl 5-(1-cyclopropyl-6-fluoro-1H-benzimidazol-2-yl)pyridine-3-carboxylate | 312.13 |
| 43 | 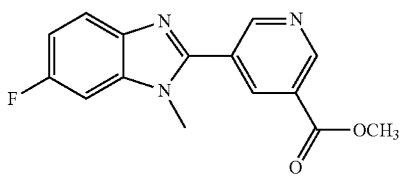 [SMILES: COC(=O)c1cncc(-c2nc3ccc(F)cc3n2C)c1] | methyl 5-(6-fluoro-1-methyl-1H-benzimidazol-2-yl)pyridine-3-carboxylate | 286.24 |
| 44 | 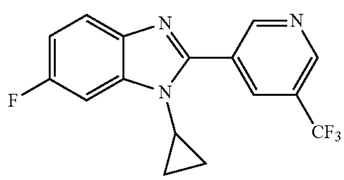 [SMILES: Fc1ccc2nc(-c3cncc(C(F)(F)F)c3)n(C3CC3)c2c1] | 1-cyclopropyl-6-fluoro-2-[5-(trifluoromethyl)pyridin-3-yl]-1H-benzimidazole | 322.19 |
| 45 | 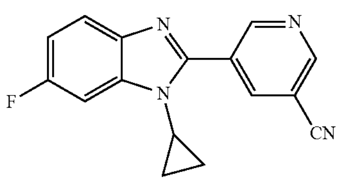 [SMILES: N#Cc1cncc(-c2nc3ccc(F)cc3n2C2CC2)c1] | 5-(1-cyclopropyl-6-fluoro-1H-benzimidazol-2-yl)pyridine-3-carbonitrile | 279.06 |
| 46 | 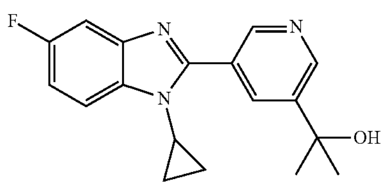 [SMILES: CC(C)(O)c1cncc(-c2nc3cc(F)ccc3n2C2CC2)c1] | 2-[5-(1-cyclopropyl-5-fluoro-1H-benzimidazol-2-yl)pyridin-3-yl]propan-2-ol | 312.06 |
| 47 | 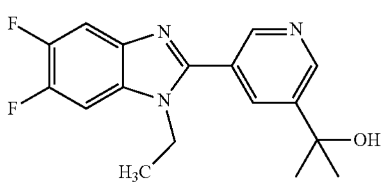 [SMILES: CCn1c(-c2cncc(C(C)(C)O)c2)nc2cc(F)c(F)cc21] | 2-[5-(1-ethyl-5,6-difluoro-1H-benzimidazol-2-yl)pyridin-3-yl]propan-2-ol | 318.07 |
| 48 | 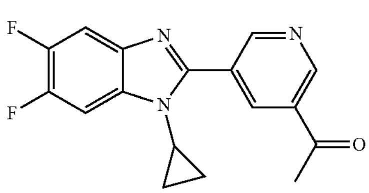 [SMILES: CC(=O)c1cncc(-c2nc3cc(F)c(F)cc3n2C2CC2)c1] | 1-[5-(1-cyclopropyl-5,6-difluoro-1H-benzimidazol-2-yl)pyridin-3-yl]ethanone | 314.42 |
| 49 | 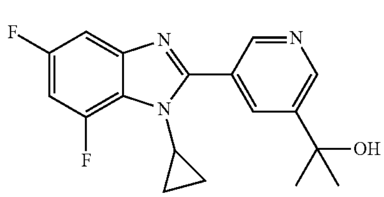 [SMILES: CC(C)(O)c1cncc(-c2nc3cc(F)cc(F)c3n2C2CC2)c1] | 2-[5-(1-cyclopropyl-5,7-difluoro-1H-benzimidazol-2-yl)pyridin-3-yl]propan-2-ol | 330.01 |

TABLE 3-continued

| Example | Structure | IUPAC Name | LCMS |
|---|---|---|---|
| 50 | 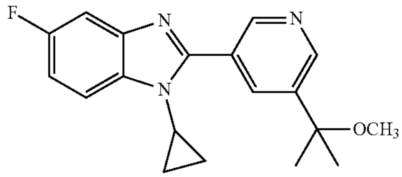 [SMILES: COC(C)(C)c1cncc(-c2nc3cc(F)ccc3n2C2CC2)c1] | 1-cyclopropyl-5-fluoro-2-[5-(2-methoxypropan-2-yl)pyridin-3-yl]-1H-benzimidazole | 326.19 |
| 51 | 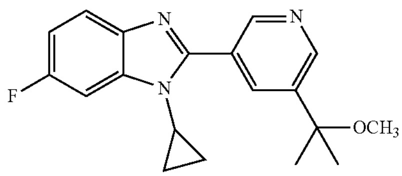 [SMILES: COC(C)(C)c1cncc(-c2nc3ccc(F)cc3n2C2CC2)c1] | 1-cyclopropyl-6-fluoro-2-[5-(2-methoxypropan-2-yl)pyridin-3-yl]-1H-benzimidazole | 326.08 |
| 52 | 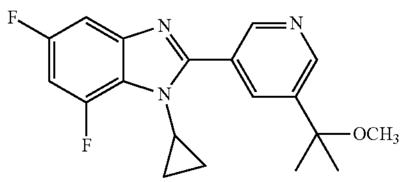 [SMILES: COC(C)(C)c1cncc(-c2nc3cc(F)cc(F)c3n2C2CC2)c1] | 1-cyclopropyl-5,7-difluoro-2-[5-(2-methoxypropan-2-yl)pyridin-3-yl]-1H-benzimidazole | 344 |

The compounds in Table 4 were all prepared using chemistry described in Example 1.

TABLE 4

| Example | Structure | IUPAC Name | LCMS |
|---|---|---|---|
| 53 | 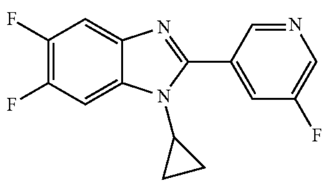 | 1-Cyclopropyl-5,6-difluoro-2-(5-fluoropyridin-3-yl)-1H-benzimidazole | 290 |
| 54 | 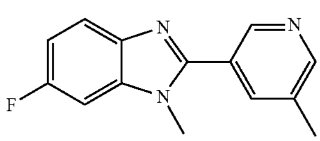 [SMILES: Cc1cncc(-c2nc3ccc(F)cc3n2C)c1] | 6-fluoro-1-methyl-2-(5-methylpyridin-3-yl)-1H-benzimidazole | 242 |
| 55 | 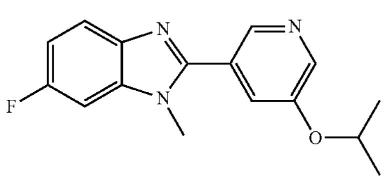 [SMILES: CC(C)Oc1cncc(-c2nc3ccc(F)cc3n2C)c1] | 6-fluoro-2-(5-isopropoxypyridin-3-yl)-1-methyl-1H-benzimidazole | 286 |
| 56 | 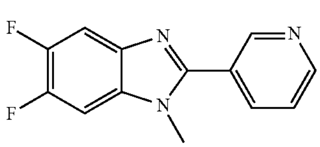 [SMILES: Cn1c(-c2cccnc2)nc2cc(F)c(F)cc21] | 5,6-Difluoro-1-methyl-2-(pyridin-3-yl)-1H-benzimidazole | 246 |
| 57 | 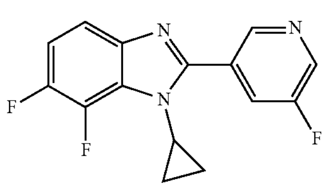 [SMILES: Fc1cncc(-c2nc3ccc(F)c(F)c3n2C2CC2)c1] | 1-Cyclopropyl-6,7-difluoro-2-(5-fluoropyridin-3-yl)-1H-benzimidazole | 290 |

TABLE 4-continued

| Example | Structure | IUPAC Name | LCMS |
|---|---|---|---|
| 58 | 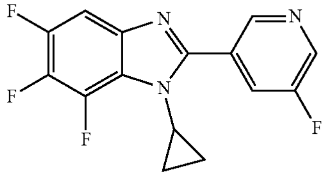 [SMILES: Fc1cncc(-c2nc3cc(F)c(F)c(F)c3n2C2CC2)c1] | 1-Cyclopropyl-2-(5-fluoropyridin-3-yl)-5,6,7-trifluoro-1H-benzimidazole | 308 |
| 59 | 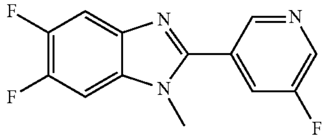 [SMILES: Cn1c(-c2cncc(F)c2)nc2cc(F)c(F)cc21] | 5,6-Difluoro-2-(5-fluoropyridin-3-yl)-1-methyl-1H-benzimidazole | 264 |
| 60 | 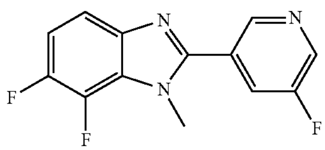 [SMILES: Cn1c(-c2cncc(F)c2)nc2ccc(F)c(F)c21] | 6,7-Difluoro-2-(5-fluoropyridin-3-yl)-1-methyl-1H-benzimidazole | 264 |
| 61 | 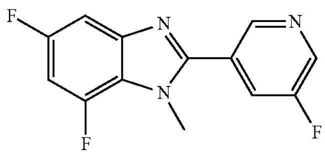 [SMILES: Cn1c(-c2cncc(F)c2)nc2cc(F)cc(F)c21] | 5,7-Difluoro-2-(5-fluoropyridin-3-yl)-1-methyl-1H-benzimidazole | 264 |
| 62 | 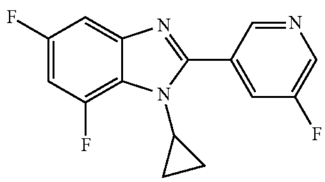 [SMILES: Fc1cncc(-c2nc3cc(F)cc(F)c3n2C2CC2)c1] | 1-Cyclopropyl-5,7-difluoro-2-(5-fluoropyridin-3-yl)-1H-benzimidazole | 290 |

EXAMPLE 63

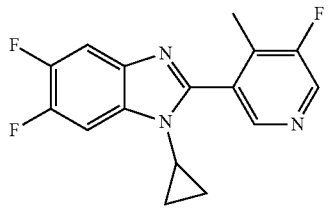 [SMILES: Cc1c(F)cncc1-c1nc2cc(F)c(F)cc2n1C1CC1]

Step A. 1-cyclopropyl-5,6-difluoro-1H-benzo[d]imidazol-2(3H)-one

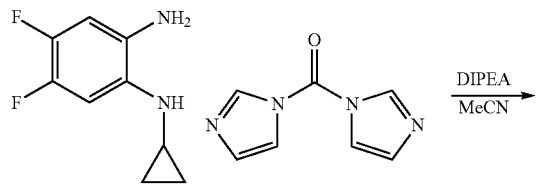 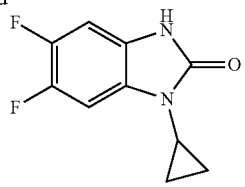

Carbonyldiimidazole (4.3 g) was added to the solution of N1-cyclopropyl-4,5-difluorobenzene-1,2-diamine (3.2 g) in THF (30 ml). The mixture was stirred at rt for 20 hours, then diluted with ethyl acetate (200 ml) and washed with hydrochloric acid (1M, 200 ml). Organic layer dried over sodium sulphate, solvent removed to give expected product as a black solid (2.5 g). $^1$H NMR (CD$_3$OD)δ: 7.20 (dd, 1H), 6.95 (dd, 1H), 2.86 (m, 1H), 1.11 (m, 2H), 0.94 (m, 2H).

Step B. 2-Bromo-1-cyclopropyl-5,6-difluorophenyl-1H-benzimidazole

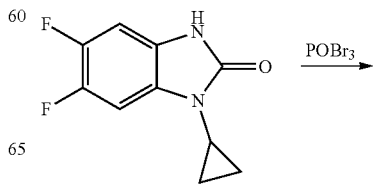

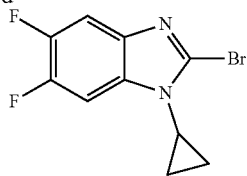

To a stirring solution of 1-cyclopropyl-5,6-difluoro-1H-benzo[d]imidazol-2(3H)-one (2.5 g) in Toluene (150 ml) was added phosphoryl tribromide (13.64 g). Reaction mixture was stirred under nitrogen at reflux overnight. Reaction cooled, diluted with DCM (150 ml) and slowly added to stirring 40° C. water. Mixture stirred for 30 min, sodium carbonate added until pH 10. Mixture poured into separating funnel, organic layer washed with water, dried over sodium sulphate and solvent removed under reduced pressure to afford 800 mg expected product. $^1$H NMR (CDCl$_3$)δ: 7.45 (dd, 1H), 7.30 (dd, 1H), 3.20 (m, 1H), 1.30 (m, 2H), 1.20 (m, 2H).

Step C. 3-bromo-5-fluoro-4-methylpyridine

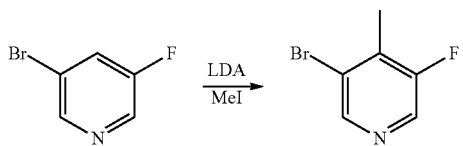

Diisopropylamine (136 mmol, 19.11 ml, 13.80 g) and THF (120 ml) were combined in a 3-necked flask under nitrogen and cooled to −78° C. N-butyllithium (2.5M in hexane) (125 mmol, 50.0 ml) was added dropwise and the mixture stirred at −78° C. for 30 minutes. A solution of 3-bromo-5-fluoropyridine (114 mmol, 20 g) in THF (40 ml) was added dropwise and stirring continued at −78° C. for a further 30 minutes. Iodomethane (136 mmol, 8.49 ml, 19.36 g) was added and the reaction mixture allowed to warm slowly to room temperature and stirred for 18 hours. The reaction was diluted with 1:1 saturated sodium bicarbonate solution/water (200 ml) and extracted with EtOAc (600 ml). Organics were washed with saturated sodium chloride solution (100 ml) and dried over sodium sulphate. Solvent was evaporated under reduced pressure to afford crude product as a brown oil. Purification by silica chromatography eluting with 0% to 15% EtOAc/heptane afforded product 3-bromo-5-fluoro-4-methylpyridine (54.1% yield) as a clear oil. $^1$H NMR (CDCl$_3$)δ: 8.49 (s, 1H), 8.31 (s, 1H), 2.37 (s, 3H).

Step D 3-fluoro-4-methyl-5-(4,4,5,5-tetramethyl-1,3,2-dioxaborolan-2-yl)pyridine

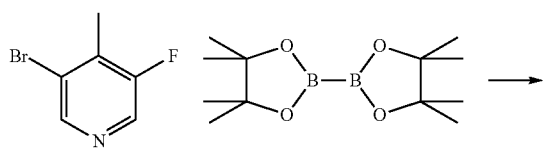

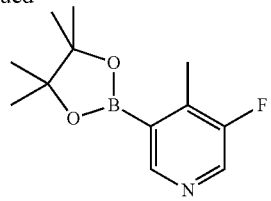

3-bromo-5-fluoro-4-methylpyridine (9.25 mmol, 2.93 g) bis(pinacolato)diboron (11.10 mmol, 2.82 g) 1,1'-bis(diphenylphosphino)ferrocenedichloropalladium(II) (0.463 mmol, 0.335 g) and potassium acetate (18.50 mmol, 1.816 g) were combined in dioxane (37.0 mL) and heated to 80° C. for 24 hours, under nitrogen. The reaction was allowed to cool to room temperature, EtOAc (400 ml) added and the mixture filtered through CELITE® and washed with 1:1 saturated sodium bicarbonate solution/water (2×200 ml) and brine (100 ml). Organics were dried over sodium sulphate and solvent evaporated under reduced pressure to yield crude product as a brown oil. Purification by silica chromatography eluting with 25 to 50% EtOAc/heptane afforded 3-fluoro-4-methyl-5-(4,4,5,5-tetramethyl-1,3,2-dioxaborolan-2-yl)pyridine. $^1$H NMR (CDCl$_3$)δ: 8.68 (s, 1H), 8.39 (s, 1H), 2.48 (s, 3H), 1.38 (s, 12H).

Step E 1-cyclopropyl-5,6-difluoro-2-(5-fluoro-4-methylpyridin-3-yl)-1H-benzimidazole

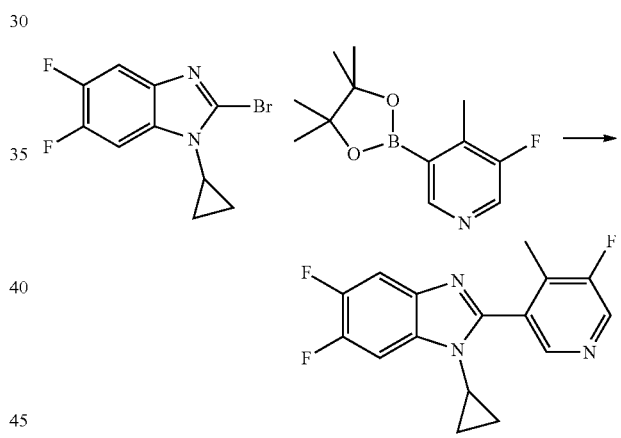

2-bromo-1-cyclopropyl-5,6-difluoro-1H-benzo[d]imidazole (0.549 mmol, 150 mg) 5-fluoro-4-methylpyridin-3-ylboronic acid (0.824 mmol, 128 mg) palladium(II)acetate (0.027 mmol, 6.17 mg) 2-dicyclohexylphosphino-2',6'-dimethoxybiphenyl (0.055 mmol, 22.55 mg) and potassium phosphate, tribasic (1.099 mmol, 233 mg) were combined in a microwave vial and dioxane (1962 μL) and water (785 μl) added. The vial was flushed with nitrogen and heated in a microwave to 180° C. for 1 hour. The reaction mixture was diluted with EtOAc (20 ml) filtered through celite and washed with saturated sodium bicarbonate solution (20 ml). Organics were dried over sodium sulphate and solvent evaporated under reduced pressure to afford crude product as a brown oil. Purification by preparative HPLC (basic phase) and evaporation of solvent in a genevac afforded product 1-cyclopropyl-5,6-difluoro-2-(5-fluoro-4-methylpyridin-3-yl)-1H-benzimidazole as a white solid. LCMS m/z 304 [M+H]$^+$; $^1$H NMR (CDCl$_3$)δ; 8.53 (s, 1H), 8.52 (s, 1H), 7.58 (t, 1H), 7.41 (t, 1H), 3.35 (m, 1H), 2.35 (s, 3H), 1.01 (m, 2H), 0.67 (m, 2H).

The compounds in Table 5 were all prepared using chemistry described in Example 63.

TABLE 5

| Example | Structure | IUPAC Name | LCMS |
|---|---|---|---|
| 64 | 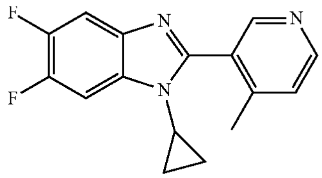 [SMILES: Cc1ccncc1-c1nc2cc(F)c(F)cc2n1C1CC1] | 1-Cyclopropyl-5,6-difluoro-2-(4-methylpyridin-3-yl)-1H-benzimidazole | 286 |
| 65 | 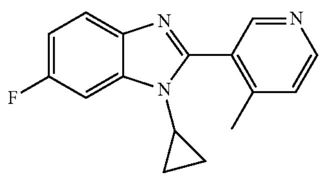 [SMILES: Cc1ccncc1-c1nc2ccc(F)cc2n1C1CC1] | 1-Cyclopropyl-6-fluoro-2-(4-methylpyridin-3-yl)-1H-benzimidazole | 268 |
| 66 | 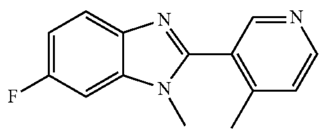 [SMILES: Cc1ccncc1-c1nc2ccc(F)cc2n1C] | 6-Fluoro-2-(4-methylpyridin-3-yl)-1-methyl-1H-benzimidazole | 242 |
| 67 | 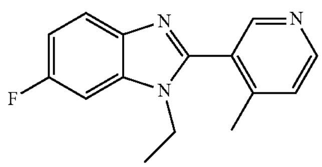 [SMILES: CCn1c(-c2cnccc2C)nc2ccc(F)cc21] | 1-Ethyl-6-fluoro-2-(4-methylpyridin-3-yl)-1H-benzimidazole | 256 |
| 68 | 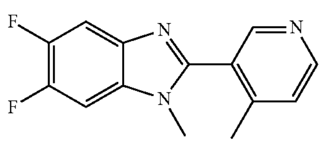 [SMILES: Cc1ccncc1-c1nc2cc(F)c(F)cc2n1C] | 5,6-Di-difluoro-2-(4-methylpyridin-3-yl)-1-methyl-1H-benzimidazole | 260 |
| 69 | 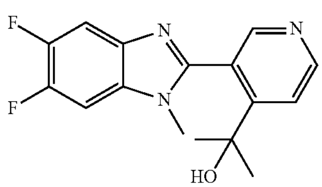 [SMILES: Cn1c(-c2cnccc2C(C)(C)O)nc2cc(F)c(F)cc21] | 5,6-Di-difluoro-2-(2-hydroxy-2-propylpyridin-3-yl)-1-methyl-1H-benzimidazole | 304 |
| 70 | 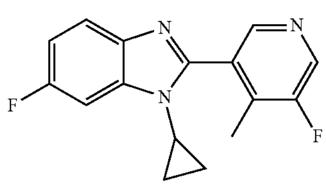 [SMILES: Cc1c(F)cncc1-c1nc2ccc(F)cc2n1C1CC1] | 1-Cyclopropyl-6-fluoro-2-(5-fluoro4-methylpyridin-3-yl)-1H-benzimidazole | 286 |
| 71 | 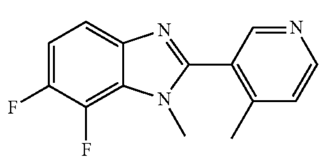 | 6,7-Difluoro-2-(4-methylpyridin-3-yl)-1-methyl-1H-benzimidazole | 260 |
| 72 | 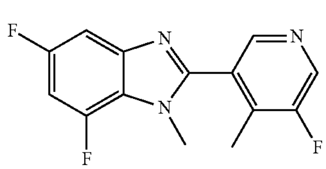 [SMILES: Cc1c(F)cncc1-c1nc2cc(F)cc(F)c2n1C] | 5,7-Difluoro-2-(5-fluoro-4-methylpyridin-3-yl)-1-methyl-1H-benzimidazole | 278 |

TABLE 5-continued

| Example | Structure | IUPAC Name | LCMS |
|---|---|---|---|
| 73 | 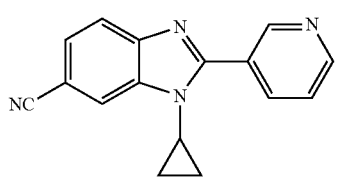 | 1-Cyclopropyl-5,7-difluoro-2-(5-fluoro-4-methylpyridin-3-yl)-1H-benzimidazole | 304 |
| 74 | 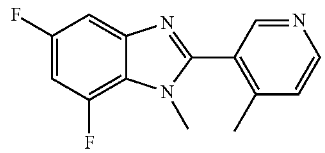 [SMILES: Cc1ccncc1-c1nc2cc(F)cc(F)c2n1C] | 5,7-Difluoro-2-(4-methylpyridin-3-yl)-1-methyl-1H-benzimidazole | 260 |

EXAMPLE 75

1-cyclopropyl-2-(pyridin-3-yl)-1H-benzo[d]imidazole-6-carbonitrile

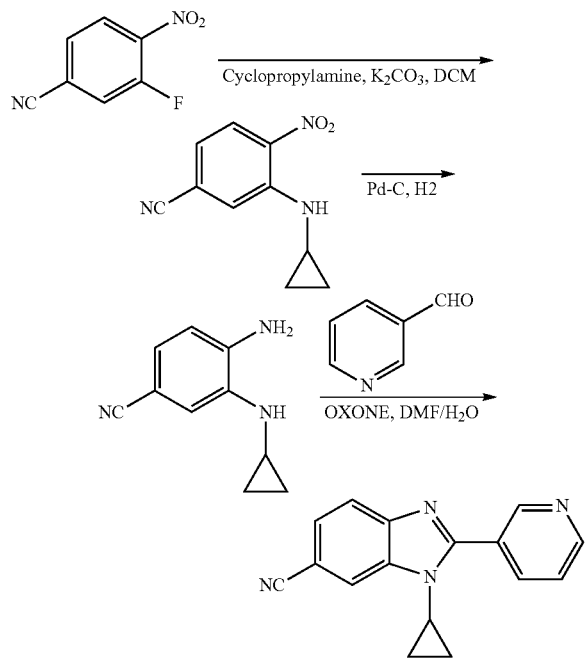

Step A. 3-(cyclopropylamino)-4-nitrobenzonitrile

To a stirred solution of 3-fluoro-4-nitrobenzonitrile (2.0 g, 0.012 mol) in DCM (20 ml), was added $K_2CO_3$ (3.3 g, 0.024 mol) and cyclopropyl amine (6.7 ml, 0.096 mol) and the resulting solution was continued to stir at room temperature for 3 h. The reaction was diluted with cold water and extracted with dichloromethane (3×100 ml). The combined organic layers were washed with brine, dried over $Na_2SO_4$ and concentrated under vacuum to afford the title compound 3-(cyclopropylamino)-4-nitrobenzonitrile as a yellow solid. $^1$H NMR (400 MHz, $CDCl_3$), δ: 8.24-8.22 (d, J=8.8 Hz, 1H), 8.07 (bs, 1H), 7.64 (s, 1H), 6.94-6.92 (d, J=8.8 Hz, 1H), 2.59-2.58 (m, 1H), 1.25-0.97 (m, 2H), 0.71-0.58 (m, 2H). MS (M+1): 204.

Step B. 4-amino-3-(cyclopropylamino) benzonitrile

To a stirred solution of 3-(cyclopropylamino)-4-nitrobenzonitrile (2.0 g, 0.009 mol) in EtOH (20 ml) was hydrogenated using Pd/C for 2 h at room temperature. The reaction was filtered through CELITE® and the filter bed was thoroughly washed with EtOH. The resulting solution was concentrated to provide 4-amino-3-(cyclopropylamino) benzonitrile as a brownish solid. $^1$H NMR (400 MHz, DMSO-$d_6$), δ: 6.92 (bs, 1H), 6.88-6.86 (d, J=8 Hz, 1H), 6.55-6.53 (d, J=8.4 Hz, 1H), 5.50 (bs, 1H), 5.44 (s, 2H), 2.36-2.34 (m, 1H), 0.76-0.71 (m, 2H), 0.39-0.34 (m, 2H). MS (M+1): 174.

Step C. 1-cyclopropyl-2-(pyridin-3-yl)-1H-benzo[d]imidazole-6-carbonitrile (75)

To a solution of 4-amino-3-(cyclopropylamino) benzonitrile, (0.2 g, 0.0011 mol) and nicotinaldehyde (0.14 g, 0.0012 mol) in DMF (5 ml) and $H_2O$ (2 ml) was added OXONE® monopersulphate (0.84 g, 0.0013 mol). Reaction mass was stirred at room temperature for 3 h. The reaction mixture was basified with 10% $K_2CO_3$ solution to pH~8-10 and extracted with EtOAc (3×20 ml). The combined organic layers were washed with brine, dried over $Na_2SO_4$ and concentrated under vacuum to afford the crude compound, which was purified by column chromatography to obtain title compound 1-cyclopropyl-2-(pyridine-3-yl)-1H-benzo[d]imidazole-6-carbonitrile. $^1$H NMR (400 MHz, DMSO-$d_6$), δ: 9.21 (s, 1H), 8.77-8.76 (d, J=4.4 Hz, 1H), 8.45-8.43 (d, J=8 Hz, 1H), 8.25 (s, 1H), 7.89-7.87 (d, J=8 Hz, 1H), 7.68-7.61 (m, 2H), 3.91-3.87 (m, 1H), 1.17-1.12 (m, 2H), 0.71-0.70 (m, 2H). MS (M+1): 261.12; purity 97.77%.

The compounds in Table 6 were prepared following the synthetic procedure as described in Example 75.

TABLE 6

| Example | Structure | IUPAC Name | LCMS (M + 1) |
|---|---|---|---|
| 76 | 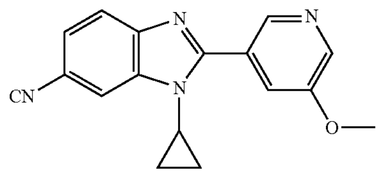 | 1-cyclopropyl-2-(5-methoxypyridin-3-yl)-1H-benzimidazole-6-carbonitrile | 291.15 |
| 77 | 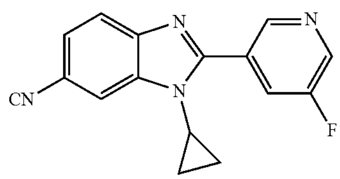 | 1-cyclopropyl-2-(5-fluoropyridin-3-yl)-1H-benzimidazole-6-carbonitrile | 279.08 |
| 78 | 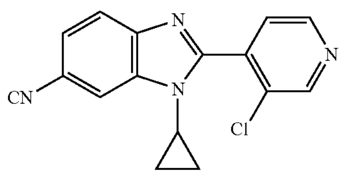 | 2-(3-chloropyridin-4-yl)-1-cyclopropyl-1H-benzimidazole-6-carbonitrile | 295.07 |
| 79 | 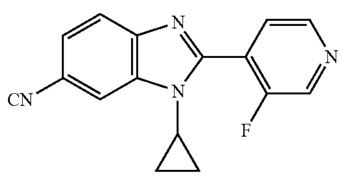 | 2-(3-fluoropyridin-4-yl)-1-cyclopropyl-1H-benzimidazole-6-carbonitrile | 279.08 |
| 80 | 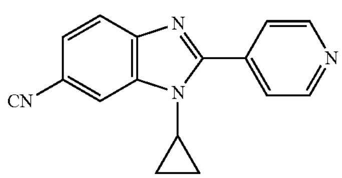 | 1-cyclopropyl-2-(pyridin-4-yl)-1H-benzimidazole-6-carbonitrile | 261.11 |
| 81 | 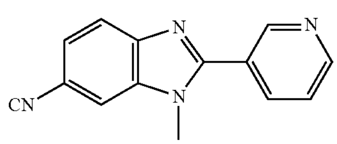 | 1-methyl-2-(pyridin-3-yl)-1H-benzimidazole-6-carbonitrile | 235.06 |
| 82 | 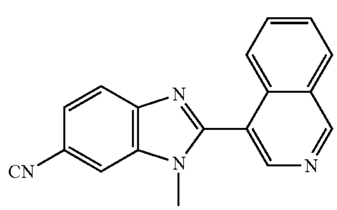 | 2-(isoquinolin-4-yl)-1-methyl-1H-benzimidazole-6-carbonitrile | 285.07 |
| 83 | 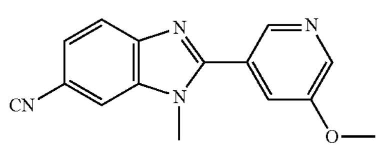 | 2-(5-methoxypyridin-3-yl)-1-methyl-1H-benzimidazole-6-carbonitrile | 265.07 |
| 84 | 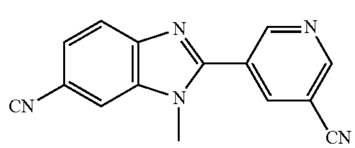 | 2-(5-cyanopyridin-3-yl)-1-methyl-1H-benzimidazole-6-carbonitrile | 260.06 |

TABLE 6-continued

| Example | Structure | IUPAC Name | LCMS (M + 1) |
|---|---|---|---|
| 85 | 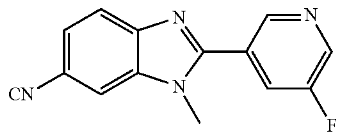 | 2-(5-fluoropyridin-3-yl)-1-methyl-1H-benzimidazole-6-carbonitrile | 253.04 |
| 86 | 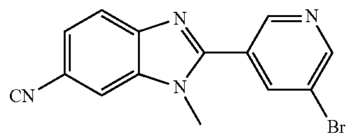 | 2-(5-bromopyridin-3-yl)-1-methyl-1H-benzimidazole-6-carbonitrile | 312.97 |
| 87 | 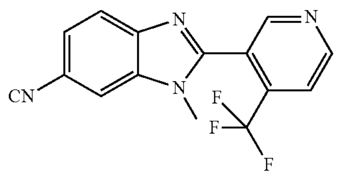 | 1-methyl-2-[4-(trifluoromethyl)pyridin-3-yl]-1H-benzimidazole-6-carbonitrile | 303.06 |
| 88 | 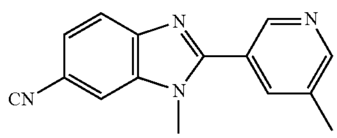 | 1-methyl-2-(5-methylpyridin-3-yl)-1H-benzimidazole-6-carbonitrile | 249.17 |
| 89 | 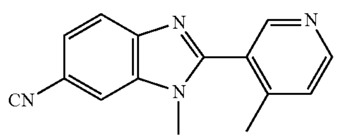 | 1-methyl-2-(4-methylpyridin-3-yl)-1H-benzimidazole-6-carbonitrile | 249.08 |
| 90 | 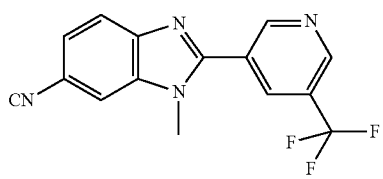 | 1-methyl-2-[5-(trifluoromethyl)pyridin-3-yl]-1H-benzimidazole-6-carbonitrile | 303.07 |
| 91 | 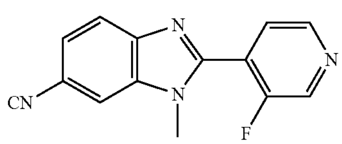 | 2-(3-fluoropyridin-4-yl)-1-methyl-1H-benzimidazole-6-carbonitrile | 253.08 |
| 92 | 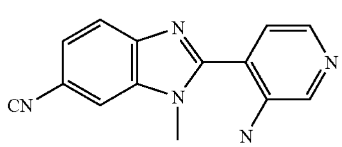 | 2-(3-aminopyridin-4-yl)-1-methyl-1H-benzimidazole-6-carbonitrile | 250.12 |
| 93 | 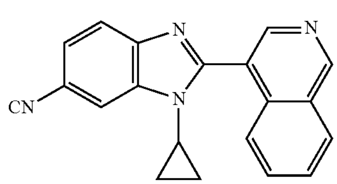 | 1-cyclopropyl-2-(isoquinolin-4-yl)-1H-benzimidazole-6-carbonitrile | 311.1 |

TABLE 6-continued

| Example | Structure | IUPAC Name | LCMS (M + 1) |
|---|---|---|---|
| 94 | 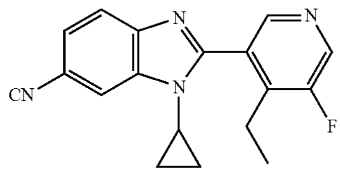 | 1-cyclopropyl-2-(4-ethyl-5-fluoropyridin-3-yl)-1H-benzimidazole-6-carbonitrile | 307.1 |
| 95 | 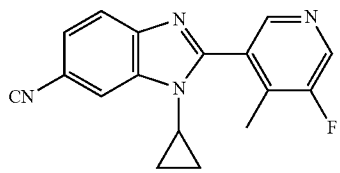 | 1-cyclopropyl-2-(5-fluoro-4-methylpyridin-3-yl)-1H-benzimidazole-6-carbonitrile | 293.1 |
| 96 | 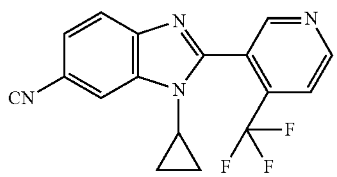 | 1-cyclopropyl-2-[4-(trifluoromethyl)pyridin-3-yl]-1H-benzimidazole-6-carbonitrile | 329.1 |
| 97 | 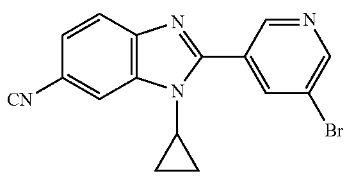 | 2-(5-bromopyridin-3-yl)-1-cyclopropyl-1H-benzimidazole-6-carbonitrile | 341.0 |
| 98 | 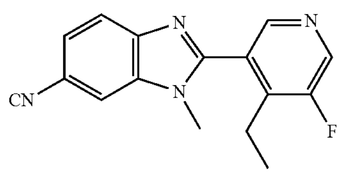 | 2-(4-ethyl-5-fluoropyridin-3-yl)-1-methyl-1H-benzimidazole-6-carbonitrile | 281.1 |
| 99 | 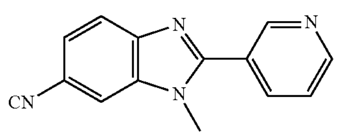 | 1-methyl-2-(pyridin-3-yl)-1H-benzimidazole-6-carbonitrile | 235.25 |
| 100 | 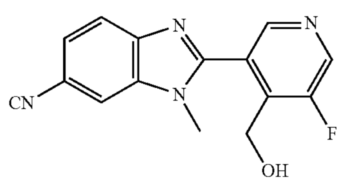 | 2-[5-fluoro-4-(hydroxymethyl)pyridin-3-yl]-1-methyl-1H-benzimidazole-6-carbonitrile | 283.1 |
| 101 | 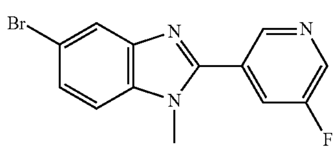 [SMILES: Cn1c(-c2cncc(F)c2)nc2cc(Br)ccc21] | 5-bromo-2-(5-fluoropyridin-3-yl)-1-methyl-1H-benzimidazole | 308.02 |
| 102 | 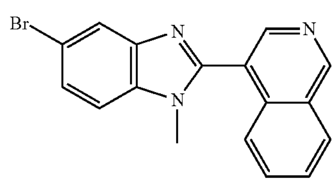 [SMILES: Cn1c(-c2cncc3ccccc23)nc2cc(Br)ccc21] | 4-(5-bromo-1-methyl-1H-benzimidazol-2-yl)isoquinoline | 338.07 |

TABLE 6-continued

| Example | Structure | IUPAC Name | LCMS (M + 1) |
|---|---|---|---|
| 103 | 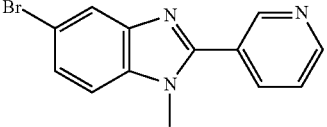 [SMILES: Cn1c(-c2cccnc2)nc2cc(Br)ccc21] | 5-bromo-1-methyl-2-(pyridin-3-yl)-1H-benzimidazole | 290.03 |
| 104 | 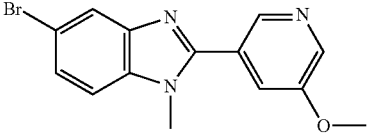 [SMILES: COc1cncc(-c2nc3cc(Br)ccc3n2C)c1] | 5-bromo-2-(5-methoxypyridin-3-yl)-1-methyl-1H-benzimidazole | 318.2 |
| 105 | 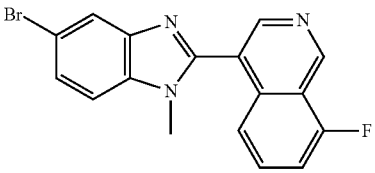 [SMILES: Cn1c(-c2cncc3c(F)cccc23)nc2cc(Br)ccc21] | 4-(5-bromo-1-methyl-1H-benzimidazol-2-yl)-8-fluoroisoquinoline | 356.04 |
| 106 | 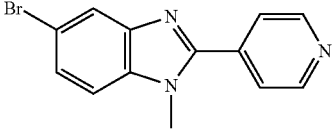 | 5-bromo-1-methyl-2-(pyridin-4-yl)-1H-benzimidazole | 287.96 |
| 107 | 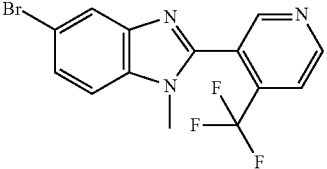 [SMILES: Cn1c(-c2cnccc2C(F)(F)F)nc2cc(Br)ccc21] | 5-bromo-1-methyl-2-[4-(trifluoromethyl)pyridin-3-yl]-1H-benzimidazole | 314.01 |
| 108 | 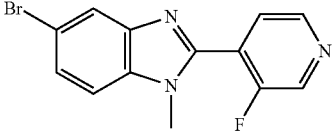 [SMILES: Cn1c(-c2ccncc2F)nc2cc(Br)ccc21] | 5-bromo-2-(3-fluoropyridin-4-yl)-1-methyl-1H-benzimidazole | 306.02 |
| 109 | 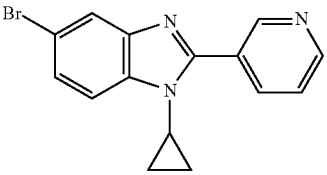 [SMILES: Brc1ccc2c(c1)nc(-c1cccnc1)n2C1CC1] | 5-bromo-1-cyclopropyl-2-(pyridin-3-yl)-1H-benzimidazole | 314.04 |
| 110 | 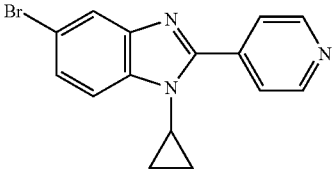 | 5-bromo-1-cyclopropyl-2-(pyridin-4-yl)-1H-benzimidazole | 314.02 |
| 111 | 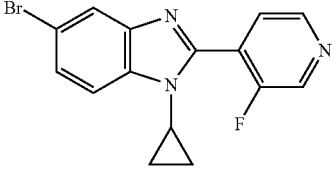 [SMILES: Fc1cnccc1-c1nc2cc(Br)ccc2n1C1CC1] | 5-bromo-1-cyclopropyl-2-(3-fluoropyridin-4-yl)-1H-benzimidazole | 333.17 |

TABLE 6-continued

| Example | Structure | IUPAC Name | LCMS (M + 1) |
|---|---|---|---|
| 112 | 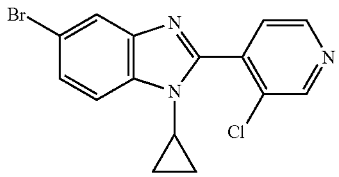 [SMILES: Clc1cnccc1-c1nc2cc(Br)ccc2n1C1CC1] | 5-bromo-2-(3-chloropyridin-4-yl)-1-cyclopropyl-1H-benzimidazole | 349.63 |
| 113 | 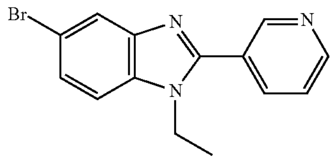 [SMILES: CCn1c(-c2cccnc2)nc2cc(Br)ccc21] | 5-bromo-1-ethyl-2-(pyridin-3-yl)-1H-benzimidazole | 302.17 |
| 114 | 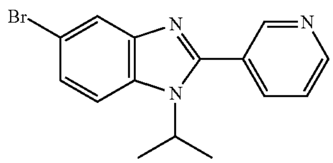 [SMILES: CC(C)n1c(-c2cccnc2)nc2cc(Br)ccc21] | 5-bromo-1-(propan-2-yl)-2-(pyridin-3-yl)-1H-benzimidazole | 318.20 |
| 115 | 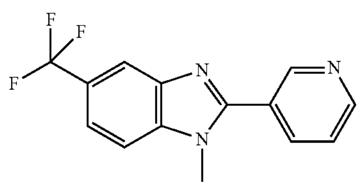 [SMILES: Cn1c(-c2cccnc2)nc2cc(C(F)(F)F)ccc21] | 1-methyl-2-(pyridin-3-yl)-5-(trifluoromethyl)-1H-benzimidazole | 278.05 |
| 116 | 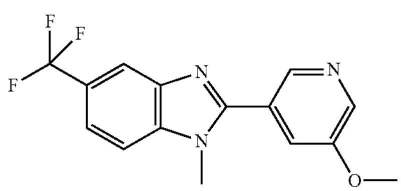 [SMILES: COc1cncc(-c2nc3cc(C(F)(F)F)ccc3n2C)c1] | 2-(5-methoxypyridin-3-yl)-1-methyl-5-(trifluoromethyl)-1H-benzimidazole | 308.04 |
| 117 | 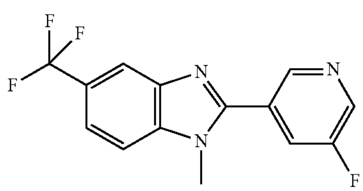 [SMILES: Cn1c(-c2cncc(F)c2)nc2cc(C(F)(F)F)ccc21] | 2-(5-fluoropyridin-3-yl)-1-methyl-5-(trifluoromethyl)-1H-benzimidazole | 295.05 |
| 118 | 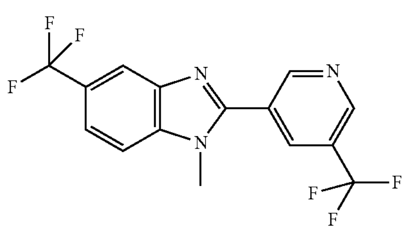 [SMILES: Cn1c(-c2cncc(C(F)(F)F)c2)nc2cc(C(F)(F)F)ccc21] | 1-methyl-5-(trifluoromethyl)-2-[5-(trifluoromethyl)pyridin-3-yl]-1H-benzimidazole | 346.10 |
| 119 | 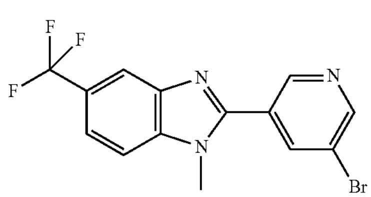 [SMILES: Cn1c(-c2cncc(Br)c2)nc2cc(C(F)(F)F)ccc21] | 2-(5-bromopyridin-3-yl)-1-methyl-5-(trifluoromethyl)-1H-benzimidazole | 357.99 |

TABLE 6-continued

| Example | Structure | IUPAC Name | LCMS (M + 1) |
|---|---|---|---|
| 120 | 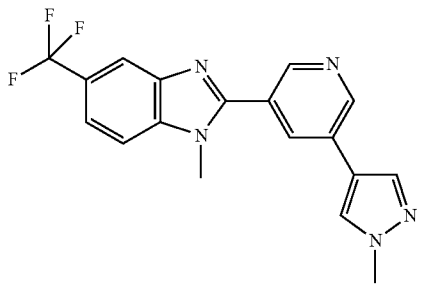 [SMILES: Cn1cc(-c2cncc(-c3nc4cc(C(F)(F)F)ccc4n3C)c2)cn1] | 1-methyl-2-[5-(1-methyl-1H-pyrazol-4-yl)pyridin-3-yl]-5-(trifluoromethyl)-1H-benzimidazole | 358.13 |
| 121 | 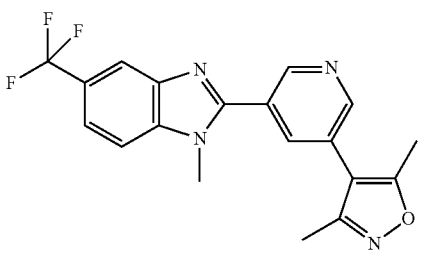 [SMILES: Cc1noc(C)c1-c1cncc(-c2nc3cc(C(F)(F)F)ccc3n2C)c1] | 2-[5-(3,5-dimethylisoxazol-4-yl)pyridin-3-yl]-1-methyl-5-(trifluoromethyl)-1H-benzimidazole | 373.11 |
| 122 | 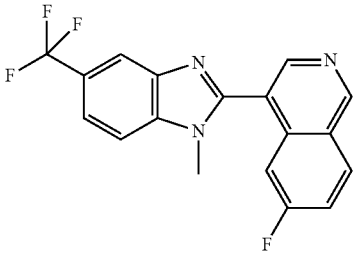 [SMILES: Cn1c(-c2cncc3ccc(F)cc23)nc2cc(C(F)(F)F)ccc21] | 6-fluoro-4-[1-methyl-5-(trifluoromethyl)-1H-benzimidazol-2-yl]isoquinoline | 346.11 |
| 123 | 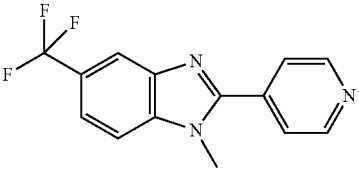 [SMILES: Cn1c(-c2ccncc2)nc2cc(C(F)(F)F)ccc21] | 1-methyl-2-(pyridin-4-yl)-5-(Trifluoromethyl)-1H-benzimidazole | 278.25 |
| 124 | 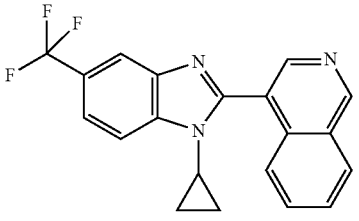 [SMILES: FC(F)(F)c1ccc2c(c1)nc(-c1cncc3ccccc13)n2C1CC1] | 4-[1-cyclopropyl-5-(trifluoromethyl)-1H-benzimidazol-2-yl]isoquinoline | 354.13 |
| 125 | 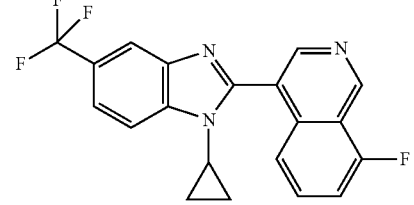 | 4-[1-cyclopropyl-5-(trifluoromethyl)-1H-benzimidazol-2-yl]-8-fluoroisoquinoline | 372.14 |

TABLE 6-continued

| Example | Structure | IUPAC Name | LCMS (M + 1) |
|---|---|---|---|
| 126 | 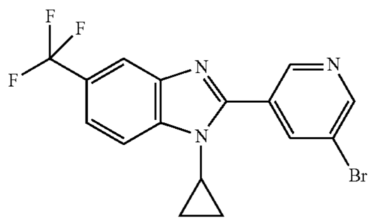 [SMILES: FC(F)(F)c1ccc2c(c1)nc(-c1cncc(Br)c1)n2C1CC1] | 2-(5-bromopyridin-3-yl)-1-cyclopropyl-5-(trifluoromethyl)-1H-benzimidazole | 384.02 |
| 127 | 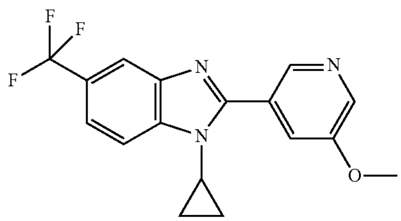 [SMILES: COc1cncc(-c2nc3cc(C(F)(F)F)ccc3n2C2CC2)c1] | 1-cyclopropyl-2-(5-methoxy-pyridin-3-yl)-5-(trifluoromethyl)-1H-benzimidazole | 334.11 |
| 128 | 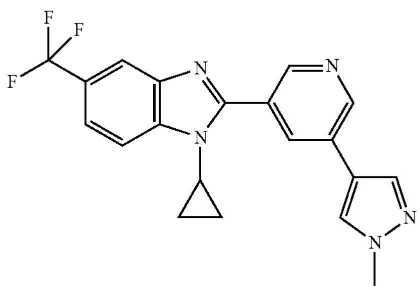 [SMILES: Cn1cc(-c2cncc(-c3nc4cc(C(F)(F)F)ccc4n3C3CC3)c2)cn1] | 1-cyclopropyl-2-[5-(1-methyl-1H-pyrazol-4-yl)pyridin-3-yl]-5-(trifluoromethyl)-1H-benzimidazole | 384.19 |
| 129 | 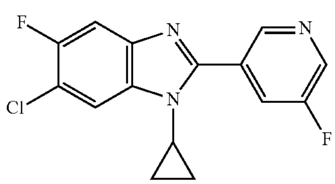 | 6-chloro-1-cyclopropyl-5-fluoro-2-(5-fluoropyridin-3-yl)-1H-benzimidazole | 306.02 |
| 130 | 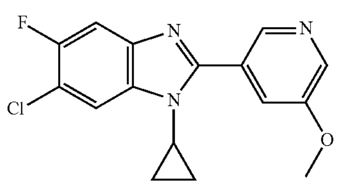 | 6-chloro-1-cyclopropyl-5-fluoro-2-(5-methoxypyridin-3-yl)-1H-benzimidazole | 318.05 |
| 131 | 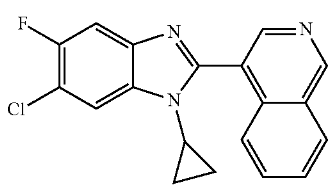 [SMILES: Fc1cc2nc(-c3cncc4ccccc34)n(C3CC3)c2cc1Cl] | 4-(6-chloro-1-cyclopropyl-5-fluoro-1H-benzimidazol-2-yl)isoquinoline | 338.07 |
| 132 | 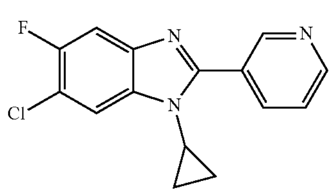 [SMILES: Fc1cc2nc(-c3cccnc3)n(C3CC3)c2cc1Cl] | 6-chloro-1-cyclopropyl-5-fluoro-2-(pyridin-3-yl)-1H-benzimidazole | 288.03 |

TABLE 6-continued

| Example | Structure | IUPAC Name | LCMS (M + 1) |
|---|---|---|---|
| 133 | 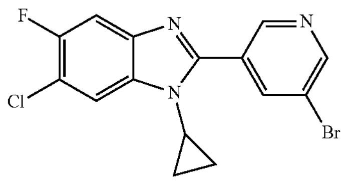 [SMILES: Fc1cc2nc(-c3cncc(Br)c3)n(C3CC3)c2cc1Cl] | 2-(5-bromopyridin-3-yl)-6-chloro-1-cyclopropyl-5-fluoro-1H-benzimidazole | 369.96 |
| 134 | 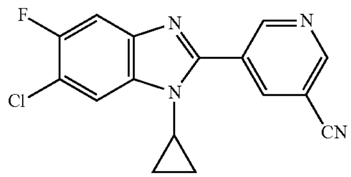 [SMILES: N#Cc1cncc(-c2nc3cc(F)c(Cl)cc3n2C2CC2)c1] | 5-(6-chloro-1-cyclopropyl-5-fluoro-1H-benzimidazol-2-yl)pyridine-3-carbonitrile | 313.04 |
| 135 | 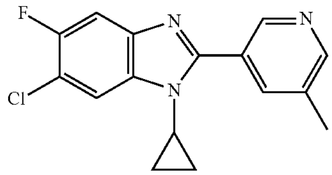 [SMILES: Cc1cncc(-c2nc3cc(F)c(Cl)cc3n2C2CC2)c1] | 6-chloro-1-cyclopropyl-5-fluoro-2-(5-methylpyridin-3-yl)-1H-benzimidazole | 302.09 |
| 136 | 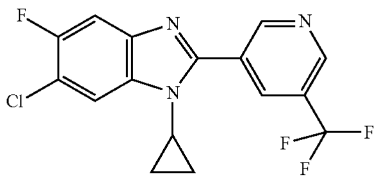 [SMILES: Fc1cc2nc(-c3cncc(C(F)(F)F)c3)n(C3CC3)c2cc1Cl] | 6-chloro-1-cyclopropyl-5-fluoro-2-[5-(trifluoromethyl)pyridin-3-yl]-1H-benzimadazole | 356.08 |
| 137 | 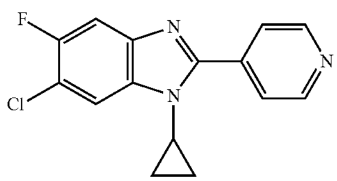 [SMILES: Fc1cc2nc(-c3ccncc3)n(C3CC3)c2cc1Cl] | 6-chloro-1-cyclopropyl-5-fluoro-2-(pyridin-4-yl)-1H-benzimidazole | 288.72 |
| 138 | 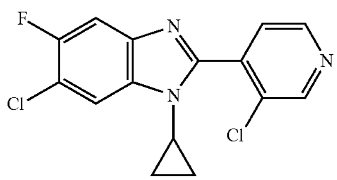 [SMILES: Fc1cc2nc(-c3ccncc3Cl)n(C3CC3)c2cc1Cl] | 6-chloro-2-(3-chloropyridin-4-yl)-1-cyclopropyl-5-fluoro-1H-benzimidazole | 323.17 |
| 139 | 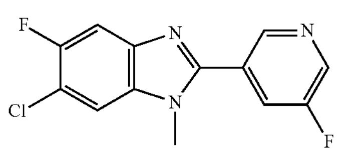 [SMILES: Cn1c(-c2cncc(F)c2)nc2cc(F)c(Cl)cc21] | 6-chloro-5-fluoro-2-(5-fluoropyridin-3-yl)-1-methyl-1H-benzimidazole | 280.23 |
| 140 | 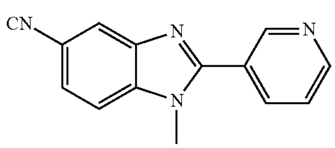 | 1-methyl-2-(pyridin-3-yl)-1H-benzimidazole-5-carbonitrile | 235.07 |
| 141 | 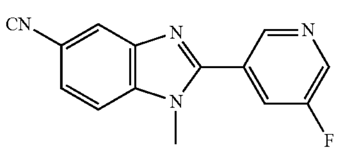 | 2-(5-fluoropyridin-3-yl)-1-methyl-1H-benzimidazole-5-carbonitrile | 253.10 |

TABLE 6-continued

| Example | Structure | IUPAC Name | LCMS (M + 1) |
|---|---|---|---|
| 142 | 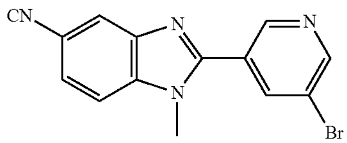 | 2-(5-bromopyridin-3-yl)-1-methyl-1H-benzimidazole-5-carbonitrile | 313.01 |
| 143 | 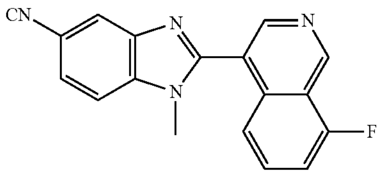 | 2-(8-fluoroisoquinolin-4-yl)-1-methyl-1H-benzimidazole-5-carbonitrile | 303.08 |
| 144 | 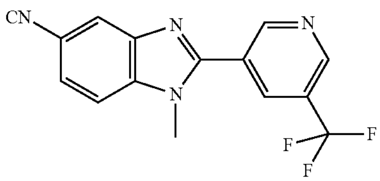 | 1-methyl-2-[5-(trifluoromethyl)pyridin-3-yl]-1H-benzimidazole-5-carbonitrile | 303.07 |
| 145 | 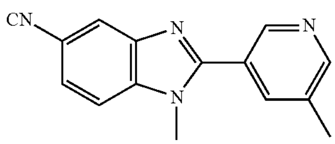 | 1-methyl-2-(5-methylpyridin-3-yl)-1H-benzimidazole-5-carbonitrile | 249.10 |
| 146 | 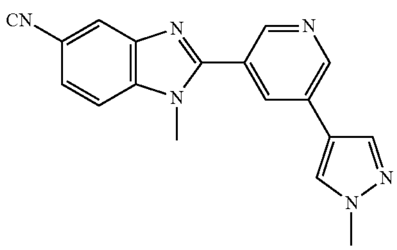 | 1-methyl-2-[5-(1-methyl-1H-pyrazol-4-yl)pyridin-3-yl]-1H-benzimidazole-5-carbonitrile | 315.15 |
| 147 | 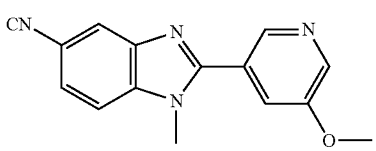 | 2-(5-methoxypyridin-3-yl)-1-methyl-1H-benzimidazole-5-carbonitrile | 265.10 |
| 148 | 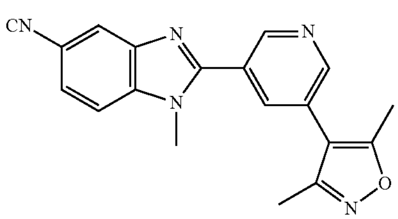 | 2-[5-(3,5-dimethylisoxazol-4-yl)pyridin-3-yl]-1-methyl-1H-benzimidazole-5-carbonitrile | 330.13 |
| 149 | 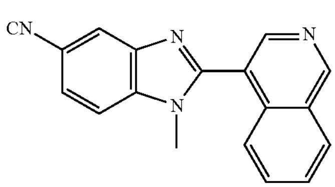 | 2-(isoquinolin-4-yl)-1-methyl-1H-benzimidazole-5-carbonitrile | 285.14 |

TABLE 6-continued

| Example | Structure | IUPAC Name | LCMS (M + 1) |
|---|---|---|---|
| 150 | 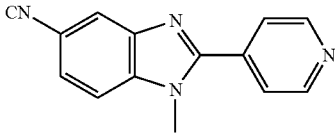 | 1-methyl-2-(pyridin-4-yl)-1H-benzimidazole-5-carbonitrile | 235.26 |
| 151 | 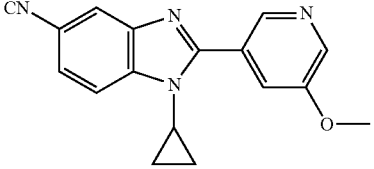 | 1-cyclopropyl-2-(5-methoxypyridin-3-yl)-1H-benzimidazole-5-carbonitrile | 291.10 |
| 152 | 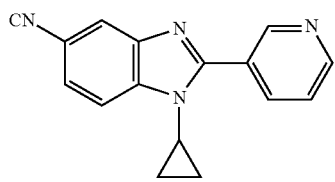 | 1-cyclopropyl-2-(pyridin-3-yl)-1H-benzimidazole-5-carbonitrile | 261.06 |
| 153 | 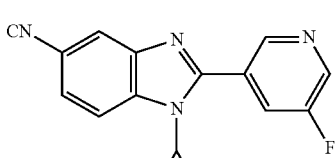 | 1-cyclopropyl-2-(5-fluoropyridin-3-yl)-1H-benzimidazole-5-carbonitrile | 279.05 |
| 154 | 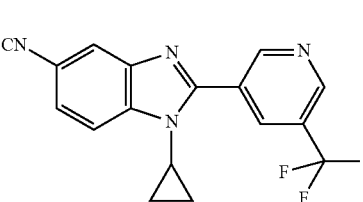 | 1-cyclopropyl-2-[5-(trifluoromethyl)pyridin-3-yl]-1H-benzimidazole-5-carbonitrile | 329.10 |
| 155 | 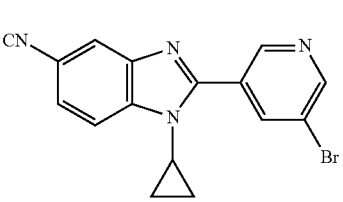 | 2-(5-bromopyridin-3-yl)-1-cyclopropyl-1H-benzimidazole-5-carbonitrile | 339.02 |
| 156 | 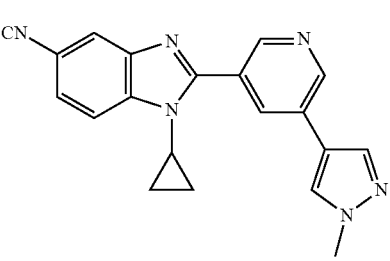 | 1-cyclopropyl-2-[5-(1-methyl-1H-pyrazol-4-yl)pyridin-3-yl]-1H-benzimidazole-5-carbonitrile | 341.16 |
| 157 | 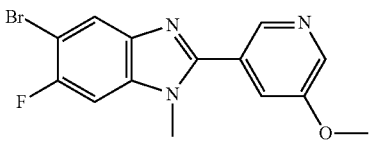 [SMILES: COc1cncc(-c2nc3cc(Br)c(F)cc3n2C)c1] | 5-bromo-6-fluoro-2-(5-methoxypyridin-3-yl)-1-methyl-1H-benzimidazole | 336.02 |

TABLE 6-continued

| Example | Structure | IUPAC Name | LCMS (M + 1) |
|---|---|---|---|
| 158 | 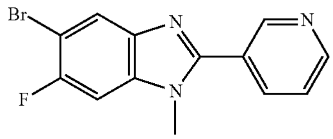 [SMILES: Cn1c(-c2cccnc2)nc2cc(Br)c(F)cc21] | 5-bromo-6-fluoro-1-methyl-2-(pyridin-3-yl)-1H-benzimidazole | 306.02 |
| 159 | 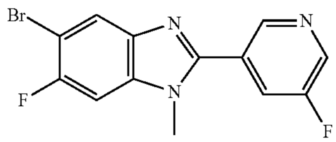 [SMILES: Cn1c(-c2cncc(F)c2)nc2cc(Br)c(F)cc21] | 5-bromo-6-fluoro-2-(5-fluoropyridin-3-yl)-1-methyl-1H-benzimidazole | 323.99 |
| 160 | 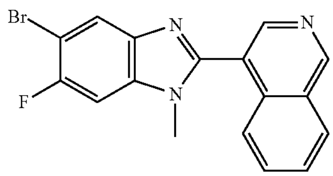 [SMILES: Cn1c(-c2cncc3ccccc23)nc2cc(Br)c(F)cc21] | 4-(5-bromo-6-fluoro-1-methyl-1H-benzimidazol-2-yl)isoquinoline | 356.04 |
| 161 | 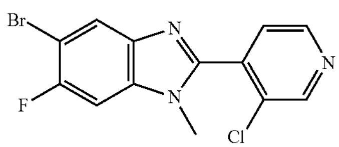 | 5-bromo-2-(3-chloropyridin-4-yl)-6-fluoro-1-methyl-1H-benzimidazole | 341.58 |
| 162 | 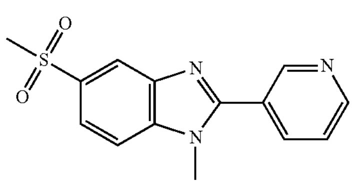 [SMILES: Cn1c(-c2cccnc2)nc2cc(S(C)(=O)=O)ccc21] | 1-methyl-5-(methylsulfonyl)-2-(pyridin-3-yl)-1H-benzimidazole | 288.05 |
| 163 | 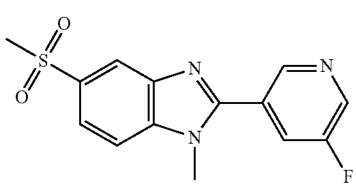 [SMILES: Cn1c(-c2cncc(F)c2)nc2cc(S(C)(=O)=O)ccc21] | 2-(5-fluoropyridin-3-yl)-1-methyl-5-(methylsulfonyl)-1H-benzimidazole | 306.10 |
| 164 | 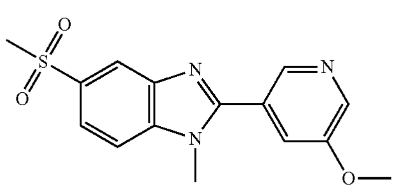 | 2-(5-methoxypyridin-3-yl)-1-methyl-5-(methylsulfonyl)-1H-benzimidazole | 318.08 |
| 165 | 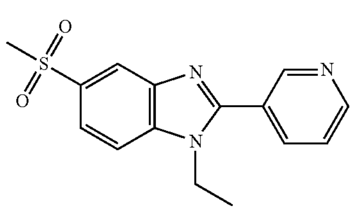 [SMILES: CCn1c(-c2cccnc2)nc2cc(S(C)(=O)=O)ccc21] | 1-ethyl-5-(methylsulfonyl)-2-(pyridin-3-yl)-1H-benzimidazole | 302.09 |

TABLE 6-continued

| Example | Structure | IUPAC Name | LCMS (M + 1) |
|---------|-----------|------------|--------------|
| 166 | 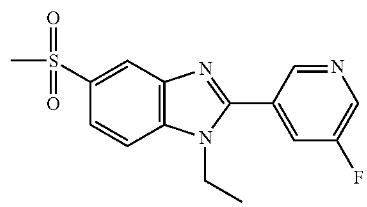 [SMILES: CCn1c(-c2cncc(F)c2)nc2cc(S(C)(=O)=O)ccc21] | 1-ethyl-2-(5-fluoropyridin-3-yl)-5-(methylsulfonyl)-1H-benzimidazole | 320.10 |
| 167 | 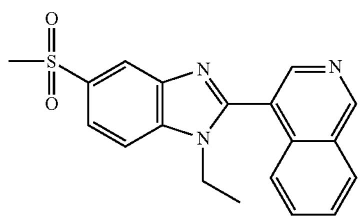 [SMILES: CCn1c(-c2cncc3ccccc23)nc2cc(S(C)(=O)=O)ccc21] | 4-[1-ethyl-5-(methylsulfonyl)-1H-benzimidazol-2-yl]isoquinoline | 352.15 |
| 168 | 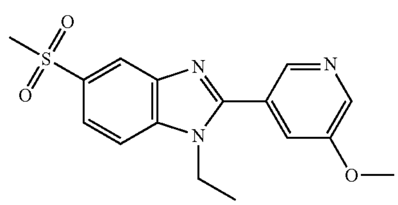 | 1-ethyl-2-(5-methoxypyridin-3-yl)-5-(methylsulfonyl)-1H-benzimidazole | 332.13 |
| 169 | 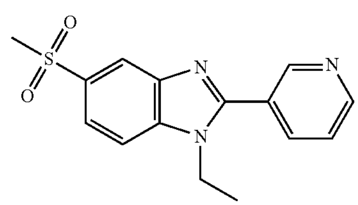 [SMILES: CCn1c(-c2cccnc2)nc2cc(S(C)(=O)=O)ccc21] | 1-ethyl-5-(methylsulfonyl)-2-(pyridin-3-yl)-1H-benzimidazole | 302.09 |
| 170 | 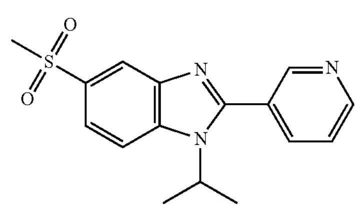 [SMILES: CC(C)n1c(-c2cccnc2)nc2cc(S(C)(=O)=O)ccc21] | 5-(methylsulfonyl)-1-(propan-2-yl)-2-(pyridin-3-yl)-1H-benzimidazole | 316.11 |
| 171 | 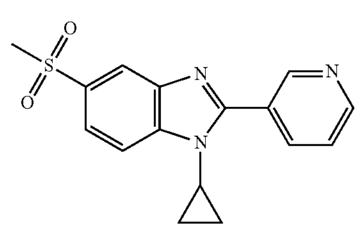 [SMILES: CS(=O)(=O)c1ccc2c(c1)nc(-c1cccnc1)n2C1CC1] | 1-cyclopropyl-5-(methylsulfonyl)-2-(pyridin-3-yl)-1H-benzimidazole | 314.13 |
| 172 | 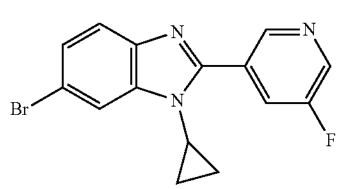 [SMILES: Fc1cncc(-c2nc3ccc(Br)cc3n2C2CC2)c1] | 6-bromo-1-cyclopropyl-2-(5-fluoropyridin-3-yl)-1H-benzimidazole | 334.01 |

TABLE 6-continued

| Example | Structure | IUPAC Name | LCMS (M + 1) |
|---|---|---|---|
| 173 | 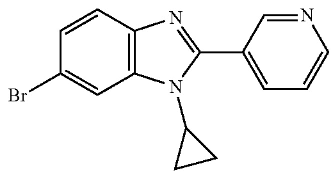 [SMILES: Brc1ccc2nc(-c3cccnc3)n(C3CC3)c2c1] | 6-bromo-1-cyclopropyl-2-(pyridin-3-yl)-1H-benzimidazole | 316.00 |
| 174 | 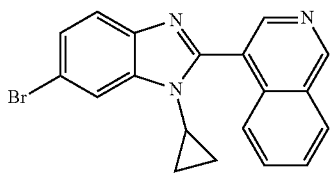 [SMILES: Brc1ccc2nc(-c3cncc4ccccc34)n(C3CC3)c2c1] | 4-(6-bromo-1-cyclopropyl-1H-benzimidazol-2-yl)isoquinoline | 364.03 |
| 175 | 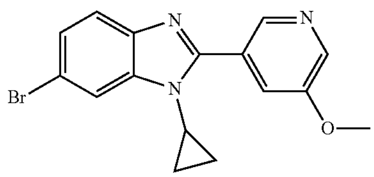 [SMILES: COc1cncc(-c2nc3ccc(Br)cc3n2C2CC2)c1] | 6-bromo-1-cyclopropyl-2-(5-methoxypyridin-3-yl)-1H-benzimidazole | 344.03 |
| 176 | 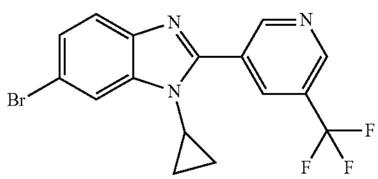 [SMILES: FC(F)(F)c1cncc(-c2nc3ccc(Br)cc3n2C2CC2)c1] | 6-bromo-1-cyclopropyl-2-[5-(trifluoromethyl)pyridin-3-yl]-1H-benzimidazole | 383.18 |
| 177 | 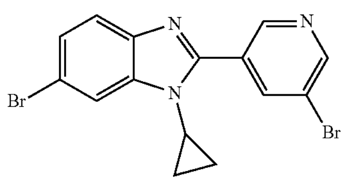 | 6-bromo-2-(5-bromopyridin-3-yl)-1-cyclopropyl-1H-benzimidazole | 395.08 |
| 178 | 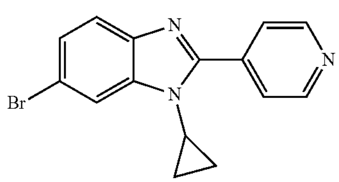 [SMILES: Brc1ccc2nc(-c3ccncc3)n(C3CC3)c2c1] | 6-bromo-1-cyclopropyl-2-(pyridin-4-yl)-1H-benzimidazole | 315.18 |
| 179 | 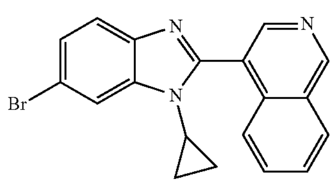 [SMILES: Brc1ccc2nc(-c3cncc4ccccc34)n(C3CC3)c2c1] | 6-bromo-1-cyclopropyl-2-(pyridin-4-yl)-1H-benzimidazole | 366.1 (M + 2) |
| 180 | 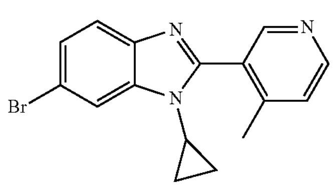 | 6-bromo-1-cyclopropyl-2-(4-methylpyridin-3-yl)-1H-benzimidazole | 330.4 (M + 2) |

TABLE 6-continued

| Example | Structure | IUPAC Name | LCMS (M + 1) |
|---|---|---|---|
| 181 | 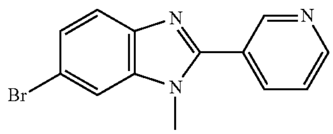 [SMILES: Cn1c(-c2cccnc2)nc2ccc(Br)cc21] | 6-bromo-1-cyclopropyl-2-(pyridin-3-yl)-1H-benzimidazole | 287.98 |
| 182 | 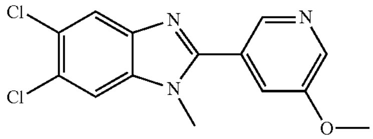 [SMILES: COc1cncc(-c2nc3cc(Cl)c(Cl)cc3n2C)c1] | 5,6-dichloro-2-(5-methoxypyridin-3-yl)-1-methyl-1H-benzimidazole | 308.12 |
| 183 | 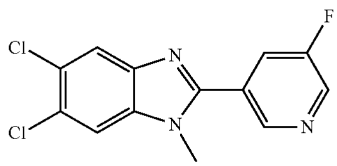 [SMILES: Cn1c(-c2cncc(F)c2)nc2cc(Cl)c(Cl)cc21] | 5,6-dichloro-2-(5-fluoropyridin-3-yl)-1-methyl-1H-benzimidazole | 296.97 |
| 184 | 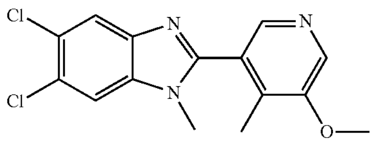 [SMILES: COc1cncc(-c2nc3cc(Cl)c(Cl)cc3n2C)c1C] | 5,6-dichloro-2-(5-methoxy-4-methylpyridin-3-yl)-1-methyl-1H-benzimidazole | 322.01 |
| 185 | 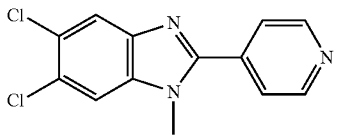 [SMILES: Cn1c(-c2ccncc2)nc2cc(Cl)c(Cl)cc21] | 5,6-dichloro-1-methyl-2-(pyridin-4-yl)-1H-benzimidazole | 279.14 |
| 186 | 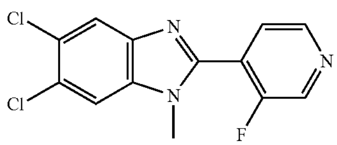 [SMILES: Cn1c(-c2ccncc2F)nc2cc(Cl)c(Cl)cc21] | 5,6-dichloro-2-(3-fluoropyridin-4-yl)-1-methyl-1H-benzimidazole | 297.13 |
| 187 | 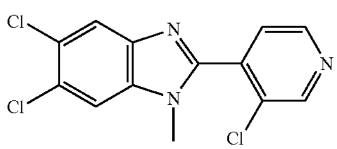 | 5,6-dichloro-2-(3-chloropyridin-4-yl)-1-methyl-1H-benzimidazole | 313.58 |
| 188 | 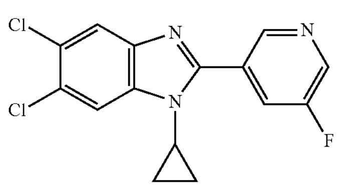 [SMILES: Fc1cncc(-c2nc3cc(Cl)c(Cl)cc3n2C2CC2)c1] | 5,6-dichloro-1-cyclopropyl-2-(5-fluoropyridin-3-yl)-1H-benzimidazole | 322.08 |
| 189 | 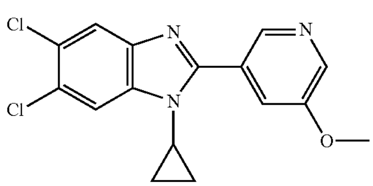 [SMILES: COc1cncc(-c2nc3cc(Cl)c(Cl)cc3n2C2CC2)c1] | 5,6-dichloro-1-cyclopropyl-2-(5-methoxypyridin-3-yl)-1H-benzimidazole | 334.05 |

TABLE 6-continued

| Example | Structure | IUPAC Name | LCMS (M + 1) |
|---|---|---|---|
| 190 | 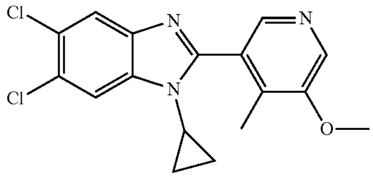 [SMILES: COc1cncc(-c2nc3cc(Cl)c(Cl)cc3n2C2CC2)c1C] | 5,6-dichloro-1-cyclopropyl-2-(5-methoxy-4-methylpyridin-3-yl)-1H-benzimidazole | 348.08 |
| 191 | 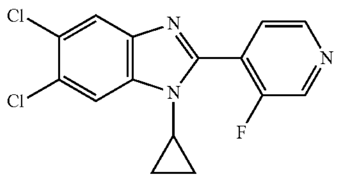 [SMILES: Fc1cnccc1-c1nc2cc(Cl)c(Cl)cc2n1C1CC1] | 5,6-dichloro-1-cyclopropyl-2-(3-fluoropyridin-4-yl)-1H-benzimidazole | 323.17 |
| 192 | 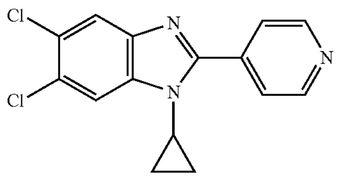 [SMILES: Clc1cc2nc(-c3ccncc3)n(C3CC3)c2cc1Cl] | 5,6-dichloro-1-cyclopropyl-2-(pyridin-4-yl)-1H-benzimidazole | 305.18 |
| 193 | 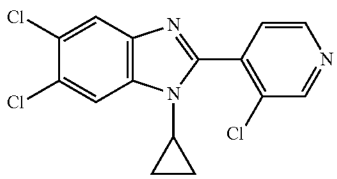 | 5,6-dichloro-2-(3-chloropyridin-4-yl)-1-cyclopropyl-1H-benzimidazole | 339.62 |
| 194 | 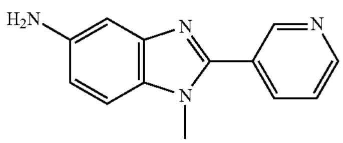 [SMILES: Cn1c(-c2cccnc2)nc2cc(N)ccc21] | 1-methyl-2-(pyridin-3-yl)-1H-benzimidazol-5-amine | 225.09 |
| 195 | 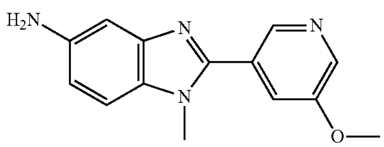 [SMILES: COc1cncc(-c2nc3cc(N)ccc3n2C)c1] | 2-(5-methoxypyridin-3-yl)-1-methyl-1H-benzimidazol-5-amine | 255.29 |
| 196 | 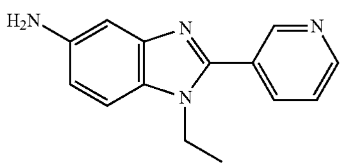 [SMILES: CCn1c(-c2cccnc2)nc2cc(N)ccc21] | 1-ethyl-2-(pyridin-3-yl)-1H-benzimidazol-5-amine | 239.29 |
| 197 | 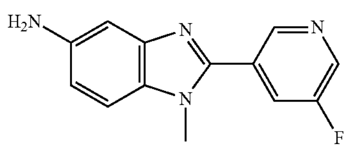 [SMILES: Cn1c(-c2cncc(F)c2)nc2cc(N)ccc21] | 2-(5-fluoropyridin-3-yl)-1-methyl-1H-benzimidazol-5-amine | 243.25 |
| 198 | 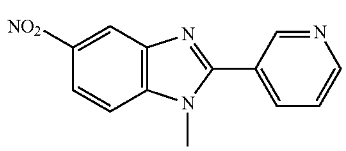 [SMILES: Cn1c(-c2cccnc2)nc2cc([N+](=O)[O-])ccc21] | 1-methyl-5-nitro-2-(pyridin-3-yl)-1H-benzimidazole | 255.07 |

TABLE 6-continued

| Example | Structure | IUPAC Name | LCMS (M + 1) |
|---|---|---|---|
| 199 | 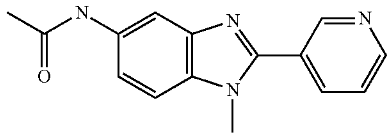 [SMILES: CC(=O)Nc1ccc2c(c1)nc(-c1cccnc1)n2C] | N-[1-methyl-2-(pyridin-3-yl)-1H-benzimidazol-5-yl]acetamide | 267.09 |
| 200 | 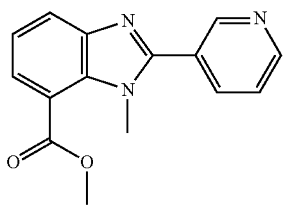 [SMILES: COC(=O)c1cccc2nc(-c3cccnc3)n(C)c12] | methyl 1-methyl-2-(pyridin-3-yl)-1H-benzimidazole-7-carboxylate | 268.17 |
| 201 | 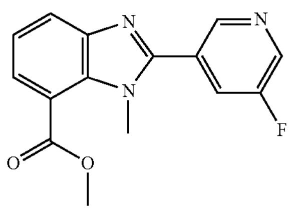 [SMILES: COC(=O)c1cccc2nc(-c3cncc(F)c3)n(C)c12] | methyl 2-(5-fluoropyridin-3-yl)-1-methyl-1H-benzimidazole-7-carboxylate | 286.13 |
| 202 | 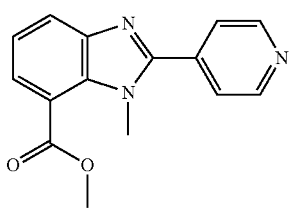 [SMILES: COC(=O)c1cccc2nc(-c3ccncc3)n(C)c12] | methyl 1-methyl-2-(pyridin-4-yl)-1H-benzimidazole-7-carboxylate | 268.28 |
| 203 | 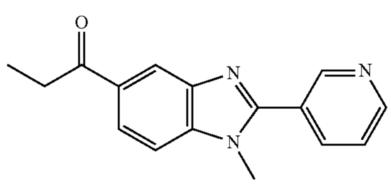 [SMILES: CCC(=O)c1ccc2c(c1)nc(-c1cccnc1)n2C] | methyl 1-methyl-2-(pyridin-3-yl)-1H-benzimidazole-5-carboxylate | 268.09 |
| 204 | 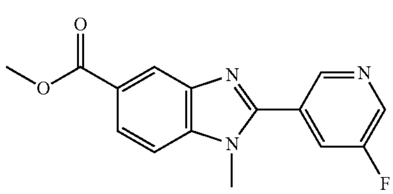 [SMILES: COC(=O)c1ccc2c(c1)nc(-c1cncc(F)c1)n2C] | methyl 2-(5-fluoropyridin-3-yl)-1-methyl-1H-benzimidazole-5-carboxylate | 286.12 |
| 205 | 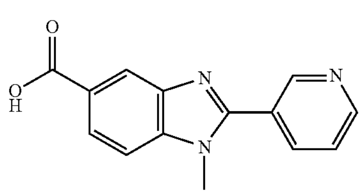 [SMILES: Cn1c(-c2cccnc2)nc2cc(C(=O)O)ccc21] | 1-methyl-2-(pyridin-3-yl)-1H-benzimidazole-5-carboxylic acid | 254.12 |
| 206 | 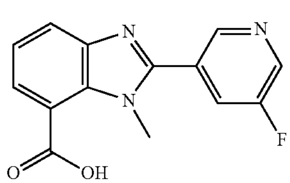 [SMILES: Cn1c(-c2cncc(F)c2)nc2cccc(C(=O)O)c21] | 2-(5-fluoropyridin-3-yl)-1-methyl-1H-benzimidazole-7-carboxylic acid | 272.2 |

TABLE 6-continued

| Example | Structure | IUPAC Name | LCMS (M + 1) |
|---|---|---|---|
| 207 | 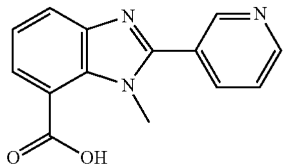 [SMILES: Cn1c(-c2cccnc2)nc2cccc(C(=O)O)c21] | 1-methyl-2-(pyridin-3-yl)-1H-benzimidazole-7-carboxylic acid | 254.26 |
| 208 | 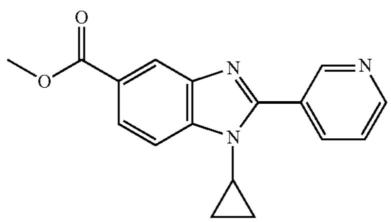 [SMILES: COC(=O)c1ccc2c(c1)nc(-c1cccnc1)n2C1CC1] | methyl 1-cyclopropyl-2-(pyridin-3-yl)-1H-benzimidazole-5-carboxylate | 294.22 |
| 209 | 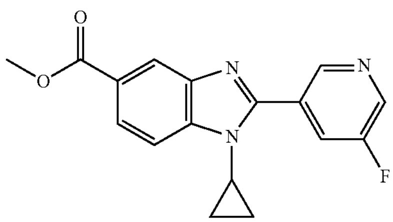 [SMILES: COC(=O)c1ccc2c(c1)nc(-c1cncc(F)c1)n2C1CC1] | methyl 1-cyclopropyl-2-(5-fluoropyridin-3-yl)-1H-benzimidazole-5-carboxylate | 312.21 |
| 210 | 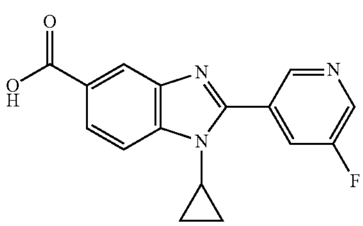 [SMILES: O=C(O)c1ccc2c(c1)nc(-c1cncc(F)c1)n2C1CC1] | 1-cyclopropyl-2-(5-fluoropyridin-3-yl)-1H-benzimidazole-5-carboxylic acid | 297.29 |
| 211 | 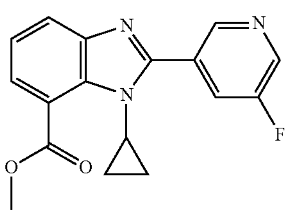 [SMILES: COC(=O)c1cccc2nc(-c3cncc(F)c3)n(C3CC3)c12] | methyl 1-cyclopropyl-2-(5-fluoropyridin-3-yl)-1H-benzimidazole-7-carboxylate | 312.21 |
| 212 | 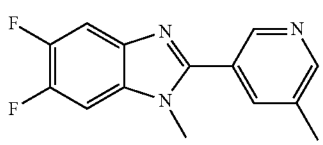 [SMILES: Cc1cncc(-c2nc3cc(F)c(F)cc3n2C)c1] | 5,6-difluoro-1-methyl-2-(5-methylpyridin-3-yl)-1H-benzimidazole | 260.05 |
| 213 | 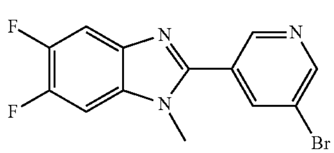 [SMILES: Cn1c(-c2cncc(Br)c2)nc2cc(F)c(F)cc21] | 2-(5-bromopyridin-3-yl)-5,6-difluoro-1-methyl-1H-benzimidazol | 325.95 |
| 214 | 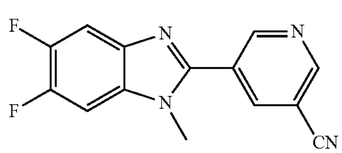 [SMILES: Cn1c(-c2cncc(C#N)c2)nc2cc(F)c(F)cc21] | 5-(5,6-difluoro-1-methyl-1H-benzimidazol-2-yl)pyridine-3-carbonitrile | 271.05 |

TABLE 6-continued

| Example | Structure | IUPAC Name | LCMS (M + 1) |
|---|---|---|---|
| 215 | 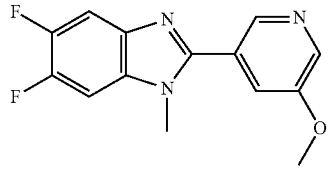 [SMILES: COc1cncc(-c2nc3cc(F)c(F)cc3n2C)c1] | 5,6-difluoro-2-(5-methoxypyridin-3-yl)-1-methyl-1H-benzimidazole | 276.07 |
| 216 | 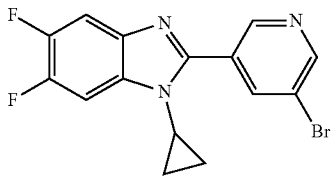 [SMILES: Fc1cc2nc(-c3cncc(Br)c3)n(C3CC3)c2cc1F] | 2-(5-bromopyridin-3-yl)-1-cyclopropyl-5,6-difluoro-1H-benzimidazole | 351.01 |
| 217 | 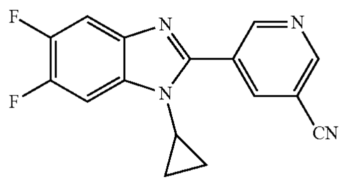 [SMILES: N#Cc1cncc(-c2nc3cc(F)c(F)cc3n2C2CC2)c1] | 5-(1-cyclopropyl-5,6-difluoro-1H-benzimidazol-2-yl)pyridine-3-carbonitrile | 297.05 |
| 218 | 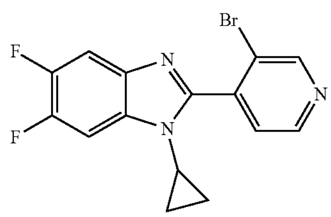 [SMILES: Fc1cc2nc(-c3ccncc3Br)n(C3CC3)c2cc1F] | 2-(3-bromopyridin-4-yl)-1-cyclopropyl-5,6-difluoro-1H-benzimidazole | 352.16 |
| 219 | 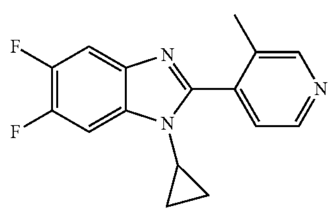 [SMILES: Cc1cnccc1-c1nc2cc(F)c(F)cc2n1C1CC1] | 1-cyclopropyl-5,6-difluoro-2-(3-methylpyridin-4-yl)-1H-benzimidazole | 286.15 |
| 220 | 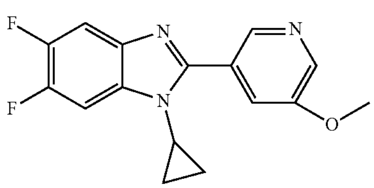 [SMILES: COc1cncc(-c2nc3cc(F)c(F)cc3n2C2CC2)c1] | 1-cyclopropyl-5,6-difluoro-2-(5-methoxypyridin-3-yl)-1H-benzimidazole | 302.14 |
| 221 | 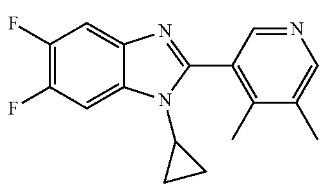 | 1-cyclopropyl-2-(4,5-dimethylpyridin-3-yl)-5,6-difluoro-1H-benzimidazole | 300.17 |
| 222 | 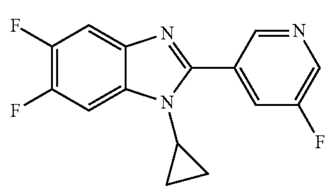 [SMILES: Fc1cncc(-c2nc3cc(F)c(F)cc3n2C2CC2)c1] | 1-cyclopropyl-5,6-difluoro-2-(4-fluoropyridin-3-yl)-1H-benzimidazole | 290.09 |

TABLE 6-continued

| Example | Structure | IUPAC Name | LCMS (M + 1) |
|---|---|---|---|
| 223 | 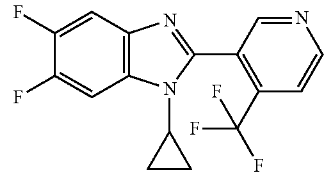 [SMILES: Fc1cc2nc(-c3cnccc3C(F)(F)F)n(C3CC3)c2cc1F] | 1-cyclopropyl-5,6-difluoro-2-[4-(trifluoromethyl)pyridin-3-yl]-1H-benzimidazole | 340.2 |
| 224 | 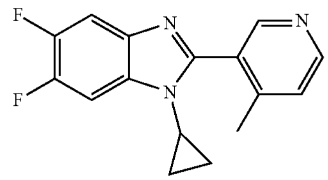 [SMILES: Cc1ccncc1-c1nc2cc(F)c(F)cc2n1C1CC1] | 1-cyclopropyl-5,6-difluoro-2-[4-(trifluoromethyl)pyridin-3-yl]-1H-benzimidazole | 286.2 |
| 225 | 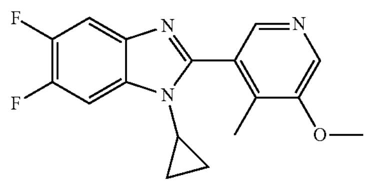 [SMILES: COc1cncc(-c2nc3cc(F)c(F)cc3n2C2CC2)c1C] | 1-cyclopropyl-5,6-difluoro-2-(5-methoxy-4-methylpyridin-3-yl)-1H-benzimidazole | 316.3 |
| 226 | 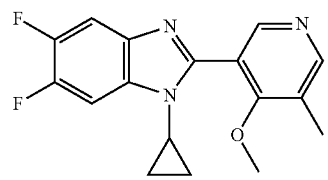 [SMILES: COc1c(C)cncc1-c1nc2cc(F)c(F)cc2n1C1CC1] | 1-cyclopropyl-5,6-difluoro-2-(4-methoxy-5-methylpyridin-3-yl)-1H-benzimidazole | 316.3 |
| 227 | 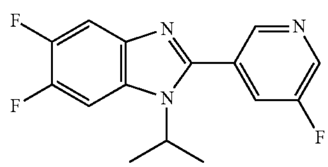 [SMILES: CC(C)n1c(-c2cncc(F)c2)nc2cc(F)c(F)cc21] | 5,6-difluoro-2-(5-fluoropyridin-3-yl)-1-(propan-2-yl)-1H-benzimidazole | 292.23 |
| 228 | 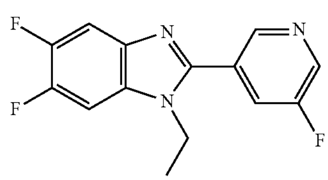 [SMILES: CCn1c(-c2cncc(F)c2)nc2cc(F)c(F)cc21] | 1-ethyl-5,6-difluoro-2-(5-fluoropyridin-3-yl)-1H-benzimidazole | 278.26 |
| 229 | 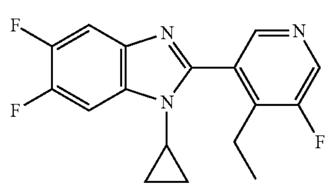 [SMILES: CCc1c(F)cncc1-c1nc2cc(F)c(F)cc2n1C1CC1] | 1-cyclopropyl-2-(4-ethyl-5-fluoropyridin-3-yl)-5,6-difluoro-1H-benzimidazole | 318.2 |
| 230 | 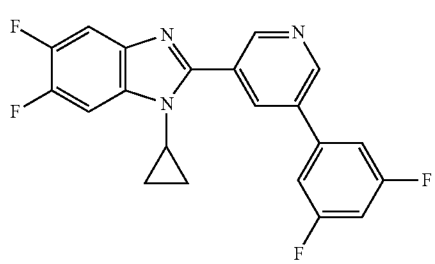 [SMILES: Fc1cc(F)cc(-c2cncc(-c3nc4cc(F)c(F)cc4n3C3CC3)c2)c1] | 1-cyclopropyl-2-[5-(3,5-difluorophenyl)pyridin-3-yl]-5,6-difluoro-1H-benzimidazole | 384.1 |

TABLE 6-continued

| Example | Structure | IUPAC Name | LCMS (M + 1) |
|---|---|---|---|
| 231 | 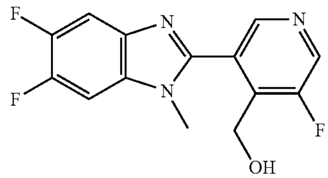 [SMILES: Cn1c(-c2cncc(F)c2CO)nc2cc(F)c(F)cc21] | [3-(5,6-difluoro-1-methyl-1H-benzimidazol-2-yl)-5-fluoropyridin-4-yl]methanol | 294.1 |
| 232 | 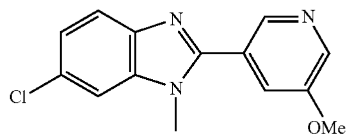 [SMILES: COc1cncc(-c2nc3ccc(Cl)cc3n2C)c1] | 6-chloro-2-(5-methoxypyridin-3-yl)-1-methyl-1H-benzimidazole | 274.12 |
| 233 | 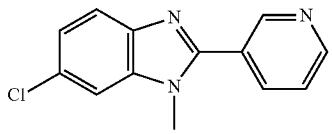 [SMILES: Cn1c(-c2cccnc2)nc2ccc(Cl)cc21] | 6-chloro-1-methyl-2-(pyridin-3-yl)-1H-benzimidazole | 244.01 |
| 234 | 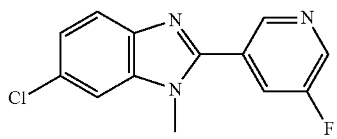 [SMILES: Cn1c(-c2cncc(F)c2)nc2ccc(Cl)cc21] | 6-chloro-2-(5-fluoropyridin-3-yl)-1-methyl-1H-benzimidazole | 262.05 |
| 235 | 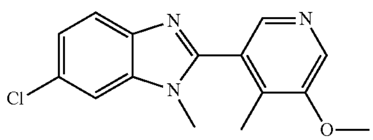 [SMILES: COc1cncc(-c2nc3ccc(Cl)cc3n2C)c1C] | 6-chloro-2-(5-methoxy-4-methylpyridin-3-yl)-1-methyl-1H-benzimidazole | 288.08 |
| 236 | 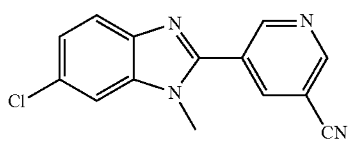 [SMILES: Cn1c(-c2cncc(C#N)c2)nc2ccc(Cl)cc21] | 5-(6-chloro-1-methyl-1H-benzimidazol-2-yl)pyridine-3-carbonitrile | 269.03 |
| 237 | 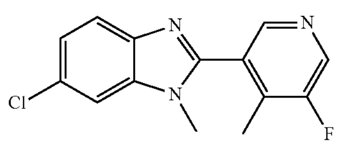 [SMILES: Cc1c(F)cncc1-c1nc2ccc(Cl)cc2n1C] | 6-chloro-2-(5-fluoro-4-methylpyridin-3-yl)-1-methyl-1H-benzimidazole | 276.1 |
| 238 | 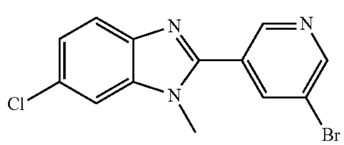 [SMILES: Cn1c(-c2cncc(Br)c2)nc2ccc(Cl)cc21] | 2-(5-bromopyridin-3-yl)-6-chloro-1-methyl-1H-benzimidazole | 323.98 |
| 239 | 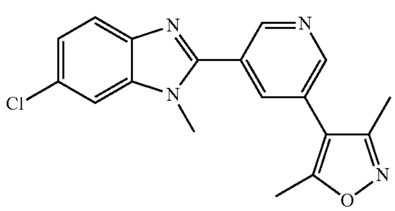 [SMILES: Cc1noc(C)c1-c1cncc(-c2nc3ccc(Cl)cc3n2C)c1] | 6-chloro-2-[5-(3,5-dimethylisoxazol-4-yl)pyridin-3-yl]-1-methyl-1H-benzimidazole | 339.12 |
| 240 | 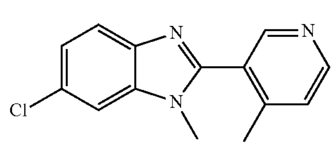 [SMILES: Cc1ccncc1-c1nc2ccc(Cl)cc2n1C] | 6-chloro-1-methyl-2-(4-methyl-pyridin-3-yl)-1H-benzimidazole | 258.1 |

TABLE 6-continued

| Example | IUPAC Name | LCMS (M + 1) |
|---|---|---|
| 241 | 6-chloro-1-methyl-2-(5-methyl-pyridin-3-yl)-1H-benzimidazole | 258.2 |
| 242 | 6-chloro-1-methyl-2-(pyridin-4-yl)-1H-benzimidazole | 244.69 |
| 243 | 6-chloro-2-(3-chloropyridin-4-yl)-1-methyl-1H-benzimidazole | 279.14 |
| 244 | 6-chloro-1-methyl-2-[4-(trifluoro-methyl)pyridin-3-yl]-1H-benzimidazole | 312.69 |
| 245 | 6-chloro-2-(3-fluoropyridin-4-yl)-1-methyl-1H-benzimidazole | 262.68 |
| 246 | 6-chloro-1-methyl-2-[5-(trifluoro-methyl)pyridin-3-yl]-1H-benzimidazole | 312.69 |
| 247 | 6-chloro-1-cyclopropyl-2-(5-fluoropyridin-3-yl)-1H-benzimidazole | 288.12 |
| 248 | 6-chloro-1-methyl-2-[5-(1-methyl-1H-pyrazol-4-yl)pyridin-3-yl]-1H-benzimidazole | 324.12 |
| 249 | 6-chloro-1-cyclopropyl-2-(4-methylpyridin-3-yl)-1H-benzimidazole | 284.1 |

TABLE 6-continued

| Example | IUPAC Name | LCMS (M + 1) |
|---|---|---|
| 250 | 6-chloro-1-cyclopropyl-2-(pyridin-3-yl)-1H-benzimidazole | 270.01 |
| 251 | 2-(5-bromopyridin-3-yl)-6-chloro-1-cyclopropyl-1H-benzimidazole | 348.99 |
| 252 | 5-(6-chloro-1-cyclopropyl-1H-benzimidazol-2-yl)pyridine-3-carbonitrile | 295.01 |
| 253 | 6-chloro-1-cyclopropyl-2-(5-methoxy-4-methylpyridin-3-yl)-1H-benzimidazole | 314.1 |
| 254 | 6-chloro-1-cyclopropyl-2-(4-ethyl-5-fluoropyridin-3-yl)-1H-benzimidazole | 316.1 |
| 255 | 4-(6-chloro-1-cyclopropyl-1H-benzimidazol-2-yl)isoquinoline | 320.1 |
| 256 | 4-(5,7-difluoro-1-methyl-1H-benzimidazol-2-yl)isoquinoline | 295.93 |
| 257 | 4-(5,7-difluoro-1-methyl-1H-benzimidazol-2-yl)isoquinoline | 246.02 |

TABLE 6-continued

| Example | Structure | IUPAC Name | LCMS (M + 1) |
|---|---|---|---|
| 258 | 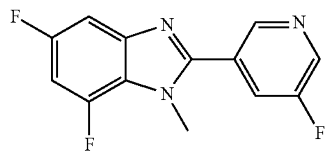 [SMILES: Cn1c(-c2cncc(F)c2)nc2cc(F)cc(F)c21] | 5,7-difluoro-2-(5-fluoropyridin-3-yl)-1-methyl-1H-benzimidazole | 264.06 |
| 259 | 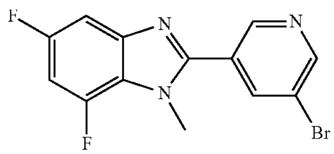 [SMILES: Cn1c(-c2cncc(Br)c2)nc2cc(F)cc(F)c21] | 2-(5-bromopyridin-3-yl)-5,7-difluoro-1-methyl-1H-benzimidazole | 325.96 |
| 260 | 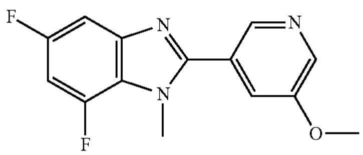 [SMILES: COc1cncc(-c2nc3cc(F)cc(F)c3n2C)c1] | 5,7-difluoro-2-(5-methoxypyridin-3-yl)-1-methyl-1H-benzimidazole | 276.13 |
| 261 | 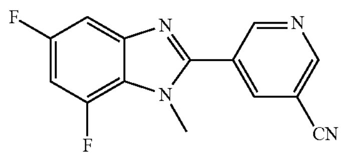 [SMILES: Cn1c(-c2cncc(C#N)c2)nc2cc(F)cc(F)c21] | 5-(5,7-difluoro-1-methyl-1H-benzimidazol-2-yl)pyridine-3-carbonitrile | 271.06 |
| 262 | 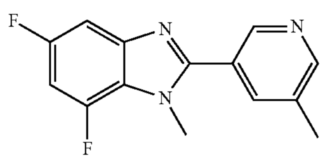 [SMILES: Cc1cncc(-c2nc3cc(F)cc(F)c3n2C)c1] | 5,7-difluoro-1-methyl-2-(5-methylpyridin-3-yl)-1H-benzimidazole | 260.08 |
| 263 | 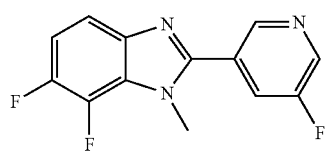 [SMILES: Cn1c(-c2cncc(F)c2)nc2ccc(F)c(F)c21] | 6,7-difluoro-2-(5-fluoropyridin-3-yl)-1-methyl-1H-benzimidazole | 264.21 |
| 264 | 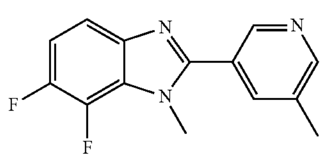 [SMILES: Cc1cncc(-c2nc3ccc(F)c(F)c3n2C)c1] | 6,7-difluoro-1-methyl-2-(5-methylpyridin-3-yl)-1H-benzimidazole | 260.23 |
| 265 | 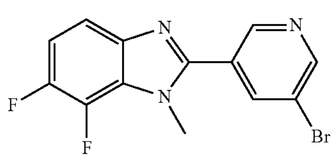 [SMILES: Cn1c(-c2cncc(Br)c2)nc2ccc(F)c(F)c21] | 2-(5-bromopyridin-3-yl)-6,7-difluoro-1-methyl-1H-benzimidazole | 324.95 |
| 266 | 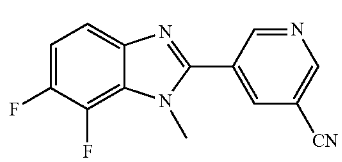 [SMILES: Cn1c(-c2cncc(C#N)c2)nc2ccc(F)c(F)c21] | 5-(6,7-difluoro-1-methyl-1H-benzimidazol-2-yl)pyridine-3-carbonitrile | 271.08 |

TABLE 6-continued

| Example | Structure | IUPAC Name | LCMS (M + 1) |
|---|---|---|---|
| 267 | 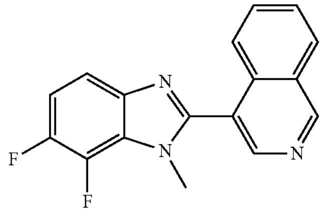 [SMILES: Cn1c(-c2cncc3ccccc23)nc2ccc(F)c(F)c21] | 5-(6,7-difluoro-1-methyl-1H-benzimidazol-2-yl)pyridine-3-carbonitrile | 296.09 |
| 268 | 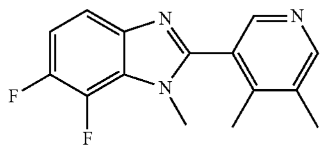 [SMILES: Cc1cncc(-c2nc3ccc(F)c(F)c3n2C)c1C] | 2-(4,5-dimethylpyridin-3-yl)-6,7-difluoro-1-methyl-1H-benzimidazole | 273.97 |
| 269 | 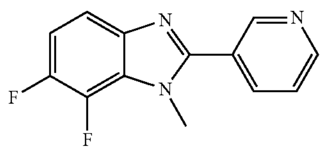 [SMILES: Cn1c(-c2cccnc2)nc2ccc(F)c(F)c21] | 6,7-difluoro-1-methyl-2-(pyridin-3-yl)-1H-benzimidazole | 246.08 |
| 270 | 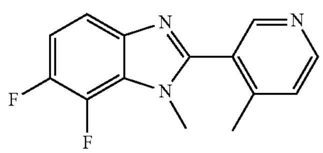 [SMILES: Cc1ccncc1-c1nc2ccc(F)c(F)c2n1C] | 6,7-difluoro-1-methyl-2-(4-methylpyridin-3-yl)-1H-benzimidazole | 260.12 |
| 271 | 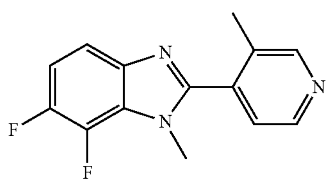 [SMILES: Cc1cnccc1-c1nc2ccc(F)c(F)c2n1C] | 6,7-difluoro-1-methyl-2-(3-methylpyridin-4-yl)-1H-benzimidazole | 260.14 |
| 272 | 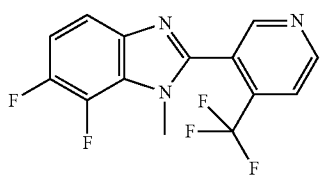 [SMILES: Cn1c(-c2cnccc2C(F)(F)F)nc2ccc(F)c(F)c21] | 6,7-difluoro-1-methyl-2-[4-(trifluoromethyl)pyridin-3-yl]-1H-benzimidazole | 314.11 |
| 273 | 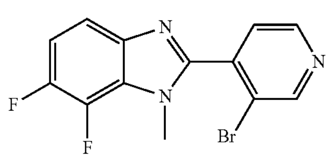 [SMILES: Cn1c(-c2ccncc2Br)nc2ccc(F)c(F)c21] | 2-(3-bromopyridin-4-yl)-6,7-difluoro-1-methyl-1H-benzimidazole | 323.99 |
| 274 | 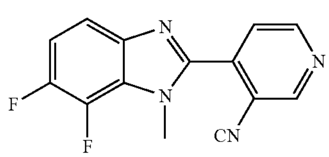 | 4-(6,7-difluoro-1-methyl-1H-benzimidazol-2-yl)pyridine-3-carbonitrile | 271.06 |
| 275 | 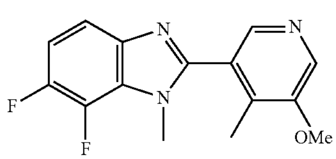 [SMILES: COc1cncc(-c2nc3ccc(F)c(F)c3n2C)c1C] | 6,7-difluoro-2-(5-methoxy-4-methylpyridin-3-yl)-1-methyl-1H-benzimidazole | 290.08 |

TABLE 6-continued

| Example | Structure | IUPAC Name | LCMS (M + 1) |
|---|---|---|---|
| 276 | 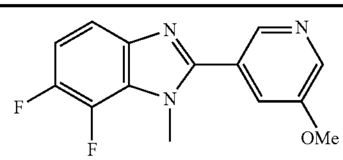 | 6,7-difluoro-2-(5-methoxypyridin-3-yl)-1-methyl-1H-benzimidazole | 276.05 |
| 277 | 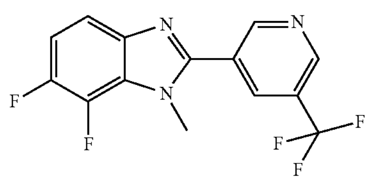 [SMILES: Cn1c(-c2cncc(C(F)(F)F)c2)nc2ccc(F)c(F)c21] | 6,7-difluoro-1-methyl-2-[5-(trifluoromethyl)pyridin-3-yl]-1H-benzimidazole | 314.05 |
| 278 | 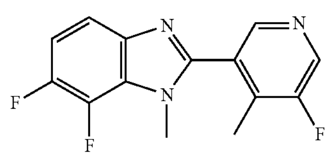 [SMILES: Cc1c(F)cncc1-c1nc2ccc(F)c(F)c2n1C] | 6,7-difluoro-2-(5-fluoro-4-methylpyridin-3-yl)-1-methyl-1H-benzimidazole | 278.04 |
| 279 | 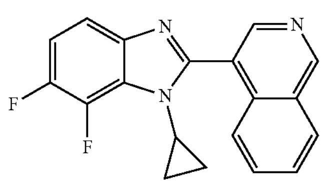 | 4-(1-cyclopropyl-6,7-difluoro-1H-benzimidazol-2-yl)isoquinoline | 322.24 |
| 280 | 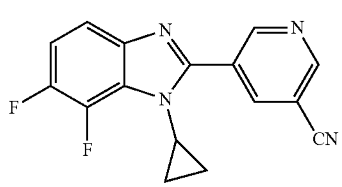 [SMILES: N#Cc1cncc(-c2nc3ccc(F)c(F)c3n2C2CC2)c1] | 5-(1-cyclopropyl-6,7-difluoro-1H-benzimidazol-2-yl)pyridine-3-carbonitrile | 297.08 |
| 281 | 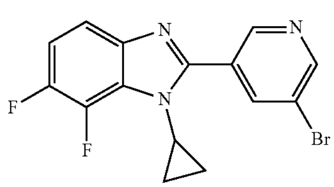 [SMILES: Fc1ccc2nc(-c3cncc(Br)c3)n(C3CC3)c2c1F] | 2-(5-bromopyridin-3-yl)-1-cyclopropyl-6,7-difluoro-1H-benzimidazole | 351.96 |
| 282 | 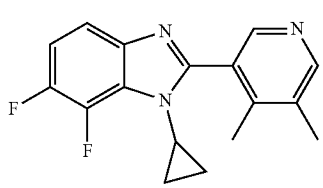 [SMILES: Cc1cncc(-c2nc3ccc(F)c(F)c3n2C2CC2)c1C] | 1-cyclopropyl-2-(4,5-dimethylpyridin-3-yl)-6,7-difluoro-1H-benzimidazole | 299.99 |
| 283 | 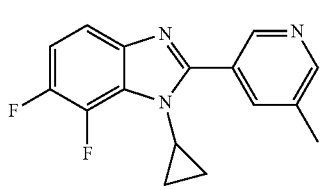 [SMILES: Cc1cncc(-c2nc3ccc(F)c(F)c3n2C2CC2)c1] | 1-cyclopropyl-6,7-difluoro-2-(5-methylpyridin-3-yl)-1H-benzimidazole | 286.13 |
| 284 | 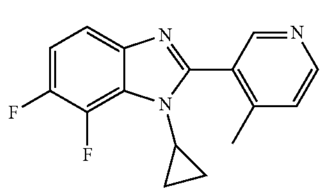 [SMILES: Cc1ccncc1-c1nc2ccc(F)c(F)c2n1C1CC1] | 1-cyclopropyl-6,7-difluoro-2-(4-methylpyridin-3-yl)-1H-benzimidazole | 286.11 |

TABLE 6-continued

| Example | Structure | IUPAC Name | LCMS (M + 1) |
|---|---|---|---|
| 285 | 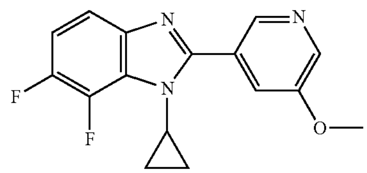 [SMILES: COc1cncc(-c2nc3ccc(F)c(F)c3n2C2CC2)c1] | 1-cyclopropyl-6,7-difluoro-2-(5-methoxypyridin-3-yl)-1H-benzimidazole | 302.15 |
| 286 | 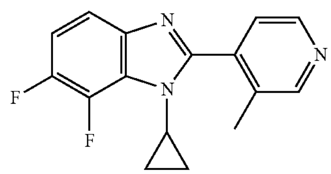 [SMILES: Cc1cnccc1-c1nc2ccc(F)c(F)c2n1C1CC1] | 1-cyclopropyl-6,7-difluoro-2-(3-methylpyridin-4-yl)-1H-benzimidazole | 286.15 |
| 287 | 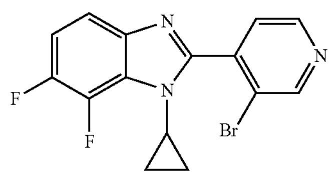 [SMILES: Fc1ccc2nc(-c3ccncc3Br)n(C3CC3)c2c1F] | 2-(3-bromopyridin-4-yl)-1-cyclopropyl-6,7-difluoro-1H-benzimidazole | 352.06 |
| 288 | 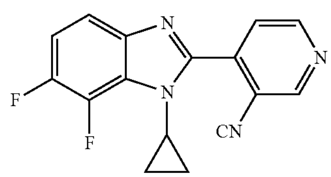 | 4-(1-cyclopropyl-6,7-difluoro-1H-benzimidazol-2-yl)pyridine-3-carbonitrile | 297.12 |
| 289 | 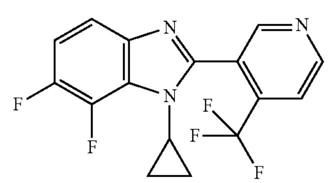 [SMILES: Fc1ccc2nc(-c3cnccc3C(F)(F)F)n(C3CC3)c2c1F] | 1-cyclopropyl-6,7-difluoro-2-[4-(trifluoromethyl)pyridin-3-yl]-1H-benzimidazole | 340.07 |
| 290 | 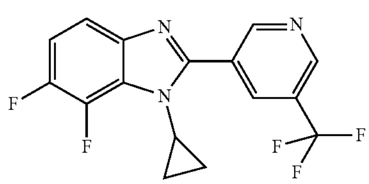 [SMILES: Fc1ccc2nc(-c3cncc(C(F)(F)F)c3)n(C3CC3)c2c1F] | 1-cyclopropyl-6,7-difluoro-2-[5-(trifluoromethyl)pyridin-3-yl]-1H-benzimidazole | 340.10 |
| 291 | 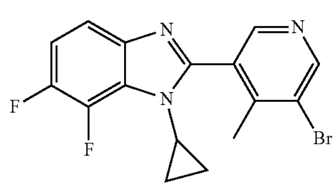 | 2-(5-bromo-4-methylpyridin-3-yl)-1-cyclopropyl-6,7-difluoro-1H-benzimidazole | 366.0 |
| 292 | 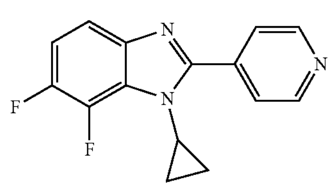 [SMILES: Fc1ccc2nc(-c3ccncc3)n(C3CC3)c2c1F] | 1-cyclopropyl-6,7-difluoro-2-(pyridin-4-yl)-1H-benzimidazole | 272.0 |

| Example | Structure | IUPAC Name | LCMS (M + 1) |
|---|---|---|---|
| 293 | 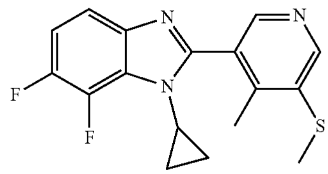 | 1-cyclopropyl-6,7-difluoro-2-[4-methyl-5-(methylsulfanyl) pyridin-3-yl]-1H-benzimidazole | 332.39 |
| 294 | 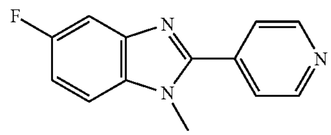 [SMILES: Cn1c(-c2ccncc2)nc2cc(F)ccc21] | 5-fluoro-1-methyl-2-(pyridin-4-yl)-1H-benzimidazole | 228.12 |
| 295 | 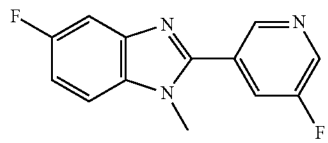 [SMILES: Cn1c(-c2cncc(F)c2)nc2cc(F)ccc21] | 5-fluoro-2-(5-fluoropyridin-3-yl)-1-methyl-1H-benzimidazole | 246.2 |
| 296 | 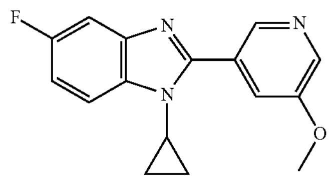 [SMILES: COc1cncc(-c2nc3cc(F)ccc3n2C2CC2)c1] | 1-cyclopropyl-5-fluoro-2-(5-methoxypyridin-3-yl)-1H-benzimidazole | 284.12 |
| 297 | 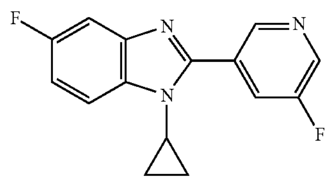 | 1-cyclopropyl-5-fluoro-2-(5-fluoropyridin-3-yl)-1H-benzimidazole | 272.14 |
| 298 | 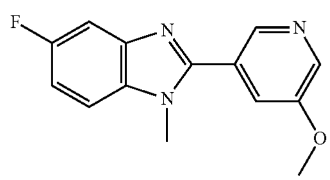 [SMILES: COc1cncc(-c2nc3cc(F)ccc3n2C)c1] | 5-fluoro-2-(5-methoxypyridin-3-yl)-1-methyl-1H-benzimidazole | 258.12 |
| 299 | 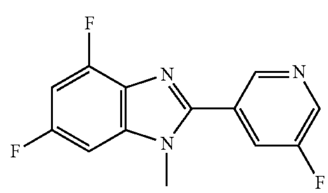 [SMILES: Cn1c(-c2cncc(F)c2)nc2c(F)cc(F)cc21] | 4,6-difluoro-2-(5-fluoropyridin-3-yl)-1-methyl-1H-benzimidazole | 264.22 |
| 300 | 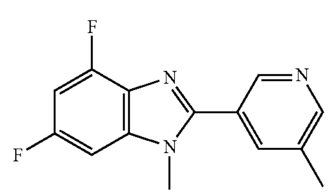 [SMILES: Cc1cncc(-c2nc3c(F)cc(F)cc3n2C)c1] | 4,6-difluoro-1-methyl-2-(5-methylpyridin-3-yl)-1H-benzimidazole | 260.11 |

TABLE 6-continued

| Example | Structure | IUPAC Name | LCMS (M + 1) |
| --- | --- | --- | --- |
| 301 | 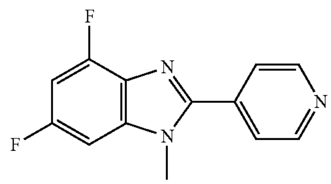 [SMILES: Cn1c(-c2ccncc2)nc2c(F)cc(F)cc21] | 4,6-difluoro-3-methyl-2-(pyridin-4-yl)-1H-benzimidazole | 246.11 |
| 302 | 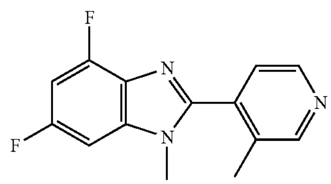 [SMILES: Cc1cnccc1-c1nc2c(F)cc(F)cc2n1C] | 2-(3-chloropyridin-4-yl)-4,6-difluoro-1-methyl-1H-benzimidazole | 280.11 |
| 303 | 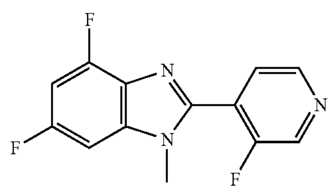 [SMILES: Cn1c(-c2ccncc2F)nc2c(F)cc(F)cc21] | 4,6-difluoro-2-(3-fluoropyridin-4-yl)-1-methyl-1H-benzimidazole | 264.22 |
| 304 | 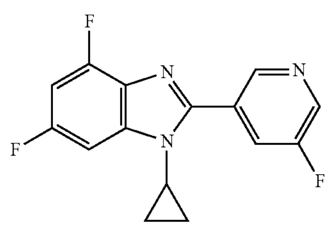 [SMILES: Fc1cncc(-c2nc3c(F)cc(F)cc3n2C2CC2)c1] | 1-cyclopropyl-4,6-difluoro-2-(5-fluoropyridin-3-yl)-1H-benzimidazole | 290.12 |
| 305 | 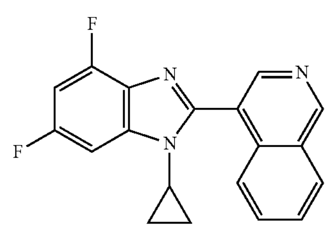 [SMILES: Fc1cc(F)c2nc(-c3cncc4ccccc34)n(C3CC3)c2c1] | 4-(1-cyclopropyl-4,6-difluoro-1H-benzimidazol-2-yl)isoquinoline | 322.11 |
| 306 | 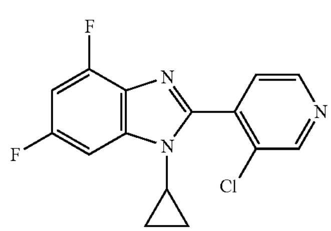 | 2-(3-chloropyridin-4-yl)-1-cyclopropyl-4,6-difluoro-1H-benzimidazole | 305.72 |
| 307 | 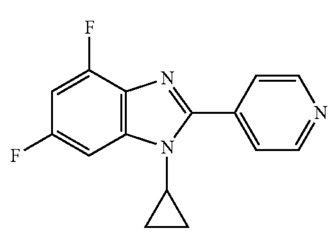 [SMILES: Fc1cc(F)c2nc(-c3ccncc3)n(C3CC3)c2c1] | 1-cyclopropyl-4,6-difluoro-2-(pyridin-4-yl)-1H-benzimidazole | 272.12 |

TABLE 6-continued

| Example | Structure | IUPAC Name | LCMS (M + 1) |
|---|---|---|---|
| 308 | 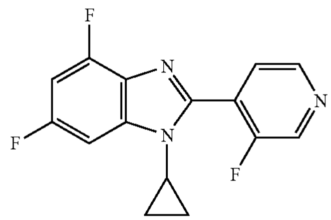 [SMILES: Fc1cc(F)c2nc(-c3ccncc3F)n(C3CC3)c2c1] | 1-cyclopropyl-4,6-difluoro-2-(3-fluoropyridin-4-yl)-1H-benzimidazole | 290.12 |
| 309 | 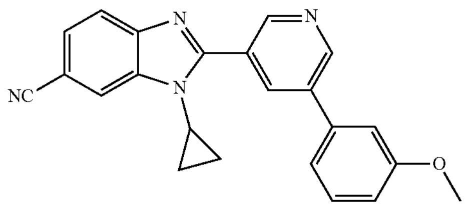 [SMILES: COc1cccc(-c2cncc(-c3nc4ccc(C#N)cc4n3C3CC3)c2)c1] | 1-cyclopropyl-2-[5-(3-methoxyphenyl)pyridin-3-yl]-1H-benzimidazole-6-carbonitrile | 367.43 |
| 310 | 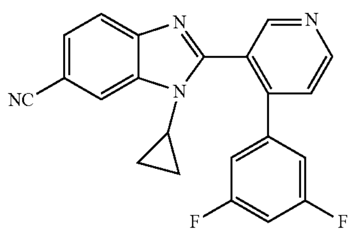 [SMILES: N#Cc1ccc2nc(-c3cnccc3-c3cc(F)cc(F)c3)n(C3CC3)c2c1] | 1-cyclopropyl-2-[4-(3,5-difluorophenyl)pyridin-3-yl]-1H-benzimidazole-6-carbonitrile | 373.38 |
| 311 | 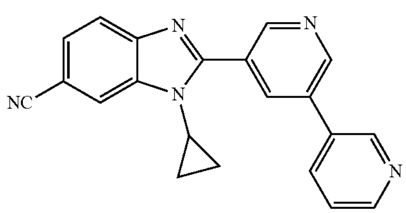 [SMILES: N#Cc1ccc2nc(-c3cncc(-c4cccnc4)c3)n(C3CC3)c2c1] | 2-(3,3'-bipyridin-5-yl)-1-cyclopropyl-1H-benzimidazole-6-carbonitrile | 338.4 |
| 312 | 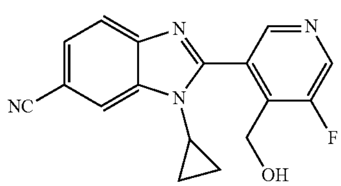 [SMILES: N#Cc1ccc2nc(-c3cncc(F)c3CO)n(C3CC3)c2c1] | 1-cyclopropyl-2-[5-fluoro-4-(hydroxymethyl)pyridin-3-yl]-1H-benzimidazole-6-carbonitrile | 310.2 |
| 313 | 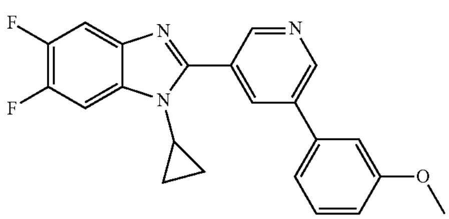 [SMILES: COc1cccc(-c2cncc(-c3nc4cc(F)c(F)cc4n3C3CC3)c2)c1] | 1-cyclopropyl-5,6-difluoro-2-[5-(3-methoxyphenyl)pyridin-3-yl]-1H-benzimidazole | 378.1 |
| 314 | 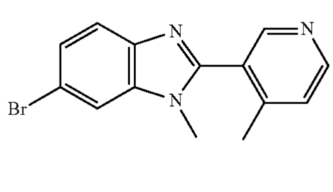 [SMILES: Cc1ccncc1-c1nc2ccc(Br)cc2n1C] | 6-bromo-1-methyl-2-(4-methyl-pyridin-3-yl)-1H-benzimidazole | 302 |

TABLE 6-continued

| Example | Structure | IUPAC Name | LCMS (M + 1) |
|---|---|---|---|
| 315 | 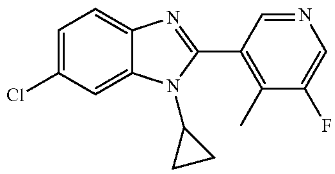 [SMILES: Cc1c(F)cncc1-c1nc2ccc(Cl)cc2n1C1CC1] | 6-chloro-1-cyclopropyl-2-(5-fluoro-4-methylpyridin-3-yl)-1H-benzimidazole | 302.75 |
| 316 | 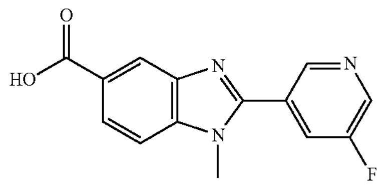 [SMILES: Cn1c(-c2cncc(F)c2)nc2cc(C(=O)O)ccc21] | 2-(5-fluoropyridin-3-yl)-1-methyl-1H-benzimidazole-5-carboxylic acid | 272.25 |
| 317 | 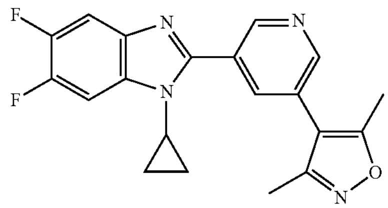 [SMILES: Cc1noc(C)c1-c1cncc(-c2nc3cc(F)c(F)cc3n2C2CC2)c1] | 1-cyclopropyl-2-[5-(3,5-dimethylisoxazol-4-yl)pyridin-3-yl]-5,6-difluoro-1H-benzimidazole | 367.37 |
| 318 | 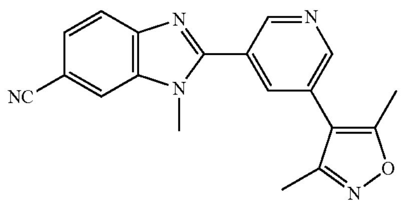 [SMILES: Cc1noc(C)c1-c1cncc(-c2nc3ccc(C#N)cc3n2C)c1] | 2-[5-(3,5-dimethylisoxazol-4-yl)pyridin-3-yl]-1-methyl-1H-benzimidazole-6-carbonitrile | 330.36 |
| 319 | 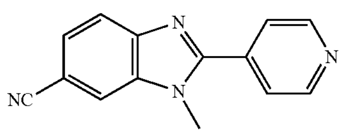 [SMILES: Cn1c(-c2ccncc2)nc2ccc(C#N)cc21] | 1-methyl-2-(pyridin-4-yl)-1H-benzimidazole-6-carbonitrile | 235.26 |
| 320 | 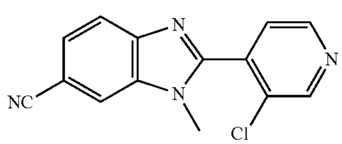 [SMILES: Cn1c(-c2ccncc2Cl)nc2ccc(C#N)cc21] | 2-(3-chloropyridin-4-yl)-1-methyl-1H-benzimidazole-6-carbonitrile | 269.71 |

EXAMPLE 321

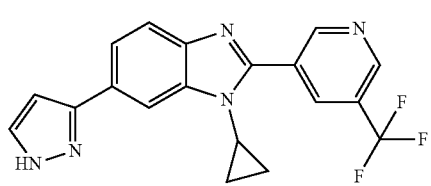 [SMILES: FC(F)(F)c1cncc(-c2nc3ccc(-c4cc[nH]n4)cc3n2C2CC2)c1]

1-Cyclopropyl-6-(1H-pyrazol-3-yl)-2-[5-(trifluoromethyl)pyridin-3-yl]-1H-benzimidazole

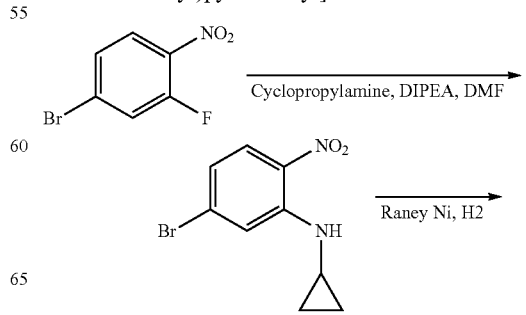

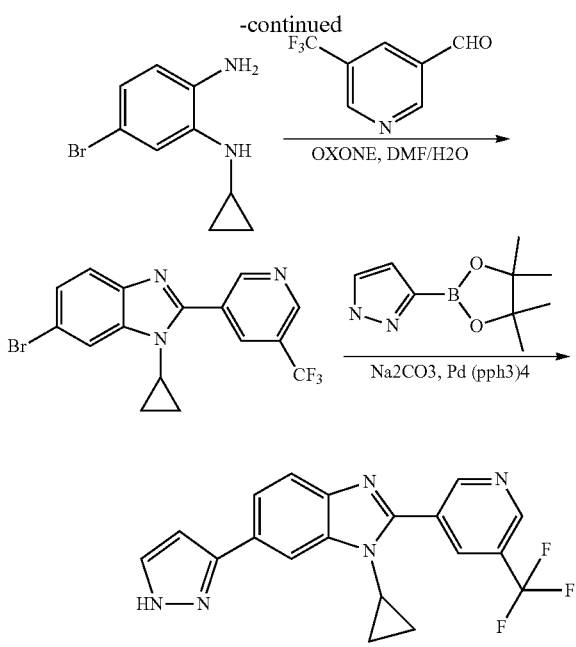

Step A. (5-bromo-2-nitro-phenyl)-cyclopropylamine

To solution of 4-bromo-2-fluoronitrobenzene (2M g, 0.0091 mol) in DMF (10 ml) was added carefully DIPEA (3.25 ml, 0.0182 mol) and cyclopropylamine (0.7 ml, 0.0091 mol) and the resulting solution was stirred at room temperature for 14 h. The reaction was quenched with ice-water and extracted with diethyl ether (3×100 ml). The combined organic layers were washed with brine dried over $Na_2SO_4$ and concentrated under vacuum to afford the title compound (5-bromo-2-nitro-phenyl)-cyclopropylamine as a yellow solid. $C_9H_9BrN_2O_2$; $^1H$ NMR (400 MHz, DMSO-$d_6$), δ: 8.08 (brs, 1H), 8.02-7.99 (d, J=8.8 Hz, 1H), 7.47 (s, 1H), 7.26 (s, 1H), 6.82-6.79 (dd, J=8.8 Hz, 1.6 Hz, 1H), 2.58-2.54 (m, 1H), 0.97-0.88 (m, 2H), 0.69-0.65 (m, 2H). MS (M+1): 258.

Step B. 4-bromo-N-cyclopropyl-benzene-1,2-diamine

A stirred solution of (5-bromo-2-nitro-phenyl)-cyclopropylamine (1.0 g, 0.0038 mol) in MeOH (20 ml) was hydrogenated using Raney-Ni for 12 h at room temperature. The reaction mixture was filtered through CELITE® and the filter bed was thoroughly washed with methanol. The resulting solution was concentrated under vacuum to provide 4-Bromo-N-cyclopropyl-benzene-1,2-diamine as a black sticky solid. $C_9H_{11}BrN_2$; Crude $^1H$ NMR (400 MHz, DMSO-$d_6$), δ: 6.80 (d, J=2.0 Hz, 1H), 6.67-6.65 (d, J=6.8 Hz, 1H), 6.55-6.62 (m, 1H), 5.28 (brs, 1H), 4.73 (brs, 1H), 2.40-2.30 (m, 1H), 0.73-0.69 (m, 2H), 0.40-0.39 (m, 2H). MS (M+1): 228.

Step C. 6-bromo-1-cyclopropyl-2-(5-trifluoromethyl-pyridin-3-yl)-1H-benzoimidazole To a solution of 4-bromo-N-cyclopropyl-benzene-1,2-diamine (0.5 g, 0.0022 mol) and 5-trifluoromethyl-pyridine-3-carbaldehyde (0.38 g, 0.0022 mol) in DMF (5 ml) and water (2 ml) was added OXONE® monopersulphate (1.62 g, 0.00264 mol). Reaction mixture was stirred at room temperature for 3 h. The reaction mixture was diluted with 10% $K_2CO_3$ solution to pH~8-10 and extracted with EtOAc (3×20 ml). The combined organic layers were washed with brine dried over $Na_2SO_4$ and concentrated under vacuum to afford the crude compound which was purified by column chromatography to obtain title compound 6-bromo-1-cyclopropyl-2-(5-trifluoromethyl-pyridin-3-yl)-1H-benzoimidazole.

Step D. 1-cyclopropyl-6-(1H-pyrazol-3-yl)-2-[5-(trifluoromethyl)pyridin-3-yl]-1H-benzimidazole (321)

To a solution of 6-bromo-1-cyclopropyl-2-(5-trifluoromethyl-pyridin-3-yl)-1H-benzoimidazole (0.15 g, 0.00026 mol) in ethanol toluene water (6 ml 3 ml 1.5 ml respectively) mixture in a sealed tube was added 3-(4,4,5,5-tetramethyl-[1,3,2]dioxaborolan-2-yl)-1H-pyrazole (0.1 g, 0.00052 mol) and $Na_2CO_3$ (0.082 g, 0.000785 mol) and argon was purged for 15 min. Then Pd (PPh$_3$)$_4$ (0.015 g, 0.000013 mol) was added and heated at 80° C. for 5 h. The solvent was evaporated and the resulting residue was added water. The aqueous layer was extracted with ethyl acetate (3×20 ml). The combined organic layers were washed with brine dried over $Na_2SO_4$ and concentrated under vacuum to afford the crude compound which was purified by column chromatography to obtain title compound 1-cyclopropyl-6-(1H-pyrazol-3-yl)-2-[5-(trifluoromethyl)pyridin-3-yl]-1H-benzimidazole (321) as an off white solid. NMR (400 MHz, DMSO-$d_6$), δ: 12.85 (s, 1H), 9.49 (s, 1H), 9.12 (s, 1H), 8.75 (s, 1H), 8.09 (s, 1H), 7.79-7.67 (m, 3H), 7.54-7.52 (m, 1H), 6.79 (s, 1H), 3.96 (bs, 1H), 1.15 (d, J=5.6 Hz, 2H), 0.73 (bs, 2H). MS (M+1): 370.6, Purity 99.94%.

The compounds in Table 7 were prepare following the synthetic procedure as described in Example 321

TABLE 7

| Example | Structure | IUPAC Name | LCMS (M + 1) |
|---|---|---|---|
| 322 | 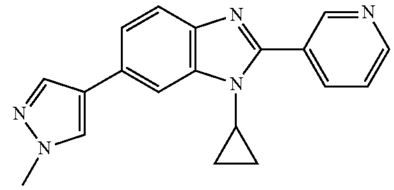 [SMILES: Cn1cc(-c2ccc3nc(-c4cccnc4)n(C4CC4)c3c2)cn1] | 1-cyclopropyl-6-(1-methyl-1H-pyrazol-4-yl)-2-(pyridin-3-yl)-1H-benzimidazole | 317.2 |

TABLE 7-continued

| Example | Structure | IUPAC Name | LCMS (M + 1) |
|---|---|---|---|
| 323 | 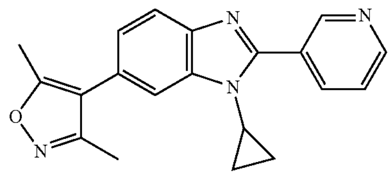 [SMILES: Cc1noc(C)c1-c1ccc2nc(-c3cccnc3)n(C3CC3)c2c1] | 1-cyclopropyl-6-(3,5-dimethylisoxazol-4-yl)-2-(pyridin-3-yl)-1H-benzimidazole | 331.6 |
| 324 | 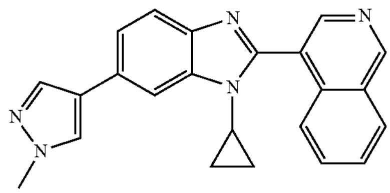 [SMILES: Cn1cc(-c2ccc3nc(-c4cncc5ccccc45)n(C4CC4)c3c2)cn1] | 4-[1-cyclopropyl-6-(1-methyl-1H-pyrazol-4-yl)-1H-benzimidazol-2-yl]isoquinoline | 366.5 |
| 325 | 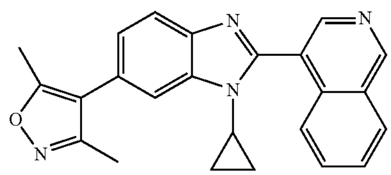 [SMILES: Cc1noc(C)c1-c1ccc2nc(-c3cncc4ccccc34)n(C3CC3)c2c1] | 4-[1-cyclopropyl-6-(3,5-dimethylisoxazol-4-yl)-1H-benzimidazol-2-yl]isoquinoline | 382.2 |
| 326 | 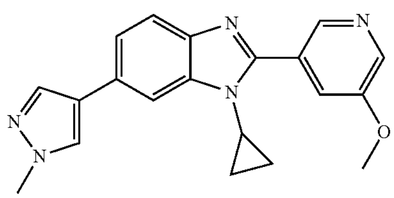 [SMILES: COc1cncc(-c2nc3ccc(-c4cnn(C)c4)cc3n2C2CC2)c1] | 1-cyclopropyl-2-(5-methoxypyridin-3-yl)-6-(1-methyl-1H-pyrazol-4-yl)-1H-benzimidazole | 346.6 |
| 327 | 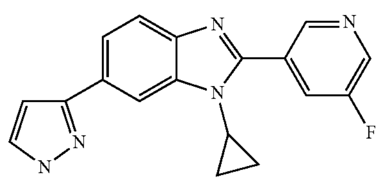 [SMILES: Fc1cncc(-c2nc3ccc(-c4cc[nH]n4)cc3n2C2CC2)c1] | 1-cyclopropyl-2-(5-fluoropyridin-3-yl)-6-(1H-pyrazol-3-yl)-1H-benzimidazole | 318.1 |
| 328 | 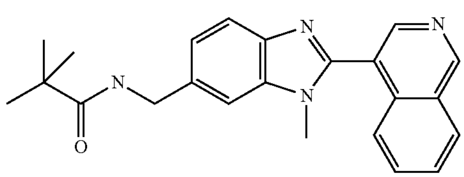 [SMILES: Cn1c(-c2cncc3ccccc23)nc2ccc(CNC(=O)C(C)(C)C)cc21] | N-{[2-(isoquinolin-4-yl)-1-methyl-1H-benzimidazol-6-yl]methyl}-2,2-dimethylpropanamide | 373.22 |
| 329 | 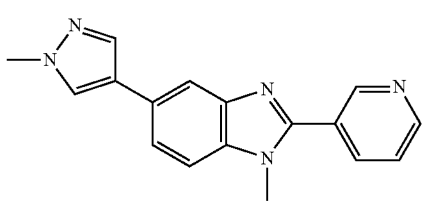 [SMILES: Cn1cc(-c2ccc3c(c2)nc(-c2cccnc2)n3C)cn1] | 1-methyl-5-(1-methyl-1H-pyrazol-4-yl)-2-(pyridin-3-yl)-1H-benzimidazole | 290.19 |
| 330 | 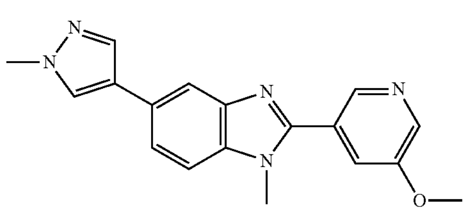 | 2-(5-methoxypyridin-3-yl)-1-methyl-5-(1-methyl-1H-pyrazol-4-yl)-1H-benzimidazole | 320.11 |

TABLE 7-continued

| Example | Structure | IUPAC Name | LCMS (M + 1) |
|---|---|---|---|
| 331 | 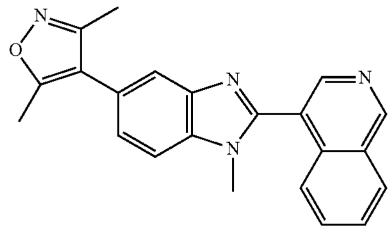 [SMILES: Cc1noc(C)c1-c1ccc2c(c1)nc(-c1cncc3ccccc13)n2C] | 5-(3,5-dimethylisoxazol-4-yl)-6-fluoro-2-(5-methoxypyridin-3-yl)-1-methyl-1H-benzimidazole | 355.14 |
| 332 | 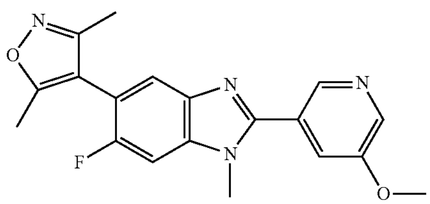 [SMILES: COc1cncc(-c2nc3cc(-c4c(C)noc4C)c(F)cc3n2C)c1] | 5-(3,5-dimethylisoxazol-4-yl)-6-fluoro-2-(5-methoxypyridin-3-yl)-1-methyl-1H-benzimidazole | 353.14 |
| 333 | 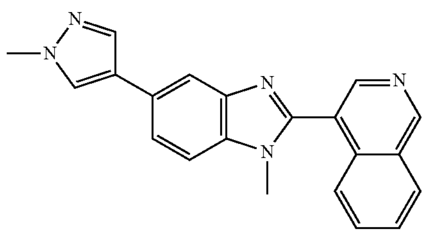 [SMILES: Cn1cc(-c2ccc3c(c2)nc(-c2cncc4ccccc24)n3C)cn1] | 4-[1-methyl-5-(1-methyl-1H-pyrazol-4-yl)-1H-benzimidazol-2-yl]isoquinoline | 340.20 |
| 334 | 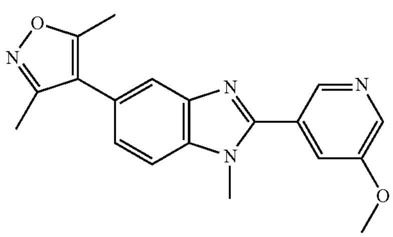 [SMILES: COc1cncc(-c2nc3cc(-c4c(C)noc4C)ccc3n2C)c1] | 5-(3,5-dimethylisoxazol-4-yl)-2-(5-methoxy-pyridin-3-yl)-1-methyl-1H-benzimidazole | 335.17 |

EXAMPLE 335

6-Chloro-5-fluoro-1-methyl-2-[4-(trifluoromethyl)pyridin-3-yl]-1/1-benzimidazole

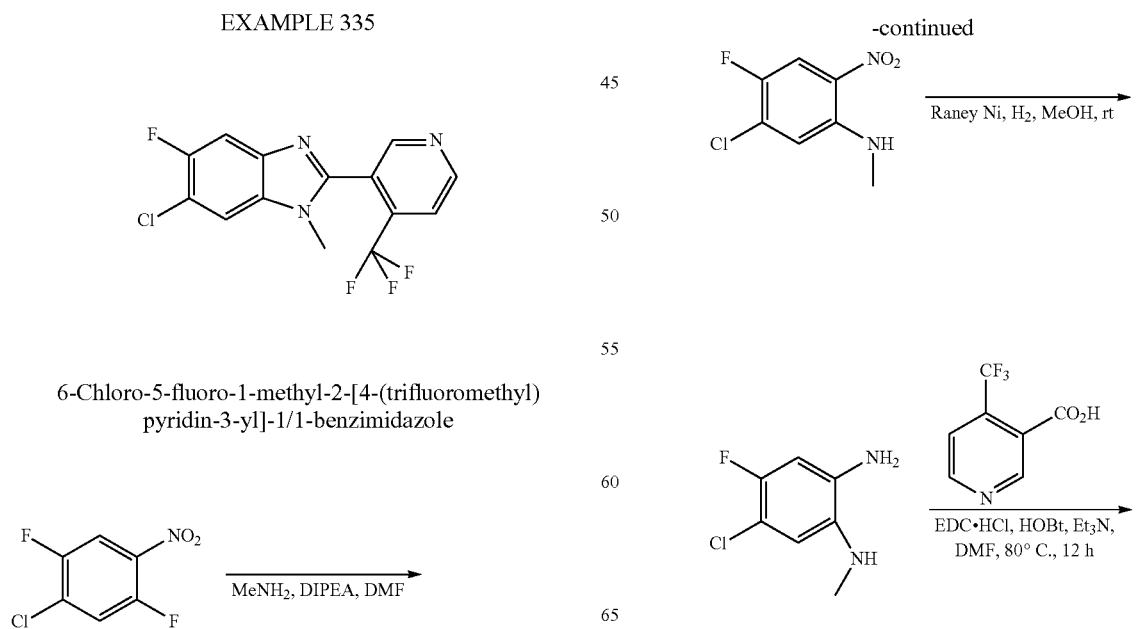

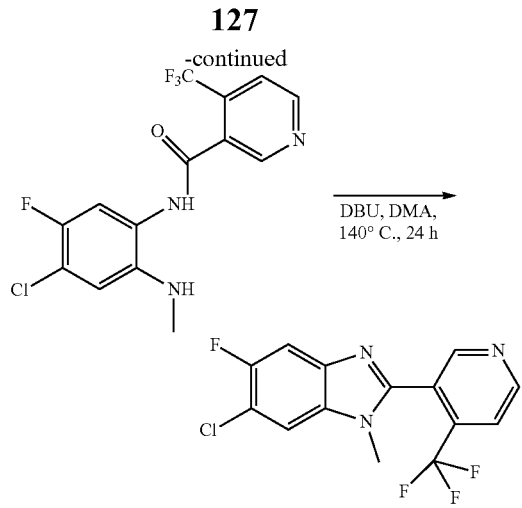

Step A. 5-chloro-4-fluoro-N-methyl-2-nitroaniline

To a solution of 4-chloro 2,5-difluoro nitrobenzene (2.0 g, 0.010 mol) in DMF (15 ml) was added DIPEA (4.5 ml, 0.026 mol) followed by MeNH$_2$ (5 ml, 0.010 mol, 2M in THF) and the resulting solution was stirred at room temperature for 12 h. The reaction was quenched with H$_2$O and extracted with EtOAc (3×30 ml). The combined organic layers were washed with brine dried over Na$_2$SO$_4$ and concentrated under vacuum to get crude product which was purified column chromatography to get the title compound 5-chloro-4-fluoro-N-methyl-2-nitroaniline as a yellow solid, $^1$H NMR (400 MHz, DMSO-d$_6$), δ: 8.20 (s, 1H), 8.09 (d, J=10 Hz, 1H), 7.22-7.20 (d, J=6.4 Hz, 1H), 2.95 (s, 3H). MS (M+1): 205.12

Step B. 5-chloro-4-fluoro-N1-methylbenzene-1 2-diamine

A stifled solution of 5-chloro-4-fluoro-N-methyl-2-nitroaniline (8; 1.5 g, 0.0078 mol) in MeOH (20 ml) was hydrogenated using Raney Ni for 6 h at room temperature. The reaction was filtered through CELITE® and the filter bed was thoroughly washed with MeOH. The resulting solution was concentrated to provide 5-chloro-4-fluoro-N1-methylbenzene-1 2-diamine as a brownish solid. $^1$H NMR (400 MHz, DMSO-d$_6$), δ: 6.49-6.47 (d, 11.6 Hz, 1H), 6.30-6.28 (d, J=7.6 Hz, 1H) 4.96 (bs, 2H), 4.74 (bs, 1H), 2.67 (s, 3H). MS (M+1): 175.1.

Step C. N-(4-chloro-5-fluoro-2-(methyl amino)phenyl)-4-(tri-fluoromethyl)nicotinamide To the solution of compound 5-chloro-4-fluoro-N1-methylbenzene-1 2-diamine (0.3 g, 0.00172 mol) and 4-trifluoromethylnicotinic acid (0.36 g, 0.00189 mol) in DMF (5 ml) was added EDC-HCl (0.27 g, 0.00206 mol) followed by HOBt (0.39 g, 0.00206 mol) and Et$_3$N (0.047 g, 0.00344 mol). Reaction mixture was heated at 80° C. for 12 h. Reaction mass was quenched with ice water and layers were separated. The aqueous layer was extracted with EtOAc (3×10 ml). The combined organic extracts were washed with sat NaHCO$_3$ solution and brine dried over Na$_2$SO$_4$ and concentrated to get crude product which was purified by column chromatography to provide N-(4-chloro-5-fluoro-2-(methyl amino)phenyl)-4-(tri-fluoromethyl)nicotinamide as a brown colored solid. $^1$H NMR (400 MHz, DMSO-d$_6$), δ: 10.08 (s, 1H), 9.20 (s, 1H), 8.99-8.98 (d, J=4.8 Hz, 1H), 8.75-8.74 (d, J=4.8 Hz, 1H), 7.91-7.89 (d, J=5.2 Hz, 1H), 7.39-7.37 (d, J=10.4 Hz, 1H), 6.72-6.71 (d, J=7.2 Hz, 1H), 5.36 (bs, 1H), 2.74-2.73 (d, J=4.0 Hz, 3H). MS (M+1): 348.12.

Step D. 6-chloro-5-fluoro-1-methyl-2-[4-(trifluoromethyl)pyridin-3-yl]-1H-benzimidazole (335)

To the solution of compound N-(4-chloro-5-fluoro-2-(methylamino) phenyl)-4-(tri-fluoromethyl) nicotinamide (0.1 g, 0.0028 mol) in DMA (5 ml) was added DBU (0.05 g, 0.0037 mol). Reaction mixture was heated at 140° C. for 24 h. Reaction mass was quenched with ice water and layers were separated. The aqueous layer was extracted with EtOAc (3×10 ml). The combined organic extracts were washed with brine dried over Na$_2$SO$_4$ and concentrated to get crude product which was purified by column chromatography to provide 6-chloro-5-fluoro-1-methyl-2-[4-(trifluoromethyl)pyridin-3-yl]-1H-benzimidazole 335; as a white colored solid. $^1$H NMR (400 MHz, DMSO-d$_6$), δ: 9.11-9.09 (d, J=5.2 Hz, 1H), 9.03 (s, 1H), 8.07-8.04 (m, 2H), 7.82-7.79 (d, J=10 Hz, 1H), 3.65 (s, 3H). MS (M+1): 330.12, Purity 99.52%.

The compounds in Table 8 were prepared following the synthetic procedure as described in Example 335.

TABLE 8

| Example | Structure | IUPAC Name | LCMS (M + 1) |
|---------|-----------|------------|--------------|
| 336 | 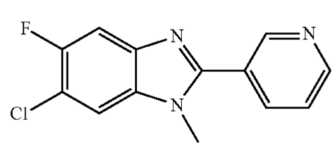 [SMILES: Cn1c(-c2cccnc2)nc2cc(F)c(Cl)cc21] | 6-chloro-5-fluoro-1-methyl-2-(pyridin-3-yl)-1H-benzimidazole | 262.01 |
| 337 | 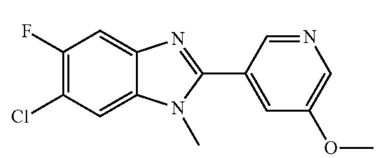 | 6-chloro-5-fluoro-2-(5-methoxypyridin-3-yl)-1-methyl-1H-benzimidazole | 292.01 |

TABLE 8-continued

| Example | Structure | IUPAC Name | LCMS (M + 1) |
|---|---|---|---|
| 338 | 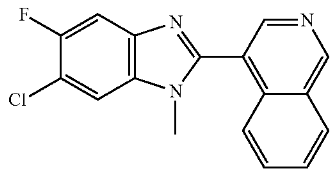 [SMILES: Cn1c(-c2cncc3ccccc23)nc2cc(F)c(Cl)cc21] | 4-(6-chloro-5-fluoro-1-methyl-1H-benzimidazol-2-yl)isoquinoline | 312.07 |
| 339 | 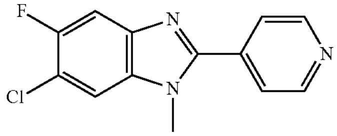 [SMILES: Cn1c(-c2ccncc2)nc2cc(F)c(Cl)cc21] | 6-chloro-5-fluoro-1-methyl-2-(pyridin-4-yl)-1H-benzimidazole | 262.68 |
| 340 | 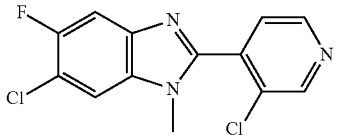 [SMILES: Cn1c(-c2ccncc2Cl)nc2cc(F)c(Cl)cc21] | 6-chloro-2-(3-chloropyridin-4-yl)-5-fluoro-1-methyl-1H-benzimidazole | 297.13 |
| 341 | 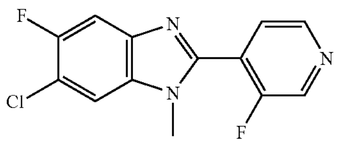 | 6-chloro-5-fluoro-2-(3-fluoropyridin-4-yl)-1-methyl-1H-benzimidazole | 280.67 |

EXAMPLE 342 AND 343

1-Methoxy-5-(methylsulfinyl)-2-(pyridin-3-yl)-1H-benzimidazole and 1-Methoxy-5-(methylsulfonyl)-2-(pyridin-3-yl)-1H-benzimidazole

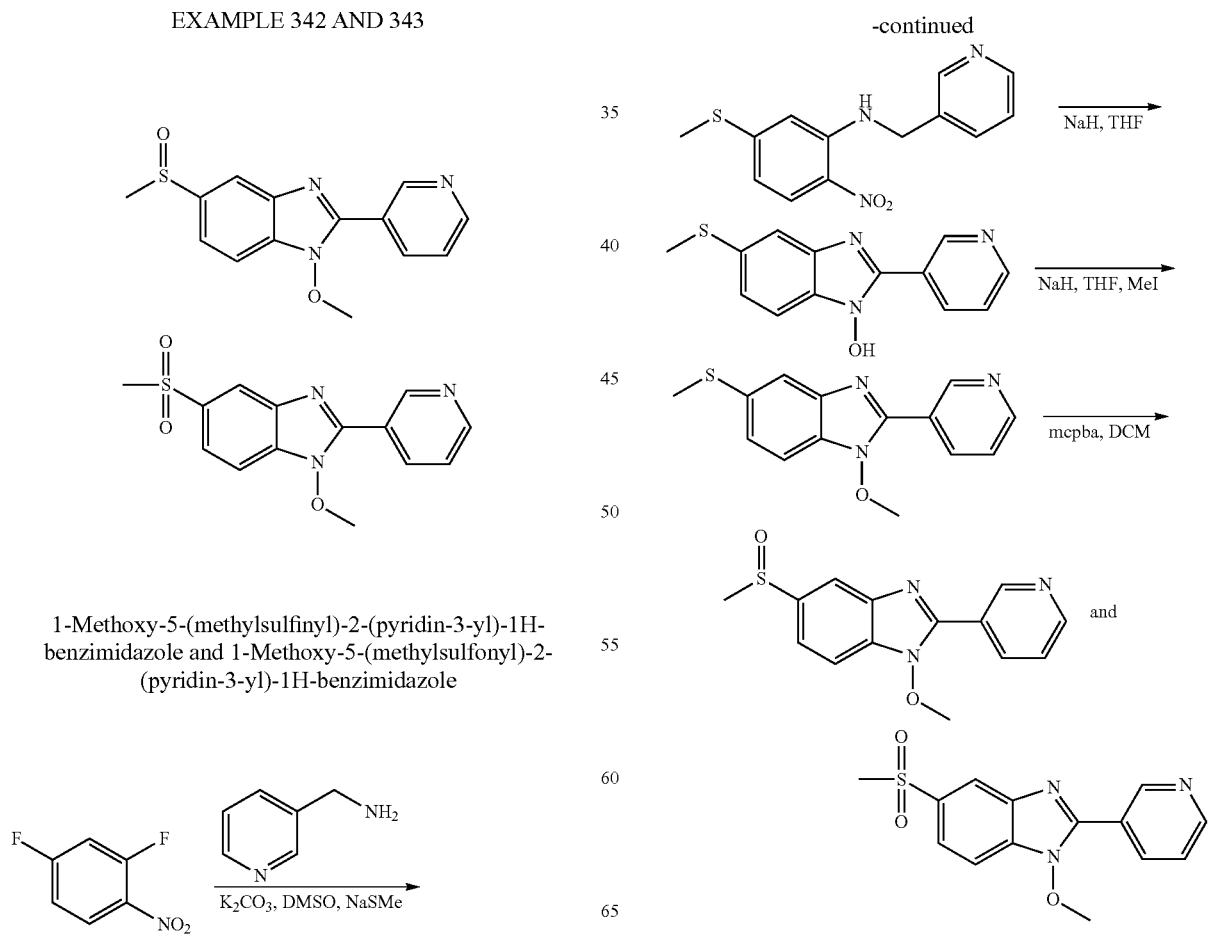

Step A. 5-(methyl-thio)-2-nitro-N-(pyridin-3-ylmethyl)aniline

To a stirred solution of 2,4-difluoro-1-nitrobenzene (2 g, 0.012 mol) in DMSO (60 ml) was added K$_2$CO$_3$ (5.2 g, 0.037 mol). Then pyridin-3-ylmethanamine (1.05 g, 0.013 mol) was added drop wise and the resulting solution was continued to stir at room temperature for 6 h. After complete conversion of 2,4-difluoro-1-nitrobenzene monitored by MS sodium thiomethoxide (1.2 g, 0.013 mol) was added and heated at 60° C. for the next 12 h. The reaction was diluted with ice cold water and extracted with ethyl acetate (3×100 ml). The combined organic layers were washed with brine dried over Na$_2$SO$_4$ and concentrated under vacuum to afford the crude compound which was purified by chromatography to obtain title compound 5-(methyl-thio)-2-nitro-N-(pyridin-3-ylmethyl) aniline as a yellow solid. $^1$H NMR (400 MHz, CDCl$_3$), δ: 8.65 (s, 1H), 8.58 (s, 2H), 8.11-8.09 (d, J=9.2 Hz, 1H), 7.69-7.67 (d, J=7.6 Hz, 1H), 7.33-7.29 (m, 1H), 6.54-6.51 (dd, J=7.2 Hz, J=1.6 Hz, 1H), 6.43 (s, 1H), 4.58-4.57 (d, J=5.6 Hz, 2H), 2.48 (s, 3H). MS (M+1): 276.

Step B. 5-(methyl-thio)-2-(pyridin-3-yl)-1H-benzo[d]imidazol-1-ol

To a stirred solution of 5-(methyl-thio)-2-nitro-N-(pyridin-3-ylmethyl) aniline (0.8 g, 0.002 mol) in THF (20 ml) was added NaH (60% suspension in mineral oil), (0.14 g, 0.006 mol) and the resulting solution was continued to stir at 60° C. for 8 h. The reaction was quenched with ice chips and extracted with dichloromethane (3×100 ml). The combined organic layers were washed with brine dried over Na$_2$SO$_4$ and concentrated under vacuum to afford to afford the crude compound which was purified by chromatography to obtain title compound 5-(methyl-thio)-2-(pyridin-3-yl)-1H-benzo[d]imidazol-1-ol as an off white solid. $^1$H NMR (400 MHz, DMSO-d$_6$), δ: 12.28 (bs, 1H), 9.36 (s, 1H), 8.71-8.70 (m, 1H), 8.55-8.53 (d, J=8 1H), 7.62-7.59 (m, 2H), 7.52-7.50 (d, J=8 Hz, 1H), 7.28-7.26 (dd, J=1.2 Hz, J=8 Hz, 1H), 2.53 (s, 3H). MS (M+1): 258.

Step C. 1-methoxy-5-(methyl-thio)-2-(pyridin-3-yl)-1H-benzo[d]imidazole

To a stirred solution of 5-(methyl-thio)-2-(pyridin-3-yl)-1H-benzo[d]imidazol-1-ol (0.36 g, 0.001 mol) in THF (20 ml) NaH (60% suspension in mineral oil), (0.14 g, 0.003 mol) was added. After stirring for the next 20 min at room temperature methyl iodide (0.39 g, 0.002 mol) was added drop wise. The resulting solution was continued to stir at room temperature for the next 3 h. The reaction was quenched with ice cold water and extracted with ethyl acetate (3×100 ml). The combined organic layers were washed with brine dried over Na$_2$SO$_4$ and concentrated under vacuum to afford to afford the crude compound which was purified by chromatography to obtain title compound 1-methoxy-5-(methyl-thio)-2-(pyridin-3-yl)-1H-benzo[ ]imidazole as a stick brown solid. $^1$H NMR (400 MHz, DMSO-d$_6$), δ 9.47 (s, 1H), 8.74-8.73 (m, 1H), 8.53-8.50 (m, 1H), 7.71 (s, 1H), 7.49-7.33 (m, 3H), 4.05 (s, 3H) 2.58 (s, 3H). MS (M+1): 272.

Step D. 1-methoxy-5-(methylsulfinyl)-2-(pyridin-3-yl)-1H-benzimidazole (342) and 1-methoxy-5-(methylsulfonyl)-2-(pyridin-3-yl)-1H-benzimidazole (343)

To a stirred solution of 1-methoxy-5-(methyl-thio)-2-(pyridin-3-yl)-1H-benzo[d]imidazole (0.22 g, 0.0008 mol) in DCM (15 ml) m-chloroperbenzoic acid (0.21 g, 0.00 mol) solution in DCM (5 ml) was added at 0° C. Then the reaction mixture was allowed to stir for the next 1 h at room temperature. Two spots were observed by TLC. The reaction was diluted with cold water and extracted with dichloromethane (3×100 ml). The combined organic layers were washed with brine dried over Na$_2$SO$_4$ and concentrated under vacuum to afford the crude compound which was purified by chromatography and isolated the both 1-methoxy-5-(methylsulfinyl)-2-(pyridin-3-yl)-1H-benzimidazole (342) as an off white solid and 1-methoxy-5-(methylsulfonyl)-2-(pyridin-3-yl)-1H-benzimidazole (343) as a off white solid. Compound 342: $^1$H NMR (400 MHz, CDCl$_3$), δ: 9.49 (s, 1H), 8.78-8.77 (d, J=4.4 Hz, 1H), 8.56-8.54 (d, J=8 Hz, 1H), 8.07 (s, 1H), 7.74-7.68 (m, 2H), 7.52-7.49 (m, 1H), 4.07 (s, 3H), 2.78 (s, 3H). MS (M+1): 288, Purity 98.37%; Compound 343: $^1$H NMR (400 MHz, CDCl$_3$), δ: 9.50 (s, 1H), 8.11-8.00 (d, J=4.4 Hz, 1H), 8.57-8.55 (d, J=8 Hz, 1H), 8.43 (s, 1H), 7.97-7.95 (d, J=8.4 Hz, 1H), 7.70-7.68 (d, J=8.4 Hz, 1H), 7.54-7.51 (m, 1H), 4.085 (s, 3H), 3.12 (s, 3H). MS (M+1): 304; Purity 98.58%.

The compound in Table 9 were prepared following the synthetic procedure as described in Examples 342 and 343

TABLE 9

| Example | Structure | IUPAC Name | LCMS (M + 1) |
| --- | --- | --- | --- |
| 344 | 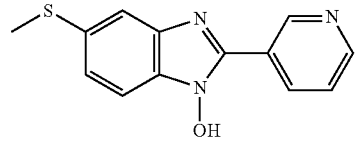 [SMILES: CSc1ccc2c(c1)nc(-c1cccnc1)n2O] | 5-(methylsulfanyl)-2-(pyridin-3-yl)-1H-benzimidazol-1-ol | 258.05 |
| 345 | 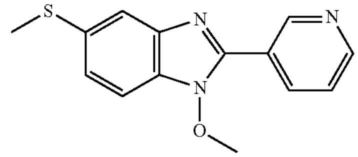 [SMILES: COn1c(-c2cccnc2)nc2cc(SC)ccc21] | 1-methoxy-5-(methylsulfanyl)-2-(pyridin-3-yl)-1H-benzimidazole | 272.06 |

TABLE 9-continued

| Example | Structure | IUPAC Name | LCMS (M + 1) |
|---------|-----------|------------|--------------|
| 346 | 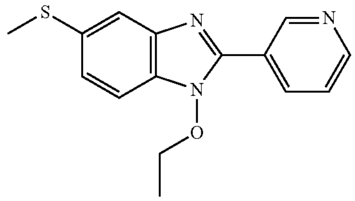 [SMILES: CCOn1c(-c2cccnc2)nc2cc(SC)ccc21] | 1-methoxy-5-(methylsulfanyl)-2-(pyridin-3-yl)-1H-benzimidazole | 286.09 |
| 347 | 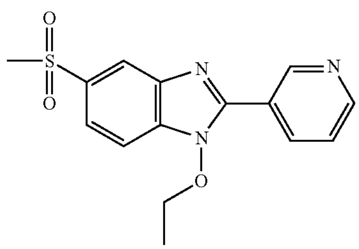 [SMILES: CCOn1c(-c2cccnc2)nc2cc(S(C)(=O)=O)ccc21] | 1-ethoxy-5-(methylsulfonyl)-2-(pyridin-3-yl)-1H-benzimidazole | 318.12 |
| 348 | 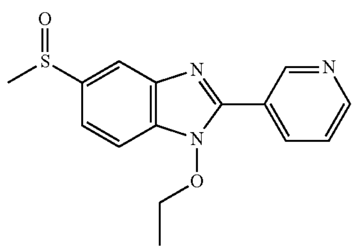 [SMILES: CCOn1c(-c2cccnc2)nc2cc(S(C)=O)ccc21] | 1-ethoxy-5-(methylsulfinyl)-2-(pyridin-3-yl)-1H-benzimidazole | 302.09 |
| 349 | 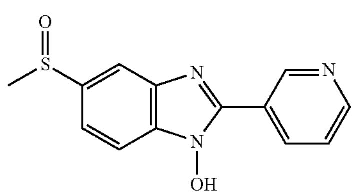 [SMILES: CS(=O)c1ccc2c(c1)nc(-c1cccnc1)n2O] | 5-(methylsulfinyl)-2-(pyridin-3-yl)-1H-benzimidazol-1-ol | 274.31 |
| 350 | 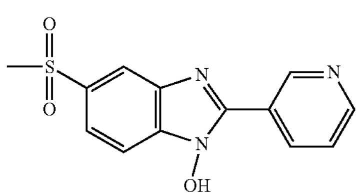 [SMILES: CS(=O)(=O)c1ccc2c(c1)nc(-c1cccnc1)n2O] | 5-(methylsulfonyl)-2-(pyridin-3-yl)-1H-benzimidazol-1-ol | 290.31 |
| 351 | 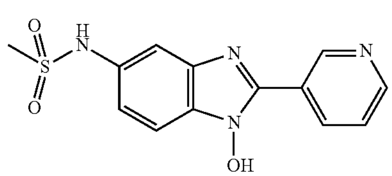 [SMILES: CS(=O)(=O)Nc1ccc2c(c1)nc(-c1cccnc1)n2O] | N-[1-hydroxy-2-(pyridin-3-yl)-1H-benzimidazol-5-yl]methanesulfonamide | 305.06 |
| 352 | 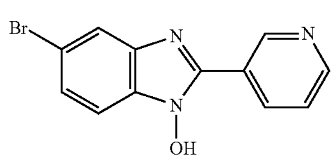 [SMILES: On1c(-c2cccnc2)nc2cc(Br)ccc21] | 5-bromo-2-(pyridin-3-yl)-1H-benzimidazol-1-ol | 292.12 |

TABLE 9-continued

| Example | Structure | IUPAC Name | LCMS (M + 1) |
|---|---|---|---|
| 353 | 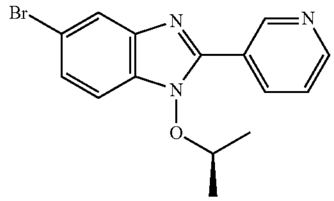 | 5-bromo-1-(propan-2-yloxy)-2-(pyridin-3-yl)-1H-benzimidazole | 334.20 |
| 354 | 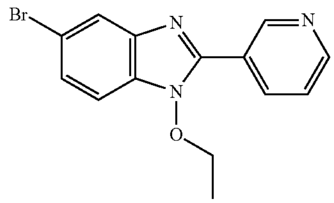 [SMILES: CCOn1c(-c2cccnc2)nc2cc(Br)ccc21] | 5-bromo-1-ethoxy-2-(pyridin-3-yl)-1H-benzimidazole | 319.17 |
| 355 | 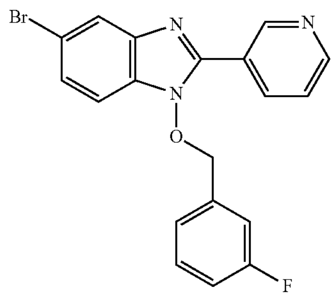 [SMILES: Fc1cccc(COn2c(-c3cccnc3)nc3cc(Br)ccc32)c1] | 5-bromo-1-[(3-fluorobenzyl)oxy]-2-(pyridin-3-yl)-1H-benzimidazole | 399.23 |
| 356 | 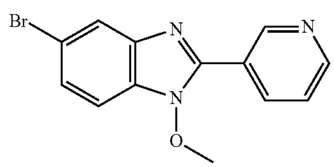 [SMILES: COn1c(-c2cccnc2)nc2cc(Br)ccc21] | 5-bromo-1-methoxy-2-(pyridin-3-yl)-1H-benzimidazole | 306.14 |
| 357 | 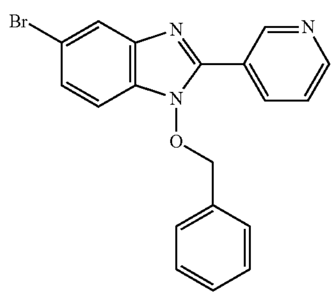 [SMILES: Brc1ccc2c(c1)nc(-c1cccnc1)n2OCc1ccccc1] | 1-(benzyloxy)-5-bromo-2-(pyridin-3-yl)-1H-benzimidazole | 381.24 |
| 358 | 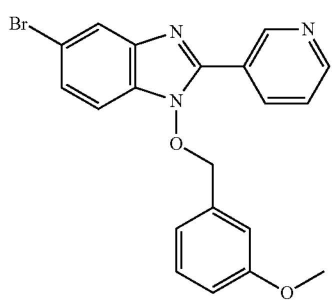 [SMILES: COc1cccc(COn2c(-c3cccnc3)nc3cc(Br)ccc32)c1] | 5-bromo-1-[(3-methoxybenzyl)oxy]-2-(pyridin-3-yl)-1H-benzimidazole | 411.27 |

TABLE 9-continued

| Example | Structure | IUPAC Name | LCMS (M + 1) |
|---|---|---|---|
| 359 | 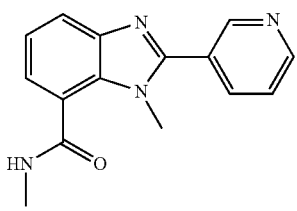 [SMILES: CNC(=O)c1cccc2nc(-c3cccnc3)n(C)c12] | 6-bromo-2-(pyridin-3-yl)-1H-benzimidazol-1-ol | 291.12 |

EXAMPLE 360

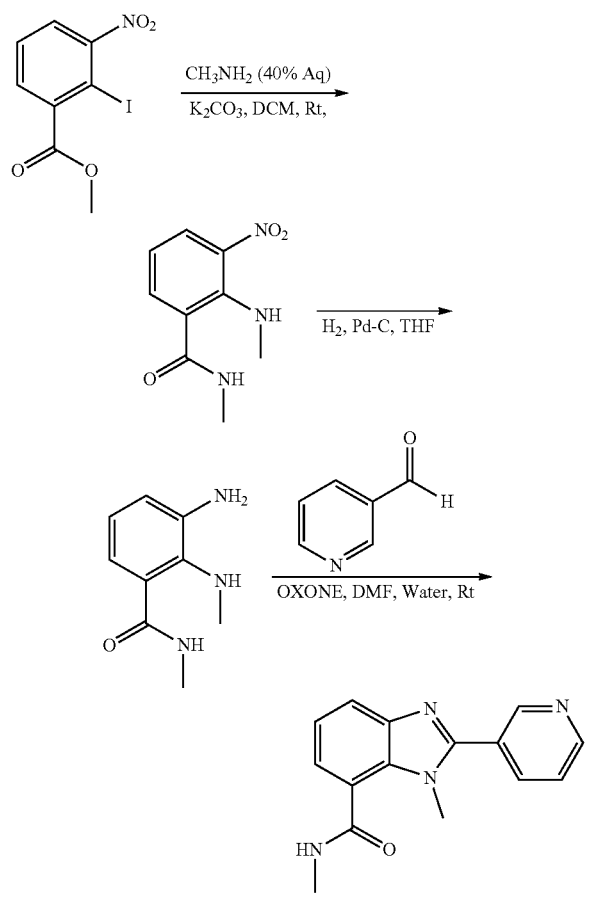

N,1-dimethyl-2-(pyridin-3-yl)-1H-benzimidazole-7-carboxamide

Step A. N-methyl-2-(methyl-amino)-3-nitrobenzamide

To a stirred solution of methyl-2-iodo-3-nitrobenzoate (0.5 g, 0.00162 mol) in DCM (20 ml) was added $K_2CO_3$ (0.45 g, 0.00325 mol) and methyl amine (5.0 ml) was added portion wise under cooling condition with constant stirring. The reaction mixture was allowed to stir at room temperature for 12 h. The reaction was diluted with cold water (15 ml) and extracted with dichloromethane (3×15 ml). The combined organic layers were washed with brine dried over $Na_2SO_4$ and concentrated in vacuo and purified by column chromatography on silica gel to afford the desired product N-methyl-2-(methyl-amino)-3-nitrobenzamide as a yellow solid. $^1$H NMR (400 MHz, DMSO-d6), δ: 8.49 (bs, 1H), 8.29 (bs, 1H), 8.02-8.0 (d, J=8.0 Hz, 1H), 7.53-7.51 (d, J=7.6 Hz, 1H), 6.71-6.67 (t, J=8.0 Hz, 1H), 2.81-2.8 (d, J=5.6 Hz, 3H), 2.75-2.74 (d, J=4.4 Hz, 3H). LCMS (ES) m/e MS (M+1=210) Purity: 87.19%.

Step B. 3-amino-N-methyl-2-(methyl-amino)benzamide

To a stirred solution of N-methyl-2-(methyl-amino)-3-nitrobenzamide (17; 0.22 g, 0.00104 mol) in THF (10 ml) was added 10% palladium on carbon (catalytic amount) portion wise at room temperature. The reaction mixture was allowed to stir under the atmosphere of hydrogen gas supplied by balloon at room temperature for 3 h. The reaction mixture was filtered through CELITE® and filtrate was concentrated to afford the desired product 3-amino-N-methyl-2-(methyl-amino) benzamide after drying and carry forward to next step by checking LCMS. LCMS (ES) m/e MS (M+1=180) Purity: 85.6%.

Step C. N,1-dimethyl-2-(pyridin-3-yl)-1H-benzimidazole-7-carboxamide (360)

To a stirred solution of 3-amino-N-methyl-2-(methyl-amino) benzamide (18; 0.2 g, 0.0011 mol) in the mixture of DMF (5 ml) and water (1 ml) was added OXONE® (0.81 g, 0.0013 mol) and followed by nicotinaldehyde (0.13 g, 0.00122 mol) was added portion wise under cooling condition with constant stirring. The reaction mixture was allowed to stir at room temperature for 3 h. The reaction mixture was concentrated on a high vacuo pump and purified by column chromatography on silica gel to afford the desired product N,1-dimethyl-2-(pyridin-3-yl)-1H-benzimidazole-7-carboxamide as brown solid. 1H NMR (400 MHz, DMSO-d6), δ: 9.0 (s, 1H), 8.76-8.75 (d, J=4.0 Hz, 1H), 8.59 (bs, 1H), 8.25-8.23 (d, J=7.6 Hz, 1H), 7.81-7.8 (d, J=7.6 Hz, 1H), 7.64-7.61 (m, 1H), 7.35-7.27 (m, 2H), 3.79 (s, 3H), 2.85-2.84 (d, J=4.4 Hz, 3H). LCMS (ES) m/e MS (M+1-267) Purity: 98.5%.

The compounds in Table 10 were prepared following the synthetic procedure as described in Example 360.

TABLE 10

| Example | Structure | IUPAC Name | LCMS (M + 1) |
|---|---|---|---|
| 361 | 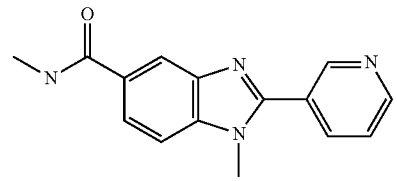 [SMILES: CNC(=O)c1ccc2c(c1)nc(-c1cccnc1)n2C] | N,1-dimethyl-2-(pyridin-3-yl)-1H-benzimidazole-5-carboxamide | 267.12 |
| 362 | 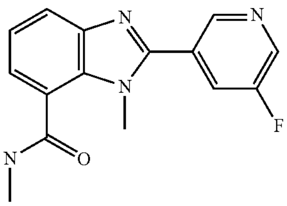 [SMILES: CNC(=O)c1cccc2nc(-c3cncc(F)c3)n(C)c12] | 2-(5-fluoropyridin-3-yl)-N,1-dimethyl-1H-benzimidazole-7-carboxamide | 285.23 |

EXAMPLE 363

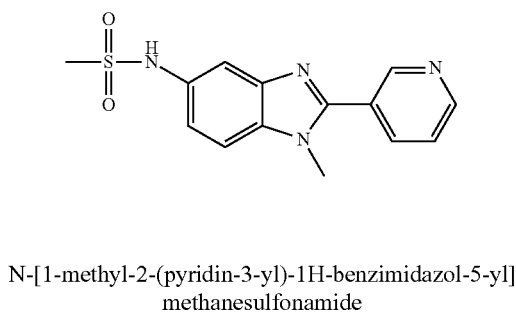

N-[1-methyl-2-(pyridin-3-yl)-1H-benzimidazol-5-yl]methanesulfonamide

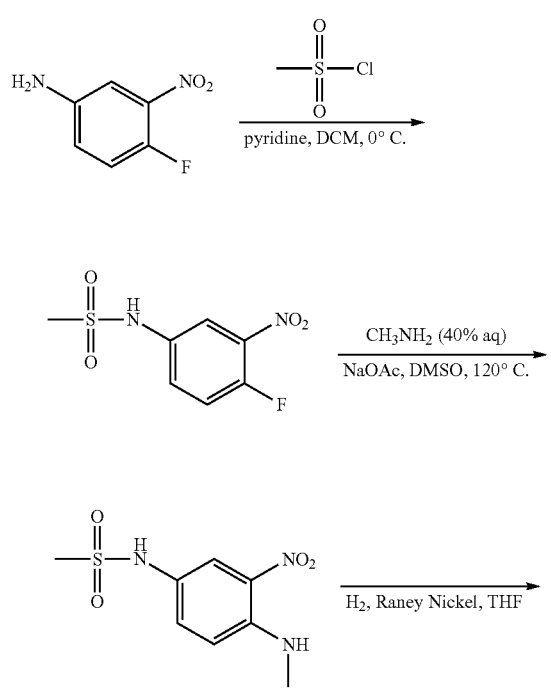

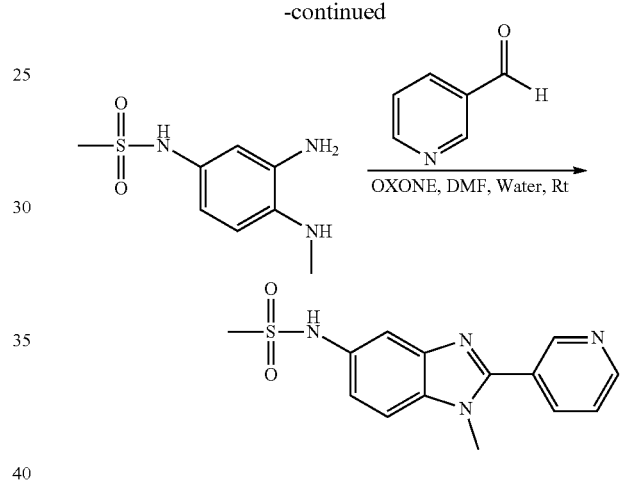

Step A. N-(4-fluoro-3-nitrophenyl)methane sulfonamide

To a stirred solution of 4-fluoro-3-nitroaniline (0.5 g, 0.023 mol) in DCM (10 ml) and pyridine (0.98 g, 0.012 mol) was added methanesulfonyl chloride (0.54 g, 0.0048 mol) portion wise at 0° C. with constant stirring. The reaction mixture was allowed to stir at 0° C. for 4 h. The reaction mixture was concentrated and diluted with water (20 ml) and extracted with DCM (3×15 ml). The combined organic layers were washed with 1 N HCl and NaHCO$_3$ solution dried over Na$_2$SO$_4$ and concentrated in vacuo to afford the desired product N-(4-fluoro-3-nitrophenyl)methane sulfonamide as off a white solid. $^1$H NMR (400 MHz, DMSO-d6), δ: 10.23 (s, 1H), 7.93-7.91 (d, J=8.4 Hz, 1H), 7.62-7.54 (m, 2H), 3.59 (s, 3H). LCMS (ES) m/e MS (M−1=233). Purity: 80%.

Step B. N-(4-(methyl amino)-3-nitrophenyl)methane sulfonamide

To a stirred solution of N-(4-fluoro-3-nitrophenyl) methane sulfonamide (0.5 g, 0.0021 mol) in DMSO (10 ml) was added NaOAc (1.75 ml, 0.0021 mol) and methyl amine (0.65 g, 0.0021 mol) portion wise with constant stirring. The reaction mixture was allowed to stir at 120° C. for 10 h. The reaction mixture was concentrated and diluted with water (10 ml) and extracted with DCM (3×15 nil). The combined organic layers were washed with brine dried over $Na_2SO_4$ and concentrated in vacuo to afford the desired product N-(4-(methyl amino)-3-nitrophenyl)methane sulfonamide (21) as a red color solid. $^1$H NMR (400 MHz, DMSO-d6), δ: 9.4 (s, 1H), 8.16 (bs, 1H), 7.93 (s, 1H), 7.46-7.43 (dd, J=9.2 Hz, 2.4 Hz, 1H), 7.04-7.01 (d, J=9.2 Hz, 1H), 2.95-2.94 (d, J=4.8 Hz, 3H), 2.92 (s, 3H). LCMS (ES) m/e MS (M−1=244). Purity: 94%.

Step C. N-(3-amino-4-(meth 1 amino) phenyl) methane sulfonamide

To a stirred solution of N-(4-(methyl amino)-3-nitrophenyl) methane sulfonamide (21; 0.4 g, 0.0016 mol) in THF (40 ml) was added raney nickel (catalytic amount) portion wise at room temperature. The reaction mixture was allowed to stir under the atmosphere of hydrogen gas supplied by balloon at room temperature for 3 h. The reaction mixture was filtered through CELITE® and filtrate was concentrated to afford the desired product N-(3-amino-4-(methyl amino) phenyl) methane sulfonamide (0.45 g, crude) after drying and carry forward to next step. LCMS (ES) m/e MS (M−1=244). Purity: 90%.

Step D. N-[1-methyl-2-(pyridin-3-yl)-1H-benzimidazol-5-yl]methanesulfonamide (363)

To a stirred solution of N-(3-amino-4-(methyl amino) phenyl) methane sulfonamide (0.3 g, 0.0013 mol) in the mixture of DMF (10 ml) and water (2 ml) was added OXONE® (1.02 g, 0.0016 mol) and followed by nicotinaldehyde (0.16 g, 0.0015 mol) was added portion wise with constant stirring. The reaction mixture was allowed to stir at room temperature for 3 h. The reaction mixture was concentrated on a high vacuo pump and diluted with cold water (10 ml) and extracted with ethyl acetate (3×15 ml). The combined organic layers were washed with brine dried over $Na_2SO_4$ and concentrated in vacuo and purified by column chromatography on silica gel to afford the desired product N-[1-methyl-2-(pyridin-3-yl)-1H-benzimidazol-5-yl]methanesulfonamide (363) as a brown solid. 1H NMR (400 MHz, DMSO-d6), δ: 9.53 (bs, 1H), 9.04 (s, 1H), 8.75-8.77 (d, J=4.0 Hz, 1H), 8.28-8.26 (d, J=8.0 Hz, 1H), 7.68-7.57 (m, 3H), 7.24-7.21 (d, J=8.4 Hz, 1H), 3.89 (s, 3H), 2.91 (s, 3H). LCMS (ES) m/e MS (M+1=244), Purity 95.64%.

The compounds in Table 11 were prepared following the synthetic procedure as described in Example 363.

TABLE 11

| Example | Structure | IUPAC Name | LCMS (M + 1) |
|---|---|---|---|
| 364 | 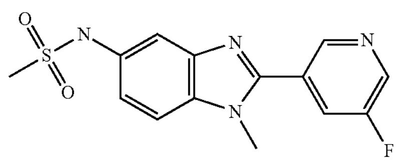 [SMILES: Cn1c(-c2cncc(F)c2)nc2cc(NS(C)(=O)=O)ccc21] | N-[2-(5-fluoropyridin-3-yl)-1-methyl-1H-benzimidazol-5-yl]methanesulfonamide | 321.23 |
| 365 | 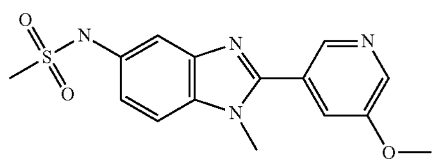 | N-[2-(5-methoxypyridin-3-yl)-1-methyl-1H-benzimidazol-5-yl]methanesulfonamide | 333.14 |
| 366 | 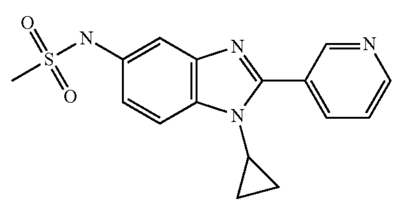 [SMILES: CS(=O)(=O)Nc1ccc2c(c1)nc(-c1cccnc1)n2C1CC1] | N-[1-cyclopropyl-2-(pyridin-3-yl)-1H-benzimidazol-5-yl]methanesulfonamide | 329.14 |
| 367 | 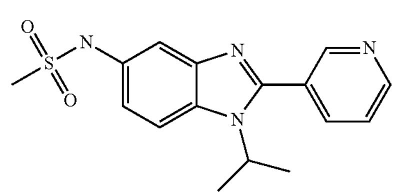 [SMILES: CC(C)n1c(-c2cccnc2)nc2cc(NS(C)(=O)=O)ccc21] | N-[1-(propan-2-yl)-2-(pyridin-3-yl)-1H-benzimidazol-5-yl]methanesulfonamide | 331.12 |
| 368 | 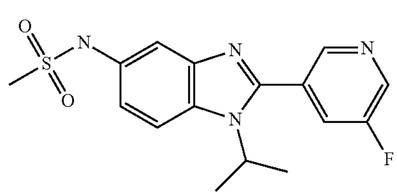 [SMILES: CC(C)n1c(-c2cncc(F)c2)nc2cc(NS(C)(=O)=O)ccc21] | N-[2-(5-fluoropyridin-3-yl)-1-(propan-2-yl)-1H-benzimidazol-5-yl]methanesulfonamide | 349.16 |

TABLE 11-continued

| Example | Structure | IUPAC Name | LCMS (M + 1) |
|---|---|---|---|
| 369 | 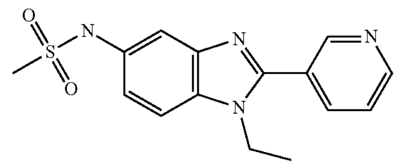 [SMILES: CCn1c(-c2cccnc2)nc2cc(NS(C)(=O)=O)ccc21] | N-[1-ethyl-2-(pyridin-3-yl)-1H-benzimidazol-5-yl]methanesulfonamide | 317.15 |
| 370 | 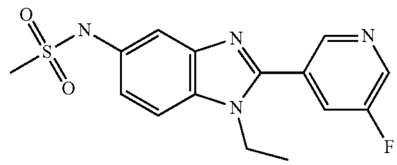 [SMILES: CCn1c(-c2cncc(F)c2)nc2cc(NS(C)(=O)=O)ccc21] | N-[1-ethyl-2-(5-fluoropyridin-3-yl)-1H-benzimidazol-5-yl]methanesulfonamide | 335.12 |

EXAMPLE 371

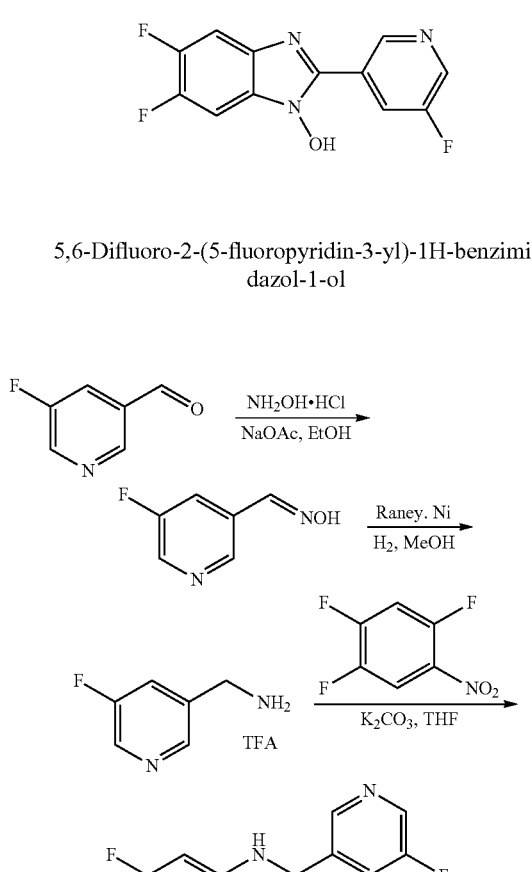

5,6-Difluoro-2-(5-fluoropyridin-3-yl)-1H-benzimidazol-1-ol

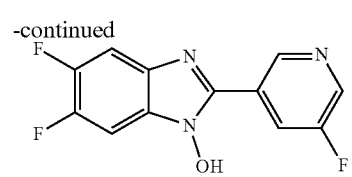

Step A. Oxime

To a solution of 5-fluoronicotinaldehyde (1.6 g, 0.012 mol) in EtOH (13 ml) was added hydroxylamine hydrochloride (1 g, 0.014 mol) and sodium acetate (1.162 g, 0.014 mol) and stirred at room temperature overnight. After the consumption of 5-fluoronicotinaldehyde (by TLC) water was added and the desired compound was extracted with EtOAc (3×30 mL). The organic phase was dried with $Na_2SO_4$ and concentrated under vacuum to give oxime as a white solid. $^1$H NMR (400 MHz, DMSO-$d_6$), δ: 11.75 (s, 1H), 8.63 (d, J=10 Hz, 1H), 8.24 (s, 1H), 7.86 (d, J=10 Hz, 1H). MS (M+1): 141

Step B. (5-fluoropyridin-3yl)methanamine TFA salt

To a solution of the oxime formed in Step A (0.58 g, 0.0041 mol) in MeOH (20 mL) was added Pd/C (0.12 g) under nitrogen atmosphere followed by TFA (2 ml) at room temperature and was stirred under a balloon of $H_2$ until the oxime is completely consumed (by TLC). The reaction mixture was then filtered through CELITE® and the filtrate was concentrated under vacuum. The crude (collected by repeating the reaction 3×) was combined and the desired product was obtained by chromatography (Alumina: 1-10% MeOH/DCM) as a viscous gel (5-fluoropyridin-3yl)methanamine TFA salt (1.02 g, ~50% LC-MS) and was used directly in the next step. $^1$H NMR (400 MHz, DMSO-$d_6$), δ: 8.49 (s, 1H), 8.43 (s, 1H), 7.72 (d, J=10 Hz, 1H), 3.82 (s, 2H), 3.42 (br, 2H). MS (M+1): 127

Step C. 4,5-difluoro-N-(5-fluoropyridin-3-yl)methyl)-2-nitroaniline 2,4,5-tri-fluoronitrobenzene (2.864 g, 0.016 mol), $K_2CO_3$ (2.236 g, 0.0161 mol) and (5-fluoropyridin-3yl)methanamine TFA salt (1.02 g, 50% LC-MS) were dissolved in THF (25 mL) and stirred at room temperature for 16 hours. The reaction mixture was then diluted with EtOAc (100 mL) and washed with $H_2O$. The organic phase was dried and concentrated under vacuum to give the ortho-substitution product, 4,5-difluoro-N-(5-fluoropyridin-3-yl) methyl)-2-nitroaniline as a yellow solid. $^1$H NMR (400 MHz, DMSO-$d_6$), δ: 8.72 (br, 1H), 8.43 (s, 1H), 8.39 (s, 1H), 8.15 (dd, J=10 Hz, 8.8 Hz, 1H), 7.65 (d, J=9.2 Hz, 1H), 6.83 (dd, J=12.8 Hz, 7.8 Hz, 1H), 4.71 (s, 2H). MS (M+1): 284

Step D. 5,6-difluoro-2-(5-fluoropyridin-3-yl)-1H-benzimidazol-1-ol (371)

To a solution of 4,5-difluoro-N-(5-fluoropyridin-3-yl) methyl)-2-nitroaniline (0.55 g, 0.0019 mop in THF (13 ml) was added NaH (0.24 g, 0.0058 mol) portion-wise at room temperature. After the consumption of the starting material (by TLC) the reaction mixture was quenched by the addition of NH$_4$OH (saturated solution) and extracted with EtOAc (2×30 mL). The organic layer was dried and concentrated under vacuum. The crude was further purified by first washing with Et$_2$O followed by triturating with Hexanes/Et$_2$O and finally washing with Hexanes to obtain the desired compound 5,6-difluoro-2-(5-fluoropyridin-3-yl)-1H-benzimidazol-1-ol (371). LC-MS ~70% purity. The compound was taken to the next step without further purification. $^1$H NMR (400 MHz, DMSO-$d_6$), δ: 12.67 (m, 1H), 9.22 (s, 1H), 8.75 (s, 1H), 8.37 (d, J=9.6 Hz, 1H), 7.81 (dd, J=10 Hz, 7.2 Hz, 1H), 7.72 (dd, J=9.2 Hz, 7.4 Hz, 1H). MS (M+1): 266; Purity 99.51%.

EXAMPLE 372

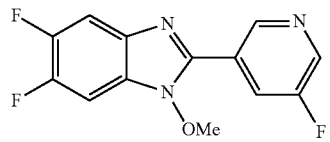 [SMILES: COn1c(-c2cncc(F)c2)nc2cc(F)c(F)cc21]

5,6-difluoro-2-(5-fluoropyridin-3-yl)-1-methoxy-11H-benzimidazole

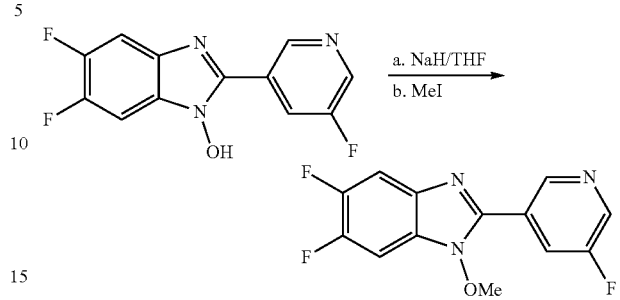

Step A. 5,6-difluoro-2-(5-fluoropyridin-3-yl)-1-methoxy-1H-benzimidazole (372)

To a solution of 5,6-difluoro-2-(5-fluoropyridin-3-yl)-1H-benzo[d]imidazol-1-ol 0.15 g, 0.0003 mol) in THF (3.5 ml) was added NaH (0.045 g, 0.0011 mol) at room temperature. After stirring for 5 min at room temperature MeI (0.04 mL, 0.00059 mol) was added in one shot and further stirred for another 1 hr. After the consumption of the starting material (by TLC) the reaction mixture was washed with H$_2$O and extracted with EtOAc (2×30 mL). The organic phase was dried and concentrated under vacuum. The crude was washed with Hexanes and further purified by chromatography (5-40% EtOAc/Hexanes) to give the desired compound 372 as a white solid. $^1$H NMR (400 MHz, DMSO-$d_6$), δ: 9.28 (s, 1H), 8.62 (s, 1H), 8.24 (s, 1H), 7.58 (s, 1H), 7.32 (s, 1H), 4.06 (s, 3H). MS (M+1): 280, Purity 99.67%.

The compounds in Table 12 were prepared following the synthetic procedure as described in Example 372.

TABLE 12

| Example | Structure | IUPAC Name | LCMS (M + 1) |
|---|---|---|---|
| 373 | 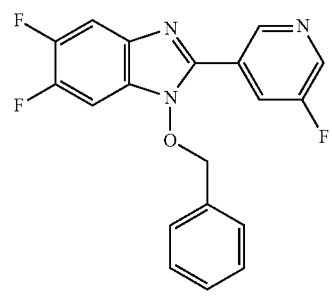 [SMILES: Fc1cncc(-c2nc3cc(F)c(F)cc3n2OCc2ccccc2)c1] | 1-(benzyloxy)-5,6-difluoro-2-(5-fluoropyridin-3-yl)-1H-benzimidazole | 356.32 |
| 374 | 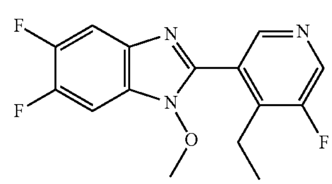 [SMILES: CCc1c(F)cncc1-c1nc2cc(F)c(F)cc2n1OC] | 2-(4-ethyl-5-fluoropyridin-3-yl)-5,6-difluoro-1-methoxy-1H-benzimidazole | 308.1 |

TABLE 12-continued

| Example | Structure | IUPAC Name | LCMS (M + 1) |
|---------|-----------|------------|--------------|
| 375 | 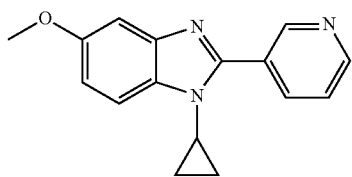 [SMILES: COc1ccc2c(c1)nc(-c1cccnc1)n2C1CC1] | 5,6-difluoro-1-methoxy-2-[4-(trifluoromethyl)pyridin-3-yl]-1H-benzimidazole | 330.3 |

EXAMPLE 376

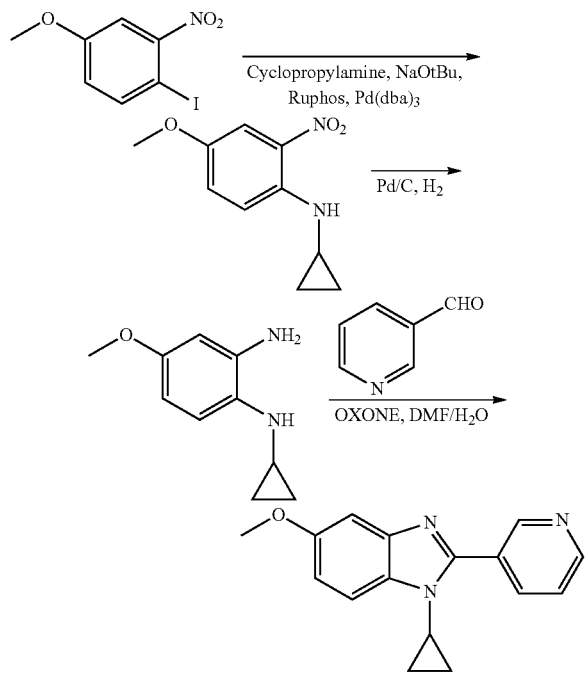

1-Cyclopropyl-5-methoxy-2-(pyridin-3-yl)-1H-benzimidazole

Step A. cyclopropyl-(4-methoxy-2-nitro-phenyl)-amine

To a stirred solution of 1-iodo-4-methoxy-2-nitrobenzene (0.2 g, 0.0007 mol) in toluene (6.0 mL) was added cyclopropylamine (0.068 ml, 0.0008 mol) potassium tert-butoxide (0.094 g, 0.0098 mol) and Ruphos (0.049 g, 0.00010 mol) at room temperature and purged with argon for 15 min. Then $Pd_2(dba)_3$ (0.064 g, 0.00007 mol) was added and resulting mixture was heated to 100° C. in CEM microwave for 30 min. After the reaction was complete the reaction mixture was filtered through CELITE® bed and the bed was thoroughly washed with ethyl acetate. The filtrate was washed with water brine dried over $Na_2SO_4$ and concentrated under reduced pressure to afford the crude compound, which was purified by column chromatography to obtain title compound cyclopropyl-(4-methoxy-2-nitro-phenyl)-amine (yellow solid). $C_{10}H_{12}N_2O_3$; $^1$H NMR (400 MHz, CDCl$_3$), δ: 7.98 (s, 1H), 7.60 (d, J=2.8 Hz, 1H), 7.30 (s, 1H), 7.19-7.16 (m, 1H), 4.12 (q, J=6.8, 1H), 3.80 (s, 1H), 0.89 (dd, J$_1$=12.0 Hz, J$_2$=6.0 Hz, 2H), 0.64 (t, J=6.8 Hz, 2H). MS (M+1): 209.1.

Step B. N1-cyclopropyl-4-methoxy-benzene-1,2-diamine

A stirred solution of cyclopropyl-(4-methoxy-2-nitro-phenyl)-amine (0.8 g, 0.0038 mol) in ethylacetate (25 ml) was hydrogenated using 10% Pd/C for 6 h at room temperature. The reaction was filtered through CELITE® and the filter bed was thoroughly washed with EtOAc. The resulting solution was concentrated to provide N1-cyclopropyl-4-methoxy-benzene-1,2-diamine as a brown liquid. $C_{10}H_{14}N_2O$; Crude $^1$H NMR (400 MHz, DMSO-d$_6$), δ: 6.66 (d, J=8.8 Hz, 1H), 6.18-6.15 (m, 1H), 6.08 (d, J=6.0 Hz, 1H), 4.03 (d, J=6.8 Hz, 1H), 3.75-3.68 (m, 2H), 3.58 (s, 3H), 0.63 (d, J=6.0 Hz, 2H), 0.40 (s, 2H). MS (M+1): 179.2.

Step C. 1-cyclopropyl-5-methoxy-2-(pyridin-3-yl)-1H-benzimidazole (376)

To a solution of N1-cyclopropyl-4-methoxy-benzene-1,2-diamine (0.2 g, 0.0011 mol) and pyridine-3-carbaldehyde (0.12 g, 0.0011 mol) in DMF (5 ml) and H$_2$O (2 ml) was added OXONE® monopersulphate (0.81 g, 0.00132 map. Reaction mass was stirred at room temperature for 3 h. The reaction mixture was basified with 10% $K_2CO_3$ solution to pH~8-10 and extracted with EtOAc (3×20 ml). The combined organic layers were washed with brine dried over $Na_2SO_4$ and concentrated under vacuum to afford the crude compound which was purified by column chromatography to obtain title compound 1-cyclopropyl-5-methoxy-2-(pyridin-3-yl)-1H-benzimidazole (376). $^1$H NMR (400 MHz, DMSO-d$_6$), δ: 9.16 (s, 1H), 8.70 (s, 1H), 8.37 (d, J=8.8 Hz, 1H), 7.55 (d, J=8.4 Hz, 2H), 7.23 (s, 1H), 6.96 (d, J=8.8 Hz, 1H), 3.80 (s, 3H), 1.10 (d, J=6.4 Hz, 2H), 0.64 (s, 2H). MS (M+1): 266.1, Purity 98.98%.

The compound in Table 13 was prepared by following the synthetic procedure as described in Example 376.

TABLE 13

| Example | Structure | IUPAC Name | LCMS (M + 1) |
|---------|-----------|------------|--------------|
| 377 | 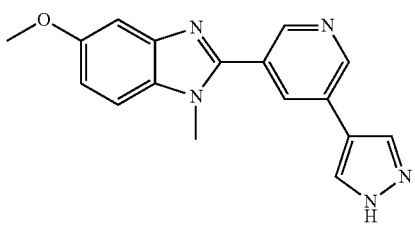 [SMILES: COc1ccc2c(c1)nc(-c1cncc(-c3cn[nH]c3)c1)n2C] | 1-cyclopropyl-2-(5-fluoropyridin-3-yl)-5-methoxy-1H-benzimidazole | 284.1 |

EXAMPLE 378

5-Methoxy-1-methyl-2-[5-(1H-pyrazol-4-yl)pyridin-3-yl]-1H-benzimidazole

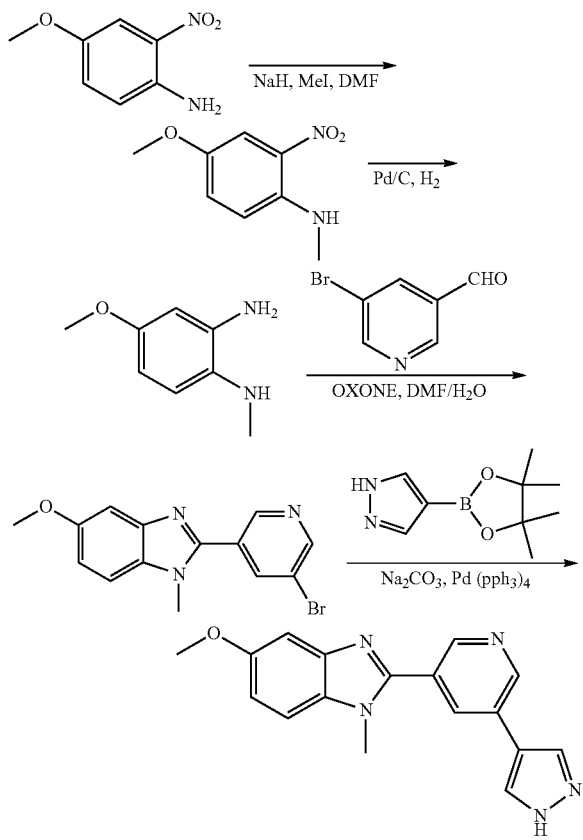

Step A. (4-methoxy-2-nitro-phenyl)-methyl-amine

To a solution of 4-methoxy-2-nitro-phenylamine (5.0 g, 0.029 mol) in DMF (25 ml) was added NaH (0.9 g, 0.035 mol) at 0° C. and stirred at that temperature for 30 min. Methyl iodide (2.17 ml, 0.035 mol) was added and the resulting solution was stirred at room temperature for 30 min. The reaction was quenched with ice-water and extracted with ethyl acetate (3×100 ml). The combined organic layers were washed with brine dried over $Na_2SO_4$ and concentrated under vacuum to afford the title compound (4-methoxy-2-nitro-phenyl)-methyl-amine as a red solid. $C_8H_{10}N_2O_3$; $^1H$ NMR (400 MHz, $CDCl_3$), δ: 8.00 (brs, 1H), 7.62 (d, J=2.4 Hz, 1H), 7.18 (dd,$_1$=9.2 Hz, $J_2$=2.0 Hz, 1H), 6.82 (d, J=9.6 Hz, 1H), 3.81 (d, J=14.8 Hz, 3H), 3.02 (s, 3H). MS (M+1): 183.1.

Step B. 4-methoxy-N1-methyl-benzene-1,2-diamine

A stirred solution of 4-methoxy-2-nitro-phenyl)-methyl-amine (2.5 g, 0.013 mol) in ethyl acetate (25 ml) was hydrogenated using 10% Pd/C for 6 h at room temperature. The reaction was filtered through CELITE® and the bed was thoroughly washed with EtOAc. The resulting solution was concentrated to provide 4-methoxy-N1-methyl-benzene-1,2-diamine as a brown solid. $C_8H_{12}N_2O$; Crude $^1H$ NMR (400 MHz, DMSO-$d_6$), δ: 6.27 (d, J=8.8 Hz, 1H), 6.19 (d, J=2.8 Hz, 1H), 6.07 (dd, $J_1$=8.4 Hz, $J_2$=2.4 Hz, 1H), 4.49 (s, 2H), 4.08 (s, 1H), 3.56 (s, 3H), 2.63 (s, 3H). MS (M+1): 153.2.

Step C. 2-(5-bromo-pyridin-3-yl)-5-methoxy-1-methyl-1H-benzoimidazole

To a solution of 4-methoxy-N1-methyl-benzene-1,2-diamine (34; 0.5 g, 0.00328 mol) and 5-bromo-pyridine-3-carbaldehyde (0.61 g, 0.00328 mol) in DMF (10 ml) and $H_2O$ (4 ml) was added OXONE® monopersulphate (2.42 g, 0.00394 mol). Reaction mass was stirred at room temperature for 3 h. The reaction mixture was basified with 10% $K_2CO_3$ solution to pH~8-10 and extracted with EtOAc (3×20 ml). The combined organic layers were washed with brine dried over $Na_2SO_4$ and concentrated under vacuum to afford the crude compound which was purified by column chromatography to obtain title compound 2-(5-bromo-pyridin-3-yl)-5-methoxy-1-methyl-1H-benzoimidazole (35).

Step D. 5-methoxy-1-methyl-2-[5-(1H-pyrazol-4-yl) pyridin-3-yl]-1H-benzimidazole (378)

To a solution of 2-(5-bromo-pyridin-3-yl)-5-methoxy-1-methyl-1H-benzoimidazole (0.15 g, 0.00047 mol) in ethanol toluene water (6 ml, 3 ml, 1.5 ml, respectively) mixture in a sealed tube was added 4-(4,4,5,5-Tetramethyl-[1,3,2]dioxaborolan-2-yl)-1H-pyrazole (0.18 g, 0.000942 mol) and $Na_2CO_3$ (0.14 g, 0.0014 mol) and argon was purged for 15 min. Then Pd (PPh₃)₄ (0.027 g, 0.000023 mol) was added and heated at 100° C. for 24 h. The solvent was evaporated and the resulting residue was added water. The aqueous layer was extracted with ethyl acetate (3×20 ml). The combined organic layers were washed with brine dried over Na₂SO₄ and concentrated under vacuum to afford the crude compound which was purified by column chromatography to obtain title compound 5-methoxy-1-methyl-2-[5-(1H-pyrazol-4-yl)pyridin-3-yl]-1H-benzimidazole as an off white solid. $^1$H NMR (400 MHz, DMSO-d₆), δ: 13.11 (s, 1H), 9.01 (s, 1H), 8.79 (s, 1H), 8.44 (s, 1H), 8.38 (s, 1H), 8.13 (s, 1H), 7.54 (d, J=8.8 Hz, 1H), 7.22 (s, 1H), 6.95 (d, J=8.8 Hz, 1H), 3.89 (s, 3H), 3.79 (s, 3H). MS (M+1): 306.1, Purity 99.0%.

The compound in Table 14 was prepared by following the synthetic procedure as described in Example 378.

TABLE 14

| Example | Structure | IUPAC Name | LCMS (M + 1) |
|---------|-----------|------------|--------------|
| 379 | 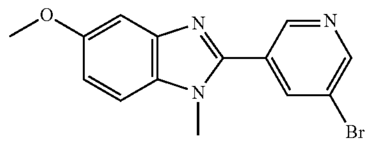 | 2-(5-bromopyridin-3-yl)-5-methoxy-1-methyl-1H-benzimidazole | 318.9 |
| 380 | 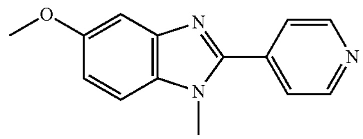 [SMILES: COc1ccc2c(c1)nc(-c1ccncc1)n2C] | 5-methoxy-1-methyl-2-(pyridin-4-yl)-1H-benzimidazole | 240.5 |
| 381 | 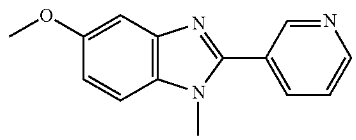 [SMILES: COc1ccc2c(c1)nc(-c1cccnc1)n2C] | 5-methoxy-1-methyl-2-(pyridin-3-yl)-1H-benzimidazole | 240.9 |
| 382 | 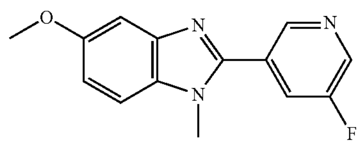 [SMILES: COc1ccc2c(c1)nc(-c1cncc(F)c1)n2C] | 2-(5-fluoropyridin-3-yl)-5-methoxy-1-methyl-1H-benzimidazole | 259.1 |
| 383 | 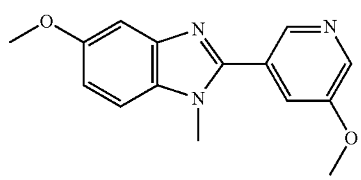 [SMILES: COc1cncc(-c2nc3cc(OC)ccc3n2C)c1] | 5-methoxy-2-(5-methoxypyridin-3-yl)-1-methyl-1H-benzimidazole | 271.1 |
| 384 | 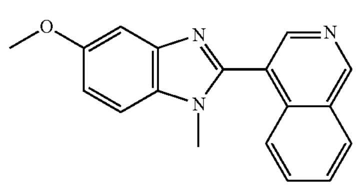 [SMILES: COc1ccc2c(c1)nc(-c1cncc3ccccc13)n2C] | 4-(5-methoxy-1-methyl-1H-benzimidazol-2-yl)-4a,8a-dihydroisoquinoline | 290.5 |
| 385 | 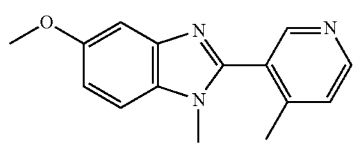 [SMILES: COc1ccc2c(c1)nc(-c1cnccc1C)n2C] | 5-methoxy-1-methyl-2-(4-methylpyridin-3-yl)-1H-benzimidazole | 254.6 |
| 386 | 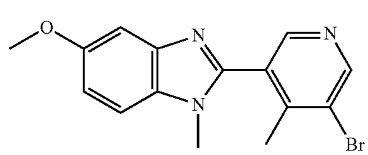 [SMILES: COc1ccc2c(c1)nc(-c1cncc(Br)c1C)n2C] | 2-(5-bromo-4-methylpyridin-3-yl)-5-methoxy-1-methyl-1H-benzimidazole | 333.3 |

TABLE 14-continued

| Example | Structure | IUPAC Name | LCMS (M + 1) |
|---|---|---|---|
| 387 | 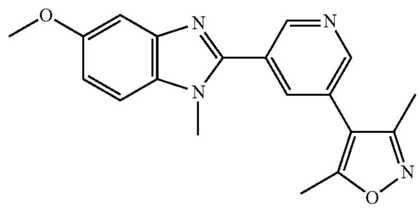 | 2-[5-(3,5-dimethylisoxazol-4-yl)pyridin-3-yl]-5-methoxy-1-methyl-1H-benzimidazole | 335.1 |
| 388 | 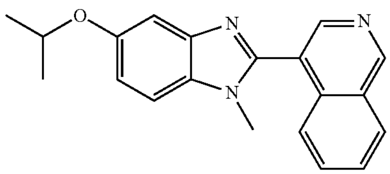 [SMILES: CC(C)Oc1ccc2c(c1)nc(-c1cncc3ccccc13)n2C] | 4-[1-methyl-5-(propan-2-yloxy)-1H-benzimidazol-2-yl]isoquinoline | 318.23 |

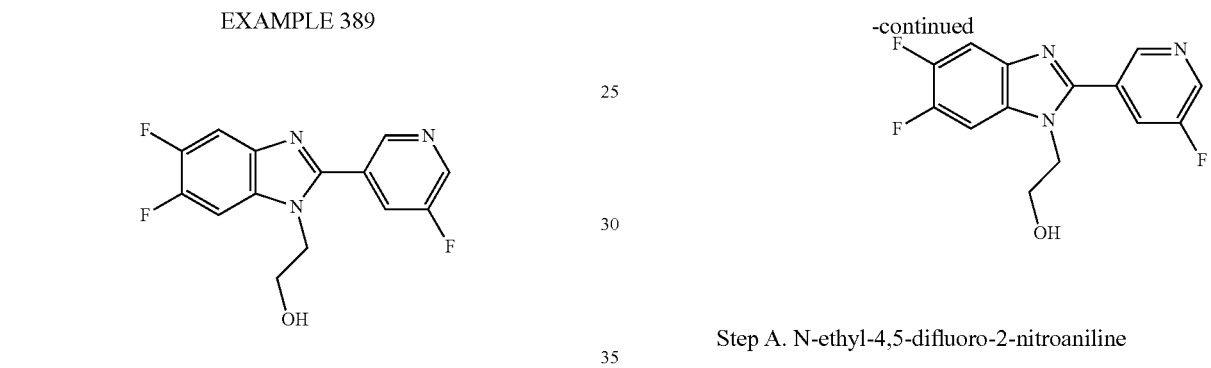

EXAMPLE 389

2-[5,6-difluoro-2-(5-fluoropyridin-3-yl)-1H-benzimidazol-1-yl]ethanol

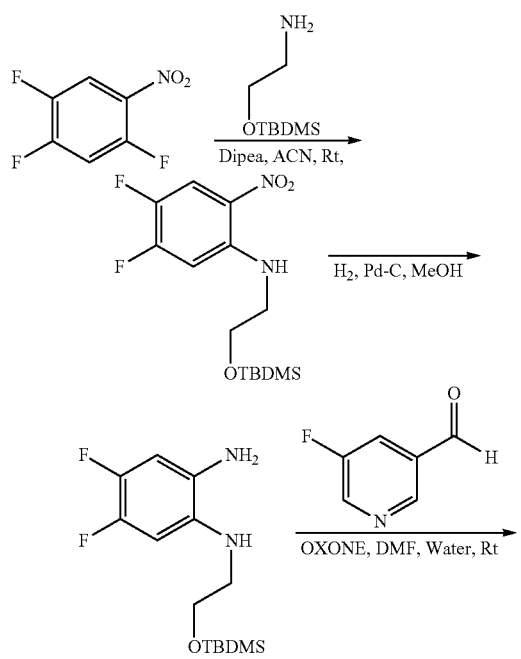

Step A. N-ethyl-4,5-difluoro-2-nitroaniline

To a stirred solution of 1,2,4-trifluoro-5-nitrobenzene (0.5 g, 0.0028 mol) in acetonitrile (5 ml) was added DIPEA (0.98 ml, 0.0056 mol) and 2-(tert-butyldimethylsilyloxy)ethanamine (0.49 g, 0.0028 mol) was added portion wise under cooling condition with constant stirring. The reaction mixture was allowed to stir at room temperature for 4 h. The reaction was concentrated and diluted with water (20 ml) and extracted with ethyl acetate (3×25 ml). The combined organic layers were washed with brine dried over $Na_2SO_4$ and concentrated in vacuo and purified by column chromatography on silica gel to afford the desired product N-ethyl-4,5-difluoro-2-nitroaniline. (37 as yellow solid. $^1$H NMR (400 MHz, DMSO-d6) δ: 8.37 (bs, 1H), 8.13-8.17 (dd, J=8.4, 8.4 Hz, 1H), 7.21-7.27 (dd, J=7.2, 7.2 Hz, 1H), 3.8-3.82 (t, J=5.2 Hz, 2H) 3.45-3.49 (m, 2H), 0.84 (s, 9H), 0.021 (s, 6H). MS (M+1=333).

Step B. N1-(2-(tert-butyldimethylsilyloxy)ethyl)-4,5-difluorobenzene-1,2-diamine To a stirred solution of N-(2-(tert-butyldimethylsilyloxy)ethyl)-4,5-difluoro-2-nitroaniline (37) in methanol (5 ml) was added 10% palladium on carbon (catalytic amount) portion wise at room temperature. The reaction mixture was allowed to stir under the atmosphere of hydrogen gas supplied by balloon at room temperature for 2 h. The reaction mixture was filtered through celite and filtrate was concentrated to afford the desired product N1-(2-(tert-butyldimethylsilyloxy)ethyl)-4,5-difluorobenzene-1,2-diamine (0.09 g; crude). LCMS (M+1=303).

Step C. 2-[5,6-difluoro-2-(5-fluoropyridin-3-yl)-1H-benzimidazol-1-yl]ethanol To a stirred solution of N1-(2-(tert-butyldimethylsilyloxy)ethyl)-4,5-difluorobenzene-1,2-diamine (38; 0.09 g, 0.0003 mol) in the mixture of DMF (3 ml) and water (0.3 ml) was added OXONE® (0.218 g, 0.0004 mol) and followed by 5-fluoronicotinaldehyde (0.041 g, 0.0003 mol) was added portion wise under cooling condition with constant stirring. The reaction mixture was allowed to stir at room temperature for 3 h. The reaction mixture was concentrated and diluted with cold water (10 ml) and extracted with ethyl acetate (3×15 ml). The combined organic layers were washed with brine dried over $Na_2SO_4$ and concentrated in vacuo and purified by column chromatography on silica gel to afford the desired product 2-[5,6-difluoro-2-(5-fluoropyridin-3-yl)-1H-benzimidazol-1-yl]ethanol as an off white solid. 1H NMR (400 MHz, DMSO-d6), δ: 8.93 (s, 1H), 8.77 (m, 1H), 8.33 (m, 1H), 7.96 (m, 1H), 7.81 (m, 1H), 5.09-5.11 (t, J=5.2 Hz, 1H), 4.35-4.38 (t, J=5.0 Hz, 2H), 3.75-3.76 (m, 2H). LCMS (ES) m/e MS (M+1=294) Purity 99.33%.

The compound in Table 15 was prepared by following the synthetic procedure as described in Example 389.

TABLE 15

| Example | Structure | IUPAC Name | LCMS (M + 1) |
|---|---|---|---|
| 390 | 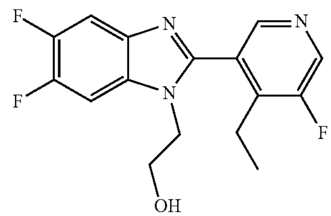 [SMILES: CCc1c(F)cncc1-c1nc2cc(F)c(F)cc2n1CCO] | 2-[2-(4-ethyl-5-fluoropyridin-3-yl)-5,6-difluoro-1H-benzimidazol-1-yl]ethanol | 322.1 |
| 391 | 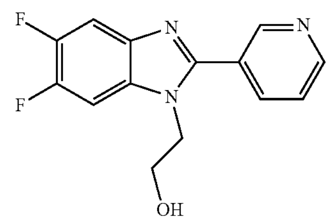 [SMILES: OCCn1c(-c2cccnc2)nc2cc(F)c(F)cc21] | 2-[5,6-difluoro-2-(pyridin-3-yl)-1H-benzimidazol-1-yl]ethanol | 276.3 |
| 392 | 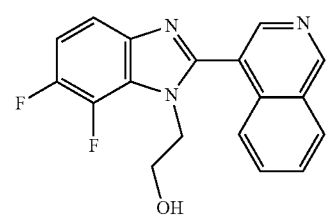 [SMILES: OCCn1c(-c2cncc3ccccc23)nc2ccc(F)c(F)c21] | 2-[6,7-difluoro-2-(isoquinolin-4-yl)-1H-benzimidazol-1-yl]ethanol | 326.5 |
| 393 | 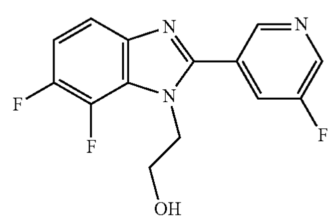 [SMILES: OCCn1c(-c2cncc(F)c2)nc2ccc(F)c(F)c21] | 2-[6,7-difluoro-2-(5-fluoropyridin-3-yl)-1H-benzimidazol-1-yl]ethanol | 294.6 |
| 394 | 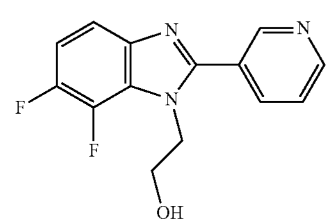 [SMILES: OCCn1c(-c2cccnc2)nc2ccc(F)c(F)c21] | 2-[6,7-difluoro-2-(pyridin-3-yl)-1H-benzimidazol-1-yl]ethanol | 276.1 |

TABLE 15-continued

| Example | Structure | IUPAC Name | LCMS (M + 1) |
|---|---|---|---|
| 395 | 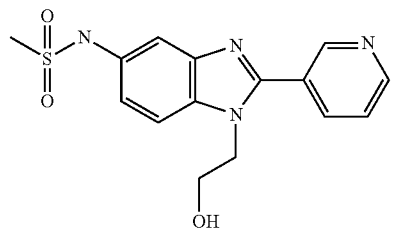 [SMILES: CS(=O)(=O)Nc1ccc2c(c1)nc(-c1cccnc1)n2CCO] | N-[1-(2-hydroxyethyl)-2-(pyridin-3-yl)-1H-benzimidazol-5-yl]methanesulfonamide | 333.38 |
| 396 | 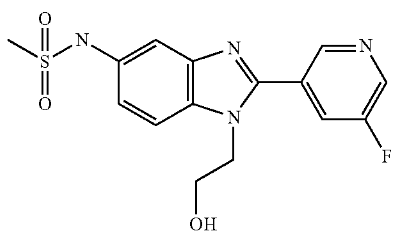 [SMILES: CS(=O)(=O)Nc1ccc2c(c1)nc(-c1cncc(F)c1)n2CCO] | N-[2-(5-fluoropyridin-3-yl)-1-(2-hydroxyethyl)-1H-benzimidazol-5-yl]methanesulfonamide | 351.37 |

EXAMPLE 397

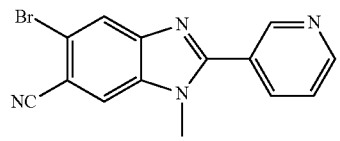 [SMILES: Cn1c(-c2cccnc2)nc2cc(Br)c(C#N)cc21]

5-Bromo-1-methyl-2-(pyridin-3-yl)-1H-benzimidazole-6-carbonitrile

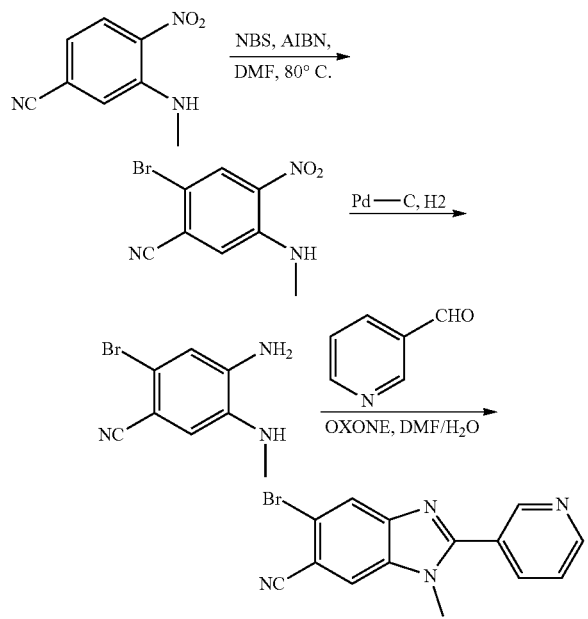

Step A.
2-bromo-5-(methylamino)-4-nitrobenzonitrile

To a stirred solution of 3-(methylamino)-4-nitrobenzonitrile (0.9 g, 0.005 mol) and NBS (0.9 g, 0.005 mol) in DMF (15 ml), AIBN (catalytic) was carefully added and the resulting solution was stirred at 80° C. for 3 h. The reaction was diluted with $H_2O$ and extracted with dichloromethane (3×30 ml). The combined organic layers were washed with brine, dried over $Na_2SO_4$ and concentrated under vacuum to afford the title compound 2-bromo-5-(methylamino)-4-nitrobenzonitrile as a yellow solid. $^1$H NMR (400 MHz, CDCl3), δ: 8.44 (s, 1H), 8.04 (bs, 1H), 7.18 (s, 1H), 3.05 (s, 3H). MS (M+1): 256.12.

Step B.
4-amino-2-bromo-5-(methylamino)benzonitrile

A stirred solution of 2-bromo-5-(methylamino)-4-nitrobenzonitrile (0.3 g, 0.001 mol) in EtOH (10 ml) was hydrogenated using Pd/C for 2 h at room temperature. The reaction was filtered through CELITE® and the filter bed was thoroughly washed with EtOH. The resulting solution was concentrated to provide 4-amino-2-bromo-5-(methylamino)benzonitrile, as a brownish a solid. Crude LCMS (M+1): 226.12. Purity: 63%.

Step C. 5-Bromo-1-methyl-2-(pyridin-3-yl)-1H-benzimidazole-6-carbonitrile

To solution of 4-amino-2-bromo-5-(methylamino)benzonitrile (0.2 g, 0.0008 mol) and nicotinaldehyde (0.094 g, 0.0008 mol) in DMF (5 ml) and $H_2O$ (2 ml) was added OXONE® monopersulphate (0.43 g, 0.0007 mol). Reaction mass was stirred at room temperature for 3 h. The reaction mixture was quenched with 10% $K_2CO_3$ solution to PH~8-10 and extracted with EtOAc (3×20 ml). The combined organic layers were washed with brine, dried over $Na_2SO_4$ and concentrated under vacuum to afford the crude compound, which was purified by column chromatography to obtain title compound 5-bromo-1-methyl-2-(pyridin-3-yl)-1H-benzimidazole-6-carbonitrile. (397 $^1$H NMR (400 MHz, DMSO-$d_6$), δ:

9.08 (s, 1H), 8.80-8.79 (d, J=4 Hz, 1H), 8.53 (s, 1H), 8.34-8.32 (d, J=7.2 Hz, 1H), 8.23 (s, 1H), 7.67-7.63 (m, 1H), 3.96 (s, 3H). MS (M+1): 313.12, Purity 93.84%.

The compound in Table 16 was prepared by following the synthetic procedure as described in Example 397.

TABLE 16

| Example | Structure | IUPAC Name | LCMS (M + 1) |
|---|---|---|---|
| 398 | 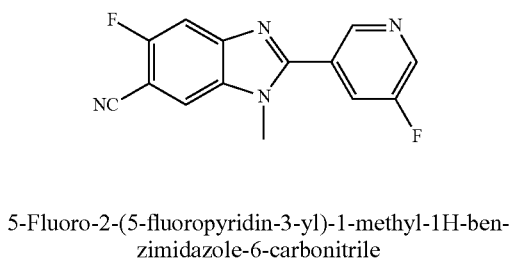 | 5-bromo-2-(5-fluoropyridin-3-yl)-1-methyl-1H-benzimidazole-6-carbonitrile | 332.12 |

EXAMPLE 399

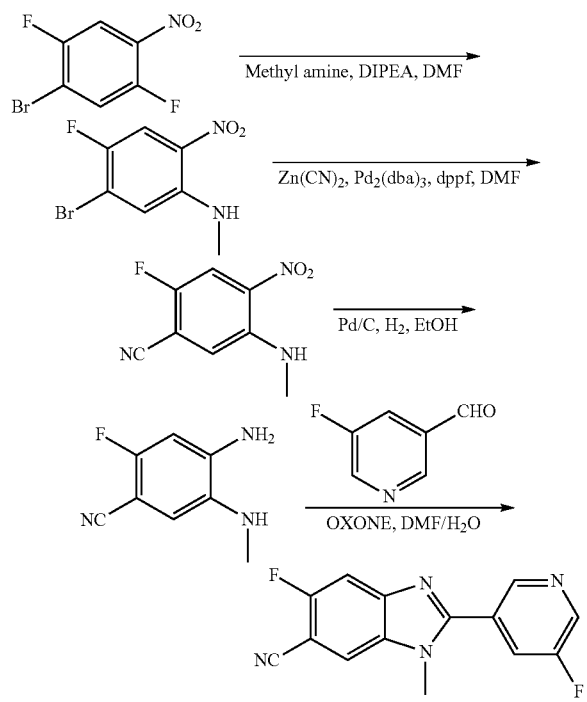

5-Fluoro-2-(5-fluoropyridin-3-yl)-1-methyl-1H-benzimidazole-6-carbonitrile

Step A. 5-bromo-4-fluoro-2-nitro-phenyl)-methyl-amine

To a solution of 1-Bromo-2,5-difluoro-4-nitro-benzene (1.5 g, 0.0063 mol) in DMF (15 mL), was added DIPEA (2.75 mL, 0.0157 mol) and methyl amine (2 M solution in THF) (4.66 ml, 0.00945 mol) carefully and the resulting solution was stirred at room temperature for 14 h. The reaction was quenched with ice-water and extracted with ethyl acetate (3×100 mL). The combined organic layers were washed with brine, dried over $Na_2SO_4$ and concentrated under vacuum to afford the crude compound, which was purified by column chromatography to obtain title compound 5-bromo-4-fluoro-2-nitro-phenyl)-methyl-amine as a brick red solid. $C_7H_6BrFN_2O_2$; $^1H$ NMR (400 MHz, $CDCl_3$) δ 7.95 (d, J=8.8 Hz, 1H), 7.88 (brs, 1H), 7.07 (d, J=5.6 Hz, 1H), 3.02 (d, J=5.6 Hz, 3H).

Step B. 2-Fluoro-5-methylamino-4-nitro-benzonitrile

A stirred solution of (5-Bromo-4-fluoro-2-nitro-phenyl)-methyl-amine (0.5 g, 0.0020 mol) in DMF (10 ml) was purged with Argon for 15 min. To the above mixture, $Pd_2(dba)_3$ (0.09 g, 0.001 mol), dppf (0.13 g, 0.0024 mol), and zinc cyanide (0.14 g, 0.0012 mol) was added carefully under argon atmosphere. The reaction mixture was heated at 120° C. for 22 h. Cooled to RT, diluted with saturated solution of ammonium chloride, filtered through CELITE® and the filter bed was thoroughly washed with ethyl acetate. The resulting mixture was separated, organic layer was washed with water, brine, dried over $Na_2SO_4$, filtered and concentrated under vacuum to afford the crude compound, which was purified by column chromatography to obtain title compound 2-fluoro-5-methylamino-4-nitro-benzonitrile as a brick red solid. $C_8H_6FN_3O_2$; $^1H$ NMR (400 MHz, $CdCl_3$) δ 8.04 (d, J=9.2 Hz, 1H), 7.85 (brs, 1H), 7.11 (d, J=4.8 Hz, 1H), 3.05 (d, J=4.8 Hz, 3H). MS (M+1): 195.1.

Step C. 4-Amino-2-fluoro-5-methylamino-benzonitrile

A stirred solution of 2-Fluoro-5-methylamino-4-nitro-benzonitrile (1.0 g, 0.0051 mol) in EtOH (20 mL) was hydrogenated using Pd/C for 3 h at room temperature. The reaction was filtered through CELITE® and the filter bed was thoroughly washed with EtOH. The resulting solution was concentrated to afford the crude 4-amino-2-fluoro-5-methylamino-benzonitrile as a brownish black solid. $C_8H_8FN_3$; Crude LCMS (M+1): 166.2; LCMS Purity: 85.05%.

Step D. 5-fluoro-2-(5-fluoropyridin-3-yl)-1-methyl-1H-benzimidazole-6-carbonitrile (399)

To a solution of 4-amino-2-fluoro-5-methylamino-benzonitrile (0.15 g, 0.00090 mol) and 5-Fluoro-pyridine-3-carbaldehyde (0.11 g, 0.0090 mol) in DMF (5 mL) and $H_2O$ (2 mL) was added OXONE® monopersulphate (0.19 g, 0.0012 mol). The reaction mixture was stirred at room temperature for 5 h, and was diluted with 10% $K_2CO_3$ solution to PH~8-10 and extracted with EtOAc (3×30 mL). The combined organic layers were washed with brine, dried over Na₂SO₄ and concentrated under vacuum to afford the crude compound, which was purified by column chromatography to obtain title compound 5-fluoro-2-(5-fluoropyridin-3-yl)-1-methyl-1H-benzimidazole-6-carbonitrile (398) as a brown solid. $C_{14}H_8F_2N_4$; $^1$H NMR (400 MHz, DMSO-$d_6$) δ 8.96 (s, 1H), 8.83 (d, J=2.4 Hz, 1H), 8.47 (d, 5.4 Hz, 1H), 8.29 (d, J=9.6 Hz, 1H), 7.88 (d, J=9.6 Hz, 1H), 3.98 (s, 3H); MS (M+1): 271.1. HPLC purity: 99.44%.

The compound in Table 17 was prepared by following the synthetic procedure as described in Example 399.

obtained. Clones V79-hCYP11B2-CLE9 and V79-hCYP11B1-8C7, were determined to produce the most aldosterone and cortisol, respectively, and were selected for inhibitor screening. For testing of inhibitors, cells were harvested at 80% confluency with 0.5% Trypsan-EDTA, washed once in PBS, and reconstituted in DMEM 0.1% BSA media at a cell concentration of 400,000 cells/mL. 25 μl of cells were added to a 384 well tissue culture treated plate and mixed with 0.25 μl of inhibitor or DMSO (1% final DMSO concentration) for 1 hour at 37° C., 5% $CO_2$. After pre-incubation with inhibitor, the reaction was initiated by adding 5 μl of substrate (final

TABLE 17

| Example | Structure | IUPAC Name | LCMS (M + 1) |
|---------|-----------|------------|--------------|
| 400 | 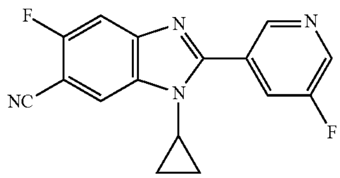 [SMILES: N#Cc1cc2c(cc1F)nc(-c1cncc(F)c1)n2C1CC1] | 1-cyclopropyl-5-fluoro-2-(5-fluoropyridin-3-yl)-1-H-benzimidazole-6-carbonitrile | 297.1 |
| 401 | 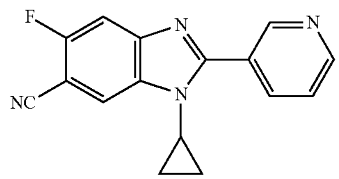 [SMILES: N#Cc1cc2c(cc1F)nc(-c1cccnc1)n2C1CC1] | 1-cyclopropyl-5-fluoro-2-(pyridin-3-yl)-1H-benzimidazole-6-carbonitrile | 279.1 |
| 402 | 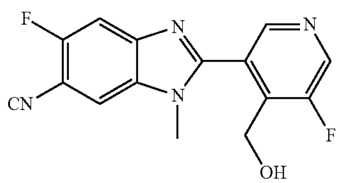 | 5-fluoro-2-[5-fluoro-4-(hydroxymethyl)pyridin-3-yl]-1-methyl-1H-benzimidazole-6-carbonitrile | 301.3 |
| 403 | 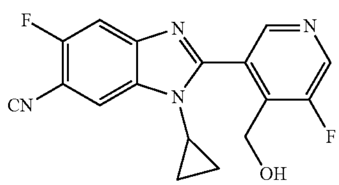 | 1-cyclopropyl-5-fluoro-2-[5-fluoro-4-(hydroxymethyl)pyridin-3-yl]-1H-benzimidazole-6-carbonitrile | 327.3 |
| 404 | 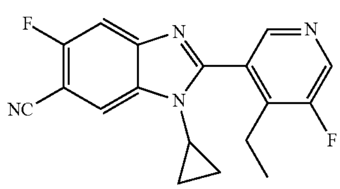 [SMILES: CCc1c(F)cncc1-c1nc2cc(F)c(C#N)cc2n1C1CC1] | 1-cyclopropyl-2-(4-ethyl-5-fluoropyridin-3-yl)-5-fluoro-1H-benzimidazole-6-carbonitrile | 325.2 |

Assay Description and Results

Methods for V79-Human-CYP11B2 and V79-Human-CYP11B1 Assays: V79 cell lines stably expressing the either the human CYP11B2 or the human CYP11B1 enzyme were generated using a standard transfection protocol. V79 cells were transfected with plasmids pTriEx3-Hygro-hCyp11B2 or pTriEx3-Hygro-hCyp11B1 using Lipofectamine2000 reagent. V79 cells that stably express the human CYP11B2 or human CYP11B1 enzyme were selected for and maintained in DMEM supplemented with 10% FBS and 400 μg/mL hygromycin for ~2 weeks. Single cell clones were generated by infinite dilution in DMEM supplemented with 10% FBS and 400 μg/mL hygromycin until single colonies were concentration of 125 nM 11-deoxycorticosterone for the CYP11B2 assay or 250 nM 11-deoxycortisol for the CYP11B1 assay). The reaction was carried out for 3 hours at 37° C., 5% $CO_2$ and was stopped by harvesting the supernatants. The amount of product in the supernatant (aldosterone for CYP11B2 assay and cortisol for the CYP11B1 assay) was measured using HTRF-based assay kit (Aldosterone HTRF-CisBio#64ALDPEB, Cortisol HTRF-CisBio #63IDC002-CORT). $IC_{50}$'s for the inhibitor were determined by plotting the amount of product formed against the concentration of inhibitor using sigmoidal dose-response curve (variable slope) fit in GraphPad.

The compounds of Examples 1-52 were tested in the V79-Human-CYP11B2 cell assay and found to have $IC_{50}$s for inhibition of human CYP11B2 of less than 1000 nM. Preferred compounds had $IC_{50}$s less than or equal to 100 nM and more preferred compounds had $IC_{50}$'s less than or equal to 20 nM.

The compounds of Examples 1-52 were also tested in the V79-Human-CYP11B1 cell assay and found to have at least 3-fold greater inhibition of CYP11B2 as compared to CYP11B1. A sub-group of compounds were at least 30-fold more selective for inhibition of CYP11B2 as compared to CYP11B1, and a further sub-group of compounds were at least 100-fold more selective for inhibition of CYP11B2. Representative examples of data collected for compounds of the present invention are shown in Table 18 below.

TABLE 18

| Example | IUPAC Name | V79 Human CYP11B2 $IC_{50}$ (nM) | V79 Human CYP11B1 $IC_{50}$ (nM) |
|---|---|---|---|
| 16 | 4-(1-cyclopropyl-6-fluoro-1H-benzimidazol-2-yl)isoquinoline | 0.1 | 59.2 |
| 32 | 4-(1-cyclopropyl-5,6-difluoro-1H-benzimidazol-2-yl)isoquinoline | 0.1 | 9.6 |
| 51 | 1-cyclopropyl-6-fluoro-2-[5-(2-methoxypropan-2-yl)pyridin-3-yl]-1H-benzimidazole | 0.2 | 4.7 |
| 38 | 2-[5-(1-cyclopropyl-5,6-difluoro-1H-benzimidazol-2-yl)pyridin-3-yl]propan-2-ol | 0.3 | 42 |
| 39 | 1-cyclopropyl-5,6-difluoro-2-[5-(2-methoxypropan-2-yl)-pyridin-3-yl]-1H-benzimidazole | 0.3 | 3.4 |
| 4 | 5-fluoro-1-methyl-2-(pyridin-3-yl)-1H-benzimidazole | 26 | 4075 |
| 17 | 1-cyclopropyl-5-fluoro-2-(pyridin-3-yl)-1H-benzimidazole | 28 | 3984 |
| 26 | 4-(1-ethyl-5-fluoro-1H-benzimidazol-2-yl)isoquinoline | 3.8 | 304 |
| 75 | 1-cyclopropyl-2-(pyridin-3-yl)-1H-benzo[d]-imidazole-6-carbonitrile | 1.226 | 374.3 |
| 76 | 1-cyclopropyl-2-(5-methoxypyridin-3-yl)-1H-benzimidazole-6-carbonitrile | 0.4222 | 1754 |
| 99 | 1-methyl-2-(pyridin-3-yl)-1H-benzimidazole-6-carbonitrile | 0.3162 | 98 |
| 129 | 6-chloro-1-cyclopropyl-5-fluoro-2-(5-fluoropyridin-3-yl)-1H-benzimidazole | 0.8102 | 161.4 |
| 131 | 4-(6-chloro-1-cyclopropyl-5-fluoro-1H-benzimidazol-2-yl)isoquinoline | 0.1264 | 122.2 |
| 132 | 6-chloro-1-cyclopropyl-5-fluoro-2-(pyridin-3-yl)-1H-benzimidazole | 0.5965 | 10000 |
| 135 | 6-chloro-1-cyclopropyl-5-fluoro-2-(5-methylpyridin-3-yl)-1H-benzimidazole | 0.2262 | 602.5 |
| 172 | 6-bromo-1-cyclopropyl-2-(5-fluoropyridin-3-yl)-1H-benzimidazole | 3.551 | 945.8 |
| 212 | 5,6-difluoro-1-methyl-2-(5-methylpyridin-3-yl)-1H-benzimidazole | 0.5852 | 149.4 |
| 226 | 1-cyclopropyl-5,6-difluoro-2-(4-methoxy-5-methylpyridin-3-yl)-1H-benzimidazole | 1.124 | 790.5 |
| 232 | 6-chloro-2-(5-methoxypyridin-3-yl)-1-methyl-1H-benzimidazole | 0.2002 | 162.2 |
| 233 | 6-chloro-1-methyl-2-(pyridin-3-yl)-1H-benzimidazole | 1.15 | 269.5 |
| 250 | 6-chloro-1-cyclopropyl-2-(pyridin-3-yl)-1H-benzimidazole | 1.594 | 425.2 |
| 256 | 4-(5,7-difluoro-1-methyl-1H-benzimidazol-2-yl)isoquinoline | 0.3457 | 490.4 |
| 267 | 5-(6,7-difluoro-1-methyl-1H-benzimidazol-2-yl)pyridine-3-carbonitrile | 0.151 | 205.5 |
| 268 | 2-(4,5-dimethylpyridin-3-yl)-6,7-difluoro-1-methyl-1H-benzimidazole | 0.2336 | 116.8 |
| 279 | 4-(1-cyclopropyl-6,7-difluoro-1H-benzimidazol-2-yl)isoquinoline | 0.2819 | 206 |
| 282 | 1-cyclopropyl-2-(4,5-dimethylpyridin-3-yl)-6,7-difluoro-1H-benzimidazole | 0.4171 | 294.8 |
| 284 | 1-cyclopropyl-6,7-difluoro-2-(4-methylpyridin-3-yl)-1H-benzimidazole | 1.353 | 300.2 |
| 335 | 6-chloro-5-fluoro-1-methyl-2-[4-(trifluoromethyl)pyridin-3-yl]-1H-benzimidazole; | 2.851 | 562.7 |
| 373 | 1-(benzyloxy)-5,6-difluoro-2-(5-fluoropyridin-3-yl)-1H-benzimidazole | 0.5 | 71.5 |

While the invention has been described with reference to certain particular embodiments thereof, numerous alternative embodiments will be apparent to those skilled in the art from the teachings described herein. Recitation or depiction of a specific compound in the claims (i.e., a species) without a specific stereoconfiguration designation, or with such a designation for less than all chiral centers, is intended to encompass the racemate, racemic mixtures, each individual enantiomer, a diastereoisomeric mixture and each individual diastereomer of the compound where such forms are possible due to the presence of one or more asymmetric centers. All patents, patent applications and publications cited herein are incorporated by reference in their entirety.

What is claimed is:

1. A compound of the formula Formula I

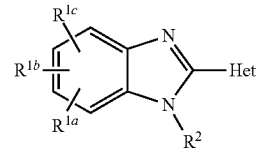

or a pharmaceutically acceptable salt thereof wherein:
Het is a heteroaromatic ring of the formula:

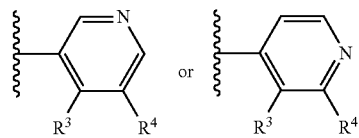

$R^{1a}$, $R^{1b}$ and $R^{1c}$ are independently selected from the group consisting of:
H; halogen; —CN; —OR$^5$; —NR$^8$R$^9$; —N(R$^{13}$)C(O)R$^{10}$; —N(R$^{13}$)SO$_2$—R$^{10}$; —C(O)R$^{10}$; —C(O)N(R$^6$)(R$^7$), —C(O)OR$^{10}$; —SO$_2$N(R$^6$)(R$^7$) or —S(O)$_m$—

R$^{10}$; alkyl optionally substituted one or more times by halogen; cycloalkyl optionally substituted one or more times by halogen, alkyl, or haloalkyl; aryl optionally substituted one or more times by halogen, —OR$^5$, alkyl, or haloalkyl or heteroaryl optionally substituted one or more times by halogen, —OR$^5$, alkyl or haloalkyl;

R$^2$ is selected from the group consisting of:
—OR$^5$, alkyl; alkyl—R$^{11}$; cycloalkyl optionally substituted one or more times by alkyl and halogen; and —C$_1$-C$_2$alkyl-cycloalkyl wherein the cycloalkyl group is optionally substituted one or more times by alkyl and halogen;

R$^3$ is selected from the group consisting of:
H; halogen; —CN; —NO$_2$; —OR$^{5a}$; —NR$^8$R$^9$; —N(R$^{13}$)C(O)R$^{10}$; —C(O)R$^{10}$—C(O)N(R$^6$)(R$^7$), —C(O)OR$^{10}$ or —S(O)$_m$—R$^{10}$; alkyl optionally substituted one or more times by halogen or —OR$^{5a}$; cycloalkyl optionally substituted one or more times by halogen, —OR$^{5a}$, alkyl, or haloalkyl; aryl optionally substituted one or more times by halogen, —OR$^{5a}$, alkyl, or haloalkyl or heteroaryl optionally substituted one or more times by halogen, —OR$^{5a}$, alkyl or haloalkyl;

R$^4$ is selected from the group consisting of:
H; halogen; —CN; —NO$_2$; —OR$^{5b}$; —NR$^8$R$^9$; —N(R$^{13}$)C(O)R$^{10}$; —C(O)R$^{10}$ —C(O)N(R$^6$)(R$^7$), —C(O)OR$^{10}$ or —S(O)$_m$—R$^{10}$; alkyl optionally substituted one or more times by halogen or OR$^{5b}$; cycloalkyl optionally substituted one or more times by halogen, alkyl, or haloalkyl; aryl optionally substituted one or more times by halogen, —OR$^{5b}$, alkyl, or haloalkyl or heteroaryl optionally substituted one or more times by halogen, —ORb$^5$, alkyl or haloalkyl;

or R$^3$ and R$^4$ are joined together to form a 5-7 membered carbocyclic or heterocyclic ring that is fused to the pyridyl ring to which R$^3$ and R$^4$ are attached, wherein the ring formed by R$^3$ and R$^4$ is optionally substituted with 1 to 3 of R$^{12}$;

R$^5$, R$^{5a}$ and R$^{5b}$ are each independently selected from the group consisting of H; alkyl optionally substituted with halogen; or aralkyl wherein the aryl ring is optionally substituted one or more times by halogen, —OR$^{5c}$, alkyl or haloalkyl;

R$^{5c}$ is H or alkyl optionally substituted with halogen;

R$^6$ and R$^7$ are each independently selected from the group consisting of:
H, alkyl optionally substituted with halogen; cycloalkyl optionally substituted with alkyl or halogen; aryl optionally substituted one or more times by halogen, —OR$^5$, alkyl, or haloalkyl or heteroaryl optionally substituted one or more times by halogen, —OR$^5$, alkyl or haloalkyl;

or R$^6$ and R$^7$ join together with the nitrogen to which they are attached to form a 3-7 membered saturated heterocyclic ring;

R$^8$ and R$^9$ are each independently selected from the group consisting of
H, alkyl or aralkyl wherein the aryl ring is optionally substituted one or more times by halogen, —OR$^5$, alkyl or haloalkyl;

R$^{10}$ is selected from the group consisting of alkyl optionally substituted one or more time with halogen; cycloalkyl optionally substituted one or more times by halogen, alkyl or haloalkyl; or aryl wherein the aryl ring is optionally substituted one or more times by halogen, —OR$^5$, alkyl or haloalkyl R$^{11}$ is selected from the group consisting of haloalkyl or —OR$^5$;

R$^{12}$ is independently selected at each occurrence from the group consisting of halogen or alkyl optionally substituted one or more time by halogen;

R$^{13}$ is H or alkyl; and m is 0, 1 or 2.

2. The compound as defined in claim 1 or a pharmaceutically acceptable salt thereof wherein:
R$^{1a}$, R$^{1b}$ or R$^{1c}$ is selected from the group consisting of —H, —F, —Cl, —Br, —CN, C$_1$-C$_6$ alkyl, C$_1$-C$_6$ alkyl substituted with —OH or halogen, —OC$_{1-6}$ alkyl, —N(R$^{13}$)C(O)—C$_1$-C$_6$ alkyl, —C(O)N(H)C$_1$-C$_6$ alkyl, —NH$_2$, —NH(C$_1$-C$_6$ alkyl), —N(C$_{1-6}$ alkyl)( C$_1$-C$_6$ alkyl), —C(O)O—C$_1$-C$_6$alkyl, —S—C$_1$-C$_6$ alkyl, —S(O)—C$_1$-C$_6$ alkyl, —S(O)$_2$—C$_1$-C$_6$ alkyl, —N(R$^{13}$)S(O)$_2$—C$_1$-C$_6$ alkyl, or optionally C$_1$-C$_6$ alkyl substituted heteroaryl, wherein the heteroaryl is an isooxazolyl, pyrazolyl, oxazolyl, imidazolyl or pyridyl ring;

R$^2$ is OH, C$_1$-C$_6$ alkyl, C$_1$-C$_6$ alkyl substituted with —OH or halogen, —O—C$_1$-C$_6$ alkyl, cyclopropyl optionally substituted by halogen, —OH or —O—C$_1$-C$_6$ alkyl or —OCH$_2$-phenyl, wherein the phenyl ring is optionally substituted by halogen, —OH or —O—C$_1$-C$_6$ alkyl; and R$^3$ and R$^4$ are independently H, halogen —CN, —C$_1$-C$_6$ alkyl substituted optionally substituted with —OH, —O—C$_1$-C$_6$ alkyl, or halogen, —O—C$_1$-C$_6$ alkyl, —C(O)C$_1$-C$_6$alkyl, —C(O)OH, —C(O)O—C$_1$-C$_6$ alkyl, —S—C$_1$-C$_6$ alkyl, —S(O) —C$_1$-C$_6$ alkyl, —S(O)$_2$—C$_1$-C$_6$alkyl, —NH$_2$, —NH(C$_{1-C6}$ alkyl), —N(C$_1$-C$_6$ alkyl)(C$_1$-C$_6$ alkyl), optionally halo substituted phenyl, or optionally C$_1$-C$_6$ alkyl substituted heteroaryl, wherein the heteroaryl is an isooxazolyl, pyrazolyl, oxazolyl, imidazolyl or pyridyl ring or R$^3$ and R$^4$ together with the pyridyl ring form:

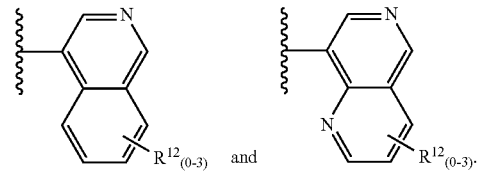

3. The compound as defined in claim 1 having the structural formula

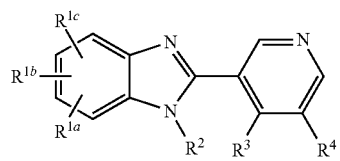

Ia or a pharmaceutically acceptable salt thereof wherein:
R$^{1a}$, R$^{1b}$ and R$^{1c}$ are independently selected from the group consisting of:
—H, —F, —Cl, —Br, —CN, —OR$^5$, —SO$_2$NR$^6$R$^7$,
—C$_1$-C$_6$ alkyl optionally substituted with 1 to 3 of —F, or
—C$_3$-C$_7$ cycloalkyl optionally substituted with 1 to 3 substituents independently selected from the group consisting of —CH$_3$ or —F;

$R^2$ is selected from the group consisting of:
- (a) —$C_1$-$C_5$ alkyl-$R^{11}$, (b) —$C_1$-$C_4$ alkyl; (c) cyclopropyl optionally substituted with 1 or 2 substituents independently selected from the group consisting of —$CH_3$ or —F or —$C_1$-$C_2$ alkyl-cyclopropyl wherein cyclopropyl is optionally substituted with 1 or 2 substituents independently selected from the group consisting of —$CH_3$ or —F;

$R^3$ is selected from the group consisting of:
- —H, —F, —Cl, —Br, —CN, —$OR^{5a}$, —$C_1$-$C_6$ perfluoroalkyl, —$C_1$-$C_6$ alkyl optionally substituted with 1 to 3 of F or optionally substituted with —OH, or —$C_3$-$C_7$ cycloalkyl optionally substituted with 1 to 3 substituents independently selected from the group consisting of —$CH_3$ and —F;

$R_4$ is selected from the group consisting of:
- (a) —H, —F, —Cl, —Br, —CN, —$OR^5b$, —$NR^8R^9$, —$CO_2R^{10}$ or —$COR^{10}$,
- (b) —$C_1$-$C_6$ perfluoroalkyl,
- (c) —$C_1$-$C_7$ alkyl optionally substituted with 1 to 6 of —F and optionally substituted with 1 or 2 substituents independently selected from the group consisting of (i) —$OR^5b$ or (ii) aryl optionally substituted with 1 to 3 substituents independently selected from the group consisting of F, —Cl or —$C_1$-$C_3$alkyl optionally substituted with 1 to 3 of —F,
- (d) —$C_3$-$C_7$ cycloalkyl optionally substituted with 1 or 2 substituents independently selected from the group consisting of —$C_1$-C6 alkyl, —$CF_3$ or F,
- (e) aryl optionally substituted with 1 to 3 substituents independently selected from the group consisting of —F, —Cl or —$C_1$-$C_3$alkyl optionally substituted with 1 to 3 of —F or
- (f) heteroaryl optionally substituted with 1 to 3 substituents independently selected from the group consisting of —F, —Cl or —$C_1$-$C_3$ alkyl optionally substituted with 1 to 3 of —F;

or $R^3$ and $R^4$ are joined together to form a 5-7 membered carbocyclic or heterocyclic ring that is fused to the pyridyl ring to which $R^3$ and $R^4$ are attached, wherein the ring formed by $R^3$ and $R^4$ is optionally substituted with 1 to 3 of $R^{12}$;

$R^5$, $R^{5a}$ and $R^{5b}$ are each independently selected from the group —consisting of —H or —$C_1$-$C_6$ alkyl optionally substituted with 1 to 3 of —F;

$R^6$ and $R^7$ are each independently selected from the group consisting of
- (a) —$C_1$-$C_6$ alkyl optionally substituted with 1 to 3 of —F, (b) —$C_3$-$C_7$ cycloalkyl optionally substituted with 1 or 2 substituents independently selected from the group consisting of —$CH_3$ and —F, (c) aryl or (d) heteroaryl, or $R^6$ and $R^7$ join together with the nitrogen to which they are attached to form a 3-7 membered saturated heterocyclic ring;

$R^8$ and $R^9$ are each independently selected from the group consisting of
- —H, —$C_1$-$C_6$ alkyl, or —$CH_2$-phenyl wherein phenyl is optionally substituted with 1 to 3 substituents independently selected from the group consisting of —F, —Cl or —$CF_3$;

$R_{10}$ is selected from the group consisting of
- —C1-C6 alkyl optionally substituted with 1 to 3 of —F, or
- —$C_3$-$C_7$ cycloalkyl optionally substituted with 1 or 2 substituents independently selected from the group consisting of —$CH_3$ and —F; or

- —phenyl wherein the phenyl is optionally substituted with 1 to 3 substituents independently selected from the group consisting of —F, —Cl or —$CF_3$;

$R^{11}$ is selected from the group consisting of —$CH_2F$, —$CHF_2$ or —$CF_3$;

$R^{12}$ is independently selected at each occurrence from the group consisting of —F, —Cl or —$C_1$-$C_3$alkyl optionally substituted with 1 to 3 of —F.

4. The compound as defined in claim 3 or a pharmaceutically acceptable salt thereof wherein $R^{1c}$ is —H and $R^2$ is cyclopropyl optionally substituted with one or two substituents independently selected from the group consisting of —$CH_3$ or —F.

5. The compound as defined claim 3 or a pharmaceutically acceptable salt thereof wherein (a) $R^3$ is —H and $R^4$ is selected from the group consisting of —H, —F, —Cl, —Br, —CN or —$C_1$-$C_7$ alkyl optionally substituted with 1 to 6 of —F or optionally substituted with 1 or 2 of —$OR^{5b}$; or (b+heterocyclic ring that is fused to the pyridyl ring to which $R^3$ and $R^4$ are attached wherein the ring formed by $R^3$ and $R^4$ is optionally substituted with 1 to 3 of $R^{12}$.

6. The compound as defined in claim 5 or a pharmaceutically acceptable salt thereof wherein $R^{1c}$ is —H and $R^2$ is cyclopropyl optionally substituted with 1 or 2 substituents independently selected from the group consisting of —$CH^3$ or —F.

7. The compound as defined claim 3 or a pharmaceutically acceptable salt thereof wherein
$R^4$ is

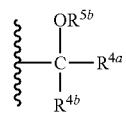

wherein $R^{5b}$ is —H or —$C_1$-$C^3$ alkyl optionally substituted with 1 to 3 of —F, and $R^{4a}$ and $R^{4b}$ are each independently selected from the group consisting of (a) —$C_1$-$C_3$ alkyl, (b) —$C_1$—$C_3$ alkyl substituted with 1 to 3 of —F or (c) aryl optionally substituted with 1 or 2 substituents independently selected from the group consisting of —F, —Cl or —$C_1$—$C_3$ alkyl optionally substituted with 1 to 3 of —F.

8. The compound as defined in claim 3 or a pharmaceutically acceptable salt thereof wherein:
$R^{1a}$, $R^{1b}$ and $R^{1c}$ are each independently selected from —H, —F, —$CF_3$ or —$OCH_3$;
$R^2$ is selected from (a) —$C_1$-$C_3$alkyl, (b) —$C_1$-$C_2$alkyl—$R^{11}$, (c) —$(CH_2)_{(1-2)}$-cyclopropyl wherein cyclopropyl is optionally substituted with —$CH_3$ or —F, or (d) cyclopropyl optionally substituted with —$CH_3$ or —F;
$R^3$ is —H or is joined together with $R^4$ to form a 5-7 membered carbocyclic or heterocyclic ring that is fused to the pyridyl ring to which $R^3$ and $R^4$ are attached selected from the group consisting of

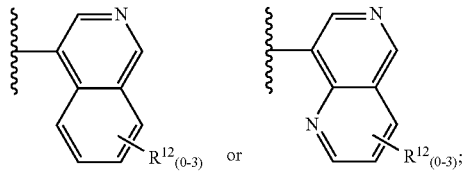

R⁴, when not joined with R³, is selected from —H, —F, —CN, —OCH₃, —COCH₃, —COOCH₃, —CF₃, or

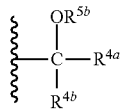

wherein $R_{5b}$ is —H or —CH₃, and $R^{4a}$ and $R^{4b}$ are each independently selected from the group consisting of —CH₃ or —CF₃; and $R^5$ and $R^{5a}$ are each independently selected from the group consisting of —H, —CH₃ and —CF₃.

9. The compound as defined in claim 1 having the structural formula

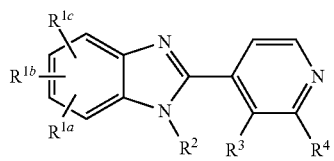

Ib or a pharmaceutically acceptable salt thereof wherein
$R^{1a}$, $R^{1b}$ and $R^{1c}$ are independently selected from the group consisting of:
  —H, —F, —Cl, —Br, —CN, —OR⁵, —SO₂NR⁶R⁷, —C(O)OR¹⁰
  —C₁-C₆ alkyl optionally substituted with 1 to 3 of —F, or —C₃-C₇ cycloalkyl optionally substituted with 1 to 3 substituents independently selected from the group consisting of —CH₃ and —F;
$R^2$ is selected from the group consisting of:
  (a) —C₁-C₅ alkyl-R¹¹, (b) —C₁-C₄ alkyl; (c) cyclopropyl optionally substituted with 1 or 2 substituents independently selected from the group consisting of —CH₃ or —F or (d) —C₁-C₂ alkyl-cyclopropyl wherein cyclopropyl is optionally substituted with 1 or 2 substituents independently selected from the group consisting of —CH₃ or —F;
$R^3$ is selected from the group consisting of:
  —H, —F, —Cl, —Br, —CN, —OR⁵ᵃ, —C₁-C₆ perfluoroalkyl,
  —C₁-C₆ alkyl optionally substituted with 1 to 3 of —F and optionally substituted with —OH, or
  —C₃-C₇ cycloalkyl optionally substituted with 1 to 3 substituents independently selected from the group consisting of —CH₃ or —F;
$R^4$ is selected from the group consisting of:
  (a) —H, —F, —Cl, —Br, —CN, —OR⁵ᵇ, —NR⁸R⁹, —CO₂R¹⁰ or —COR¹⁰,
  (b) —C₁-C₆ perfluoroalkyl,
  (c) —C₁-C₇ alkyl optionally substituted with 1 to 6 of —F and optionally substituted with 1 or 2 substituents independently selected from the group consisting of
    (i) —OR⁵ᵇ or (ii) aryl optionally substituted with 1 to 3 substituents independently selected from the group consisting of —F, —Cl or —C₁-C₃alkyl optionally substituted with 1 to 3 of —F,
  (d) —C₃-C₇ cycloalkyl optionally substituted with 1 or 2 substituents independently selected from the group consisting of —C₁-C₆ alkyl, —CF₃ or —F,
  (e) aryl optionally substituted with 1 to 3 substituents independently selected from the group consisting of —F, —Cl or —C₁-C₃alkyl optionally substituted with 1 to 3 of —F and
  (f) heteroaryl optionally substituted with 1 to 3 substituents independently selected from the group consisting of —F, —Cl or —C₁-C₃alkyl optionally substituted with 1 to 3 of —F;
or $R^3$ and $R^4$ are joined together to form a 5-7 membered carbocyclic or heterocyclic ring that is fused to the pyridyl ring to which $R^3$ and $R^4$ are attached, wherein the ring formed by $R^3$ and $R^4$ is optionally substituted with 1 to 3 of $R^{12}$;
$R^5$, $R^{5a}$ and $R^{5b}$ are each independently selected from the group consisting of —H or —C₁-C₆ alkyl optionally substituted with 1 to 3 of —F;
$R^6$ and $R^7$ are each independently selected from the group consisting of
  (a) —C₁-C₆ alkyl optionally substituted with 1 to 3 of —F, (b) —C₃-C₇ cycloalkyl optionally substituted with 1 or 2 substituents independently selected from the group consisting of —CH₃ or —F, (c) aryl or (d) heteroaryl,
or $R^6$ and $R^7$ join together with the nitrogen to which they are attached to form a 3-7 membered saturated heterocyclic ring;
$R^8$ and $R^9$ are each independently selected from the group consisting of —H, —C₁-C₆ alkyl or —CH₂-phenyl wherein phenyl is optionally substituted with 1 to 3 substituents independently selected from the group consisting of —F, —Cl or —CF₃;
$R^{10}$ is selected from the group consisting of
  —C₁-C₆ alkyl optionally substituted with 1 to 3 of —F,
  —C₃-C₇ cycloalkyl optionally substituted with 1 or 2 substituents independently selected from the group consisting of —CH₃ or —F; or
  —phenyl which is optionally substituted with 1 to 3 substituents independently selected from the group consisting of —F, —Cl or —CF₃;
$R^{11}$ is selected from the group consisting of —CH₂F, —CHF₂ or —CF₃;
$R^{12}$ is independently selected at each occurrence from the group consisting of —F, —Cl or —C₁-C₃alkyl optionally substituted with 1 to 3 of —F.

10. The compound as defined in claim 9 or a pharmaceutically acceptable salt thereof wherein:
$R^{1a}$, $R^{1b}$ and $R^{1c}$ are independently selected from the group consisting of:
  —H, —F, —Cl, —Br, —CN, —OR⁵, —C(O)OR¹⁰, or —C₁-C₆ alkyl optionally substituted with 1 to 3 of —F;
$R^2$ is selected from the group consisting of:
  C₁-C₄ alkyl or cyclopropyl;
$R^3$ is selected from the group consisting of:
  —H, —F, —Cl, —Br, —CN, —OR⁵ᵃ, —C₁-C₆ perfluoroalkyl, or —C₁-C₆ alkyl;
$R^4$ is selected from the group consisting of:
  —H, —F, —Cl —Br, —CN, —OR⁵ᵇ and —C₁-C₆ perfluoroalkyl,
$R^5$ and $R^{5b}$ are each independently selected from the group consisting of —H and —C₁-C₆ alkyl optionally substituted with 1 to 3 of —F; and
$R^{10}$ is selected from the group consisting of
  C₁-C₆ alkyl optionally substituted with 1 to 3 of —F.

11. The compound of claim 1 selected from the group consisting of:
   4 (1-cyclopropyl-6-fluoro-1H-benzimidazol-2-yl)isoquinoline;
   4(1-cyclopropyl-5,6-difluoro-1H-benzimidazol-2-yl)isoquinoline;
   1-cyclopropyl-6-fluoro-2-[5-(2-methoxypropan-2-yl)pyridin-3-yl]-1H-benzimidazole;
   4-(1-ethyl-5,6-difluoro-1H-benzimidazol-2-yl)isoquinoline;
   4-(1-cyclopropyl-5-fluoro-1H-benzimidazol-2-yl)isoquinoline;
   2-[5-(1-ethyl-5,6-difluoro-1H-benzimidazol-2-yl)pyridin-3-yl]propan-2-ol;
   methyl 5-(1-cyclopropyl-6-fluoro-1H-benzimidazol-2-yl)pyridine-3-carboxylate;
   4-(1-ethyl-5-fluoro-1H-benzimidazol-2-yl)isoquinoline;
   1-cyclopropyl-6-fluoro-2-(5-fluoropyridin-3-yl)-1H-benzimidazole;
   1-cyclopropyl-6,7-difluoro-2-(pyridin-3-yl)-1H-benzimidazole;
   6-fluoro-1 -(1 -methylcyclopropyl)-2-(pyridin-3-yl)-1H-benzimidazole;
   2-[5-(1-cyclopropyl-5,7-difluoro-1H-benzimidazol-2-yl)pyridin-3-yl]propan-2-ol;
   5-fluoro-1-methyl-2-(pyridin-3-yl)-1H-benzimidazole;
   8-(1-cyclopropyl-6-fluoro-1H-benzimidazol-2-yl)-1,6-naphthyridine;
   8-(1-ethyl-5,6-difluoro-1H-benzimidazol-2-yl)-1,6-naphthyridine;
   1-cyclopropyl-6-fluoro-2-(pyridin-3-yl)-1H-benzimidazole;
   1-cyclopropyl-5-fluoro-2-(pyridin-3-yl)-1 H-benzimidazole;
   2[5-(1 -cyclopropyl-6-fluoro-1H-benzimidazol-2-yl)pyridin-3-yl]propan-2-ol;
   1-cyclopropyl-5,6-difluoro-2-(pyridin-3-yl)-1H-benzimidazole;
   1-cyclopropyl-4,6-difluoro-2-(pyridin-3-yl)-1H-benzimidazole;
   1-cyclopropyl-5,7-difluoro-2-(pyridin-3-yl)-1H-benzimidazole;
   2[5-(1 -cyclopropyl-5-fluoro-1H-benzimidazol-2-yl)pyridin-3-yl]propan-2-ol;
   8(1-cyclopropyl-5,6-difluoro-1H-benzimidazol-2-yl)-1,6-naphthyridine;
   2-[5-(1 -cyclopropyl-5,6-difluoro-1H-benzimidazol-2-yl)pyridin-3-yl]propan-2-ol;
   2-[5-(1-cyclopropyl-5,6-difluoro-1H-benzimidazol-2-yl)pyridin-3-yl]-1,1,1-trifluoropropan-2-ol,
   1-cyclopropyl-5,6-difluoro-2-(5-fluoropyridin-3-yl)-1H-benzimidazole;
   1-cyclopropyl-5,6-difluoro-2-(5-fluoro-4-methylpyridin-3-yl)-1H-benzimidazole;
   1-cyclopropyl-5,6-difluoro-2-(4-methylpyridin-3-yl)-1H-benzimidazole;
   6-fluoro-2-(4-methylpyridin-3-yl)-1 -methyl-1H-benzimidazole;
   1 -ethyl-6-fluoro-2-(4-methylpyridin-3-yl)- 1H-benzimidazole;
   5,6-di-difluoro-2-(4-methylpyridin-3-yl)-1 -methyl-1H-benzimidazole;
   5,6-di-difluoro-2-(2-hydroxy-2-propylpyridin-3-yl)-1-methyl-1H-benzimidazole;
   1-cyclopropyl-6-fluoro-2-(5-fluoro4-methylpyridin-3-yl)-1H-benzimidazole;
   6,7-difluoro-2-(4-methylpyridin-3-yl)-1 -methyl-1H-benzimidazole;
   5,7-difluoro-2-(5-fluoro-4-methylpyridin-3-yl)-1-methyl-1H-benzimidazole;
   1-cyclopropyl-5,7-difluoro-2-(5-fluoro-4-methylpyridin-3-yl)-1H-benzimidazole;
   5,7-difluoro-2-(4-methylpyridin-3-yl)-1 -methyl-1H-benzimidazole;
   or a the pharmaceutically acceptable salts thereof.

12. The compound as defined in claim 1 selected from the group consisting of:
   1-cyclopropyl-6-fluoro-2-(pyridin-3-yl)-1H-benzimidazole;
   1-cyclopropyl-5-fluoro-2-(pyridin-3-yl)-1H-benzimidazole;
   2-[5-(1-cyclopropyl-6-fluoro-1H-benzimidazol-2-yl)pyridin-3-yl]propan-2-ol;
   1-cyclopropyl-5,6-difluoro-2-(pyridin-3-yl)-1H-benzimidazole;
   1-cyclopropyl-4,6-difluoro-2-(pyridin-3-yl)-1H-benzimidazole;
   1-cyclopropyl-5,7-difluoro-2-(pyridin-3-yl)-1H-benzimidazole;
   2-[5-(1-cyclopropyl-5-fluoro-1H-benzimidazol-2-yl)pyridin-3-yl]propan-2-ol;
   8(1-cyclopropyl-5,6-difluoro-1H-benzimidazol-2-yl)-1,6-naphthyridine;
   2-[5-(1 -cyclopropyl-5,6-difluoro-1H-benzimidazol-2-yl)pyridin-3-yl]propan-2-ol;
   2-[5-(1-cyclopropyl-5,6-difluoro-1H-benzimidazol-2-yl)pyridin-3-yl]-1 ,1,1-trifluoropropan-2-ol;
   1-cyclopropyl-5,6-difluoro-2-(5-fluoropyridin-3-yl)-1H-benzimidazole;
   1-cyclopropyl-5,6-difluoro-2-(5-fluoro-4-methylpyridin-3-yl)-1H-benzimidazole;
   1-cyclopropyl-5,6-difluoro-2-(4-methylpyridin-3-yl)-1H-benzimidazole;
   6-fluoro-2-(4-methylpyridin-3-yl)-1-methyl-1H-benzimidazole;
   1-ethyl-6-fluoro-2-(4-methylpyridin-3-yl)- 1H-benzimidazole;
   5,6-di-difluoro-2-(4-methylpyridin-3-yl)-1 -methyl-1H-benzimidazole;
   5,6-di-difluoro-2-(2-hydroxy-2-propylpyridin-3-yl)-1-methyl-1H-benzimidazole;
   1-cyclopropyl-6-fluoro-2-(5-fluoro4-methylpyridin-3-yl)-1H-benzimidazole;
   6,7-difluoro-2-(4-methyl pyridin-3-yl)-1 -methyl-1H-benzimidazole;
   5,7-difluoro-2-(5-fluoro-4-methylpyridin-3-yl)-1-methyl-1H-benzimidazole;
   1 -cyclopropyl-5,7-difluoro-2-(5-fluoro-4-methylpyridin-3-yl)-1H-benzimidazole;
   5,7-difluoro-2-(4-methylpyridin-3-yl)-1 -methyl-1H-benzimidazole;
   or the pharmaceutically acceptable salts thereof.

13. The compound of claim 1 selected from the group consisting of:
   1-cyclopropyl-2-(pyridin-3-yl)-1H-benzo[d]imidazole-6-carbonitrile;
   1-cyclopropyl-2-(5-methoxypyridin-3-yl)-1H-benzimidazole-6-carbonitrile;
   1-methyl-2-(pyridin-3-yl)-1H-benzimidazole-6-carbonitrile;
   6-chloro-1-cyclopropyl-5-fluoro-2-(5-fluoropyridin-3-yl)-1H-benzimidazole;

4-(6-chloro-1-cyclopropyl-5-fluoro-1H-benzimidazol-2-yl)isoquinoline;
6-chloro-1-cyclopropyl-5-fluoro-2-(pyridin-3-yl)-1H-benzimidazole;
6-chloro-1-cyclopropyl-5-fluoro-2-(5-methylpyridin-3-yl)-1H-benzimidazole;
6-bromo-1-cyclopropyl-2-(5-fluoropyridin-3-yl)-1H-benzimidazole;
5,6-difluoro-1-methyl-2-(5-methylpyrid in-3-yl)-1H-benzimidazole;
1-cyclopropyl-5,6-difluoro-2-(4-methoxy-5-methylpyridin-3-yl)-1H-benzimidazole;
6-chloro-2-(5-methoxypyridin-3-yl)-1-methyl-1H-benzimidazole;
6-chloro-2-(5-methoxypyridin-3-yl)-1-methyl-1H-benzimidazole;
6-chloro-1-cyclopropyl-2-(pyridin-3-yl)-1H-benzimidazole;
4-(5,7-difluoro-1-methyl-1 H-benzimidazol-2-yl)isoquinoline;
5-(6,7-difluoro-1-methyl-1 H-benzimidazol-2-yl)pyridine-3-carbonitrile;
2-(4,5-dimethylpyridin-3-yl)-6,7-difluoro-1 -methyl-1H-benzimidazole;
4(1-cyclopropyl-6,7-difluoro-1H-benzimidazol-2-yl)isoquinoline;
1-cyclopropyl-2-(4,5-dimethylpyridin-3-yl)-6,7-difluoro-1H-benzimidazole;
1-cyclopropyl-6,7-difluoro-2-(4-methylpyridin-3-yl)-1H-benzimidazole;
6-chloro-5-fluoro-1-methyl-2-[4-(trifluoromethyl)pyridin-3-yl]-1H-benzimidazole;
1 -(benzyloxy)-5,6-difluoro-2-(5-fluoropyridin-3-yl)-1H-benzimidazole;
or a pharmaceutically acceptable salt thereof.

14. A pharmaceutical composition comprised of a compound as defined in claim 1 or a pharmaceutically acceptable salt thereof and a pharmaceutically acceptable carrier.

15. A compound selected from the group consisting of:
6-fluoro-2-(5-methoxl-2-(pyridin-3-yl)-1-methyl-1H-benzimidazole;
6-fluoro-1-methyl-2-(pyridin-3-yl)-1H-benzimidazole;
6-fluoro-1-(propan-2-yl)-2-(pyridin-3-yl)-1H-benzimidazole;
5-fluoro-1-methyl-2-(pyridin-3-yl)-1H-benzimidazole;
6-Methoxy-2-(5-methoxypyridin-3-yl)-i-methyl-1H-benzimidazole;
6-fluoro-2-(5-fluoropyridin-3-yl)-1-methyl-1H-benzimidazole;
1-ethyl-6-fluoro-2-(pyridin-3-yl)-1H-benzimidazole;
6-fluoro-2-(5-fluoropyridin-3-yl)-1-(propan-2-yl)-1H-benzimidazole;
1-cyclopropyl-4-fluoro-2-(pyridin-3-yl)-1H-benzimidazole;
1-ethyl-5-fluoro-2-(pyridin-3-yl)-1H-benzimidazole;
4-(1-ethyl-5-fluoro-1H-benzimidazol-2-yl)isoquinoline;
4-(1-ethyl-5,6-difluoro-1H-benzimidazol-2-yl)isoquinoline;
1-ethyl-5,6-difluoro-2-(pyridin-3-yl)-1H-benzimidazole;
8-(1-ethyl-5,6-difluoro-1H-benzimidazol-2-yl)-1,6-naphthyridine; methyl5-(6-fluoro-1-methyl-1H-benzimidazol-2-yl)pyridine-3-carboxylate;
2-[5-(1-ethyl-5,6-difluoro-1H-benzimidazol-2-yl)pyridin-3-yl]propan-2-ol;
6-fluoro-1-methyl-2-(5-methylpyridin-3-yl)-1H-benzimidazole;
6-fluoro-2-(5-isopropoxypyridin-3-yl)-1-methyl-1H-benzimidazole;
5,6-Difluoro-1-methyl-2-(pyridin-3-yl)-1H-benzimidazole;
5,6-Difluoro-2-(5-fluoropyridin-3-yl)-1-methyl-1H-benzimidazole;
6,7-Difluoro-2-(5-fluoropyridin-3-yl)-1-methyl-1H-benzimidazole;
5,7-Difluoro-2-(5-fluoropyridin-3-yl)-1-methyl-1H-benzimidazole;
6-Fluoro-2-(4-methylpyridin-3-yl)-1-methyl-1H-benzimidazole;
1-Ethyl-6-fluoro-2-(4-methylpyridin-3-yl)-1H-benzimidazole;
5,6-Di-difluoro-2-(4-methylpyridin-3-yl)-1-methyl-1H-benzimidazole;
5,6-Di-difluoro-2-(2-hydroxy-2-propylpyridin-3-yl)-1-methyl-1H-benzimidazole;
6,7-Difluoro-2-(4-methylpyridin-3-yl)-1-methyl-1H-benzimidazole;
5,7-Difluoro-2-(5-fluoro-4-methylpyridin-3-yl)-1-methyl-1H-benzimidazole;
5,7-Difluoro-2-(4-methylpyridin-3-yl)-1-methyl-1H-benzimidazole;
2-(isoquinolin-4-yl)-1-methyl-1H-benzimidazole-6-carbonitrile;
2-(5-methoxypyridin-3-yl)-1-methyl-1H-benzimidazole-6-carbonitrile;
2-(5-cyanopyridin-3-yl)-1-methyl-1H-benzimidazole-6-carbonitrile;
2-(5-fluoropyridin-3-yl)-1-methyl-1H-benzimidazole-6-carbonitrile;
2-(5-bromopyridin-3-yl)-1-methyl-1H-benzimidazole-6-carbonitrile;
1-methyl-2-[4-(trifluoromethyl)pyridin-3-yl]-1H-benzimidazole-6-carbonitrile;
1-methyl-2-(5-methylpyridin-3-yl)-1H-benzimidazole-6-carbonitrile;
1-methyl-2-(4-methylpyridin-3-yl)-1H-benzimidazole-6-carbonitrile;
1-methyl-2-[5-(trifluoromethyl)pyridin-3-yl]-1H-benzimidazole-6-carbonitrile;
2-(3-fluoropyridin-4-yl)-1-methyl-1H-benzimidazole-6-carbonitrile;
2-(3-aminopyridin-4-yl)-1-methyl-1H-benzimidazole-6-carbonitrile;
2-(4-ethyl-5-fluoropyridin-3-yl)-1-methyl-1H-benzimidazole-6-carbonitrile;
2-[5-fluoro-4-(hydroxymethyl)pyridin-3-yl]-1-methyl-1H-benzimidazole-6-carbonitrile;
5-bromo-2-(5-fluoropyridin-3-yl)-1-methyl-1H-benzimidazole;
4-(5-bromo-1-methyl-1H-benzimidazol-2-yl)isoquinoline;
5-bromo-1-methyl-2-(pyridin-3-yl)-1H-benzimidazole;
5-bromo-2-(5-methoxypyridin-3-yl)-1-methyl-1H-benzimidazole;
4-(5-bromo-1-methyl-1H-benzimidazol-2-yl)-8-fluoroisoquinoline;
5-bromo-1-methyl-2-(pyridin-4-yl)-1H-benzimidazole;
5-bromo-1-methyl-2-[4-(trifluoromethyl)pyridin-3-yl]-1H-benzimidazole;
5-bromo-2-(3-fluoropyridin-4-yl)-1-methyl-1H-benzimidazole;
5-bromo-1-ethyl-2-(pyridin-3-yl)-1H-benzimidazole;
5-bromo-1-(propan-2-yl)-2-(pyridin-3-yl)-1H-benzimidazole;

1-methyl-2-(pyridin-3-yl)-5-(trifluoromethyl)-1H-benzimidazole;
2-(5-methoxypyridin-3-yl)-1-methyl-5-(trifluoromethyl)-1H-benzimidazole;
2-(5-fluoropyridin-3-yl)-1-methyl-5-(trifluoromethyl)-1H-benzimidazole;
1-methyl-5-(trifluoromethyl)-2-[5-(trifluoromethyl)pyridin-3-yl]-1H-benzimidazole;
2-(5-bromopyridin-3-yl)-1-methyl-5-(trifluoromethyl)-1H-benzimidazole;
1-methyl-2-[5-(1-methyl-1H-pyrazol-4-yl)pyridin-3-yl]-5-(trifluoromethyl)-1H-benzimidazole;
2-[5-(3,5-dimethylisoxazol-4-yl)pyridin-3-yl]-1-methyl-5-(trifluoromethyl)-1H-benzimidazole;
6-fluoro-4-[1-methyl-5-(trifluoromethyl)-1H-benzimidazol-2-yl]isoquinoline;
1-methyl-2-(pyridin-4-yl)-5-(trifluoromethyl)-1H-benzimidazole;
6-chloro-5-fluoro-2-(5-fluoropyridin-3-yl)-1-methyl-1H-benzimidazole;
1-methyl-2-(pyridin-3-yl)-1H-benzimidazole-5-carbonitrile;
2-(5-fluoropyridin-3-yl)-1-methyl-1H-benzimidazole-5-carbonitrile;
2-(5-bromopyridin-3-yl)-1-methyl-1H-benzimidazole-5-carbonitrile;
2-(8-fluoroisoquinolin-4-yl)-1-methyl-1H-benzimidazole-5-carbonitrile;
1-methyl-2-[5-(trifluoromethyl)pyridin-3-yl]-1H-benzimidazole-5-carbonitrile;
1-methyl-2-(5-methylpyridin-3-yl)-1H-benzimidazole-5-carbonitrile;
1-methyl-2-[5-(1-methyl-1H-pyrazol-4-yl)pyridin-3-yl]-1H-benzimidazole-5-carbonitrile;
2-(5-methoxypyridin-3-yl)-1-methyl-1H-benzimidazole-5-carbonitrile;
2-[5-(3,5-dimethylisoxazol-4-yl)pyridin-3-yl]-1-methyl-1H-benzimidazole-5-carbonitrile;
2-(isoquinolin-4-yl)-1-methyl-1H-benzimidazole-5-carbonitrile;
1-methyl-2-(pyridin-4-yl)-1H-benzimidazole-5-carbonitrile;
5-bromo-6-fluoro-2-(5-methoxypyridin-3-yl)-1-methyl-1-H-benzimidazole;
5-bromo-6-fluoro-1-methyl-2-(pyridin-3-yl)-1H-benzimidazole;
5-bromo-6-fluoro-2-(5-fluoropyridin-3-yl)-1-methyl-1H-benzimidazole;
4-(5-bromo-6-fluoro-1-methyl-1H-benzimidazol-2-yl)isoquinoline;
5-bromo-2-(3-chloropyridin-4-yl)-6-fluoro-1-methyl-1H-benzimidazole;
1-methyl-5-(methyl sulfonyl)-2-(pyridin-3-yl)-1H-benzimidazole;
2-(5-fluoropyridin-3-yl)-1-methyl-5-(methylsulfonyl)-1H-benzimidazole;
2-(5-methoxypyridin-3-yl)-1-methyl-5-(methylsulfonyl)-1H-benzimidazole;
1-ethyl-5-(methylsulfonyl)-2-(pyridin-3-yl)-1H-benzimidazole;
1-ethyl-2-(5-fluoropyridin-3-yl)-5-(methylsulfonyl)-1H-benzimidazole;
4-[1-ethyl-5-(methylsulfonyl)-1H-benzimidazol-2-yl]isoquinoline;
1-ethyl-2-(5-methoxypyridin-3-yl)-5-(methylsulfonyl)-1H-benzimidazole;
1-ethyl-5-(methylsulfonyl)-2-(pyridin-3-yl)-1H-benzimidazole;
5-(methylsulfonyl)-1-(propan-2-yl)-2-(pyridin-3-yl)-1H-benzimidazole;
6-bromo-1-cyclopropyl-2-(pyridin-3-yl)-1H-benzimidazole;
5,6-dichloro-2-(5-methoxypyridin-3-yl)-1-methyl-1H-benzimidazole;
5,6-dichloro-2-(5-fluoropyridin-3-yl)-1-methyl-1H-benzimidazole;
5,6-dichloro-2-(5-methoxy-4-methylpyridin-3-yl)-1-methyl-1H-benzimidazole;
5,6-dichloro-1-methyl-2-(pyridin-4-yl)-1H-benzimidazole;
5,6-dichloro-2-(3-fluoropyridin-4-yl)-1-methyl-1H-benzimidazole;
5,6-dichloro-2-(3-chloropyridin-4-yl)-1-methyl-1H-benzimidazole;
1-methyl-2-(pyridin-3-yl)-1H-benzimidazol-5-amine;
2-(5-methoxypyridin-3-yl)-1-methyl-1H-benzimidazol-5-amine;
1-ethyl-2-(pyridin-3-yl)-1H-benzimidazol-5-amine;
2-(5-fluoropyridin-3-yl)-1-methyl-1H-benzimidazol-5-amine;
1-methyl-5-nitro-2-(pyridin-3-yl)-1H-benzimidazole;
N-[1-methyl-2-(pyridin-3-yl)-1H-benzimidazol-5-yl]acetamide;
methyl 1-methyl-2-(pyridin-3-yl)-1H-benzimidazole-7-carboxylate;
methyl 2-(5-fluoropyridin-3-yl)-1-methyl-1H-benzimidazole-7-carboxylate;
methyl 1-methyl-2-(pyridin-4-yl)-1H-benzimidazole-7-carboxylate;
methyl 1-methyl-2-(pyridin-3-yl)-1H-benzimidazole-5-carboxylate;
methyl 2-(5-fluoropyridin-3-yl)-1-methyl-1H-benzimidazole-5-carboxylate;
1-methyl-2-(pyridin-3-yl)-1H-benzimidazole-5-carboxylic acid;
2-(5-fluoropyridin-3-yl)-1-methyl-1H-benzimidazole-7-carboxylic acid;
1-methyl-2-(pyridin-3-yl)-1H-benzimidazole-7-carboxylic acid;
5,6-difluoro-1-methyl-2-(5-methylpyridin-3-yl)-1H-benzimidazole;
2-(5-bromopyridin-3-yl)-5,6-difluoro-1-methyl-1H-benzimidazole;
5-(5,6-difluoro-1-methyl-1H-benzimidazol-2-yl)pyridine-3-carbonitrile;
5,6-difluoro-2-(5-methoxypyridin-3-yl)-1-methyl-1H-benzimidazole;
5,6-difluoro-2-(5-fluoropyridin-3-yl)-1-(propan-2-yl)-1H-benzimidazole;
1-ethyl-5,6-difluoro-2-(5-fluoropyridin-3-yl)-1H-benzimidazole;
[3-(5,6-difluoro-1-methyl-1H-benzimidazol-2-yl)-5-fluoropyridin-4-yl]methanol;
6-chloro-2-(5-methoxypyridin-3-yl)-1-methyl-1H-benzimidazole;
6-chloro-1-methyl-2-(pyridin-3-yl)-1H-benzimidazole;
6-chloro-2-(5-fluoropyridin-3-yl)-1-methyl-1H-benzimidazole;
6-chloro-2-(5-methoxy-4-methylpyridin-3-yl)-1-methyl-1H-benzimidazole;
5-(6-chloro-1-methyl-1H-benzimidazol-2-yl)pyridine-3-carbonitrile;

6-chloro-2-(5-fluoro-4-methylpyridin-3-yl)-1-methyl-1H-benzimidazole;
2-(5-bromopyridin-3-yl)-6-chloro-1-methyl-1H-benzimidazole;
6-chloro-2-[5-(3,5-dimethylisoxazol-4-yl)pyridin-3-yl]-1-methyl-1H-benzimidazole;
6-chloro-1-methyl-2-(4-methyl-pyridin-3-yl)-1H-benzimidazole;
6-chloro-1-methyl-2-(5-methyl-pyridin-3-yl)-1H-benzimidazole;
6-chloro-1-methyl-2-(pyridin-4-yl)-1H-benzimidazole;
6-chloro-2-(3-chloropyridin-4-yl)-1-methyl-1H-benzimidazole;
6-chloro-1-methyl-2-[4-(trifluoro-methyl)pyridin-3-yl]-1H-benzimidazole;
6-chloro-2-(3-fluoropyridin-4-yl)-1-methyl-1H-benzimidazole;
6-chloro-1-methyl-2-[5-(trifluoro-methyl)pyridin-3-yl]1H-benzimidazole;
6-chloro-1-methyl-2-[5-(1-methyl-1H-pyrazol-4-yl)pyridin-3-yl]-1H-benzimidazole;
4-(5,7-difluoro-1-methyl-1H-benzimidazol-2-yl)isoquinoline;
4-(5,7-difluoro-1-methyl-1H-benzimidazol-2-yl)isoquinoline;
5,7-difluoro-2-(5-fluoropyridin-3-yl)-1-methyl-1H-benzimidazole;
2-(5-bromopyridin-3-yl)-5,7-difluoro-1-methyl-1H-benzimidazole;
5,7-difluoro-2-(5-methoxypyridin-3-yl)-1-methyl-1H-benzimidazole;
5-(5,7-difluoro-1-methyl-1H-benzimidazol-2-yl)pyridine-3-carbonitrile;
5,7-difluoro-1-methyl-2-(5-methylpyridin-3-yl)-1H-benzimidazole;
6,7-difluoro-2-(5-fluoropyridin-3-yl)-1-methyl-1H-benzimidazole;
6,7-difluoro-1-methyl-2-(5-methylpyridin-3-yl)-1H-benzimidazole;
2-(5-bromopyridin-3-yl)-6,7-difluoro-1-methyl-1H-benzimidazole;
5-(6,7-difluoro-1-methyl-1H-benzimidazol-2-yl)pyridine-3-carbonitrile;
5-(6,7-difluoro-1-methyl-1H-benzimidazol-2-yl)pyridine-3-carbonitrile;
2-(4,5-dimethylpyridin-3-yl)-6,7-difluoro-1-methyl-1H-benzimidazole;
6,7-difluoro-1-methyl-2-(pyridin-3-yl)-1H-benzimidazole;
6,7-difluoro-1-methyl-2-(4-methylpyridin-3-yl)-1H-benzimidazole;
1   6,7-difluoro-1-methyl-2-(3-methylpyridin-4-yl)-1H-benzimidazole;
6,7-difluoro-1-methyl-2-[4-(trifluoromethyl)pyridin-3-yl]-1H-benzimidazole;
2-(3-bromopyridin-4-yl)-6,7-difluoro-1-methyl-1H-benzimidazole;
4-(6,7-difluoro-1-methyl-1H-benzimidazol-2-yl)pyridine-3-carbonitrile;
6,7-difluoro-2-(5-methoxy-4-methylpyridin-3-yl)-1-methyl-1H-benzimidazole;
6,7-difluoro-2-(5-methoxypyridin-3-yl)-1-methyl-1H-benzimidazole;
6,7-difluoro-1-methyl-2-[5-(trifluoromethyl)pyridin-3-yl]-1H-benzimidazole;
6,7-difluoro-2-(5-fluoro-4-methylpyridin-3-yl)-1-methyl-1H-benzimidazole;
5-fluoro-1-methyl-2-(pyridin-4-yl)-1H-benzimidazole;
5-fluoro-2-(5-fluoropyridin-3-yl)-1-methyl-1H-benzimidazole;
5-fluoro-2-(5-methoxypyridin-3-yl)-1-methyl-1H-benzimidazole;
4,6-difluoro-2-(5-fluoropyridin-3-yl)-1-methyl-1H-benzimidazole;
4,6-difluoro-1-methyl-2-(5-methylpyridin-3-yl)-1H-benzimidazole;
4,6-difluoro-1-methyl-2-(pyridin-4-yl)-1H-benzimidazole;
2-(3-chloropyridin-4-yl)-4,6-difluoro-1-methyl-1H-benzimidazole;
4,6-difluoro-2-(3-fluoropyridin-4-yl)-1-methyl-1H-benzimidazole;
6-bromo-1-methyl-2-(4-methyl-pyridin-3-yl)-1H-benzimidazole;
2-(5-fluoropyridin-3-yl)-1-methyl-1H-benzimidazole-5-carboxylic acid;
2-[5-(3,5-dimethylisoxazol-4-yl)pyridin-3-yl]-1-methyl-1H-benzimidazole-6-carbonitrile;
1-methyl-2-(pyridin-4-yl)-1H-benzimidazole-6-carbonitrile;
2-(3-chloropyridin-4-yl)-1-methyl-1H-benzimidazole-6-carbonitrile;
1-methyl-5-(1-methyl-1H-pyrazol-4-yl)-2-(pyridin-3-yl)-1H-benzimidazole;
2-(5-methoxypyridin-3-yl)-1-methyl-5-(1-methyl-1H-pyrazol-4-yl)-1H-benzimidazole;
5-(3,5-dimethylisoxazol-4-yl)-6-fluoro-2-(5-methoxypyridin-3-yl)-1-methyl-1H-benzimidazole;
5-(3,5-dimethylisoxazol-4-yl)-6-fluoro-2-(5-methoxypyridin-3-yl)-1-methyl-1H-benzimidazole;
4-[1-methyl-5-(1-methyl-1H-pyrazol-4-yl)-1H-benzimidazol-2-yl]isoquinoline;
5-(3,5-dimethylisoxazol-4-yl)-2-(5-methoxy-pyridin-3-yl)-1-methyl-1H-benzimidazole;
6-Chloro-5-fluoro-1-methyl-2-[4-(trifluoromethyl)pyridin-3-yl]-1H-benzimidazole;
6-chloro-5-fluoro-1-methyl-2-(pyridin-3-yl)-1H-benzimidazole;
6-chloro-5-fluoro-2-(5-methoxypyridin-3-yl)-1-methyl-1H-benzimidazole;
4-(6-chloro-5-fluoro-1-methyl-1H-benzimidazol-2-yl)isoquinoline;
6-chloro-5-fluoro-1-methyl-2-(pyridin-4-yl)-1H-benzimidazole;
6-chloro-2-(3-chloropyridin-4-yl)-5-fluoro-1-methyl-1H-benzimidazole;
6-chloro-5-fluoro-2-(3-fluoropyridin-4-yl)-1-methyl-1H-benzimidazole;
N, 1-dimethyl-2-(pyridin-3-yl)-1H-benzimidazole-7-carboxamide;
N, 1-dimethyl-2-(pyridin-3-yl)-1H-benzimidazole-5-carboxamide;
2-(5-fluoropyridin-3-yl)-N,1-dimethyl-1H-benz-imidazole-7-carboxamide;
N-[1-methyl-2-(pyridin-3-yl)-1H-benzimidazol-5-yl]methanesulfonamide;
N-[2-(5-fluoropyridin-3-yl)-1-methyl-1H-benzimidazol-5-yl]methanesulfonamide;
N-[2-(5-methoxypyridin-3-yl)-1-methyl-1H-benzimidazol-5-yl]methanesulfonamide;
N-[1-(propan-2-yl)-2-(pyridin-3-yl)-1H-benzimidazol-5-yl]methanesulfonamide;
N-[2-(5-fluoropyridin-3-yl)-1-(propan-2-yl)-1H-benzimidazol-5-yl]methanesulfonamide;

N-[1-ethyl-2-(pyridin-3-yl)-1H-benzimidazol-5-yl]methanesulfonamide;
N-[1-ethyl-2-(5-fluoropyridin-3-yl)-1H-benzimidazol-5-yl]methanesulfonamide;
5-Methoxy-1-methyl-2-[5-(1H-pyrazol-4-yl)pyridin-3-yl]-1H-benzimidazole;
2-(5-bromopyridin-3-yl)-5-methoxy-1-methyl-1H-benzimidazole;
5-methoxy-1-methyl-2-(pyridin-4-yl)-1H-benzimidazole;
5-methoxy-1-methyl-2-(pyridin-3-yl)-1H-benzimidazole;
2-(5-fluoropyridin-3-yl)-5-methoxy-1-methyl-1H-benzimidazole;
5-methoxy-2-(5-methoxypyridin-3-yl)-1-methyl-1H-benzimidazole;
4-(5-methoxy-i-methyl-iH-benzimidazol-2-yl)-4a,8a-dihydroisoquinoline;
5-methoxy-1-methyl-2-(4-methylpyridin-3-yl)-1H-benzimidazole;
2-(5-bromo-4-methylpyridin-3-yl)-5-methoxy-1-methyl-1H-benzimidazole;
2-[5-(3,5-dimethylisoxazol-4-yl)pyridin-3-yl]-5-methoxy-1-methyl-1H-benzimidazole;
4-[1-methyl-5-(propan-2-yloxy)-1H-benzimidazol-2-yl]isoquinoline;
5-Bromo-1-methyl-2-(pyridin-3-yl)-1H-benzimidazole-6-carbonitrile;
5-bromo-2-(5-fluoropyridin-3-yl)-1-methyl-1H-benzimidazole-6-carbonitrile;
5-fluoro-2-[5-fluoro-4-(hydroxymethyl)pyridin-3-yl]-1-methyl-1H-benzimidazole-6-carbonitrile;
or a pharmaceutically acceptable salt thereof.

16. A compound selected from the group consisting of:
1-methyl-5-nitro-2-(pyridin-3-yl)-1H-benzimidazole;
1-methyl-2-(pyridin-3-yl)-1H-benzimidazole-5-carboxylic acid;
2-(5-fluoropyridin-3-yl)-1-methyl-1H-benzimidazole-7-carboxylic acid;
1-methyl-2-(pyridin-3-yl)-1H-benzimidazole-7-carboxylic acid;
1-cyclopropyl-2-(5-fluoropyridin-3-yl)-1H-benzimidazole-5-carboxylic acid;
2-(5-fluoropyridin-3-yl)-1-methyl-1H-benzimidazole-5-carboxylic acid;
or a pharmaceutically acceptable salt thereof

\* \* \* \* \*